United States Patent
Parihar et al.

(10) Patent No.: US 9,826,976 B2
(45) Date of Patent: Nov. 28, 2017

(54) MOTOR DRIVEN SURGICAL INSTRUMENTS WITH LOCKABLE DUAL DRIVE SHAFTS

(71) Applicant: Ethicon Endo-Surgery, Inc., Cincinnati, OH (US)

(72) Inventors: Shailendra K. Parihar, Mason, OH (US); Robert L. Koch, Jr., Cincinnati, OH (US); Chester O. Baxter, III, Loveland, OH (US); Frederick E. Shelton, IV, Hillsboro, OH (US)

(73) Assignee: Ethicon LLC, Los Frailes Industrial Park, Guaynabo, PR (US)

( * ) Notice: Subject to any disclaimer, the term of this patent is extended or adjusted under 35 U.S.C. 154(b) by 557 days.

(21) Appl. No.: 14/248,590

(22) Filed: Apr. 9, 2014

(65) Prior Publication Data

US 2014/0305987 A1   Oct. 16, 2014

Related U.S. Application Data

(60) Provisional application No. 61/812,365, filed on Apr. 16, 2013, provisional application No. 61/812,376, (Continued)

(51) Int. Cl.
  *A61B 17/072* (2006.01)
  *A61B 17/068* (2006.01)
  (Continued)

(52) U.S. Cl.
  CPC .......... *A61B 17/068* (2013.01); *A61B 17/072* (2013.01); *A61B 17/07207* (2013.01);
  (Continued)

(58) Field of Classification Search
  CPC ................ A61B 17/068; A61B 17/072; A61B 17/07207; A61B 17/115; A61B 17/1155;
  (Continued)

(56) References Cited

U.S. PATENT DOCUMENTS 66,052 A   6/1867   Smith
662,587 A   11/1900   Blake
(Continued)

FOREIGN PATENT DOCUMENTS

AU   2008207624 A1   3/2009
AU   2010214687 A1   9/2010
(Continued)

OTHER PUBLICATIONS

U.S. Appl. No. 12/031,573, filed Feb. 14, 2008.
(Continued)

*Primary Examiner* — Scott A. Smith

(57) ABSTRACT

Motor driven surgical instruments that include a first rotary drive system and a second rotary drive system. Various forms include a transmission assembly that is selectively shiftable between a first drive position wherein rotary motion generated by the motor is transferred to the first rotary drive system and a second drive position wherein rotary motion generated by the motor is transferred to the second rotary drive system. Various forms further include a locking assembly configured to mechanically prevent rotation of the second rotary drive system when the transmission assembly is in the first drive position as well as to prevent rotation of the first rotary drive system when the transmission assembly is in the second drive position.

18 Claims, 115 Drawing Sheets

Related U.S. Application Data filed on Apr. 16, 2013, provisional application No. 61/812,382, filed on Apr. 16, 2013, provisional application No. 61/812,385, filed on Apr. 16, 2013, provisional application No. 61/812,372, filed on Apr. 16, 2013.

(51) Int. Cl.
   A61B 17/00 (2006.01)
   A61B 17/115 (2006.01)
   A61B 90/00 (2016.01)

(52) U.S. Cl.
   CPC ......... *A61B 17/115* (2013.01); *A61B 17/1155* (2013.01); *A61B 2017/00398* (2013.01); *A61B 2017/07214* (2013.01); *A61B 2090/0811* (2016.02)

(58) Field of Classification Search
   CPC ........... A61B 2017/00367; A61B 2017/00398; A61B 2017/07214; A61B 2017/00734
   USPC .. 227/19, 175.1, 175.2, 176.1, 179.1, 180.1; 606/139, 143, 153, 213, 219
   See application file for complete search history.

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,799,151 A | 3/1974 | Fukaumi et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |

(56) References Cited

U.S. PATENT DOCUMENTS

| | | |
|---|---|---|
| 4,451,743 A | 5/1984 | Suzuki et al. |
| 4,454,887 A | 6/1984 | Kruger |
| 4,467,805 A | 8/1984 | Fukuda |
| 4,470,414 A | 9/1984 | Imagawa et al. |
| 4,473,077 A | 9/1984 | Noiles et al. |
| 4,475,679 A | 10/1984 | Fleury, Jr. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,856,078 A | 8/1989 | Konopka |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |

(56) References Cited

U.S. PATENT DOCUMENTS

| | | |
|---|---|---|
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,343,391 A | 8/1994 | Mushabac |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |

(56) References Cited

U.S. PATENT DOCUMENTS

| | | |
|---|---|---|
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman |
| 5,409,498 A | 4/1995 | Braddock et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |

(56) References Cited

U.S. PATENT DOCUMENTS

| | | |
|---|---|---|
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |

(56) References Cited

U.S. PATENT DOCUMENTS

| | | |
|---|---|---|
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |

(56) References Cited

U.S. PATENT DOCUMENTS

| | | |
|---|---|---|
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,049,145 A | 4/2000 | Austin et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,106,511 A | 8/2000 | Jensen |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |

(56) References Cited

U.S. PATENT DOCUMENTS

| | | | |
|---|---|---|---|
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,430,298 B1 | 8/2002 | Kettl et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| 6,443,973 B1 * | 9/2002 | Whitman ......... A61B 17/07207 227/176.1 |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Kornbluh et al. |
| 6,585,144 B2 | 7/2003 | Adams et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |

(56) References Cited

U.S. PATENT DOCUMENTS

| | | |
|---|---|---|
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,697,048 B2 | 2/2004 | Rosenberg et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nakamura et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |

(56) References Cited

U.S. PATENT DOCUMENTS

| | | |
|---|---|---|
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,025,743 B2 | 4/2006 | Mann et al. |
| 7,029,435 B2 | 4/2006 | Nakao |
| 7,029,439 B2 | 4/2006 | Roberts et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,980 B2 | 11/2006 | Buysse et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |

(56) References Cited

U.S. PATENT DOCUMENTS

| | | |
|---|---|---|
| 7,210,609 B2 | 5/2007 | Leiboff et |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,241,288 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |

(56) References Cited

U.S. PATENT DOCUMENTS

| | | |
|---|---|---|
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,583,063 B2 | 9/2009 | Dooley |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |

(56) References Cited

U.S. PATENT DOCUMENTS

| | | | |
|---|---|---|---|
| 7,735,703 | B2 | 6/2010 | Morgan et al. |
| 7,736,374 | B2 | 6/2010 | Vaughan et al. |
| 7,738,971 | B2 | 6/2010 | Swayze et al. |
| 7,740,159 | B2 | 6/2010 | Shelton, IV et al. |
| 7,742,036 | B2 | 6/2010 | Grant et al. |
| 7,743,960 | B2 | 6/2010 | Whitman et al. |
| 7,744,624 | B2 | 6/2010 | Bettuchi |
| 7,744,627 | B2 | 6/2010 | Orban, III et al. |
| 7,744,628 | B2 | 6/2010 | Viola |
| 7,748,587 | B2 | 7/2010 | Haramiishi et al. |
| 7,749,204 | B2 | 7/2010 | Dhanaraj et al. |
| 7,751,870 | B2 | 7/2010 | Whitman |
| 7,753,245 | B2 | 7/2010 | Boudreaux et al. |
| 7,753,904 | B2 | 7/2010 | Shelton, IV et al. |
| 7,758,612 | B2 | 7/2010 | Shipp |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,776,037 | B2 | 8/2010 | Odom |
| 7,776,060 | B2 | 8/2010 | Mooradian et al. |
| 7,778,004 | B2 | 8/2010 | Nerheim et al. |
| 7,780,054 | B2 | 8/2010 | Wales |
| 7,780,055 | B2 | 8/2010 | Scirica et al. |
| 7,780,663 | B2 | 8/2010 | Yates et al. |
| 7,780,685 | B2 | 8/2010 | Hunt et al. |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2* | 9/2010 | Moore .............. A61B 17/07207 227/176.1 |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,815,092 | B2 | 10/2010 | Whitman et al. |
| 7,815,565 | B2 | 10/2010 | Stefanchik et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,884 | B2 | 10/2010 | Lee et al. |
| 7,819,886 | B2 | 10/2010 | Whitfield et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,694 | B2 | 11/2010 | Tethrake et al. |
| 7,838,789 | B2 | 11/2010 | Stoffers et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,846,149 | B2 | 12/2010 | Jankowski |
| 7,850,642 | B2 | 12/2010 | Moll et al. |
| 7,850,982 | B2 | 12/2010 | Stopek et al. |
| 7,854,736 | B2 | 12/2010 | Ryan |
| 7,857,183 | B2 | 12/2010 | Shelton, IV |
| 7,857,185 | B2 | 12/2010 | Swayze et al. |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,879,070 | B2 | 2/2011 | Ortiz et al. |
| 7,883,465 | B2 | 2/2011 | Donofrio et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,891,531 | B1 | 2/2011 | Ward |
| 7,891,532 | B2 | 2/2011 | Mastri et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,877 | B2 | 3/2011 | Hall et al. |
| 7,896,895 | B2 | 3/2011 | Boudreaux et al. |
| 7,900,805 | B2 | 3/2011 | Shelton, IV et al. |
| 7,905,380 | B2 | 3/2011 | Shelton, IV et al. |
| 7,905,381 | B2 | 3/2011 | Baxter, III et al. |
| 7,905,889 | B2 | 3/2011 | Catanese, III et al. |
| 7,905,902 | B2 | 3/2011 | Huitema et al. |
| 7,909,191 | B2 | 3/2011 | Baker et al. |
| 7,909,220 | B2 | 3/2011 | Viola |
| 7,909,221 | B2 | 3/2011 | Viola et al. |
| 7,913,891 | B2 | 3/2011 | Doll et al. |
| 7,913,893 | B2 | 3/2011 | Mastri et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,848 | B2 | 4/2011 | Lau et al. |
| 7,918,867 | B2 | 4/2011 | Dana et al. |
| 7,922,061 | B2 | 4/2011 | Shelton, IV et al. |
| 7,922,063 | B2* | 4/2011 | Zemlok ............ A61B 17/07207 227/175.1 |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,927,328 | B2 | 4/2011 | Orszulak et al. |
| 7,928,281 | B2 | 4/2011 | Augustine |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,934,630 | B2 | 5/2011 | Shelton, IV et al. |
| 7,934,631 | B2 | 5/2011 | Balbierz et al. |
| 7,935,773 | B2 | 5/2011 | Hadba et al. |
| 7,938,307 | B2 | 5/2011 | Bettuchi |
| 7,941,865 | B2 | 5/2011 | Seman, Jr. et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,950,560 | B2 | 5/2011 | Zemlok et al. |
| 7,950,561 | B2 | 5/2011 | Aranyi |
| 7,951,071 | B2 | 5/2011 | Whitman et al. |

(56) References Cited

U.S. PATENT DOCUMENTS

| | | |
|---|---|---|
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,987,405 B2 | 7/2011 | Turner et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,576 B2 | 11/2011 | Cappola |
| 8,062,330 B2 | 11/2011 | Prommersberger et al. |
| 8,063,619 B2 | 11/2011 | Zhu et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,079,950 B2 | 12/2011 | Stern et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,122,128 B2 | 2/2012 | Burke |
| 8,123,103 B2 | 2/2012 | Milliman |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,840 B2 | 5/2012 | Milliman |
| 8,186,555 B2 | 5/2012 | Shelton, IV et al. |

(56) References Cited

U.S. PATENT DOCUMENTS

| | | |
|---|---|---|
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,286,845 B2 | 10/2012 | Perry et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |

(56) References Cited

U.S. PATENT DOCUMENTS

| | | |
|---|---|---|
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,574,199 B2 | 11/2013 | bon Bülow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,673,210 B2 | 3/2014 | Deshays |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |

(56) References Cited

U.S. PATENT DOCUMENTS

| | | |
|---|---|---|
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,967,443 B2 | 3/2015 | McCuen |
| 8,967,446 B2 | 3/2015 | Beardsley et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,016,542 B2 | 4/2015 | Shelton, IV et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,055,941 B2 | 6/2015 | Schmid et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Skarbnik et al. |
| 9,138,225 B2 | 9/2015 | Huang et al. |
| 9,149,274 B2 | 10/2015 | Spivey et al. |

(56) References Cited

U.S. PATENT DOCUMENTS

| | | |
|---|---|---|
| 9,149,325 B2 | 10/2015 | Worrell et al. |
| 9,161,803 B2 | 10/2015 | Yates et al. |
| 9,168,038 B2 | 10/2015 | Shelton, IV et al. |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,192,380 B2 | 11/2015 | Racenet et al. |
| 9,192,384 B2 | 11/2015 | Bettuchi |
| 9,193,045 B2 | 11/2015 | Saur et al. |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,750 B2 | 1/2016 | Weir et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,241,714 B2 | 1/2016 | Timm et al. |
| 9,259,274 B2 | 2/2016 | Prisco |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,308,011 B2 | 4/2016 | Chao et al. |
| 9,314,246 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,358,005 B2 | 6/2016 | Shelton, IV et al. |
| 9,364,220 B2 | 6/2016 | Williams |
| 9,364,230 B2 | 6/2016 | Shelton, IV et al. |
| 9,364,233 B2 | 6/2016 | Alexander, III et al. |
| 9,364,279 B2 | 6/2016 | Houser et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,433,419 B2 | 9/2016 | Gonzalez et al. |
| 9,445,813 B2 | 9/2016 | Shelton, IV et al. |
| 9,451,958 B2 | 9/2016 | Shelton, IV et al. |
| 9,480,476 B2 | 11/2016 | Aldridge et al. |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0026126 A1 | 2/2002 | Burdorff et al. |
| 2002/0029032 A1 | 3/2002 | Arkin |
| 2002/0029036 A1 | 3/2002 | Goble et al. |
| 2002/0049472 A1 | 4/2002 | Coleman et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0157481 A1 | 10/2002 | Kogiso et al. |
| 2002/0165541 A1 | 11/2002 | Whitman |
| 2002/0188170 A1 | 12/2002 | Santamore et al. |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0032345 A1 | 2/2004 | Kazuya et al. |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |

(56) References Cited

U.S. PATENT DOCUMENTS

| | | |
|---|---|---|
| 2004/0116952 A1 | 6/2004 | Sakurai et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267297 A1 | 12/2004 | Malackowski |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0116673 A1 | 6/2005 | Carl et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159184 A1 | 7/2005 | Kerner et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0267530 A1 | 12/2005 | Cummins |
| 2005/0272973 A1 | 12/2005 | Kawano et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |

(56) References Cited

U.S. PATENT DOCUMENTS

| | | |
|---|---|---|
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0027553 A1 | 2/2007 | Biran et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0090788 A1 | 4/2007 | Hansford et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1* | 8/2007 | Shelton ............ A61B 17/07207 227/176.1 |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0198039 A1 | 8/2007 | Jones et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0250113 A1 | 10/2007 | Hegeman et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0097563 A1 | 4/2008 | Petrie et al. |
| 2008/0108443 A1 | 5/2008 | Jinno et al. |
| 2008/0114250 A1 | 5/2008 | Urbano et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0241667 A1 | 10/2008 | Kohn et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0281254 A1 | 11/2008 | Humayun et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0069842 A1 | 3/2009 | Lee et al. |
| 2009/0076506 A1 | 3/2009 | Baker |
| 2009/0078736 A1 | 3/2009 | Van Lue |

(56) References Cited

U.S. PATENT DOCUMENTS

| | | |
|---|---|---|
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0101692 A1* | 4/2009 | Whitman ......... A61B 17/07207 227/175.1 |
| 2009/0108048 A1* | 4/2009 | Zemlok ............ A61B 17/07207 227/175.1 |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0179757 A1 | 7/2009 | Cohn et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248007 A1 | 10/2009 | Falkenstein et al. |
| 2009/0248038 A1 | 10/2009 | Blumenkranz et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0290016 A1 | 11/2009 | Suda |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0041945 A1 | 2/2010 | Isbell, Jr. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0191292 A1 | 7/2010 | DeMeo et al. |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0249759 A1 | 9/2010 | Hinman et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0009890 A1 | 1/2011 | Palmer et al. |
| 2011/0011916 A1 | 1/2011 | Levine |
| 2011/0016960 A1 | 1/2011 | Debrailly |
| 2011/0017799 A1 | 1/2011 | Whitman et al. |
| 2011/0021871 A1 | 1/2011 | Berkelaar |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0034910 A1 | 2/2011 | Ross et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060356 A1 | 3/2011 | Reschke et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0112517 A1 | 5/2011 | Peine et al. |
| 2011/0114697 A1 | 5/2011 | Baxter, III et al. |
| 2011/0118778 A1 | 5/2011 | Burbank |
| 2011/0121049 A1 | 5/2011 | Malinouskas et al. |
| 2011/0125138 A1 | 5/2011 | Malinouskas et al. |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0167619 A1 | 7/2011 | Smith et al. |
| 2011/0174099 A1* | 7/2011 | Ross .................. A61B 17/072 74/89.32 |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0199225 A1 | 8/2011 | Touchberry et al. |

(56) References Cited

U.S. PATENT DOCUMENTS

| | | |
|---|---|---|
| 2011/0208093 A1 | 8/2011 | Gross et al. |
| 2011/0210156 A1 | 9/2011 | Smith et al. |
| 2011/0241597 A1 | 10/2011 | Zhu et al. |
| 2011/0253765 A1 | 10/2011 | Nicholas et al. |
| 2011/0257650 A1 | 10/2011 | Deville et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0282446 A1 | 11/2011 | Schulte et al. |
| 2011/0290855 A1* | 12/2011 | Moore ............... A61B 17/072 227/180.1 |
| 2011/0290856 A1 | 12/2011 | Shelton, IV et al. |
| 2011/0293690 A1 | 12/2011 | Griffin et al. |
| 2011/0295269 A1 | 12/2011 | Swensgard et al. |
| 2011/0295295 A1 | 12/2011 | Shelton, IV et al. |
| 2011/0307023 A1 | 12/2011 | Tweden et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0045303 A1 | 2/2012 | Macdonald |
| 2012/0046692 A1 | 2/2012 | Smith et al. |
| 2012/0064483 A1 | 3/2012 | Lint et al. |
| 2012/0074200 A1 | 3/2012 | Schmid et al. |
| 2012/0078071 A1 | 3/2012 | Bohm et al. |
| 2012/0078244 A1 | 3/2012 | Worrell et al. |
| 2012/0078278 A1 | 3/2012 | Bales, Jr. et al. |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080498 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116367 A1 | 5/2012 | Houser et al. |
| 2012/0116388 A1 | 5/2012 | Houser et al. |
| 2012/0116391 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0228355 A1 | 9/2012 | Combrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241492 A1 | 9/2012 | Shelton, IV et al. |
| 2012/0241493 A1 | 9/2012 | Baxter, III et al. |
| 2012/0248167 A1 | 10/2012 | Flanagan et al. |
| 2012/0248169 A1 | 10/2012 | Widenhouse et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0277780 A1 | 11/2012 | Smith et al. |
| 2012/0283707 A1 | 11/2012 | Giordano et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0026973 A1 | 1/2013 | Luke et al. |
| 2013/0030608 A1 | 1/2013 | Taylor et al. |
| 2013/0032626 A1 | 2/2013 | Smith et al. |
| 2013/0037596 A1 | 2/2013 | Bear et al. |
| 2013/0046290 A1 | 2/2013 | Palmer et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103023 A1 | 4/2013 | Monson et al. |
| 2013/0103024 A1 | 4/2013 | Monson et al. |
| 2013/0105548 A1 | 5/2013 | Hodgkinson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126379 A1 | 5/2013 | Medhal et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233905 A1 | 9/2013 | Sorrentino et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0256371 A1 | 10/2013 | Shelton, IV et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0267945 A1 | 10/2013 | Behnke et al. |
| 2013/0270322 A1 | 10/2013 | Scheib et al. |
| 2013/0277412 A1 | 10/2013 | Gresham et al. |

(56) References Cited

U.S. PATENT DOCUMENTS

| | | |
|---|---|---|
| 2013/0282052 A1 | 10/2013 | Aranyi et al. |
| 2013/0310873 A1 | 11/2013 | Stopek et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0012238 A1 | 1/2014 | Chen et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207125 A1 | 7/2014 | Applegate et al. |
| 2014/0207166 A1 | 7/2014 | Shelton, IV et al. |
| 2014/0224857 A1 | 8/2014 | Schmid |
| 2014/0230595 A1 | 8/2014 | Butt et al. |
| 2014/0232316 A1 | 8/2014 | Philipp |
| 2014/0236184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |

(56) References Cited

U.S. PATENT DOCUMENTS

| | | |
|---|---|---|
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0157354 A1 | 6/2015 | Bales, Jr. et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0209041 A1 | 7/2015 | Milliman et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0069449 A1 | 3/2016 | Kanai et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |

(56) References Cited

U.S. PATENT DOCUMENTS

| | | |
|---|---|---|
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | Timm et al. |
| 2016/0220249 A1 | 8/2016 | Shelton, IV et al. |
| 2016/0220254 A1 | 8/2016 | Baxter, III et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0238108 A1 | 8/2016 | Kanai et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249930 A1 | 9/2016 | Hall et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, IV et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262760 A1 | 9/2016 | Shelton, IV et al. |
| 2016/0270780 A1 | 9/2016 | Hall et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |
| 2016/0331375 A1 | 11/2016 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 86100996 A | 9/1986 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101254126 A | 9/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101541251 A | 9/2009 |
| CN | 101675898 A | 3/2010 |
| CN | 101683280 A | 3/2010 |
| CN | 101028205 A | 1/2011 |
| CN | 101934098 A | 5/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |

(56) References Cited

FOREIGN PATENT DOCUMENTS

| | | | |
|---|---|---|---|
| CN | 101310680 B | 4/2012 |
| CN | 202397539 U | 8/2012 |
| CN | 101317782 B | 10/2012 |
| CN | 101507633 B | 2/2013 |
| CN | 101023879 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| CN | 102166129 B | 3/2015 |
| CN | 102247177 B | 2/2016 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |

(56) References Cited

FOREIGN PATENT DOCUMENTS

| | | |
|---|---|---|
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A2 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A1 | 11/2008 |
| EP | 1990014 A2 | 11/2008 |
| EP | 1992296 A1 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |

(56) References Cited

FOREIGN PATENT DOCUMENTS

| | | |
|---|---|---|
| EP | 2025293 A1 | 2/2009 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A1 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 2377472 A1 | 10/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A | 2/2012 |
| EP | 2090253 B1 | 3/2012 |
| EP | 2430986 A2 | 3/2012 |
| EP | 1347638 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 A2 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 2606834 A2 | 6/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777528 A2 | 9/2014 |
| EP | 2777538 A2 | 9/2014 |
| EP | 2446835 B1 | 1/2015 |
| EP | 2923660 A2 | 9/2015 |
| EP | 1774914 B1 | 12/2015 |
| EP | 2090235 B1 | 4/2016 |
| EP | 2510891 B1 | 6/2016 |
| ES | 2396594 T3 | 2/2013 |
| FR | 459743 A | 11/1913 |
| FR | 999646 A | 2/1952 |
| FR | 1112936 A | 3/1956 |

(56) References Cited

FOREIGN PATENT DOCUMENTS

| | | |
|---|---|---|
| FR | 2598905 A1 | 11/1987 |
| FR | 2765794 A1 | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 47-11908 Y1 | 5/1972 |
| JP | 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-63054 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 07-9622 U | 2/1995 |
| JP | H 7-47070 A | 2/1995 |
| JP | H 07-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |

(56) References Cited

FOREIGN PATENT DOCUMENTS

| | | |
|---|---|---|
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-237881 A | 10/2008 |
| JP | 2008-259860 A | 10/2008 |
| JP | 2008-264535 A | 11/2008 |
| JP | 2008-283459 A | 11/2008 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504813 A | 2/2010 |
| JP | 2010-504846 A | 2/2010 |
| JP | 2010-505524 A | 2/2010 |
| JP | 2010-069310 A | 4/2010 |
| JP | 2010-075695 A | 4/2010 |
| JP | 2010-088876 A | 4/2010 |
| JP | 2010-098844 A | 4/2010 |
| JP | 2010-214166 A | 9/2010 |
| JP | 4549018 B2 | 9/2010 |
| JP | 2010-540192 A | 12/2010 |
| JP | 2011-524199 A | 9/2011 |
| JP | 4783373 B2 | 9/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 1814161 A1 | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |

(56) References Cited

FOREIGN PATENT DOCUMENTS

| | | |
|---|---|---|
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/30659 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A2 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A2 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/048809 A1 | 6/2005 |
| WO | WO 2005/055846 A1 | 6/2005 |
| WO | WO 2005/072634 A2 | 8/2005 |
| WO | WO 2005/078892 A1 | 8/2005 |

(56) References Cited

FOREIGN PATENT DOCUMENTS

| | | |
|---|---|---|
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021687 A1 | 2/2008 |
| WO | WO 2008/021969 A2 | 2/2008 |
| WO | WO 2008/039237 A1 | 4/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/112912 A2 | 9/2008 |
| WO | WO 2008/118728 A1 | 10/2008 |
| WO | WO 2008/118928 A2 | 10/2008 |
| WO | WO 2008/124748 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2012/166503 A1 | 12/2012 |
| WO | WO 2013/009252 A2 | 1/2013 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |
| WO | WO 2014/004294 A2 | 1/2014 |
| WO | WO 2015/153642 A1 | 10/2015 |

OTHER PUBLICATIONS

International Search Report for PCT/US2014/033893, dated Oct. 1, 2014 (4 pages).
International Search Report for PCT/US2014/033894, dated Feb. 12, 2015 (5 pages).
International Search Report for PCT/US2014/033895, dated Jan. 26, 2015 (9 pages).
International Search Report for PCT/US2014/033896, dated Jan. 22, 2015 (8 pages).
International Search Report for PCT/US2014/033897, dated Feb. 11, 2015 (9 pages).
International Search Report for PCT/US2014/033898, dated Nov. 19, 2014 (6 pages).
International Search Report for PCT/US2014/033899, dated Feb. 5, 2015 (5 pages).
International Search Report for PCT/US2014/033900, dated Nov. 19, 2014 (5 pages).
International Search Report for PCT/US2014/033901, dated Sep. 8, 2014 (3 pages).
European Search Report for Application No. 14164924.4, dated Dec. 5, 2014 (6 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract;

(56) References Cited

OTHER PUBLICATIONS http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
International Preliminary Report on Patentability for PCT/US2014/033893, dated Oct. 20, 2015 (7 pages).
International Preliminary Report on Patentability for PCT/US2014/033894, dated Oct. 20, 2015 (8 pages).
International Preliminary Report on Patentability for PCT/US2014/033895, dated Oct. 20, 2015 (16 pages).
International Preliminary Report on Patentability for PCT/US2014/033896, dated Oct. 20, 2015 (13 pages).
International Preliminary Report on Patentability for PCT/US2014/033897, dated Oct. 20, 2015 (13 pages).
International Preliminary Report on Patentability for PCT/US2014/033898, dated Oct. 20, 2015 (9 pages).
International Preliminary Report on Patentability for PCT/US2014/033899, dated Oct. 20, 2015 (8 pages).
International Preliminary Report on Patentability for PCT/US2014/033900, dated Oct. 20, 2015 (9 pages).
International Preliminary Report on Patentability for PCT/US2014/033901, dated Oct. 20, 2015 (5 pages).
European Examination Report for Application No. 14164924.4, dated Aug. 4, 2016 (6 pages).
European Search Report for Application No. 14165011.9, dated Nov. 12, 2014 (6 pages).
European Examination Report for Application No. 14165011.9, dated Jan. 19, 2017 (5 pages).
Partial European Search Report for Application No. 14164975.6, dated Sep. 17, 2014 (5 pages).
European Search Report for Application No. 14164975.6, dated Feb. 5, 2015 (8 pages).
Partial European Search Report for Application No. 14164936.8, dated Feb. 3, 2015 (7 pages).
European Search Report for Application No. 14164982.2, dated Nov. 26, 2014 (8 pages).
European Search Report for Application No. 14164968.1, dated Nov. 21, 2014 (8 pages).
Partial European Search Report for Application No. 14164935.0, dated Dec. 17, 2014 (5 pages).
European Search Report for Application No. 14164935.0, dated Apr. 13, 2015 (7 pages).
European Search Report for Application No. 14164925.1, dated Sep. 10, 2014 (5 pages).
European Search Report for Application No. 14164948.3, dated Nov. 18, 2014 (10 pages).

(56) References Cited

OTHER PUBLICATIONS

European Examination Report for Application No. 14164925.1, dated Jan. 23, 2017 (3 pages).
European Search Report for Application No. 14164936.8, dated Jun. 5, 2015 (14 pages).
European Search Report for Application No. 14185832.4, dated Jun. 17, 2015 (12 pages).

* cited by examiner

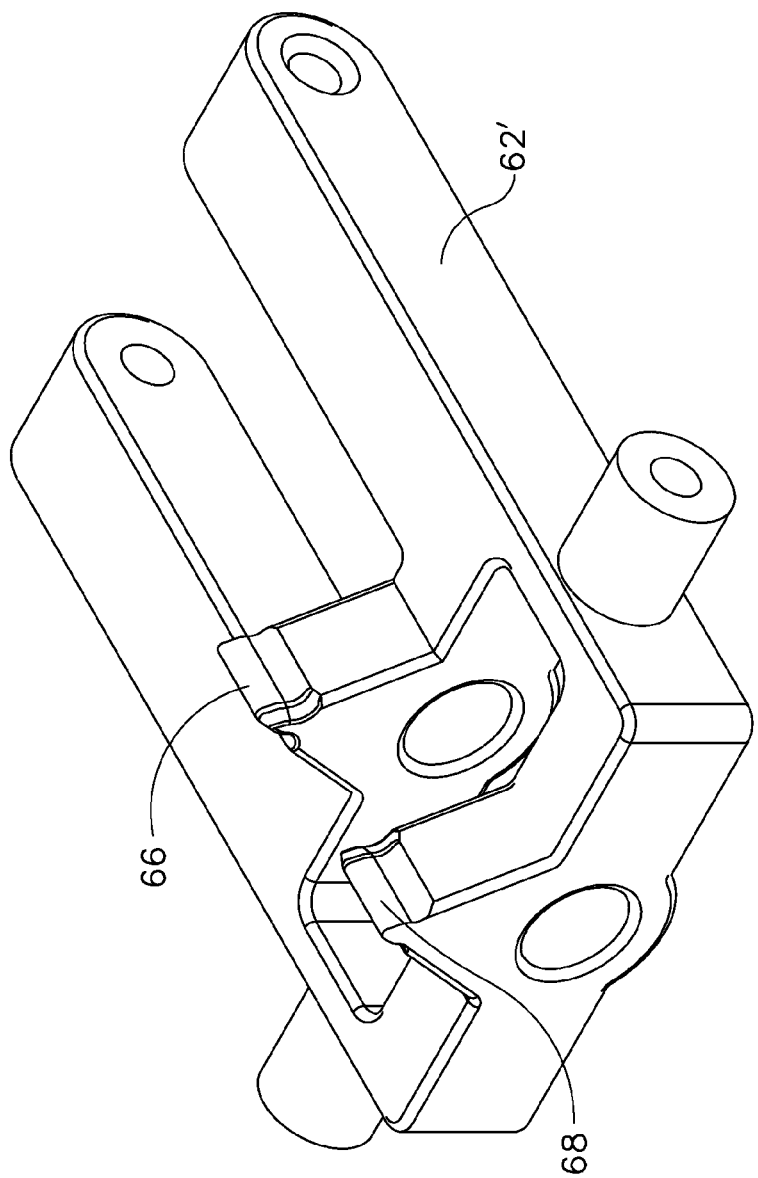

| DEVICE / SHAFT | OPERATION | TOTAL TIME FOR ONE COMPLETE STROKE (SECS) | LOAD CURRENT REQUIREMENT (AMPS) |
|---|---|---|---|
| CIRCULAR | CLOSING | 5 | 5.58 |
| CIRCULAR | OPENING | 5 | 5.58 |
| CIRCULAR | FIRING | 1.25 | 15.69 |
| CONTOUR | CLOSING | 2 | 4.88 |
| CONTOUR | OPENING | 2 | 4.88 |
| CONTOUR | FIRING | 1.5 | 9.41 |
| TLC | CLOSING | 1.5 | 5.23 |
| TLC | OPENING | 1.5 | 5.23 |
| TLC | FIRING | 5 | 0.69 |

FIG. 62

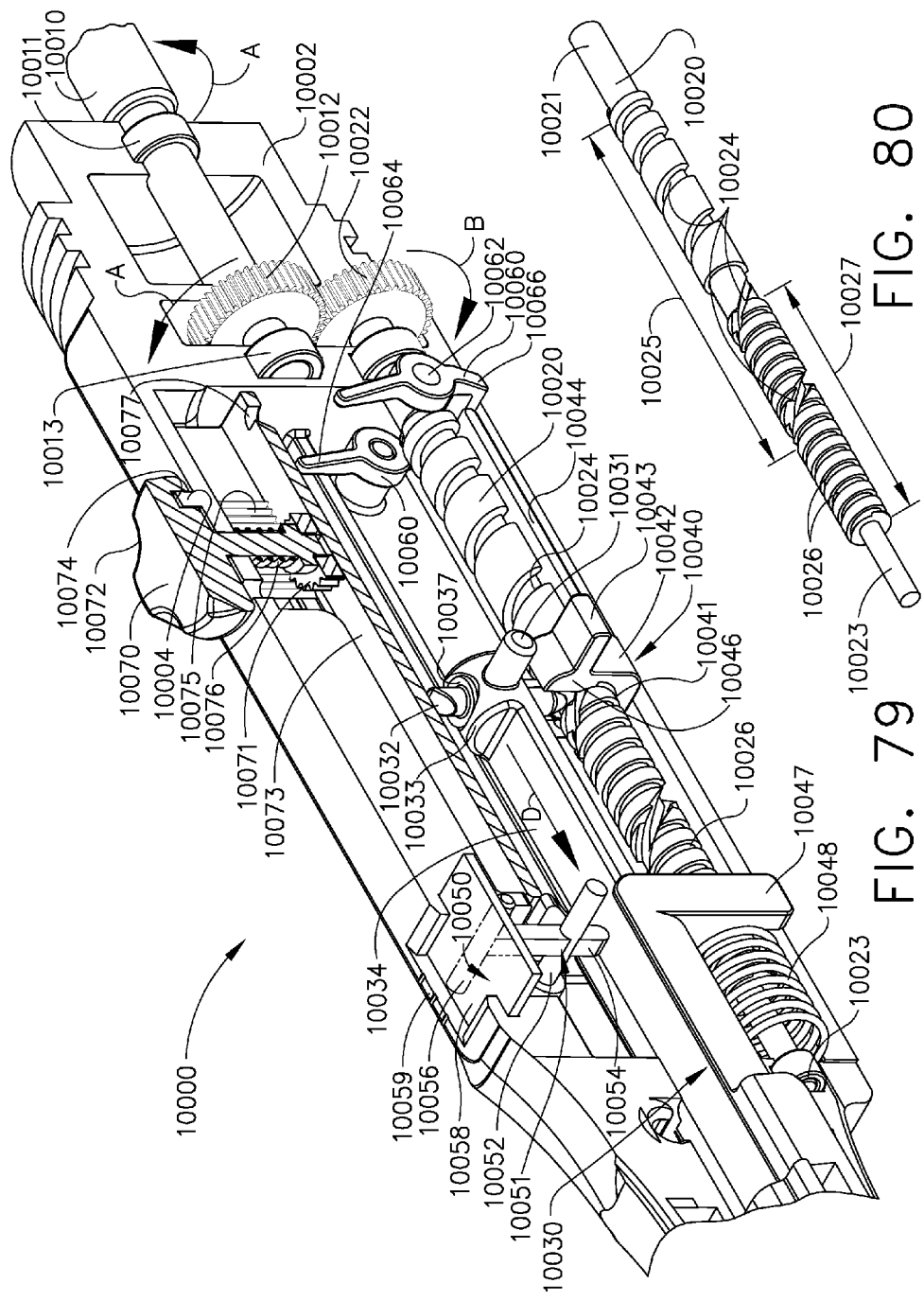

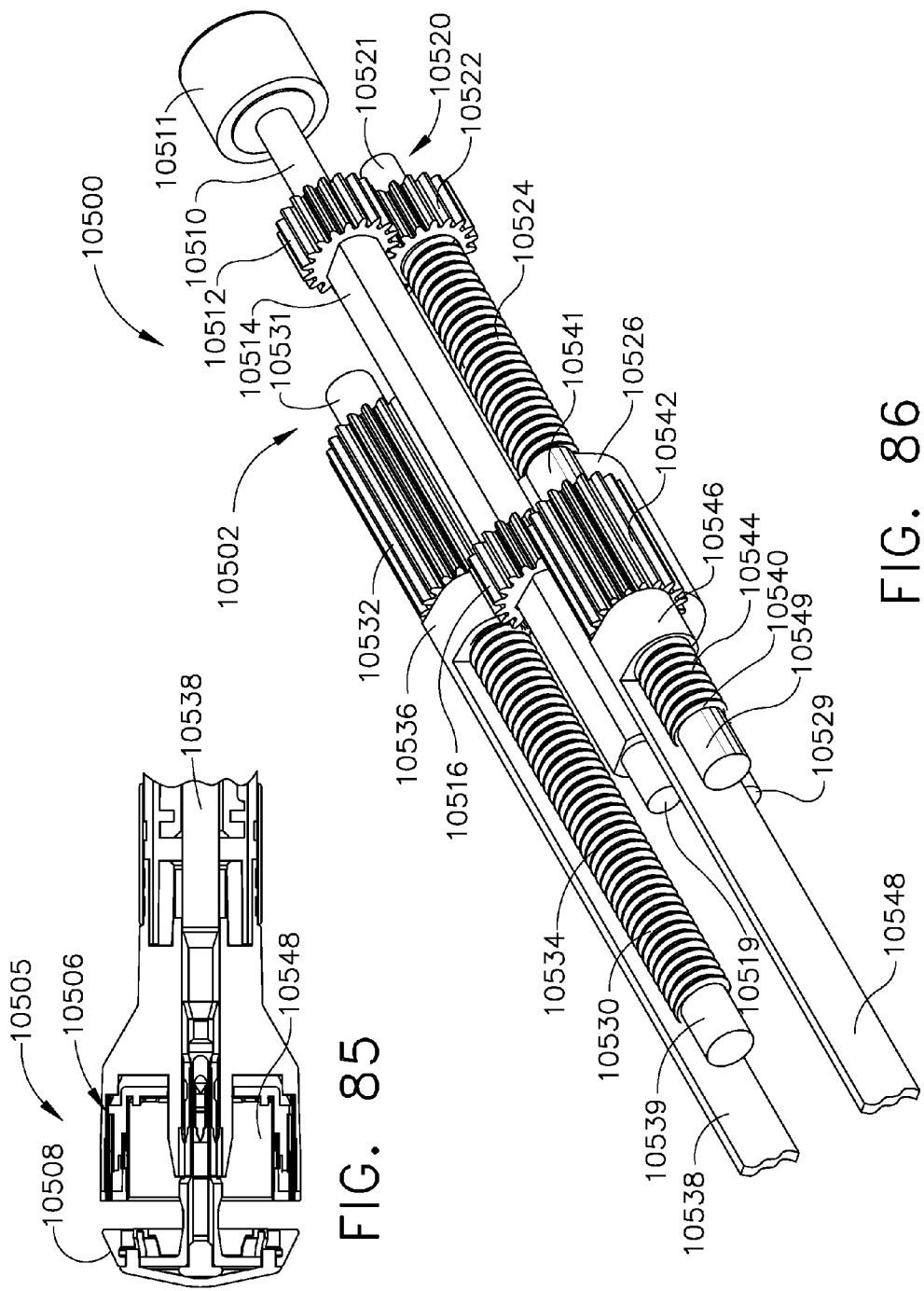

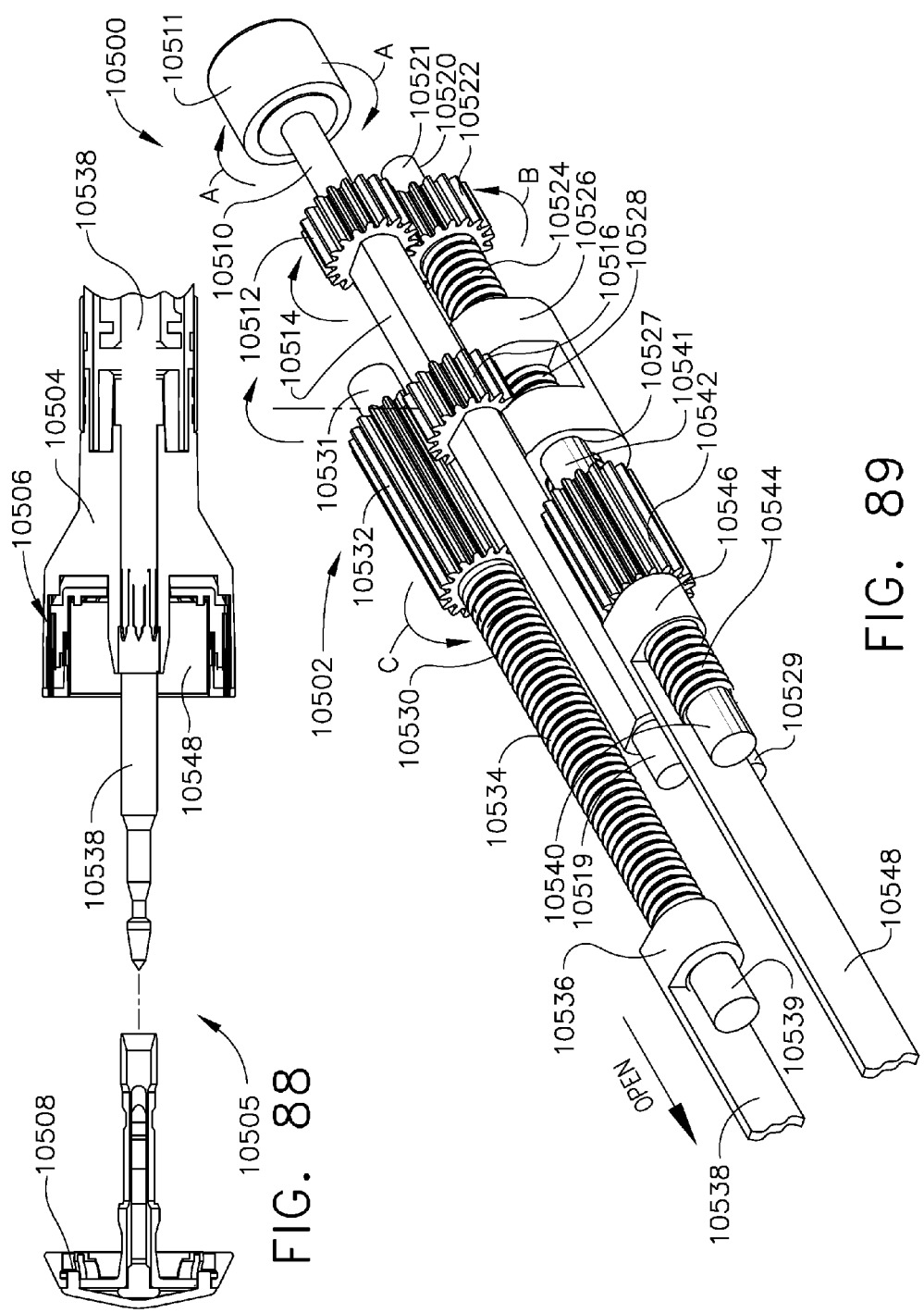

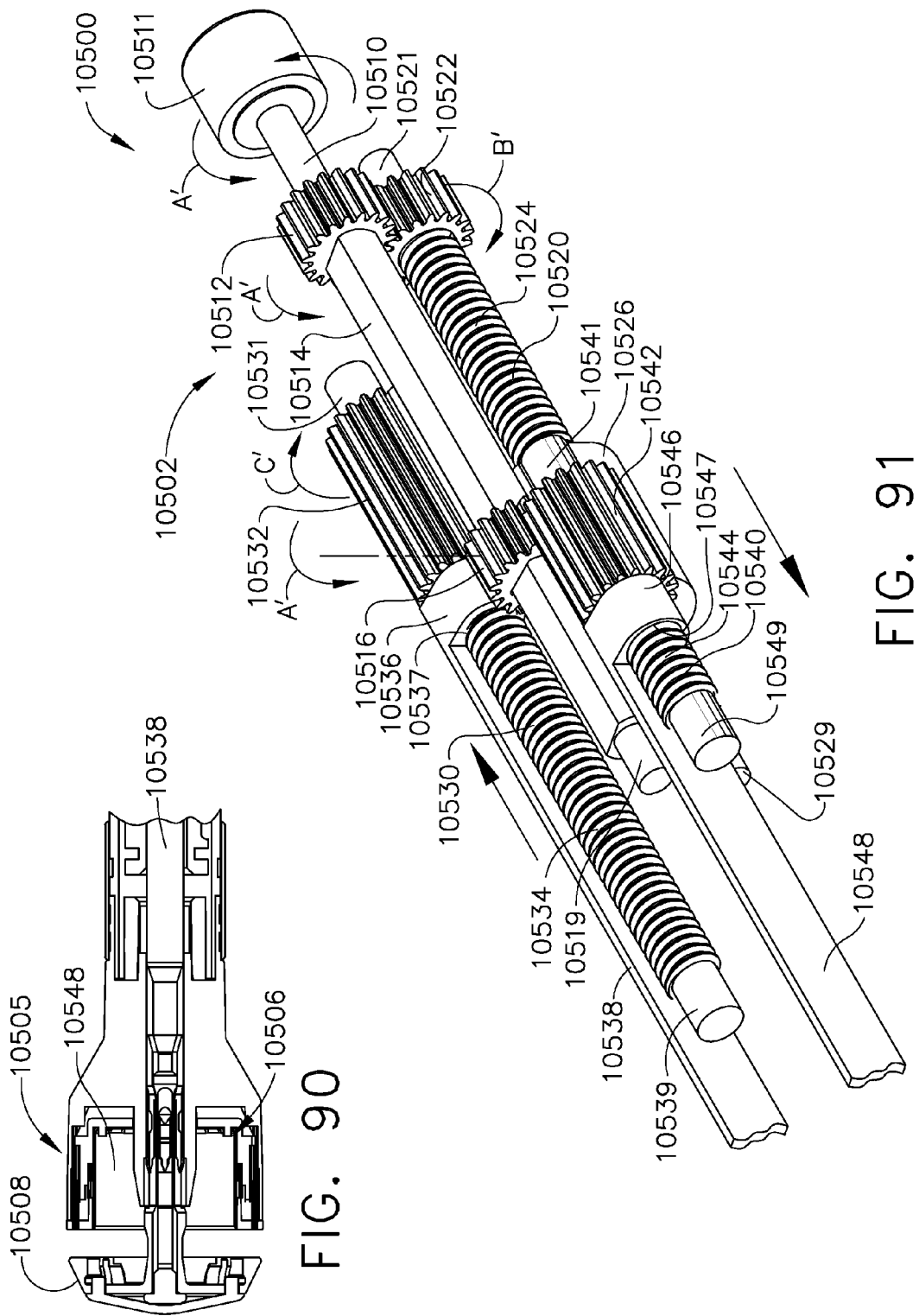

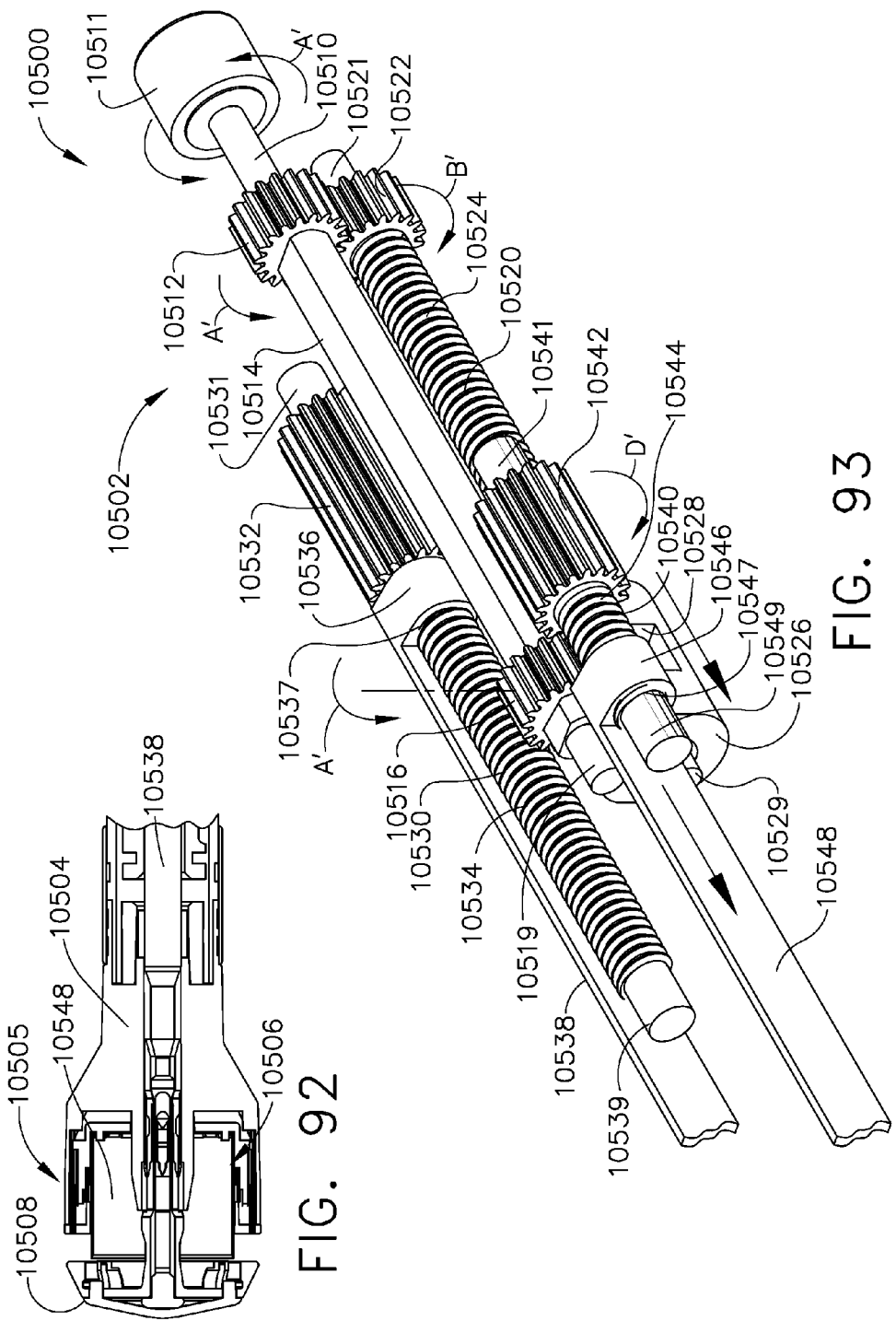

MOTOR DRIVEN SURGICAL INSTRUMENTS WITH LOCKABLE DUAL DRIVE SHAFTS

CROSS-REFERENCE TO RELATED APPLICATIONS

This non-provisional patent application claims the benefit under 35 U.S.C. §119(e) of U.S. Provisional Patent Application Ser. No. 61/812,365, entitled SURGICAL INSTRUMENT WITH MULTIPLE FUNCTIONS PERFORMED BY A SINGLE MOTOR, filed Apr. 16, 2013, which is incorporated by reference herein in its entirety. This non-provisional patent application also claims the benefit under 35 U.S.C. §119(e) of U.S. Provisional Patent Application Ser. No. 61/812,376, entitled LINEAR CUTTER WITH POWER, filed Apr. 16, 2013, which is incorporated by reference herein in its entirety. This non-provisional patent application also claims the benefit under 35 U.S.C. §119(e) of U.S. Provisional Patent Application Ser. No. 61/812,382, entitled LINEAR CUTTER WITH MOTOR AND PISTOL GRIP, filed Apr. 16, 2013, which is incorporated by reference herein in its entirety. This non-provisional patent application also claims the benefit under 35 U.S.C. §119(e) of U.S. Provisional Patent Application Ser. No. 61/812,385, entitled SURGICAL INSTRUMENT HANDLE WITH MULTIPLE ACTUATION MOTORS AND MOTOR CONTROL, filed Apr. 16, 2013, which is incorporated by reference herein in its entirety. This non-provisional patent application also claims the benefit under 35 U.S.C. §119(e) of U.S. Provisional Patent Application Ser. No. 61/812,372, entitled SURGICAL INSTRUMENT WITH MULTIPLE FUNCTIONS PERFORMED BY A SINGLE MOTOR, filed Apr. 16, 2013, which is incorporated by reference herein in its entirety.

BACKGROUND

Various forms of the invention relate to surgical instruments and, in various embodiments, to surgical cutting and stapling instruments and staple cartridges therefor that are designed to cut and staple tissue.

BRIEF DESCRIPTION OF THE DRAWINGS

The various features and advantages of this invention and the manner of attaining them will become more apparent and the invention itself will be better understood by reference to the following description of embodiments of the invention taken in conjunction with the accompanying drawings, wherein:

FIG. 6A is a perspective view of an alternative transmission carriage with locking means;

FIG. 50A is an enlarged view of a portion of the surgical end effector of FIG. 50;

FIG. 62 is a table depicting total time to complete a stroke and load current requirements for various operations of various device shafts;

FIG. 79 is a partial cross-sectional perspective view of a surgical instrument including a rotatable drive shaft, a closure drive operable by said drive shaft, and a firing drive operable by said drive shaft, wherein the closure drive is illustrated in a partially open configuration and the firing drive is illustrated in an unfired configuration;

FIG. 80 is a perspective view of the rotatable drive shaft of FIG. 79;

FIG. 85 is a partial cross-sectional view of an end effector and a shaft of a surgical instrument illustrated in a closed, unfired configuration;

FIG. 86 is a perspective view of a transmission for operating the surgical instrument of FIG. 85 illustrated in a configuration which corresponds with the configuration of FIG. 85;

FIG. 88 is a partial cross-sectional view of the end effector and the shaft of FIG. 85 illustrated in an open, unfired configuration;

FIG. 89 is a perspective view of the transmission of FIG. 86 illustrated in a configuration which corresponds with the configuration illustrated in FIG. 88;

FIG. 90 is a partial cross-sectional view of the end effector and the shaft of FIG. 85 illustrated in a closed, unfired configuration;

FIG. 91 is a perspective view of the transmission of FIG. 86 illustrated in a configuration which corresponds with the configuration illustrated in FIG. 90;

FIG. 92 is a partial cross-sectional view of the end effector and the shaft of FIG. 85 illustrated in a closed, fired configuration;

FIG. 93 is a perspective view of the transmission of FIG. 86 illustrated in a configuration which corresponds with the configuration illustrated in FIG. 92;

FIG. 115 is a partial cross-sectional view of the handle of FIG. 111 illustrating the transmission of FIG. 114 operably engaged with a firing system of the surgical stapling instrument of FIG. 111;

FIG. 116 is an exploded view of the transmission of FIG. 114;

FIG. 117 is a perspective view of a surgical stapling instrument in accordance with at least one embodiment illustrated with some components removed and illustrated in an open configuration;

FIG. 118 is a perspective view of the surgical stapling instrument of FIG. 117 illustrated with some components removed and illustrated in a closed configuration;

FIG. 119 is a perspective view of another end effector arrangement and a staple pack embodiment therefor prior to installing the staple pack into the end effector;

FIG. 120 is another perspective view of the end effector and staple pack of FIG. 119 with the staple pack installed into the end effector; and FIG. 121 is another perspective view of the end effector and staple pack of FIG. 120 with the keeper member of the staple pack removed therefrom.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 1:
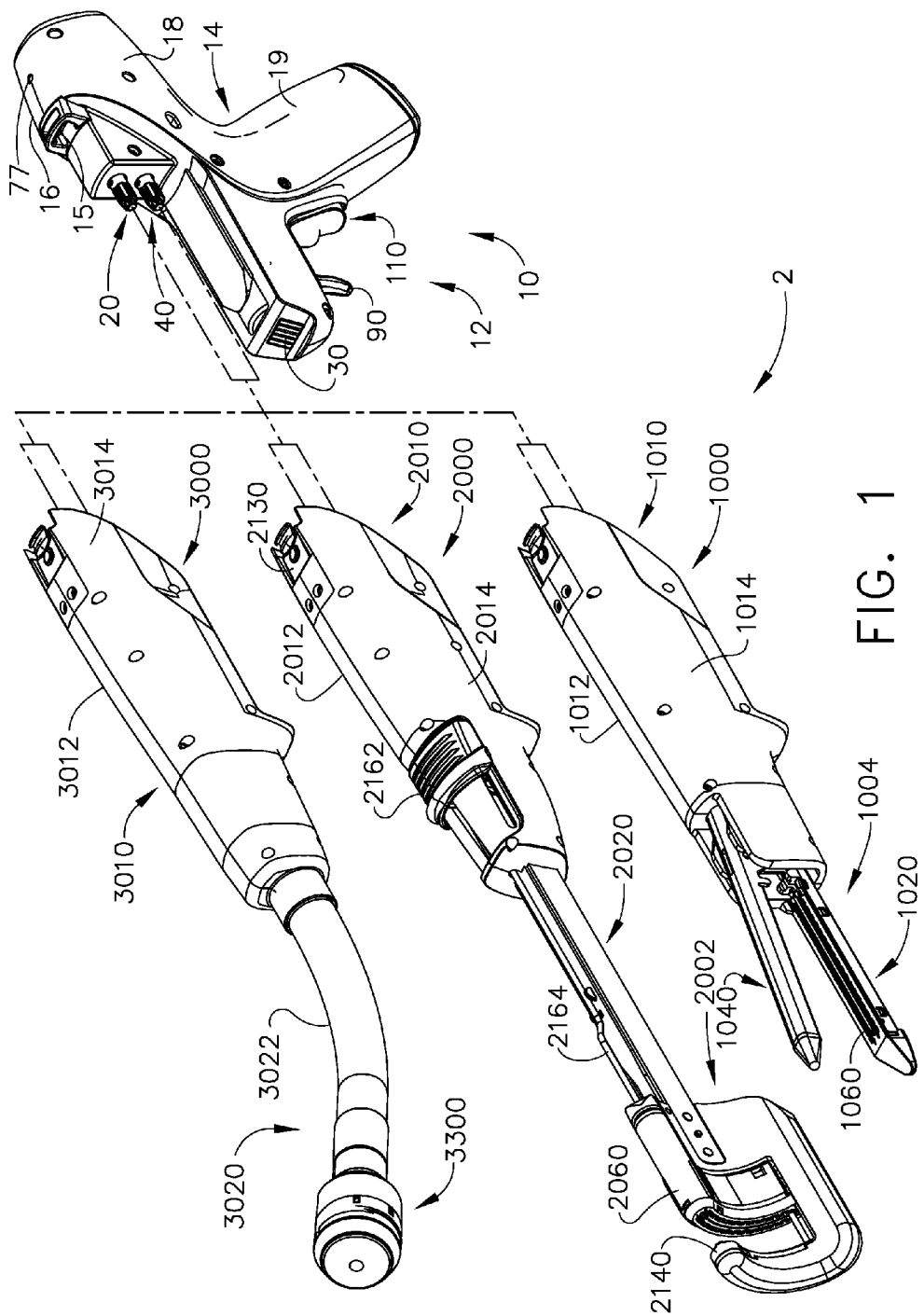
FIG. 1 is a perspective view of a modular surgical system that includes a motor-driven surgical instrument and three interchangeable end effectors.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION;

U.S. patent application Ser. No. 13/782,323, entitled ROTARY POWERED ARTICULATION JOINTS FOR SURGICAL INSTRUMENTS;

U.S. patent application Ser. No. 13/782,338, entitled THUMBWHEEL SWITCH ARRANGEMENTS FOR SURGICAL INSTRUMENTS;

U.S. patent application Ser. No. 13/782,499, entitled ELECTROMECHANICAL SURGICAL DEVICE WITH SIGNAL RELAY ARRANGEMENT;

U.S. patent application Ser. No. 13/782,460, entitled MULTIPLE PROCESSOR MOTOR CONTROL FOR MODULAR SURGICAL INSTRUMENTS;

U.S. patent application Ser. No. 13/782,358, entitled JOYSTICK SWITCH ASSEMBLIES FOR SURGICAL INSTRUMENTS;

U.S. patent application Ser. No. 13/782,481, entitled SENSOR STRAIGHTENED END EFFECTOR DURING REMOVAL THROUGH TROCAR;

U.S. patent application Ser. No. 13/782,518, entitled CONTROL METHODS FOR SURGICAL INSTRUMENTS WITH REMOVABLE IMPLEMENT PORTIONS;

U.S. patent application Ser. No. 13/782,375, entitled ROTARY POWERED SURGICAL INSTRUMENTS WITH MULTIPLE DEGREES OF FREEDOM; and U.S. patent application Ser. No. 13/782,536, entitled SURGICAL INSTRUMENT SOFT STOP are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE;

U.S. patent application Ser. No. 13/803,193, entitled CONTROL ARRANGEMENTS FOR A DRIVE MEMBER OF A SURGICAL INSTRUMENT;

U.S. patent application Ser. No. 13/803,053, entitled INTERCHANGEABLE SHAFT ASSEMBLIES FOR USE WITH A SURGICAL INSTRUMENT;

U.S. patent application Ser. No. 13/803,086, entitled ARTICULATABLE SURGICAL INSTRUMENT COMPRISING AN ARTICULATION LOCK;

U.S. patent application Ser. No. 13/803,210, entitled SENSOR ARRANGEMENTS FOR ABSOLUTE POSITIONING SYSTEM FOR SURGICAL INSTRUMENTS;

U.S. patent application Ser. No. 13/803,148, entitled MULTI-FUNCTION MOTOR FOR A SURGICAL INSTRUMENT;

U.S. patent application Ser. No. 13/803,066, entitled DRIVE SYSTEM LOCKOUT ARRANGEMENTS FOR MODULAR SURGICAL INSTRUMENTS;

U.S. patent application Ser. No. 13/803,117, entitled ARTICULATION CONTROL SYSTEM FOR ARTICULATABLE SURGICAL INSTRUMENTS;

U.S. patent application Ser. No. 13/803,130, entitled DRIVE TRAIN CONTROL ARRANGEMENTS FOR MODULAR SURGICAL INSTRUMENTS; and U.S. patent application Ser. No. 13/803,159, entitled METHOD AND SYSTEM FOR OPERATING A SURGICAL INSTRUMENT.

Applicant of the present application also owns the following patent applications that were filed on Mar. 25, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS;

U.S. patent application Ser. No. 14/226,099, entitled STERILIZATION VERIFICATION CIRCUIT;

U.S. patent application Ser. No. 14/226,094, entitled VERIFICATION OF NUMBER OF BATTERY EXCHANGES/PROCEDURE COUNT;

U.S. patent application Ser. No. 14/226,117, entitled POWER MANAGEMENT THROUGH SLEEP OPTIONS OF SEGMENTED CIRCUIT AND WAKE UP CONTROL;

U.S. patent application Ser. No. 14/226,075, entitled MODULAR POWERED SURGICAL INSTRUMENT WITH DETACHABLE SHAFT ASSEMBLIES;

U.S. patent application Ser. No. 14/226,093, entitled FEEDBACK ALGORITHMS FOR MANUAL BAILOUT SYSTEMS FOR SURGICAL INSTRUMENTS;

U.S. patent application Ser. No. 14/226,116, entitled SURGICAL INSTRUMENT UTILIZING SENSOR ADAPTATION;

U.S. patent application Ser. No. 14/226,071, entitled SURGICAL INSTRUMENT CONTROL CIRCUIT HAVING A SAFETY PROCESSOR;

U.S. patent application Ser. No. 14/226,097, entitled SURGICAL INSTRUMENT COMPRISING INTERACTIVE SYSTEMS;

U.S. patent application Ser. No. 14/226,126, entitled INTERFACE SYSTEMS FOR USE WITH SURGICAL INSTRUMENTS;

U.S. patent application Ser. No. 14/226,133, entitled MODULAR SURGICAL INSTRUMENT SYSTEM;

U.S. patent application Ser. No. 14/226,081, entitled SYSTEMS AND METHODS FOR CONTROLLING A SEGMENTED CIRCUIT;

U.S. patent application Ser. No. 14/226,076, entitled POWER MANAGEMENT THROUGH SEGMENTED CIRCUIT AND VARIABLE VOLTAGE PROTECTION;

U.S. patent application Ser. No. 14/226,111, entitled SURGICAL STAPLING INSTRUMENT SYSTEM; and U.S. patent application Ser. No. 14/226,125, entitled SURGICAL INSTRUMENT COMPRISING A ROTATABLE SHAFT.

Applicant of the present application also owns the following patent applications that were filed on Apr. 9, 2014, and which are each herein incorporated by reference in their respective entireties:

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Turning to the Drawings wherein like numerals denote like components throughout the several views, FIG. 1 depicts a modular surgical instrument system generally designated as 2 that, in one form, includes a motor driven surgical instrument 10 that may be used in connection with a variety of surgical end effectors such as, for example, end effectors 1000, 2000 and 3000. In the illustrated embodiment, the motor driven surgical instrument 10 includes a housing 12 that consists of a handle 14 that is configured to be grasped, manipulated and actuated by a clinician. As the present Detailed Description proceeds, it will be understood that the various unique and novel drive system arrangements depicted in connection with handle 14 as well as the various end effector arrangements disclosed herein may also be effectively employed in connection with robotically-controlled surgical systems. Thus, the term "housing" may also encompass a housing or similar portion of a robotic system that may house or otherwise operably support various forms of the drive systems depicted herein and which may be configured to generate control motions which could be used to actuate the end effector arrangements described herein and their respective equivalent structures. The term "frame" may refer to a portion of a handheld surgical instrument. The term "frame" may also represent a portion of a motor driven system or a robotically controlled surgical instrument and/or a portion of the robotic system that may be used to operably control a surgical instrument. For example, the drive system arrangements and end effector arrangements disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719 which is hereby incorporated by reference herein in its entirety.

Referring now to FIGS. 2-5, the handle 14 may comprise a pair of handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports two rotary drive systems 20, 40 therein that are configured to generate and apply various control motions to corresponding drive shaft portions of a particular end effector coupled thereto. The first rotary drive system 20 may, for example, be employed to apply "closure" motions to a corresponding closure drive shaft arrangement that is operably supported in an end effector and the second rotary drive system 40 may be employed to apply "firing" motions to a corresponding firing drive shaft arrangement in the end effector that is coupled thereto.

The first and second rotary drive systems 20, 40 are powered by a motor 80 through a unique and novel "shiftable" transmission assembly 60 that essentially shifts power/motion between two power trains. The first rotary drive system 20 includes a first rotary drive shaft 22 that is rotatably supported in the housing 12 of the handle 14 and defines a first drive shaft axis "FDA-FDA". A first drive gear 24 is keyed onto or otherwise non-rotatably affixed to the first rotary drive shaft 22 for rotation therewith about the first drive shaft axis FDA-FDA. Similarly, the second rotary drive system 40 includes a second rotary drive shaft 42 that is rotatably supported in the housing 12 of the handle 14 and defines a second drive shaft axis "SDA-SDA". In at least one arrangement, the second drive shaft axis SDA-SDA is offset from and parallel or is substantially parallel to the first drive shaft axis FDA-FDA. As used in this context, the term "offset" means that the first and second drive shaft axes are not coaxial for example. The second rotary drive shaft 42 has a second drive gear 44 keyed onto or otherwise non-rotatably affixed to the second drive shaft 42 for rotation therewith about the second drive shaft axis SDA-SDA. In addition, the second drive shaft 42 has an intermediate drive gear 46 rotatably journaled thereon such that the intermediate drive gear 46 is freely rotatable on the second rotary drive shaft 42 about the second drive shaft axis SDA-SDA.

Figure 2:
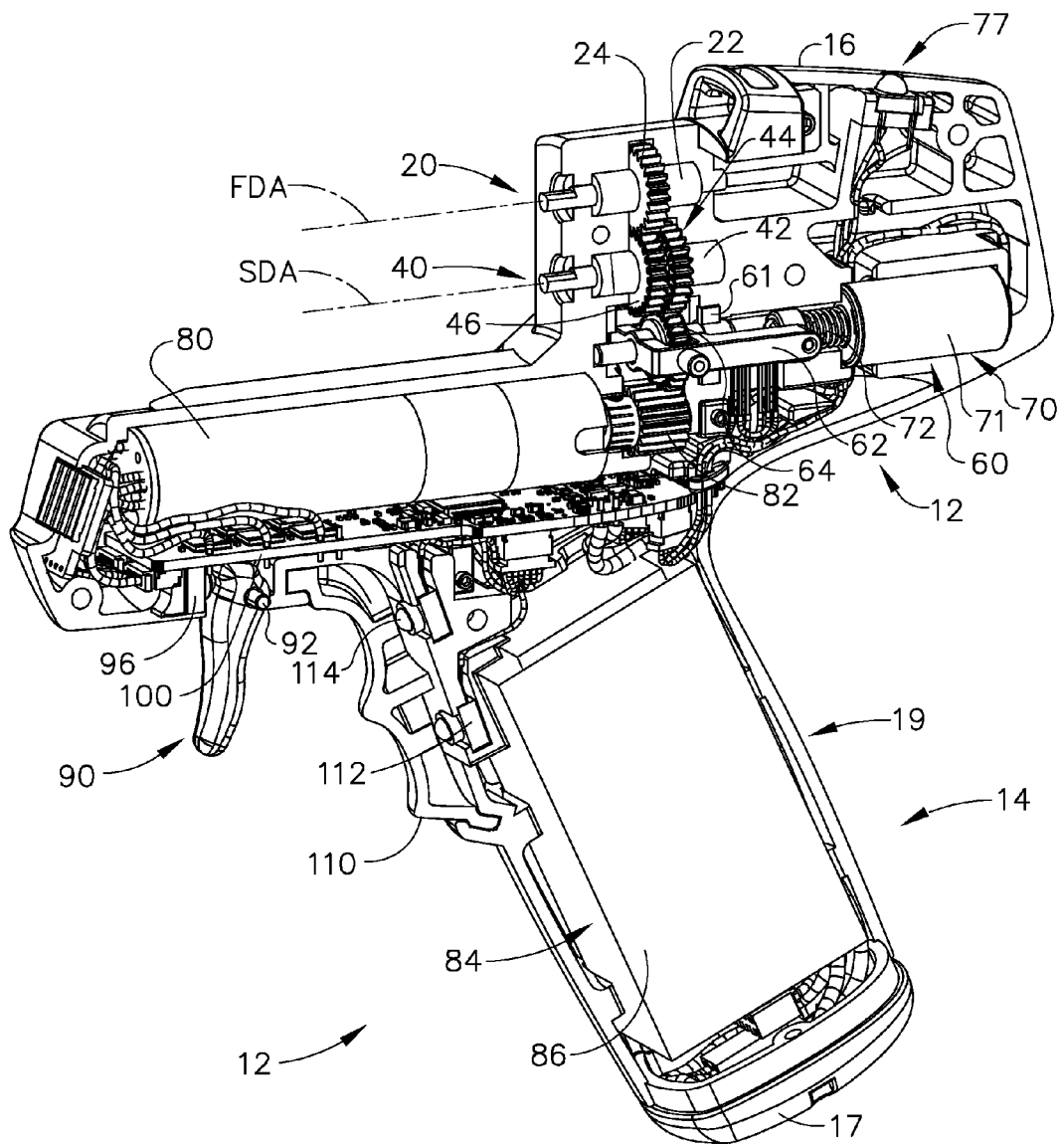
FIG. 2 is a side perspective view of the motor-driven surgical instrument with a portion of the handle housing removed for clarity.
Figure 3:
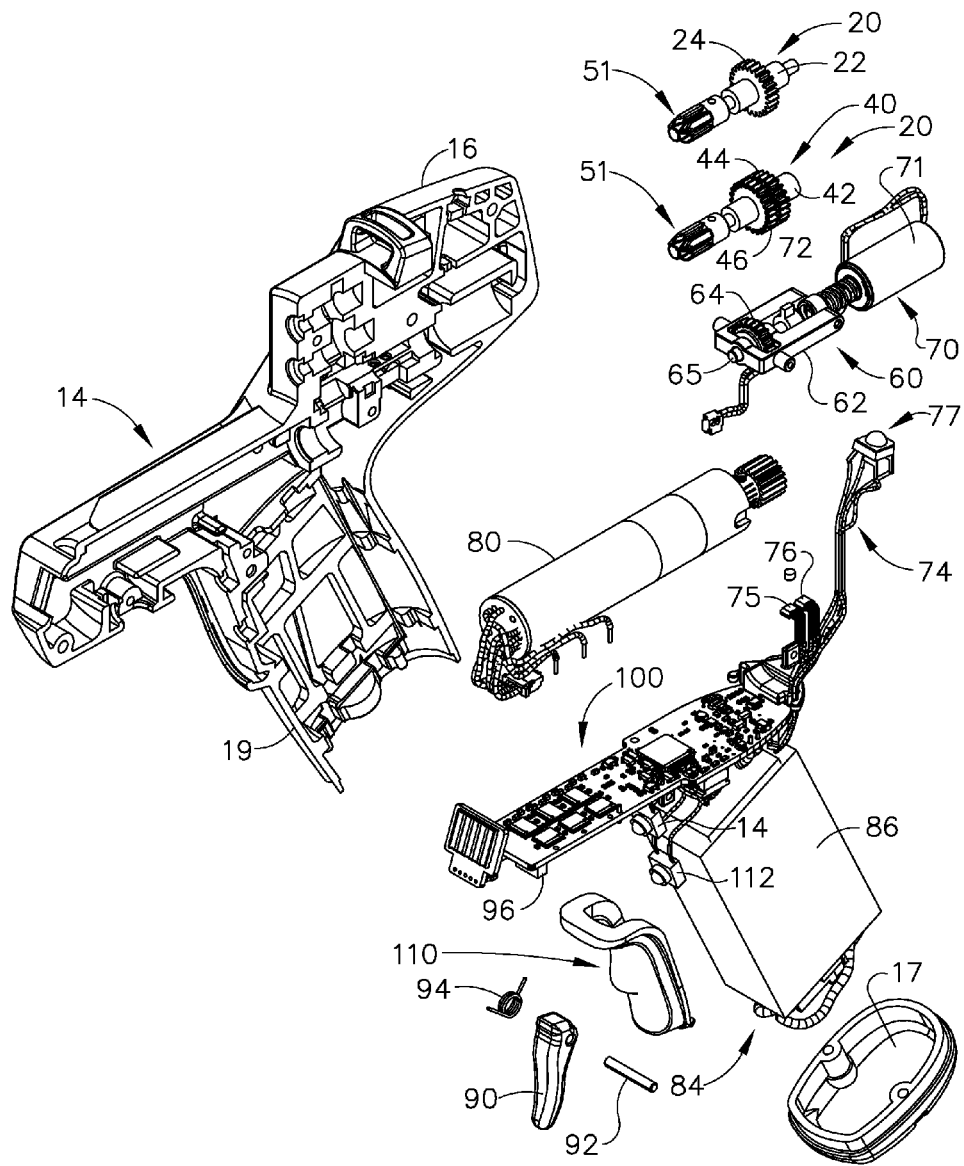
FIG. 3 is a partial exploded assembly view of the surgical instrument of FIG. 2.
Figure 4:
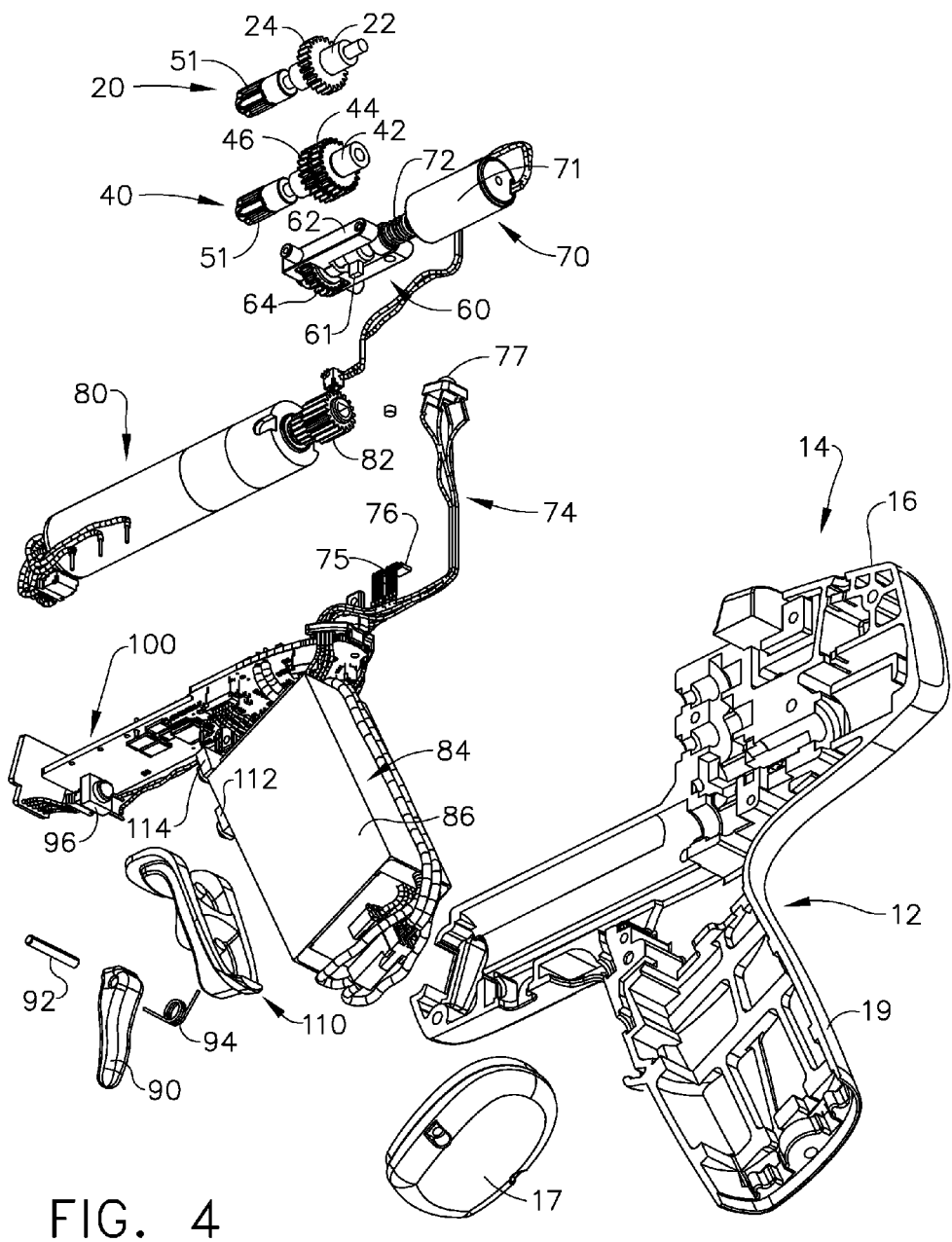
FIG. 4 is another partial exploded assembly view of the surgical instrument of FIGS. 2 and 3.
Figure 5:
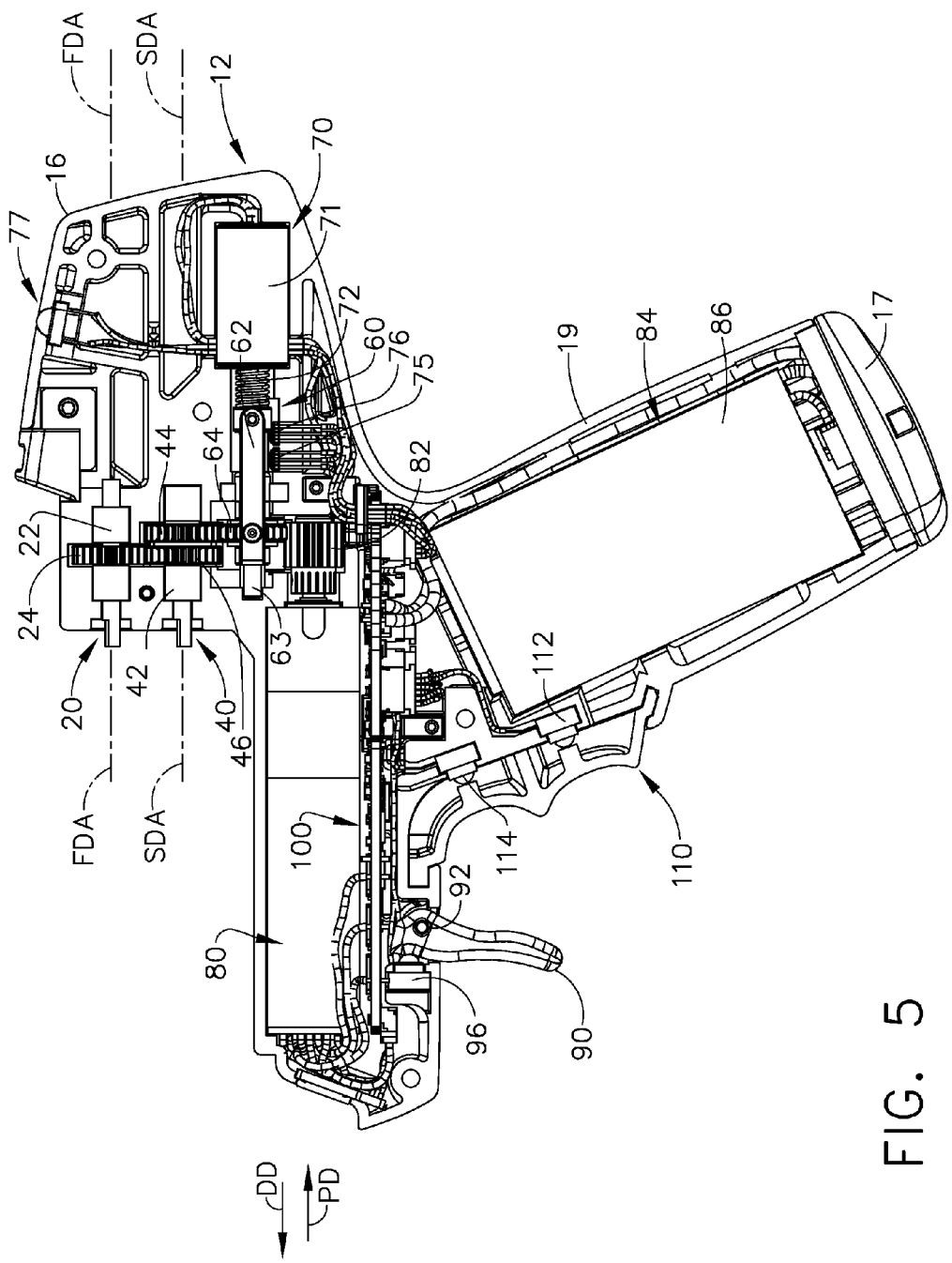
FIG. 5 is a side elevational view of the motor-driven surgical instrument with a portion of the handle housing removed.
Figure 7:
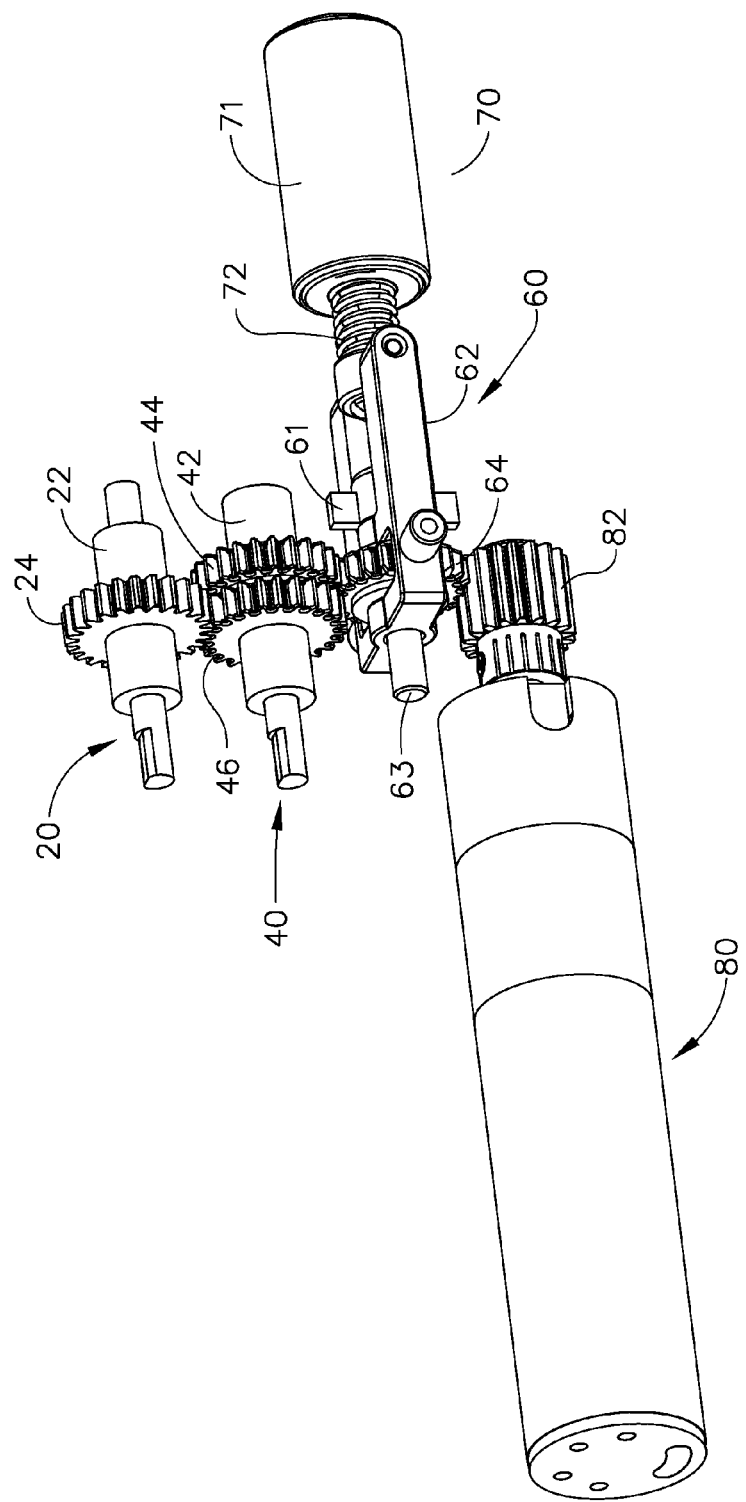
FIG. 7 is another perspective view of the motor drive system and transmission assembly of FIG. 6 with the transmission assembly in the second drive position wherein actuation of the motor will result in the actuation of the second drive system.

Referring to FIGS. 2-5, in one form, the motor 80 includes a motor output shaft 81 that has a motor drive gear 82 non-rotatably attached thereto. The motor drive gear 82 is configured for intermeshing "operable" engagement with the transmission assembly 60 as will be discussed in further detail below. In at least one form, the transmission assembly 60 includes a transmission carriage 62 that is supported for axial travel between the drive gear 82 and gears 44 and 46 on the second rotary drive shaft 42. For example, the transmission carriage 62 may be slidably journaled on a support shaft 63 that is mounted within the housing 12 on a shaft mount 61 such that the line of action of the transmission carriage is perpendicular to the gear trains of the rotary drive systems. The shaft mount 61 is configured to be rigidly supported within slots or other features within the housing 10. The transmission carriage 62 includes a carriage gear 64 that is rotatably supported on the support shaft 63 and is configured for selective meshing engagement with gears 44 and 46 while in driving engagement with drive gear 82. In the arrangement depicted in FIGS. 2-5, the transmission carriage 62 is operably attached to a shifter or a "means for shifting" 70 that is configured to axially shift the transmission carriage 62 between a "first drive position" and a "second drive position". In one form, for example, the means for shifting 70 includes a shifter solenoid 71 that is supported within the housing 12 of the handle 14. The shifter solenoid 71 may comprise a bi-stable solenoid or, for example, may comprise a "dual position, spring loaded" solenoid. The illustrated arrangement, for example, includes a spring 72 that biases the transmission carriage 62 in the distal direction "DD" to the first drive position wherein the carriage gear 64 is in meshing engagement with the intermediate drive gear 46 while also in meshing engagement with the drive gear 82. When in that first drive position, activation of the motor 80 will result in rotation of gears 82, 46 and 24 which will ultimately result in rotation of the first drive shaft 22. As will be further discussed herein, the shifter solenoid 71 may be actuated by a firing trigger 90 that is pivotally supported on the housing 12 of handle 14 as shown in FIGS. 2 and 5. In the illustrated embodiment, the firing trigger 90 is pivotally supported on a firing trigger shaft 92 mounted in the handle 14. The firing trigger 90 is normally biased in an unactuated position by a firing trigger spring 94. See FIG. 3. The firing trigger 90 is mounted for operable actuation of a firing switch 96 that is operably supported on a control circuit board assembly 100. In the illustrated arrangement, actuation of the firing trigger 90 results in the actuation of the shifter solenoid 71. As described in more detail hereinbelow in connection with FIGS. 61, 63, 64, the handle processor 7024 provides the drive signal to shifter solenoid 7032 (71). With reference now back to FIGS. 2-5, thus, actuation of the firing trigger 90 will result in the shifter solenoid 71 pulling the transmission carriage 62 in the proximal direction "PD" to thereby move the carriage gear 64 into meshing engagement with the second drive gear 44. See FIG. 7. Actuation of motor 80 when the carriage gear 64 is in meshing engagement with the drive gear 82 and the second drive gear 44 will result in the rotation of the second drive shaft 42 about the second drive shaft axis "SDA". As can also be seen in FIGS. 2-5, the shiftable transmission assembly 60 may also include an indicator system 74 that includes a pair of switches 75 and 76 that are operably coupled to the control board 100 as well as a transmission indicator light 77. The switches 75, 76 serve to detect the position of the transmission carriage 62 which results in the control system actuating the indicator light 77 depending upon the position of the transmission carriage 62. For example, the indicator light 77 may be energized when the transmission carriage 62 is in the first drive position. This provides the clinician with an indication that actuation of the motor 80 will result in the actuation of the first drive system 20.

Figure 6:
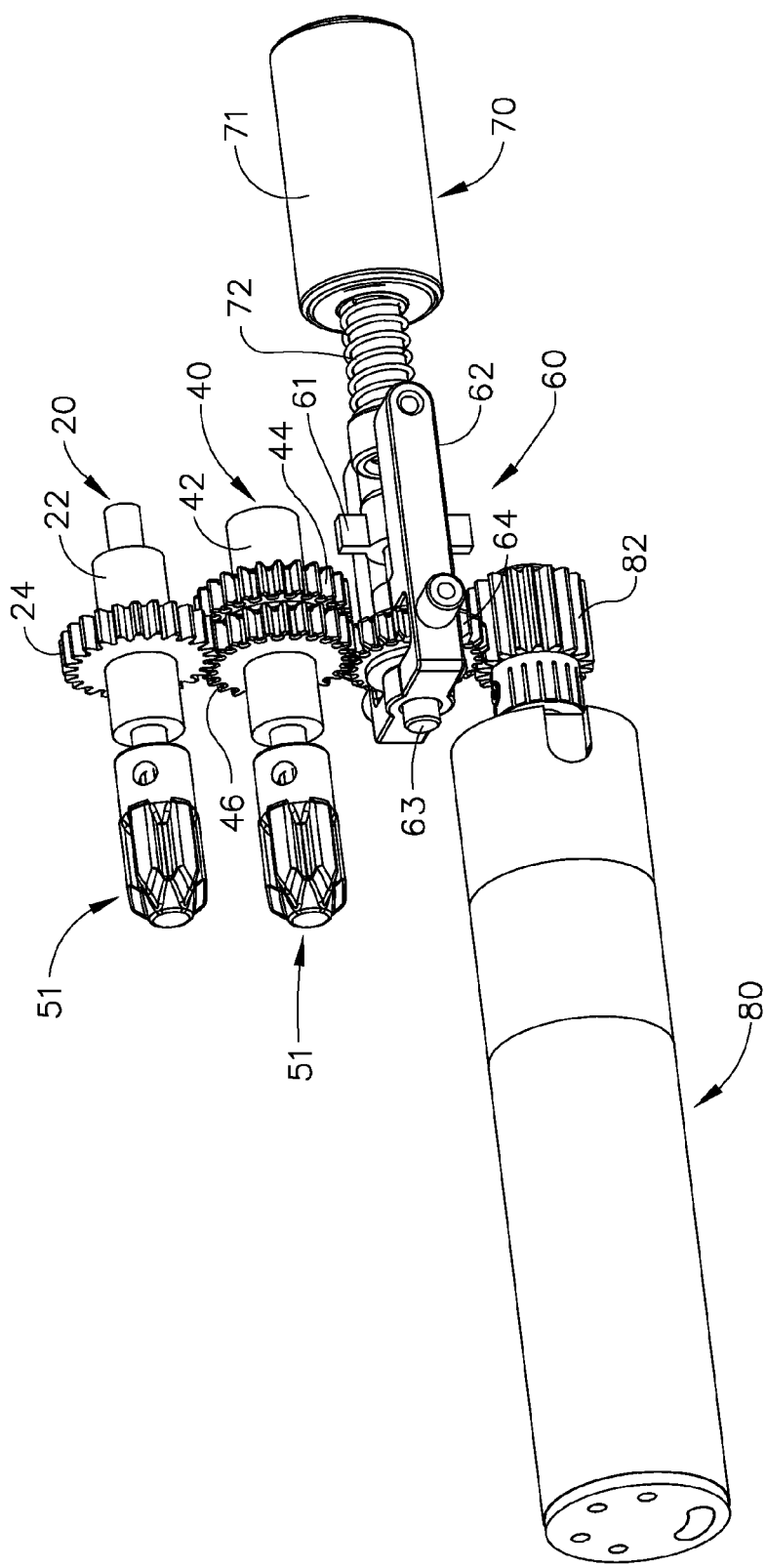
FIG. 6 is a perspective view of a motor drive system and transmission assembly with the transmission assembly in the first drive position wherein actuation of the motor will result in the actuation of a first drive system of the surgical instrument of FIGS. 2-5.
Figure 6B:
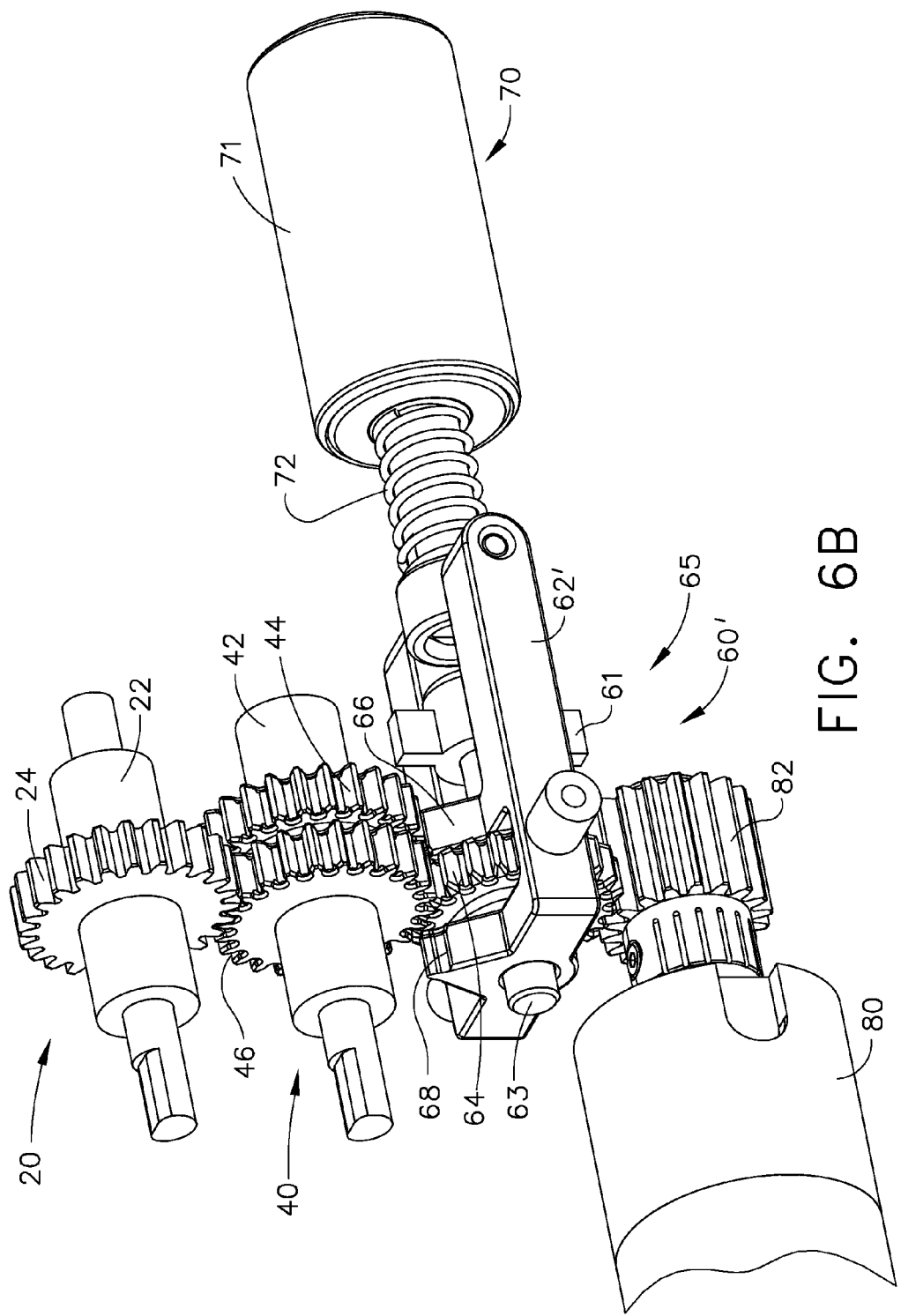
FIG. 6B is a perspective view of a motor drive system and transmission assembly including the transmission carriage of FIG. 6A with the transmission assembly in the first drive position wherein actuation of the motor will result in the actuation of the first drive system and the second drive system is locked by the locking means.
Figure 6C:
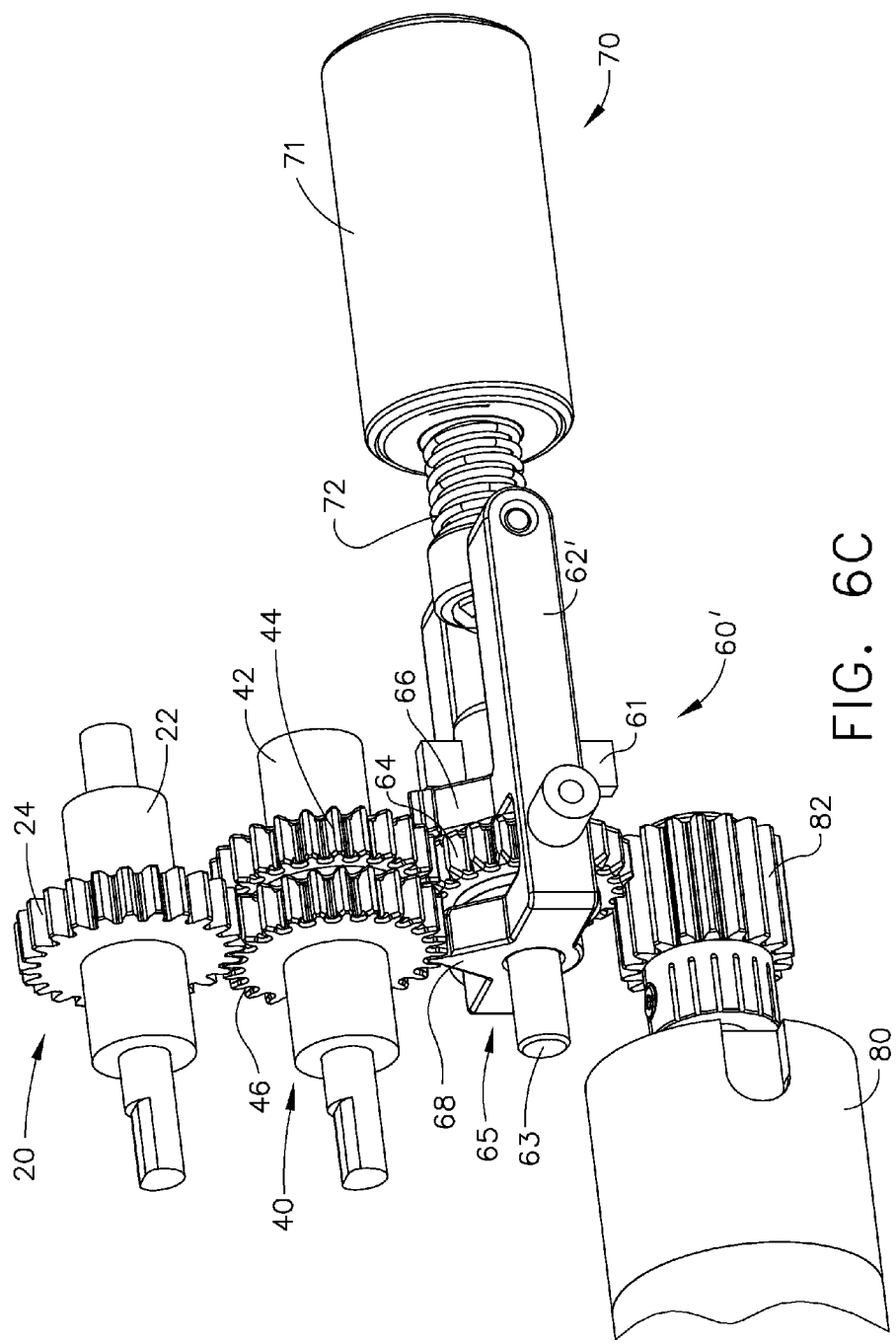
FIG. 6C is a perspective view of the motor drive system and transmission assembly of FIG. 6B with the transmission assembly in the second drive position wherein actuation of the motor will result in the actuation of the second drive system and the first drive system is locked by the locking means.

Various surgical instruments disclosed herein may also include a transmission assembly 60' that is substantially identical to transmission assembly 60, but also include a locking assembly or means (generally designated as 65) for locking the first and second drive systems 20, 40 to prevent their inadvertent actuation when they are not intended to be actuated. For example, FIG. 6A illustrates an alternative transmission carriage 62' that includes a first drive lock 66 and a second drive lock 68. The first drive lock 66 comprises a first gear engagement member or tooth on the transmission carriage 62' that is located for intermeshing engagement with the second drive gear 44 when the carriage gear 64 is in driving engagement with the intermediate gear 46 (i.e., when the transmission assembly 60' is in the first drive position). See FIG. 6B. Thus, when the transmission assembly 60' is in the first drive position, the first drive lock 66 is in meshing engagement with the second drive gear 44 and prevents relative rotation thereof while the first drive shaft 22 is rotated in the above-described manner. Likewise, when the transmission assembly 60' is in the second drive position (i.e., the carriage gear 64 is in meshing engagement with the second drive gear 44), the second drive lock 68 is in meshing engagement with the intermediate drive gear 46. See FIG. 6C. Thus, when the transmission assembly 60' is in the second drive position, the second drive lock 68 prevents the intermediate gear 46 from rotating which also prevents the first drive gear 24 from rotating. As such, when the clinician operates the motor 80 to actuate the first drive system 20, the second drive system 40 is locked in position. Likewise, when the clinician actuates the second drive system 40, the first drive system 20 is locked in position.

The control system for the motor 80, as described hereinbelow in connection with FIGS. 61, 63, 64, may be programmed in such a way that it always stops in an orientation when one tooth of gears 42, 44 remains vertical or other defined position depending upon the orientation of the other matching gear. This feature will serve to avoid any interference between the gear teeth while shifting. When shifting, the locking members also shift and locks the position of the non-rotating gear train. When employed in connection with an end effector that includes a cartridge/anvil arrangement or other clamping configuration, another advantage gained by locking the non-rotating (i.e., non-powered) gear train is the retention of the clamp/anvil in a stable position while firing.

The motor 80 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor, including motors which can be autoclavable. The motor 80 may be powered by a power source 84 that in one form may comprise a power pack 86 that is removably stored in the handle 14. As can be seen in FIGS. 2-5, for example, the power pack 86 may be removably housed within the pistol grip portion 19 of the handle 14. To access the power pack 86, the clinician removes a removable cap 17 that is attached to the pistol grip portion 19 as shown. The power pack 86 may operably support a plurality of batteries (not shown) therein. The batteries may each comprise, for example, a Lithium Ion ("LI") or other suitable battery. The power pack 86 is configured for removable operable attachment to the control circuit board assembly 100 which is also operably coupled to the motor 80 and mounted within the handle 14. A number of batteries may be connected in series may be used as the power source for the surgical instrument. In addition, the power source 84 may be replaceable and/or rechargeable and, in at least one instance, can include CR123 batteries, for example. The motor 80 may be actuated by a "rocker-trigger" 110 that is pivotally mounted to the pistol grip portion 19 of the handle 14. The rocker trigger 110 is configured to actuate a first motor switch 112 that is operably coupled to the control board 100. The first motor switch 112 may comprise a pressure switch which is actuated by pivoting the rocker trigger 110 into contact therewith. Actuation of the first motor switch 112 will result in actuation of the motor 80 such that the drive gear 82 rotates in a first rotary direction. A second motor switch 114 is also attached to the circuit board 100 and mounted for selective contact by the rocker trigger 110. Actuation of the second motor switch 114 will result in actuation of the motor 80 such that the drive gear 82 is rotated in a second direction. For example, in use, a voltage polarity provided by the power source 84 can operate the electric motor 80 in a clockwise direction wherein the voltage polarity applied to the electric motor by the battery can be reversed in order to operate the electric motor 80 in a counter-clockwise direction. As with the other forms described herein, the handle 14 can also include a sensor that is configured to detect the directions in which the drive systems are being moved. One particular implementation of the motor 80 is described hereinbelow in connection with FIGS. 61, 63, 64 where a brushless DC motor 7038 is described. DC motor 7038 can be autoclavable.

Figure 8:
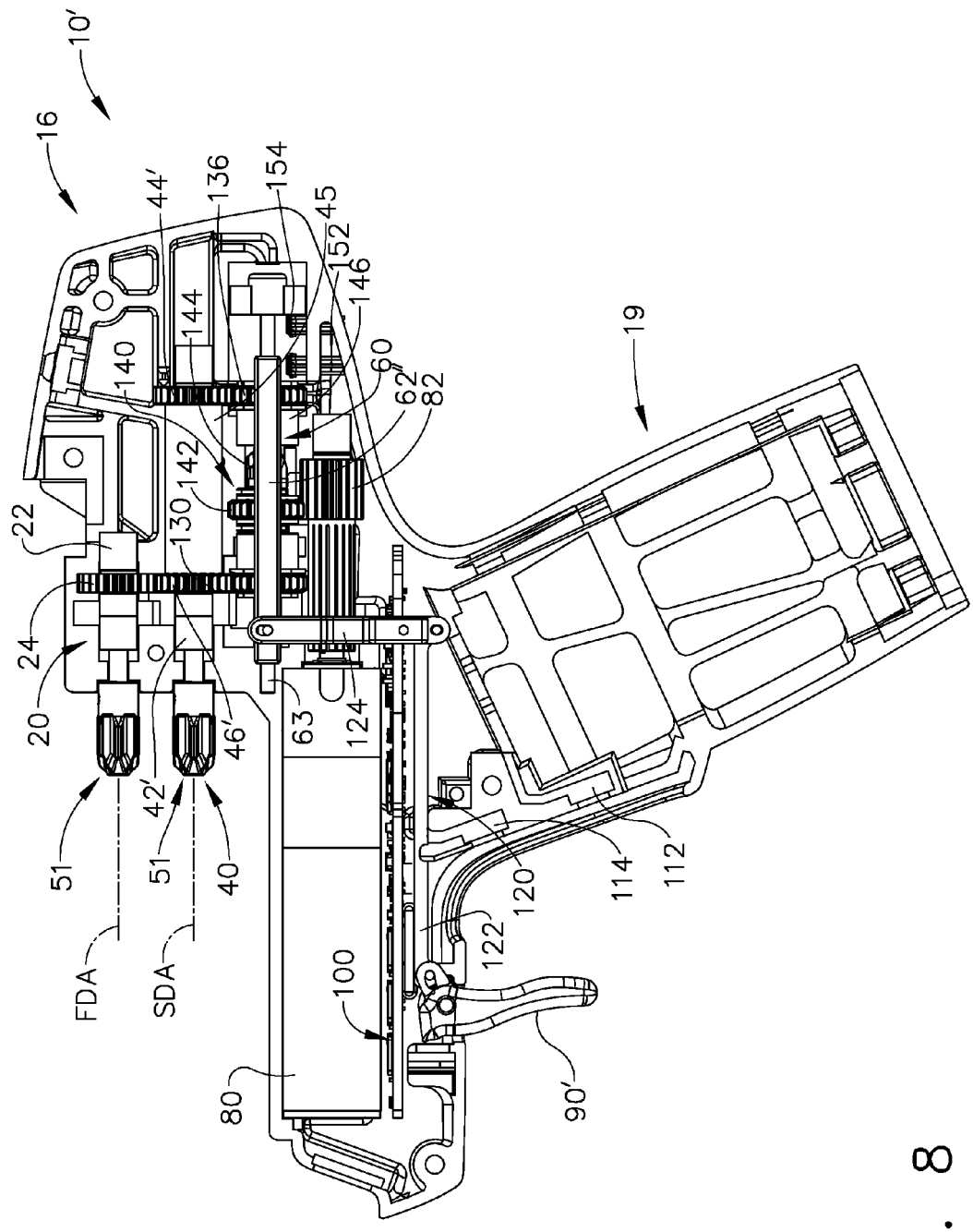
FIG. 8 is a side elevational view of another motor-driven surgical instrument with a portion of the handle housing and other portions thereof omitted for clarity.
Figure 9:
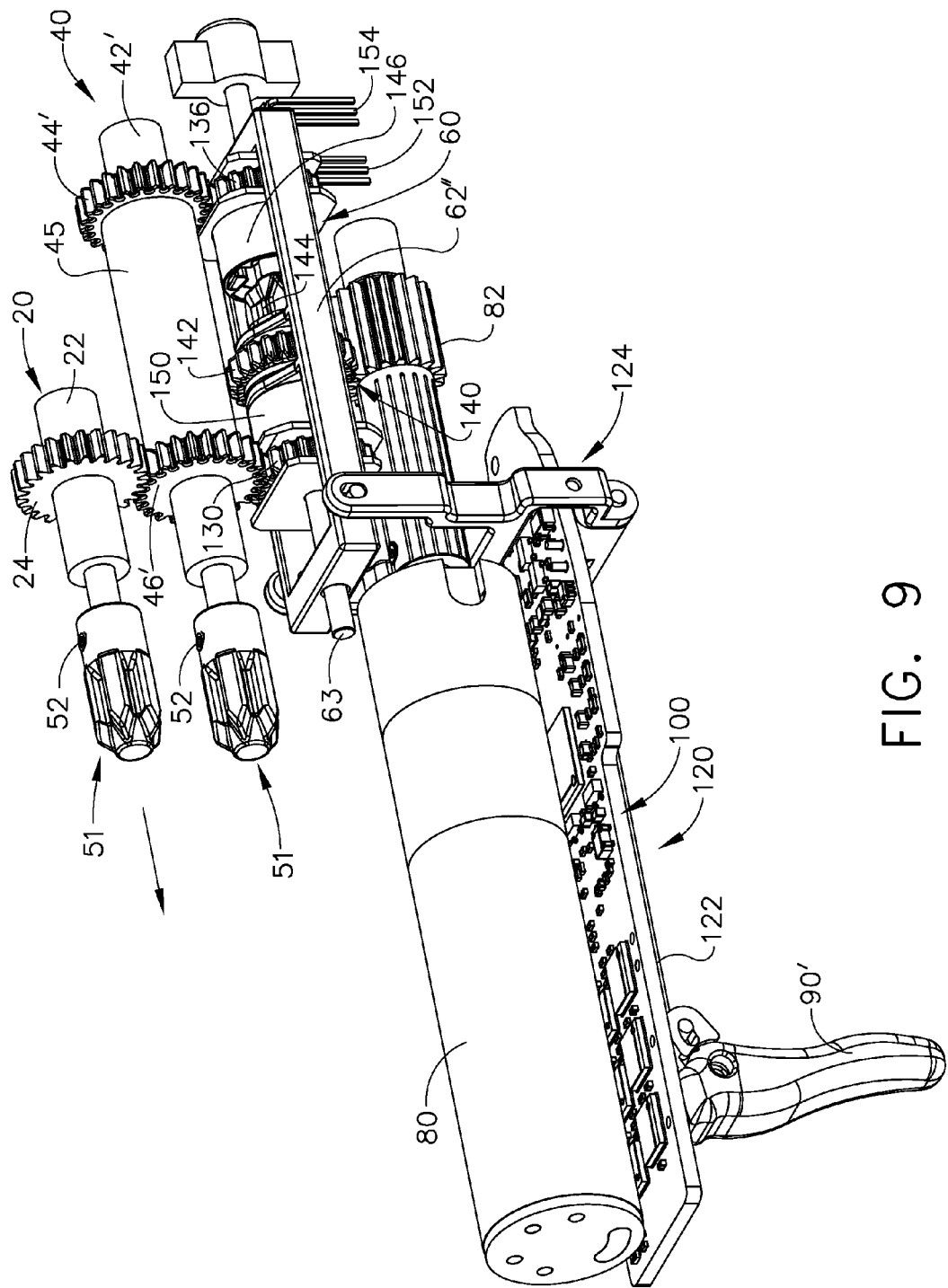
FIG. 9 is a perspective view of the motor, transmission assembly and first and second drive systems of the surgical instrument of FIG. 8 with the transmission assembly thereof in the first drive position.
Figure 10:
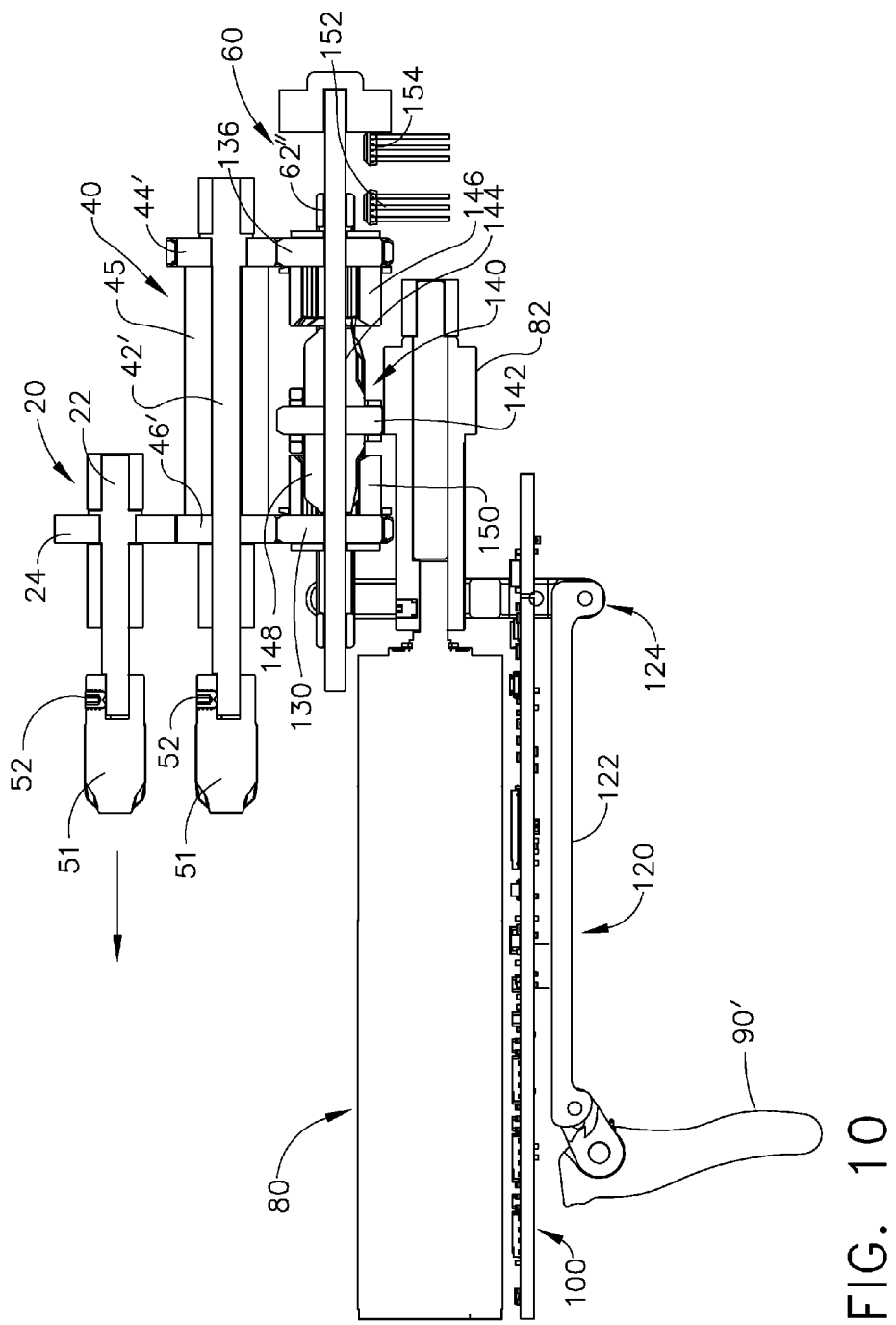
FIG. 10 is a cross-sectional elevational view of the motor, transmission assembly and first and second drive systems of FIG. 9 with the transmission assembly in the first drive position.
Figure 11:
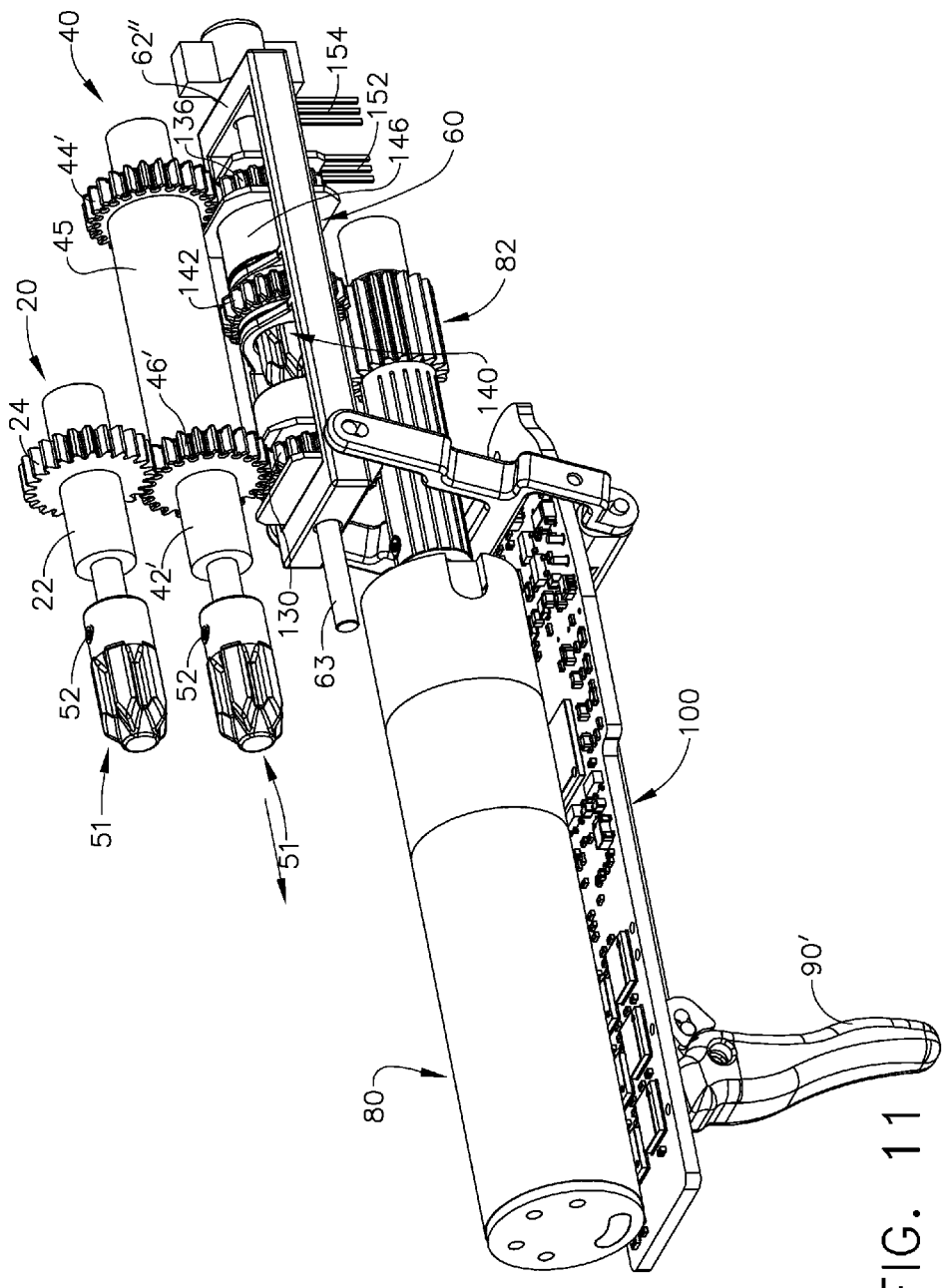
FIG. 11 is another perspective view of the motor, transmission assembly and first and second drive systems of FIGS. 9 and 10 with the transmission assembly in the second drive position.
Figure 12:
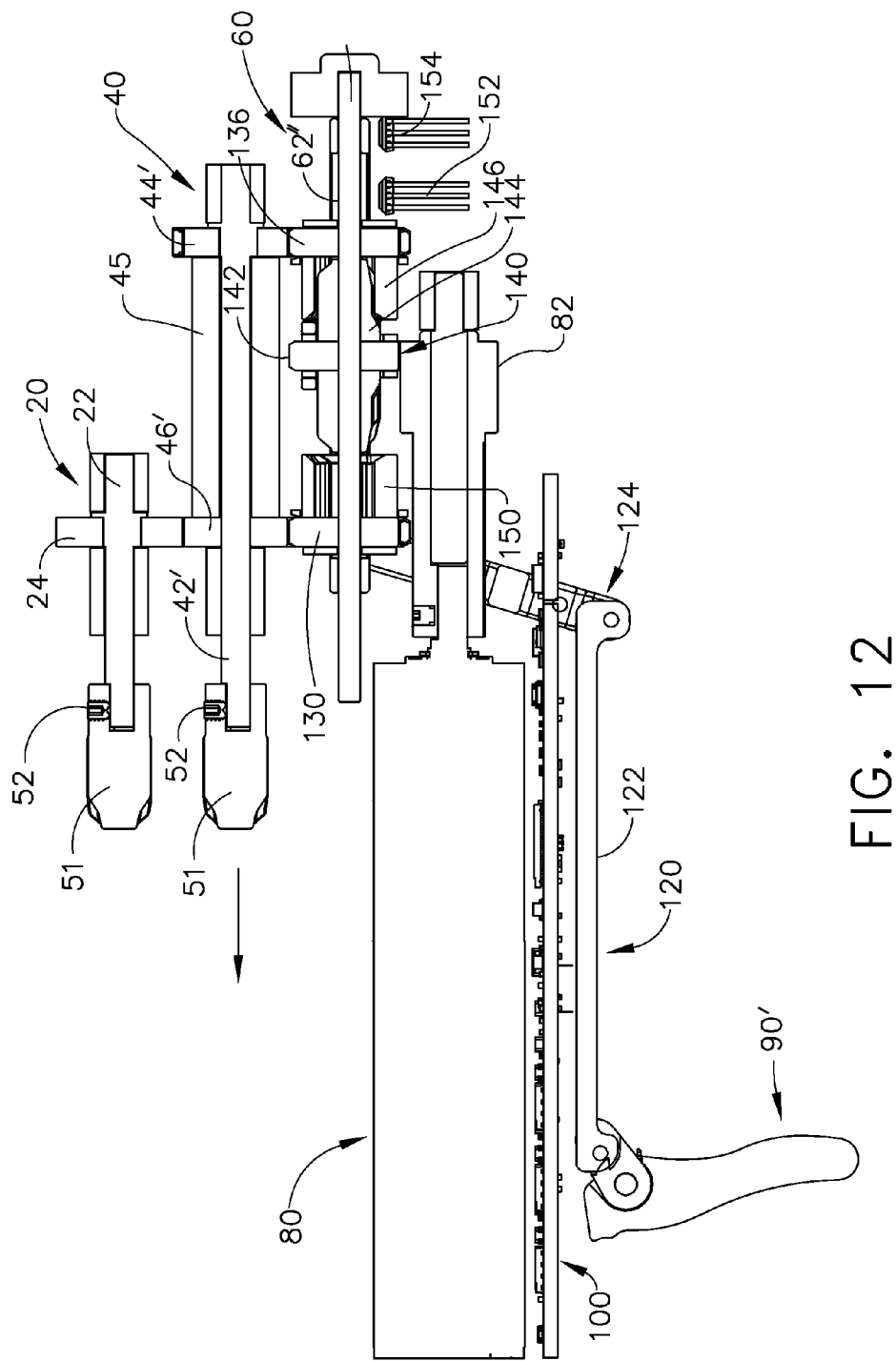
FIG. 12 is another cross-sectional elevational view of the motor, transmission assembly and first and second drive systems of FIGS. 9-11 with the transmission assembly in the second drive position.
Figure 13:
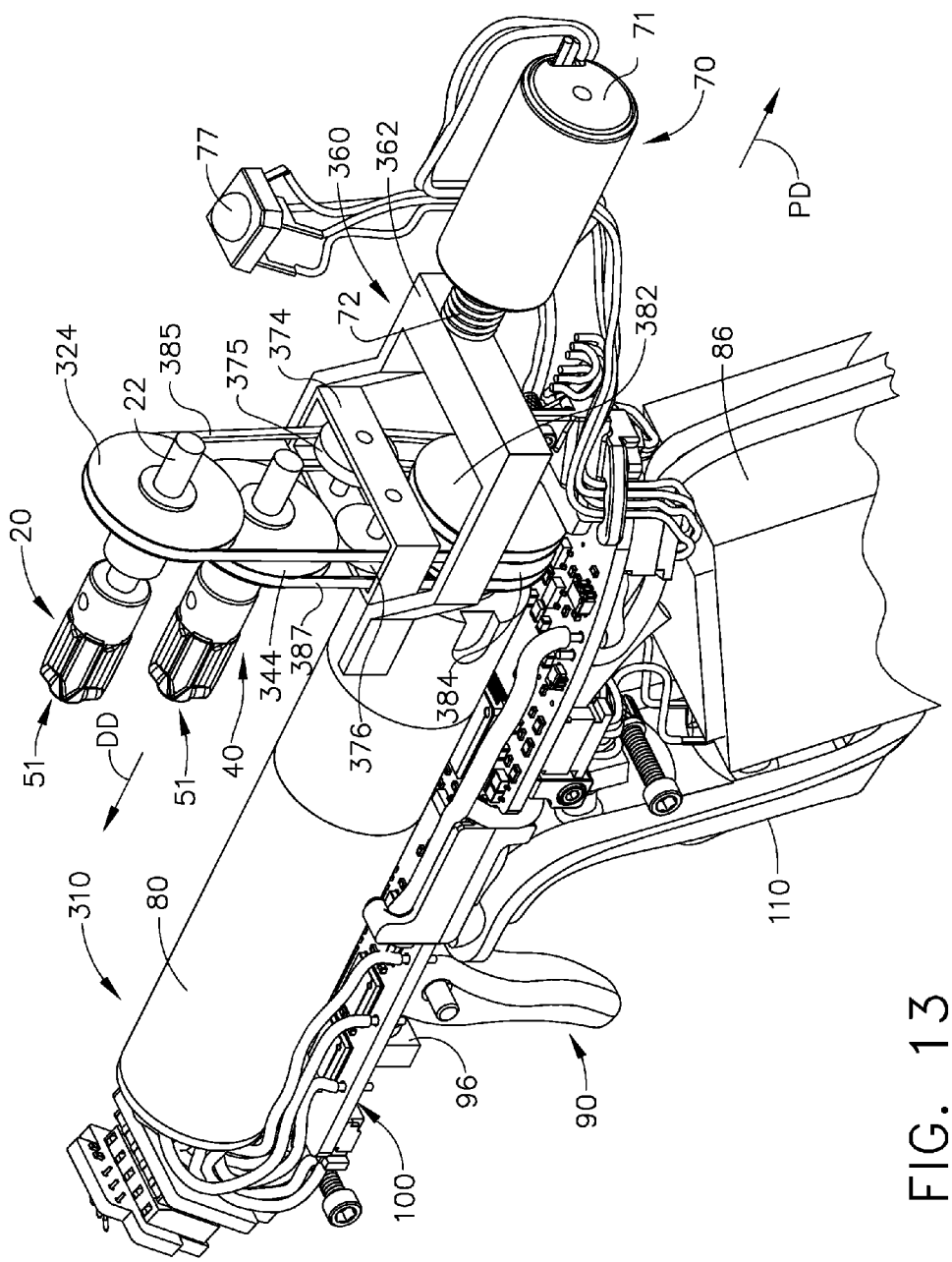
FIG. 13 is a partial rear perspective view of a portion of another motor driven surgical instrument.

FIGS. 8-12 illustrate another form of surgical instrument 10' that may be identical to surgical instrument 10 except for the differences noted below. Those components of surgical instrument 10' that are the same as the components in the surgical instrument 10 described above will be designated with the same element numbers. Those components of surgical instrument 10' that may be similar in operation, but not identical to corresponding components of surgical instrument 10, will be designated with the same component numbers along with a "'" or in some cases a "''". As can be seen in FIG. 8, for example, the first drive shaft axis "FDA" is offset from and parallel with or is substantially parallel with the second drive shaft axis "SDA". Referring primarily to FIG. 9, for example, the transmission assembly 60 and, more specifically, the transmission carriage 62'' is manually shiftable by a linkage assembly 120 that is operably attached to the firing trigger 90'. As can be seen in that Figure, for example, the linkage assembly 120 includes a first transmission link 122 that is pivotally coupled to the firing trigger 90' and extends axially to be pivotally coupled to a transmission yoke 124. The transmission yoke 124 is movably pinned to the transmission carriage 62". Thus, actuation of the firing trigger 90' results in the axial movement of the transmission carriage 62". It will therefore be understood that the linkage assembly 120 essentially performs similar actuation motions to those performed by the shifter solenoid 71 that was described above. As used in the context of this embodiment with respect to movement of the transmission carriage 62", the term "manually shiftable" refers to moving the transmission carriage between the first and second drive positions without the use of electricity or other power means other than depressing the firing trigger 90'.

As can also be seen in FIGS. 8-12, the second drive gear 44' is spaced apart from the intermediate gear 46' on the second drive shaft 42' by a spacer 45. The second drive gear 44' is keyed onto or otherwise non-rotatably affixed to the second drive shaft 42', while the intermediate drive gear 46' is rotatably journaled on the second drive shaft 42' for free rotation relative thereto. In one form, for example, a distal drive gear 130 is supported in meshing engagement with the intermediate drive gear 46'. Similarly, a proximal drive gear 136 is supported in meshing engagement with the second drive gear 44'. In this arrangement, however, the transmission carriage 62" also includes a centrally-disposed, transmission gear assembly 140 that is operably attached to the transmission carriage 62' for axial travel therewith. Still referring to FIGS. 8-12, the transmission gear assembly 140 includes a centrally-disposed shifter drive gear 142 that is in slidable meshing engagement with the motor drive gear 82. Thus, rotation of motor drive gear 82 results in rotation of the shifter drive gear 142. In addition, a proximally extending, conically-shaped drive gear 144 is coupled to the shifter drive gear 142 and is configured for selective meshing engagement with a proximal gear socket 146 that is attached to the proximal drive gear 136. Likewise a distally extending, conically shaped drive gear 148 is configured for selective meshing engagement with a distal gear socket 150 attached to the distal drive gear 130.

When the clinician desires to actuate the first drive system 20, the clinician moves the firing trigger 90' to axially move the transmission gear assembly 140 to bring the distally extending conically-shaped drive gear 148 into seated meshing engagement with the distal gear socket 150 that is attached to distal drive gear 130. See FIGS. 8-10. When in that position, operation of motor 80 will result in the rotation of motor drive gear 82, shifter drive gear 142, distal drive gear 130, intermediate drive gear 46', the first drive gear 24 and the first drive shaft 22. When the clinician desires to actuate the second drive system 40, the clinician moves the firing trigger 90' to the position shown in FIGS. 11 and 12 to thereby bring the proximally extending conically-shaped drive gear 144 into seated meshing engagement with the proximal gear socket 146 that is attached to the proximal drive gear 136. When in that position, operation of motor 80 will result in the rotation of drive gear 82, shifter drive gear 142, proximal drive gear 136, the second drive gear 44' and the second drive shaft 42'. As can also be seen in FIGS. 8-12, sensors 152 and 154 may be employed to detect the position of the transmission carriage 62" as will be discussed in further detail below. For example, the sensors 152 and 154 may be implemented using the Hall effect sensors 7028 described hereinbelow in connection with FIGS. 61, 63, 64.

Figure 14:
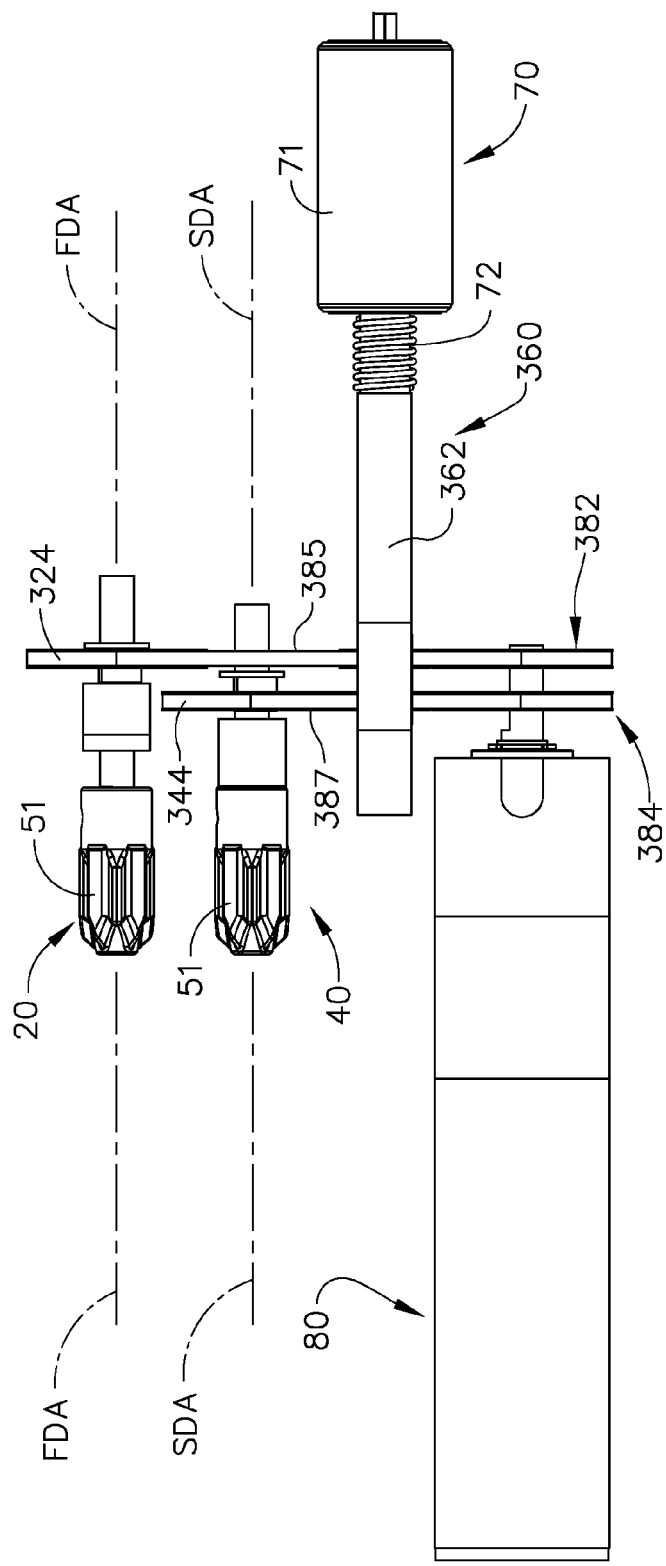
FIG. 14 is a side elevational view of the motor, transmission assembly and first and second drive systems of the surgical instrument of FIG. 13.
Figure 15:
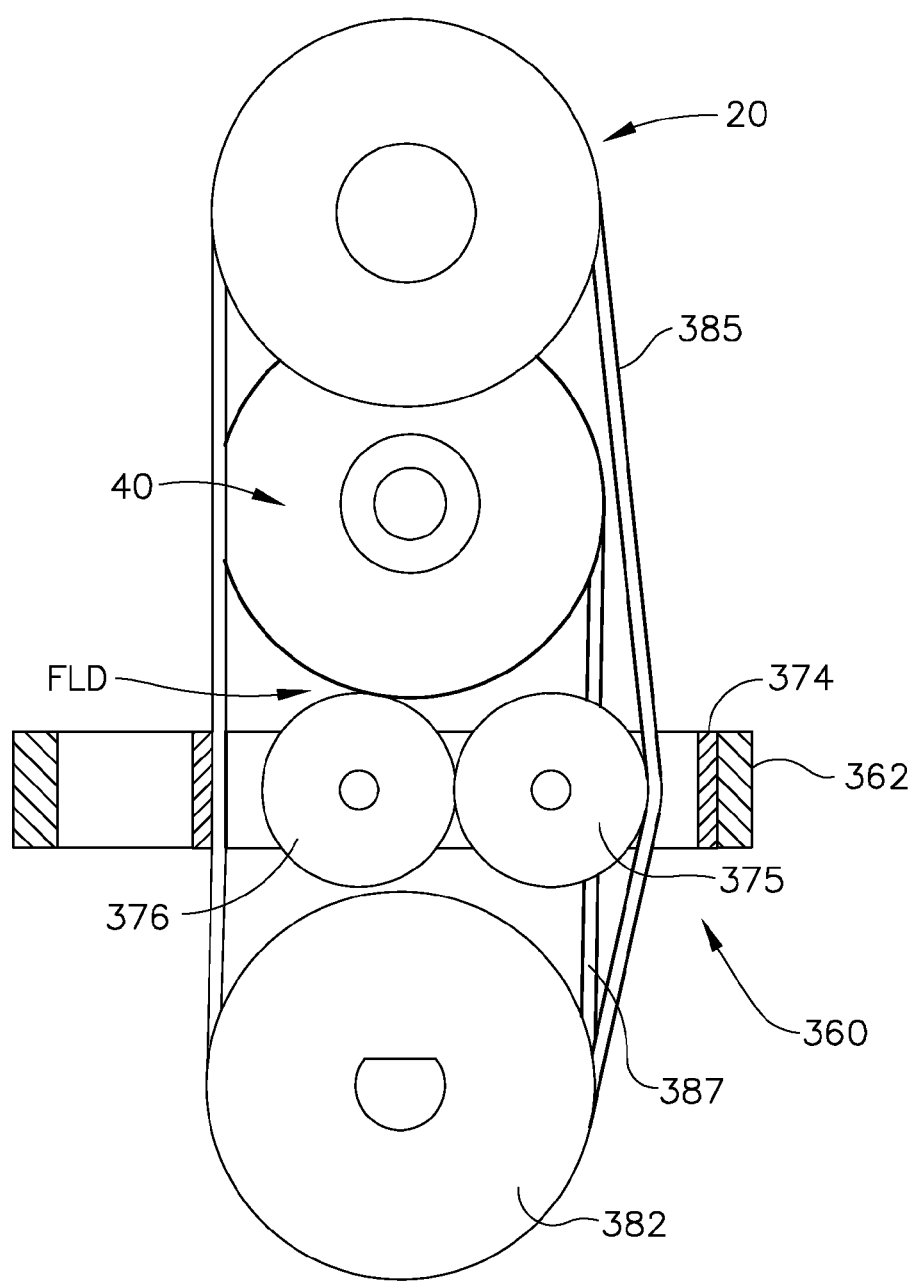
FIG. 15 is a cross-sectional view of the transmission assembly of the surgical instrument of FIGS. 13 and 14 in a first drive position.
Figure 16:
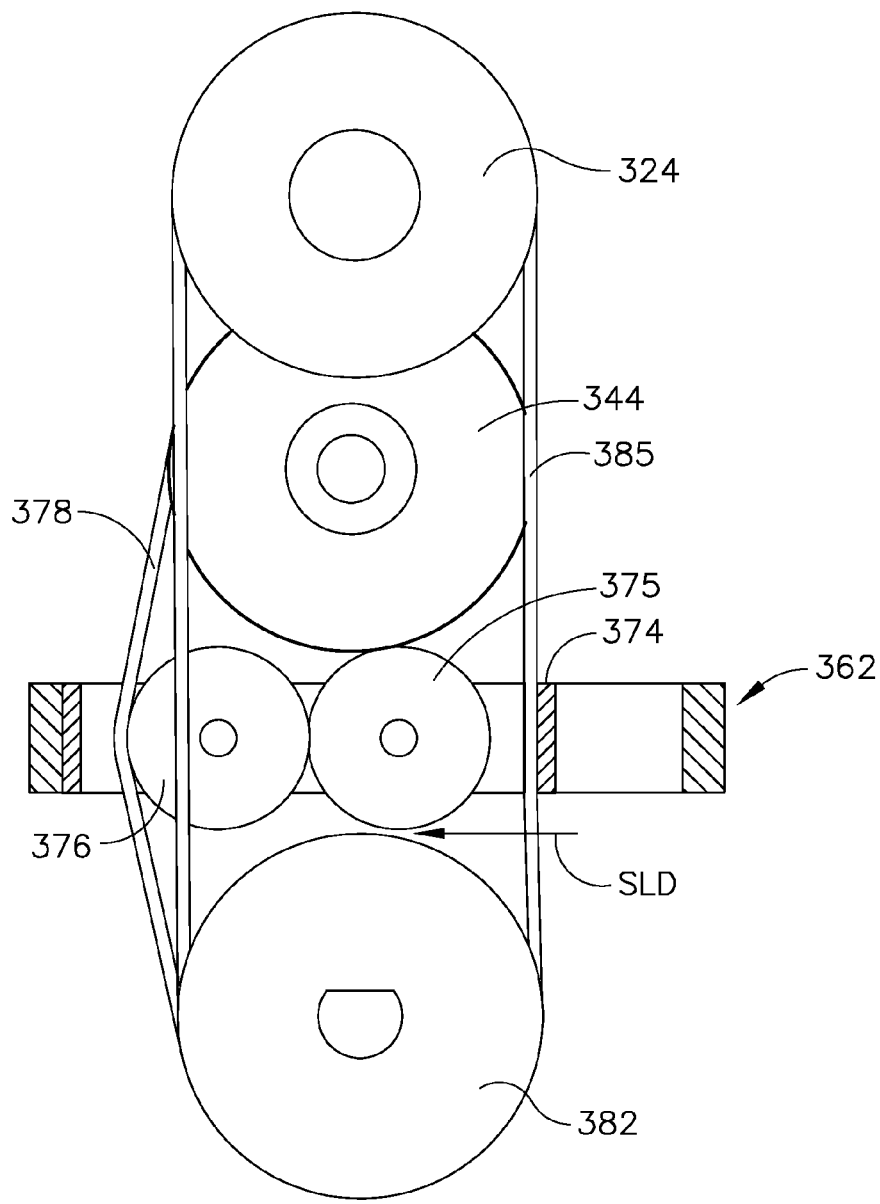
FIG. 16 is another cross-sectional view of the transmission assembly of the surgical instrument of FIGS. 13-15 in a second drive position.
Figure 17:
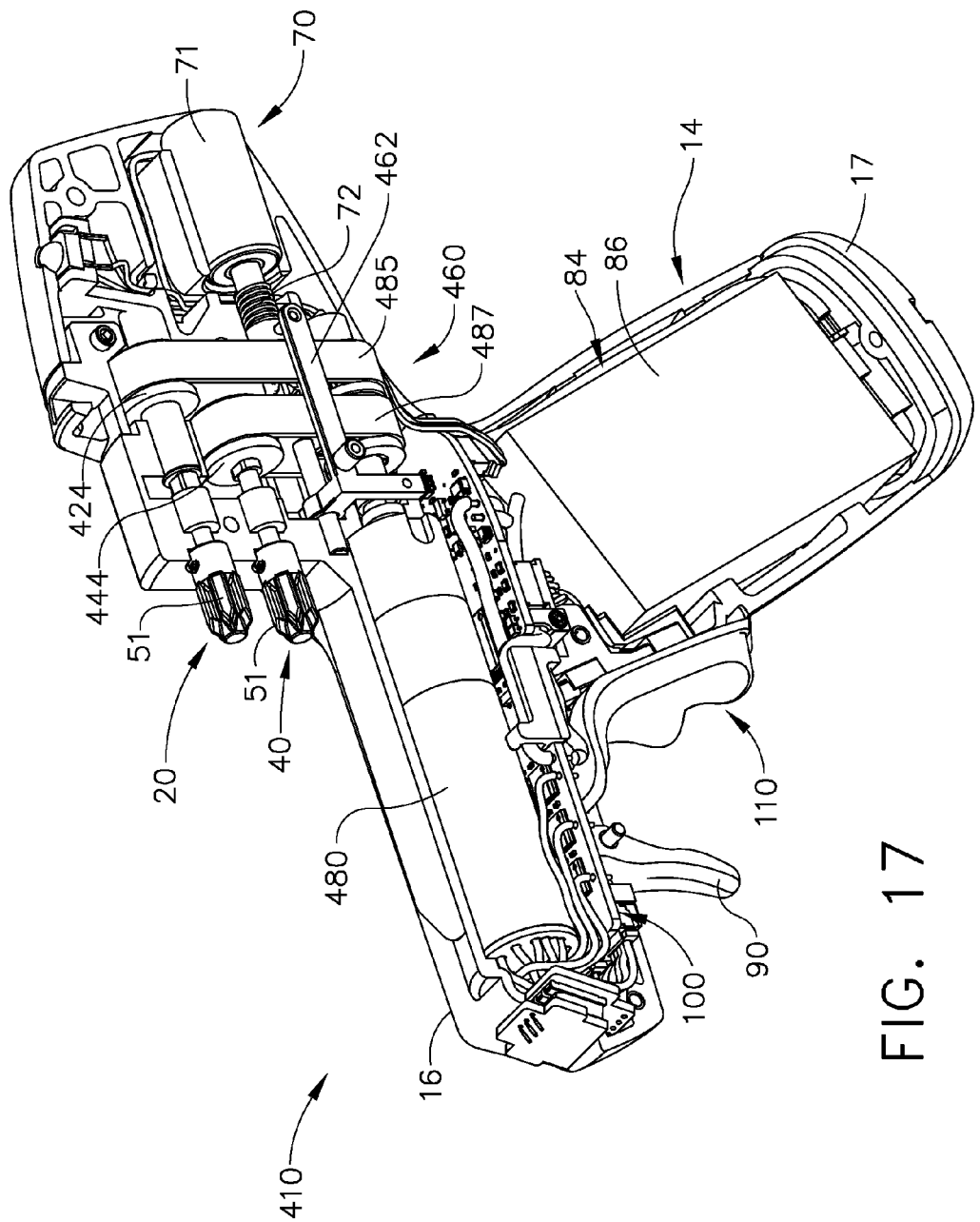
FIG. 17 is a perspective view of another motor driven surgical instrument arrangement with a portion of the housing removed for clarity.

FIGS. 13-16 illustrate another form of motor driven surgical instrument 310 that may be identical to surgical instrument 10 except for the differences noted below. Those components of surgical instrument 310 that are the same as the components in the surgical instrument 10 described above will be designated with the same element numbers. In this arrangement, the first and second drive systems 20, 40 are powered by motor 80 through a unique and novel "shiftable" transmission assembly 360. The first drive system 20 includes a first drive shaft 22 that has a first drive pulley 324 keyed thereon or otherwise non-rotatably affixed thereto. Similarly, the second drive system 40 includes a second drive shaft 42 that has a second drive pulley 344 keyed thereon or otherwise non-rotatably thereto. As can be seen in FIG. 14, for example, the first drive shaft axis "FDA" is offset from and parallel with or is substantially parallel with the second drive shaft axis "SDA".

Still referring to FIGS. 13-16, in one form, the motor 80 includes a first motor pulley 382 that is non-rotatably attached to the shaft of the motor 80. The first motor pulley 382 drives a first drive belt 385 that is received on the first drive pulley 324. In addition, a second motor pulley 384 is non-rotatably mounted to the motor shaft and operably supports a second drive belt 387 thereon. The second drive belt 387 is also received on the second drive pulley 344 on the second drive shaft 42. The first and second drive belts 385, 387 may comprise V-belts, for example.

The instrument 310 also includes a transmission assembly 360 that includes a transmission carriage 362 that is supported for axial travel within the instrument housing. The transmission carriage 362 operably interacts with an idler carriage 374 that is supported to move laterally in response to contact with transmission carriage 362 as the transmission carriage 362 is moved axially by the shifter solenoid 71. The idler carriage 374 includes a first idler pulley 375 and a second idler pulley 376 mounted thereon. In the illustrated arrangement, the spring 72 biases the transmission carriage 362 in the distal direction "DD" to a first drive position wherein the transmission carriage 362 causes the idler carriage 374 to move in a first lateral direction "FLD" which causes the first idler pulley 375 to remove the slack from the first drive belt 385. When in that position, the second idler pulley 376 is located out of engagement with the second drive belt 387. Thus, operation of motor 80 will result in the rotation of the first drive shaft 22. Although the second motor pulley 384 will also be rotated when the motor 80 is activated, the slack in the second drive belt 387 prevents that rotary motion from being transferred to the second drive pulley 344. Thus, no rotary motion is transferred to the second drive system 40. As discussed above, the shifter solenoid 71 may be actuated by the firing trigger 90. However, in alternative arrangements, the shifter solenoid 71 may also be replaced by a manually actuatable linkage assembly of the type described above, for example. In the illustrated arrangement, actuation of the firing trigger 90 will result in the shifter solenoid 71 pulling the transmission carriage 362 in the proximal direction "PD" to thereby laterally displace the idler carriage 374 in a second lateral direction "SLD" to bring the second idler 376 into contact with the second drive belt 387 to remove the slack therefrom. Such lateral movement of the idler carriage 374 also moves the first idler 375 out of engagement with the first drive belt 385 to permit the first drive belt 385 to slacken. Thus, when in such second drive position, actuation of the motor 80 results in the actuation of the second drive system 40. The slack in the first drive belt 385 prevents the rotary motion from being transferred to the first drive system 20.

The transmission assembly 360 may provide several distinct advantages. For example, the use of V-belts eliminates meshing gears or gear alignments with a clutch.

Furthermore, such transmission arrangement may be activated or deactivated under load. In addition, the transmission assembly 360 requires little displacement to disengage and engage.

Figure 18:
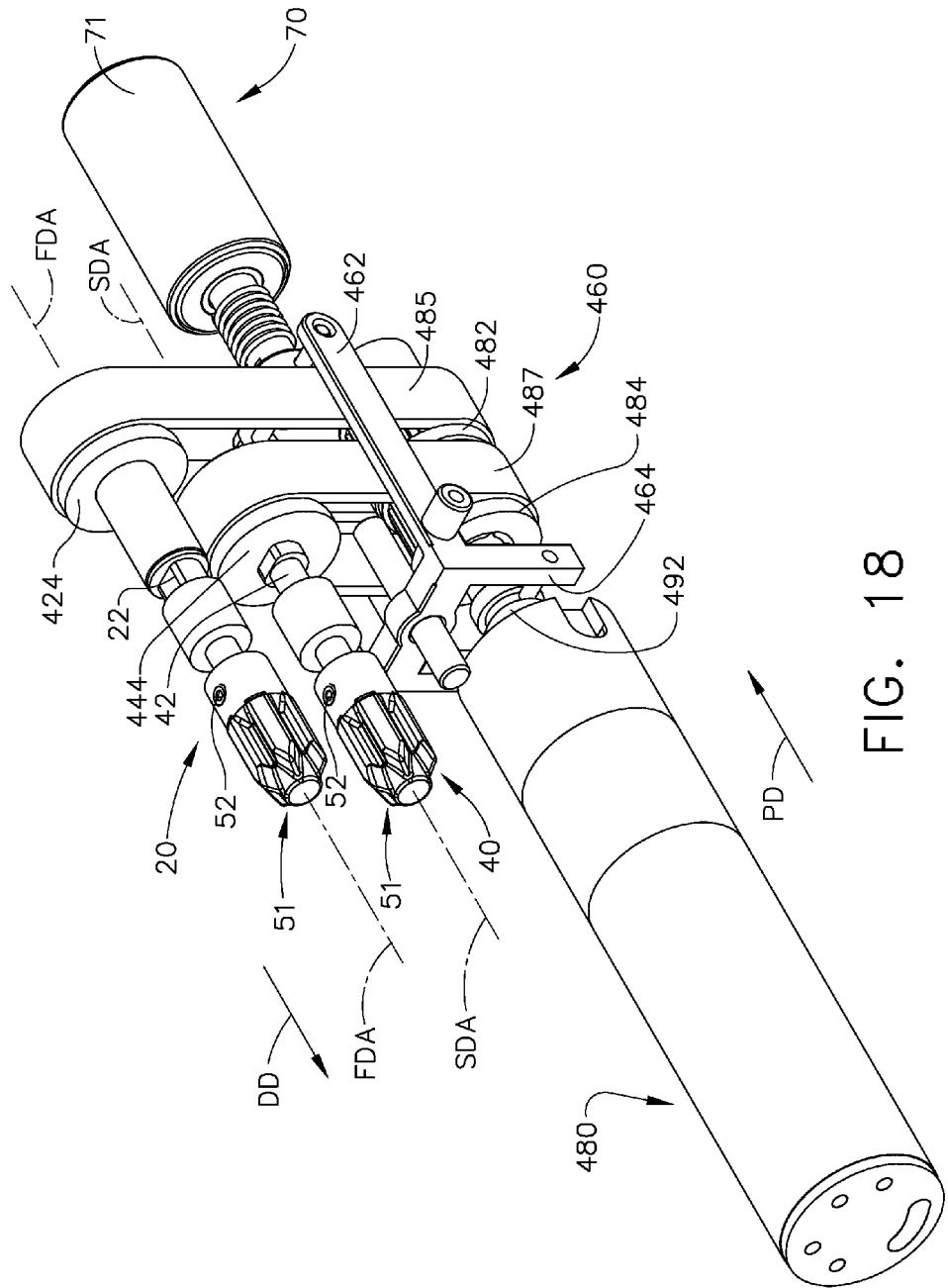
FIG. 18 is a perspective view of a motor, transmission assembly and first and second drive systems of the surgical instrument of FIG. 17.

FIGS. 17-21 illustrate another form of motor driven surgical instrument 410 that may be identical to surgical instrument 10 except for the differences noted below. Those components of surgical instrument 410 that are the same as the components in the surgical instrument 10 described above will be designated with the same element numbers. In this arrangement, the first and second drive systems 20, 40 are powered by motor 480 through a unique and novel "shiftable" transmission assembly 460. The first drive system 20 includes a first drive shaft 22 that has a first drive pulley 424 keyed thereon or otherwise non-rotatably affixed thereto. Similarly, the second drive system 40 includes a second drive shaft 42 that has a second drive pulley 444 keyed thereon or otherwise non-rotatably fixed thereto. As can be seen in FIG. 18, for example, the first drive shaft axis "FDA" is offset from and parallel with or is substantially parallel with the second drive shaft axis "SDA".

Figure 19:
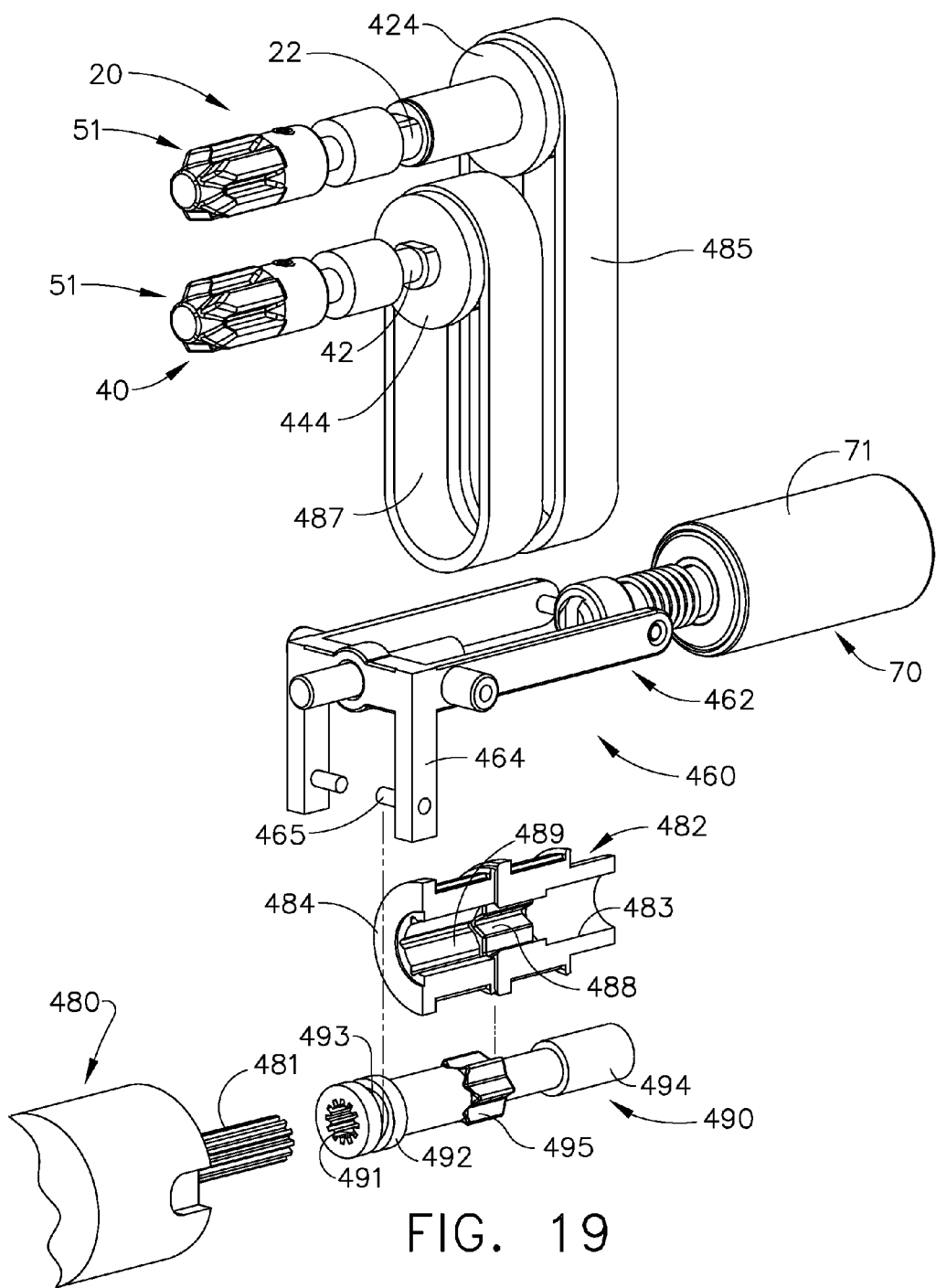
FIG. 19 is an exploded assembly view of the motor, transmission assembly and first and second drive systems of FIG. 18.

Referring now to FIG. 19, in one form, the motor 480 includes a splined drive shaft 481 that is adapted to slidably engage a transmission shaft assembly 490 that is configured to interact with a transmission carriage 462 such that axial movement of the transmission carriage 462 results in axial movement of the transmission shaft assembly 490 on the splined drive shaft 481. As can be seen in FIG. 19, the transmission shaft assembly 490 has a splined bore 491 therein for slidably and operably receiving the splined drive shaft 481 therein. In addition, a distal engagement collar 492 is formed on a distal end of the transmission shaft assembly 490. The distal engagement collar 492 is configured with an annular groove 493 that is configured to receive therein two opposed yoke rods 465 that are attached to a yoke portion 464 of the transmission carriage 462. Such arrangement serves to couple the transmission carriage 462 to the transmission shaft assembly 490 while permitting the transmission shaft assembly 490 to rotate relative to the transmission carriage 462.

Still referring to FIG. 19, a first motor pulley 482 is configured for selective driving engagement with the transmission shaft assembly 490. As can be seen in FIG. 19, for example, the transmission shaft assembly 490 has a bearing collar 494 formed on the proximal end thereof that is sized to be slidably and rotatably received within bore 483 in the first motor pulley 482. In addition, the first motor pulley 482 also includes a star-shaped proximal drive cavity 488 that is adapted to meshingly engage a complementary-shaped drive portion 495 formed on the transmission shaft assembly 490. The first motor pulley 482 drives a first drive belt 485 that is also received on the first drive pulley 424. The surgical instrument 410 also includes a second motor pulley 484 that has a star-shaped bore 489 that is configured to meshingly engage the drive portion 495 of the transmission shaft assembly 490 therein. A second motor pulley 484 operably supports a second drive belt 487 thereon that is also received on the second drive pulley 444.

Figure 20:
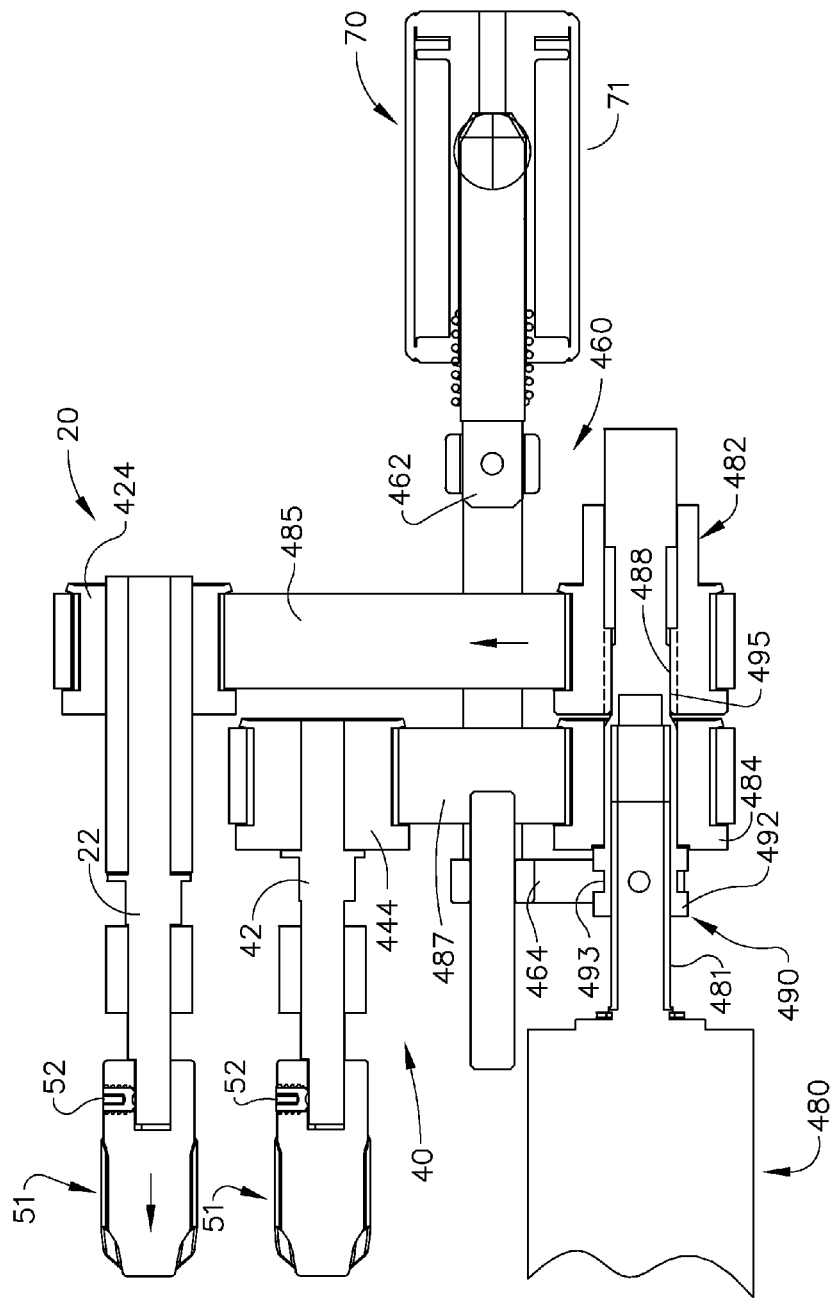
FIG. 20 is a cross-sectional view of portions of the motor, transmission assembly and first and second drive systems of FIGS. 18 and 19 with the transmission shaft assembly thereof in a first drive position.
Figure 21:
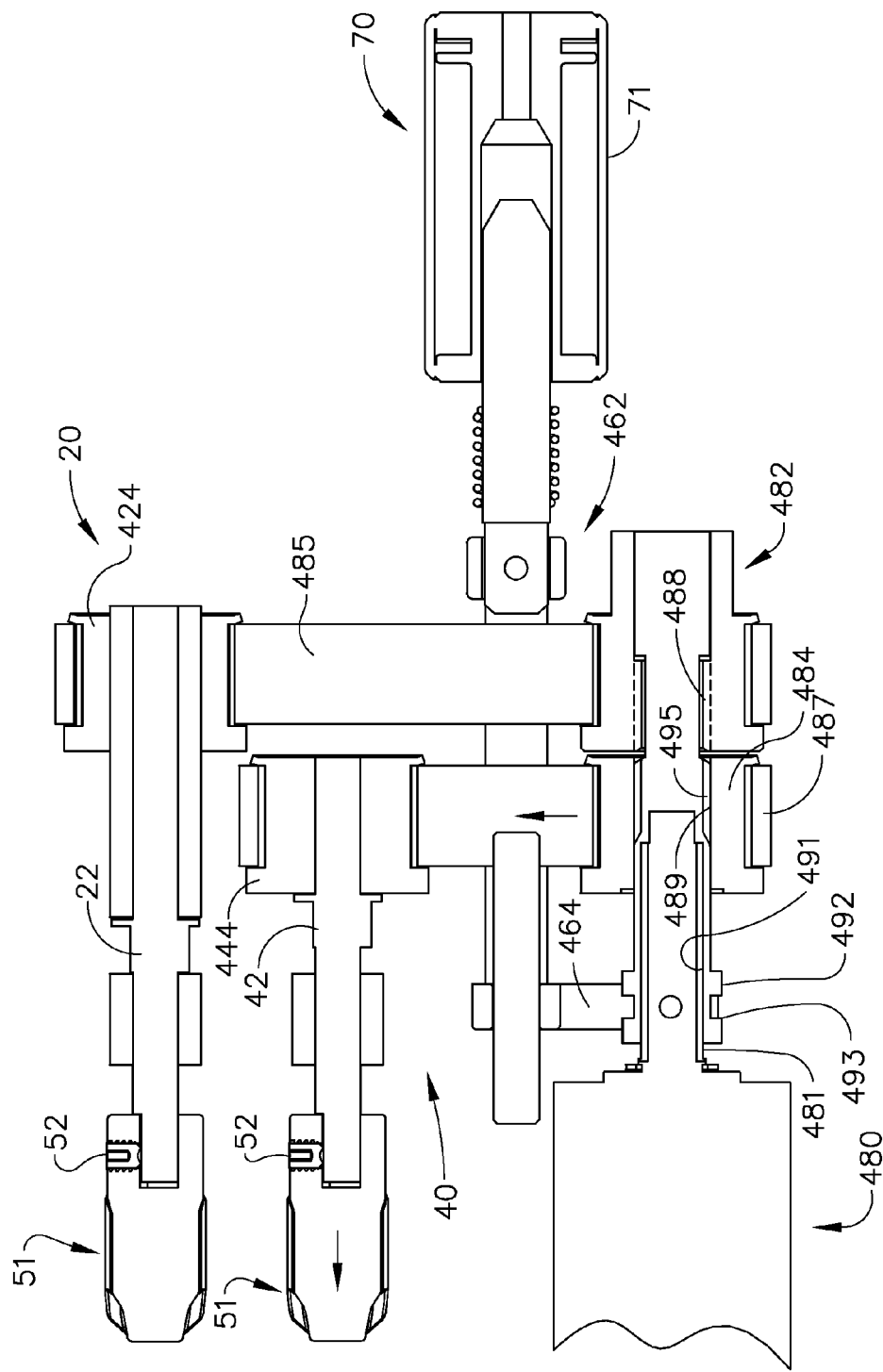
FIG. 21 is another cross-sectional view of the portions of the motor, transmission assembly and first and second drive systems of FIG. 20 with the transmission shaft assembly thereof in a second drive position.
Figure 22:
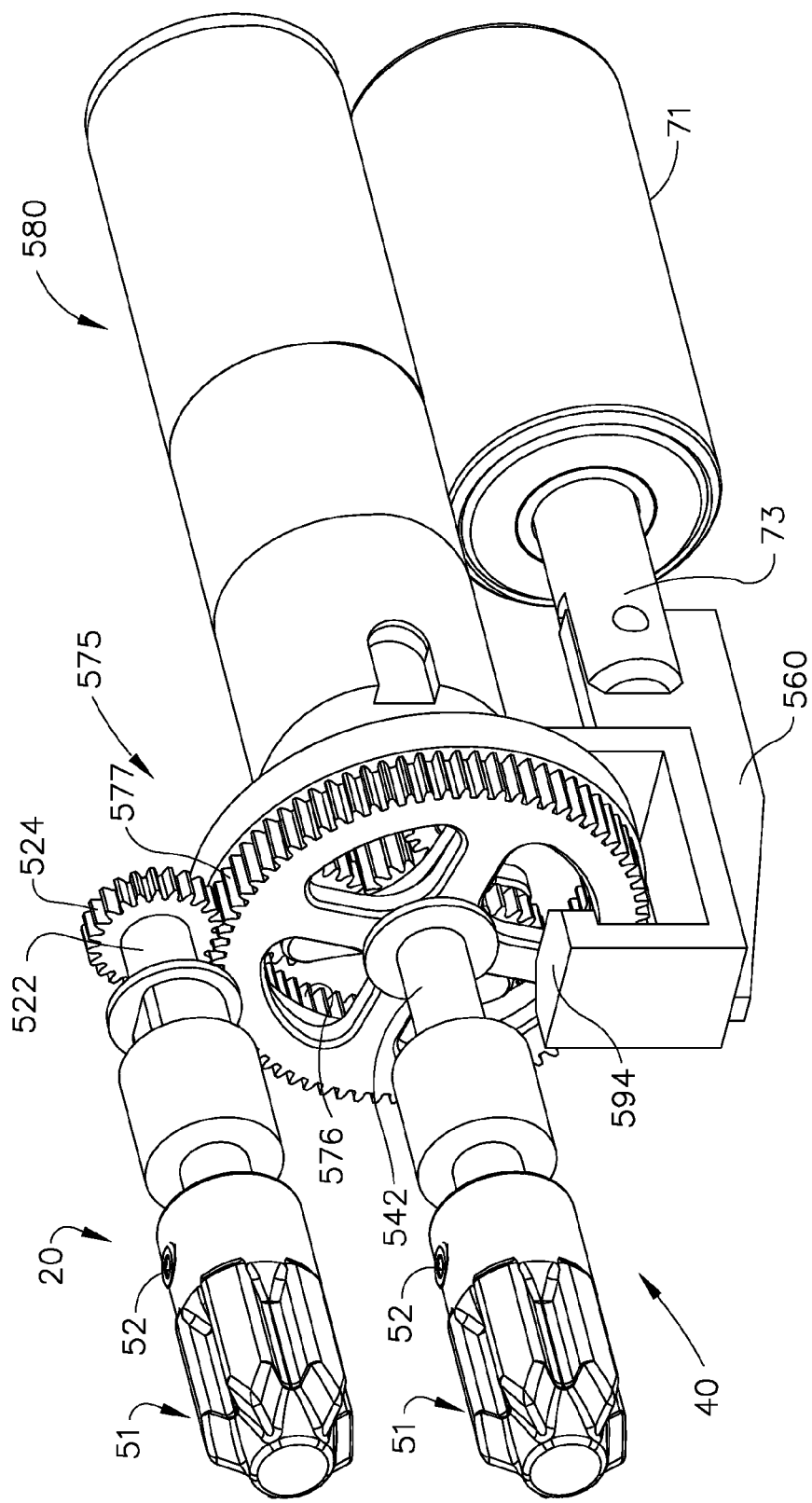
FIG. 22 is a perspective view of another motor, transmission assembly and first and second drive systems of one form of a surgical instrument of the present invention.

As indicated above, the instrument 410 also includes a transmission assembly 460 that includes a transmission carriage 462 that is supported for axial travel within the instrument housing. The transmission carriage 462 operably interacts with transmission shaft assembly 490 to also move the transmission shaft assembly 490 axially while the transmission shaft assembly 490 remains engaged with the motor shaft 481. FIG. 20 illustrates the shifter solenoid 71 in the unactuated position. As can be seen in that Figure, the transmission carriage 462 has moved the transmission shaft assembly 490 to its proximal-most position which may also be referred to as the "first drive position" wherein the drive portion 495 is in driving engagement with the star-shaped bore 488 in the first motor pulley 482. Thus, rotation of the motor shaft 481 will result in rotation of the transmission shaft assembly 490 and the first motor pulley 482. Rotation of the first motor pulley 482 results in rotation of the first drive belt 485 which ultimately results in rotation of the first drive shaft 22. When the transmission shaft assembly 490 is in the first drive position, the transmission shaft assembly 490 rotates freely relative to the second motor pulley 484. Thus, when the first drive system 20 is actuated, the second drive system 40 remains unactuated. When the shifter solenoid 71 is actuated to the position shown in FIG. 21 (by actuating the firing trigger 90), the transmission carriage 462 moves the transmission shaft assembly 490 to its distal-most position on the motor shaft 481 which may also be referred to as the 'second drive position". As can be seen in FIG. 21, when the transmission shaft assembly 490 is in the second drive position, the drive portion 495 thereof is moved into meshing engagement with the star-shaped bore 489 in the second motor pulley 484. Thus, rotation of the motor shaft 481 will result in the rotation of the second motor pulley 484. Rotation of the second motor pulley 484 will result in the rotation of the second drive belt 487 which results in the rotation of the second drive shaft 42. When in that second drive position, the transmission shaft assembly 490 rotates freely within the first motor pulley 482. Thus, when the second drive system 40 is actuated, the first drive system 20 is in an unactuated state.

Figure 23:
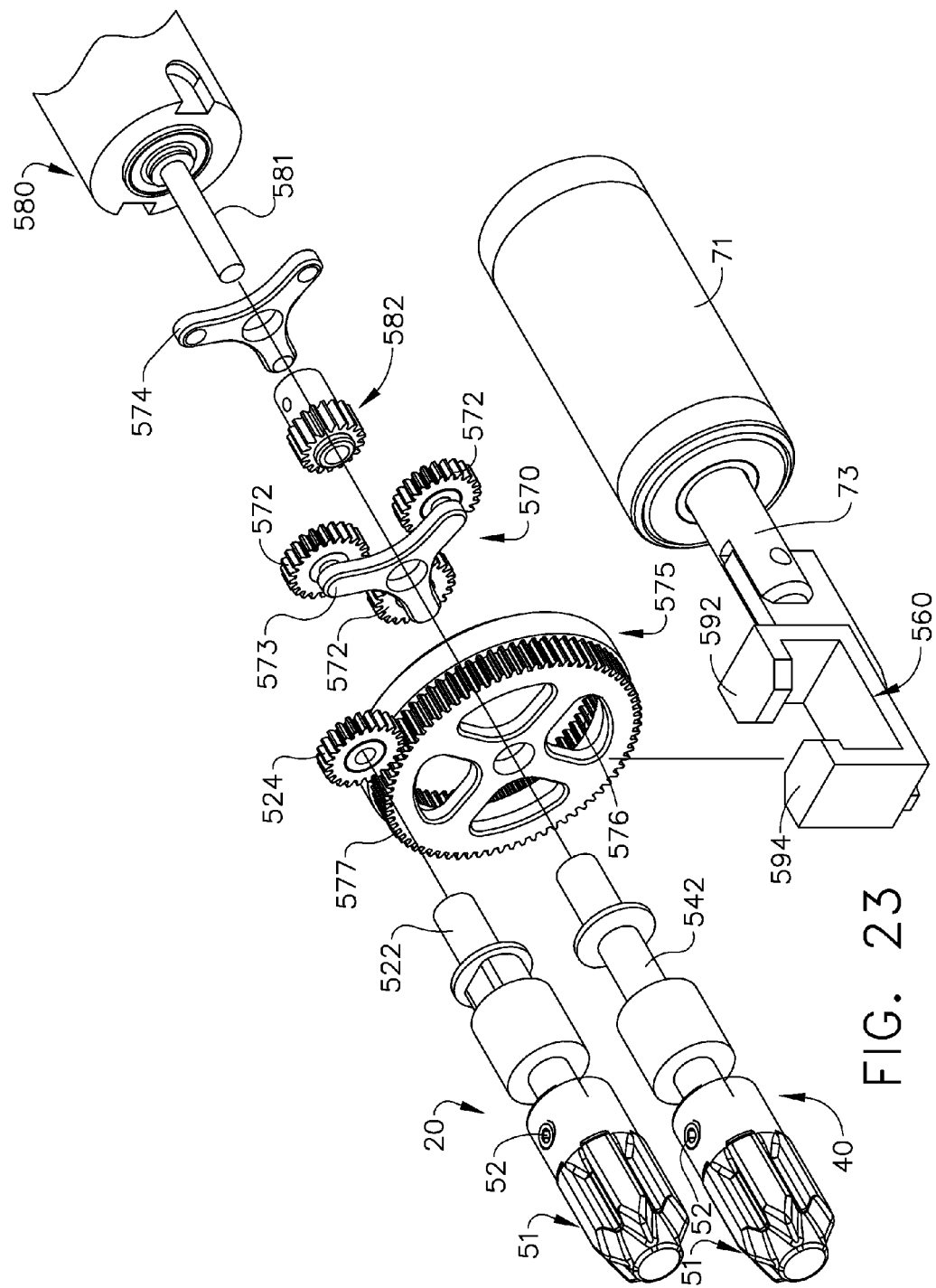
FIG. 23 is an exploded assembly view of the motor, transmission assembly and first and second drive systems of FIG. 22.
Figure 24:
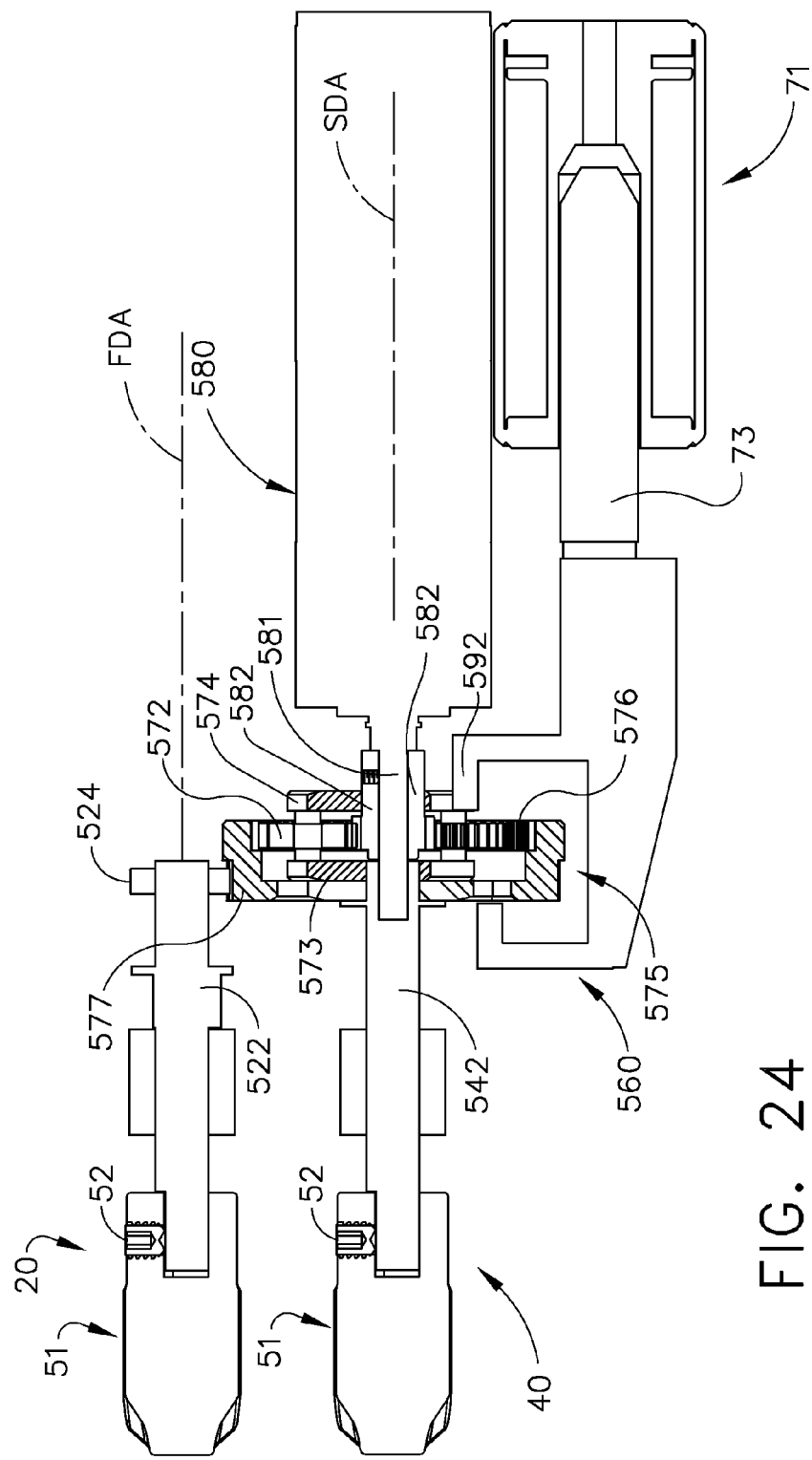
FIG. 24 is a cross-sectional view of the motor, transmission assembly and first and second drive systems of FIGS. 22 and 23 with the transmission assembly in first drive position.
Figure 25:
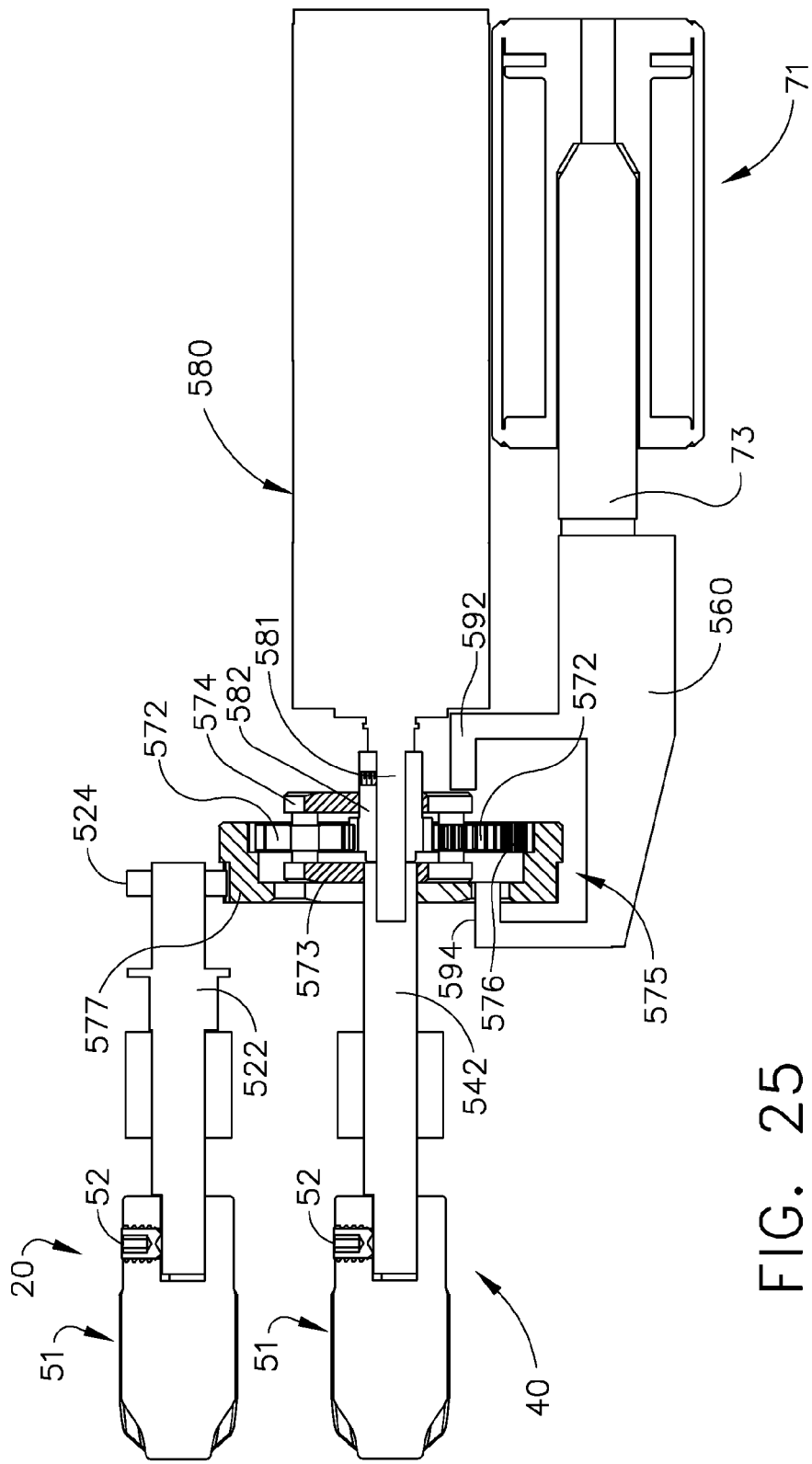
FIG. 25 is another cross-sectional view of the motor, transmission assembly and first and second drive systems of FIGS. 22-24 with the transmission assembly in a second drive position.
Figure 26:
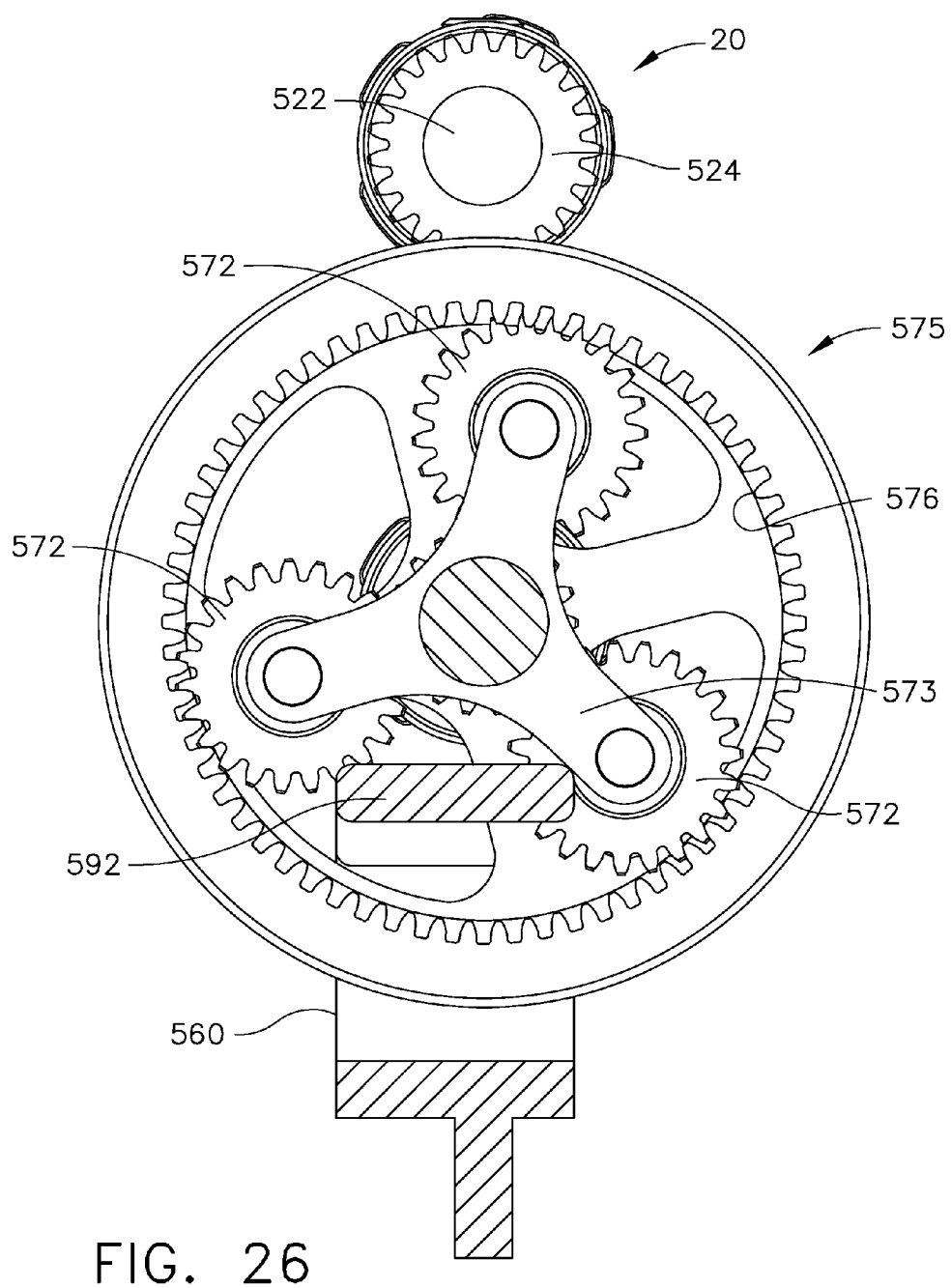
FIG. 26 is another cross-sectional view of the motor and transmission assembly of FIGS. 22-25 with the transmission assembly in the first drive position.
Figure 27:
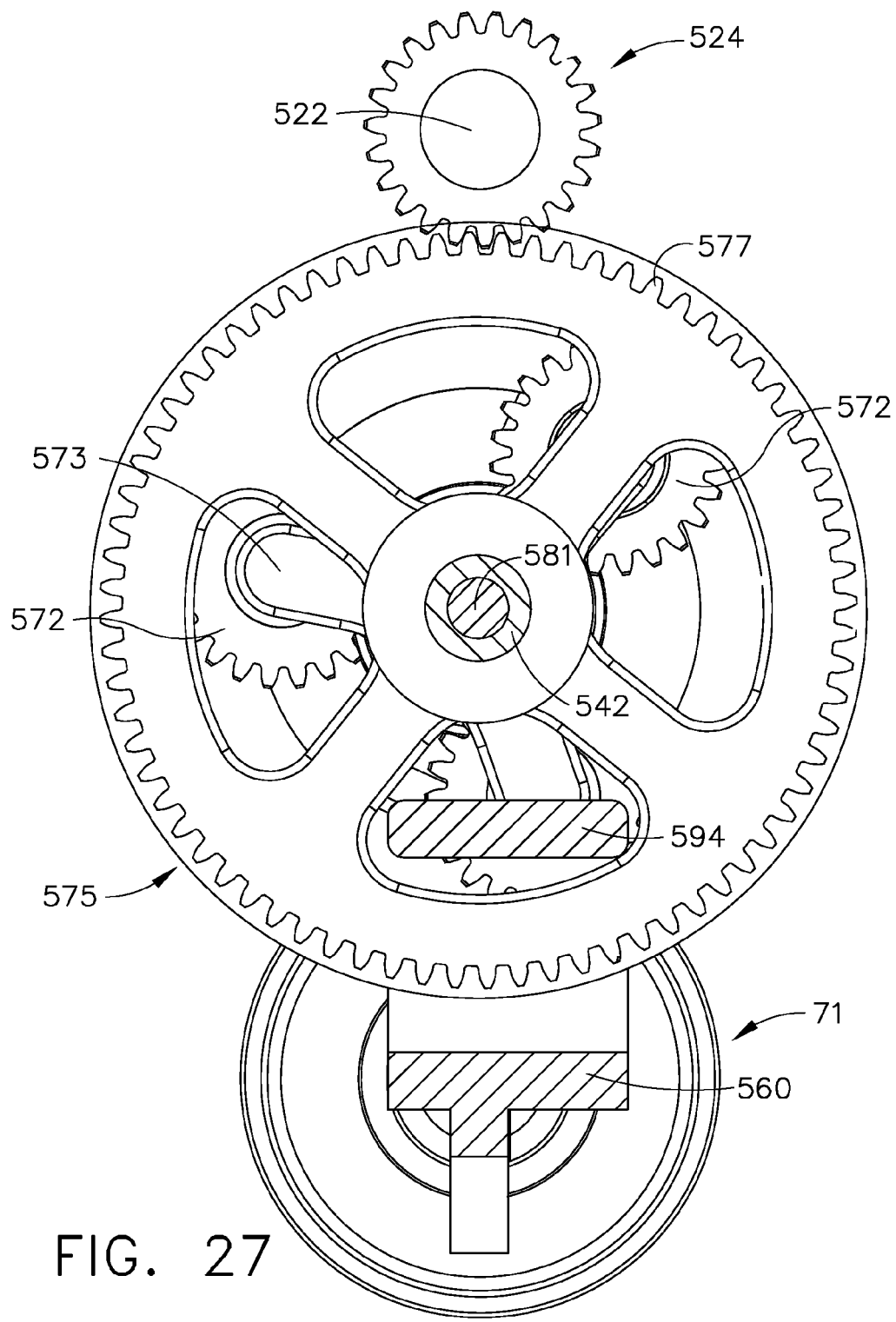
FIG. 27 is another cross-sectional view of the motor and transmission assembly of FIGS. 22-26 with the transmission assembly in the second drive position.

FIGS. 22-27 illustrate another motor, transmission assembly and first and second drive systems that may be employed with various surgical instruments described herein. The illustrated arrangement includes a motor 580 that has a motor shaft 581. See FIGS. 23 and 24. A motor drive gear 582 or "sun gear" 582 is non-rotatably affixed to the motor shaft 581 for rotation therewith. The arrangement further includes a planetary gear assembly 570 that includes three planetary gears 572 that are rotatably supported between a distal carrier bracket 573 and proximal carrier bracket 574. The proximal carrier bracket 574 is supported on a hub portion of the sun gear 582 such that the sun gear 582 may rotate relative to the proximal carrier bracket 574. The distal carrier bracket 573 is affixed to a second drive shaft 542 of a second drive system 40 such that rotation of the distal carrier bracket 573 will result in the rotation of the second drive shaft 542 of the second drive system 40. The three planetary gears 572 are supported in meshing engagement with a ring gear assembly 575. More specifically, the planetary gears 572 are in meshing engagement with an internal ring gear 576 on the ring gear assembly 575. The ring gear assembly 575 further includes an external ring gear 577 that is in meshing engagement with a first drive gear 524 that is affixed to a first drive shaft 522 of the first drive system 20. As can be seen in FIG. 24, for example, the first drive shaft axis "FDA" is offset from and parallel with or is substantially parallel with the second drive shaft axis "SDA".

As can be seen in FIG. 23, the arrangement further includes a solenoid 71 that may be operated by the firing trigger in the various manners described herein. In this arrangement, the transmission assembly 560 is attached to the shaft 73 of the solenoid 71. FIG. 24 illustrates the transmission assembly 560 in the first drive position. In one form, the transmission assembly 560 includes a locking assembly, generally designated as 590 that comprises a first or proximal lock lug portion 592 and a second or distal lock lug portion 594 on the transmission assembly 560. As can be seen in that Figure, the transmission assembly 560 is positioned such that the proximal lock lug portion 592 is in engagement with the proximal carrier bracket 574. When in that first drive position, the proximal lock lug portion 592 prevents the planetary gear assembly 570 from rotating as a unit with the sun gear 582. However, rotation of the sun gear 582 results in rotation of the planetary gears 572. Rotation of the planetary gears 572 results in rotation of the ring gear assembly 575. Rotation of the ring gear assembly 575 results in rotation of the first drive gear 524 and the first drive shaft 522. Because the proximal carrier bracket 574 is prevented from rotating, the distal carrier bracket 573 is also prevented from rotating. Thus, the second drive shaft 544 is also prevented from rotating while the first drive shaft 522 is rotated. A spring (not shown) may be employed to bias the solenoid 71 (and the transmission assembly 560 attached thereto) into this "first drive position". When the clinician desires to actuate the second drive system 40, the solenoid 71 may be actuated using the firing trigger as described above to move the solenoid shaft 73 to the position shown in FIG. 25. When the transmission assembly 560 is in that "second drive position", the distal lock lug portion 594 retainingly engages the ring gear assembly 575 to prevent rotation thereof. Thus, when the sun gear 582 is rotated, the planetary gear carrier (i.e., the distal carrier bracket 573 and proximal carrier bracket 574) will also rotate. The planetary gears 572 will rotate within the fixed internal ring gear 576. Such rotary motion will be transferred to the second drive shaft 542 while the first drive shaft 522 remains unactuated.

Figure 28:
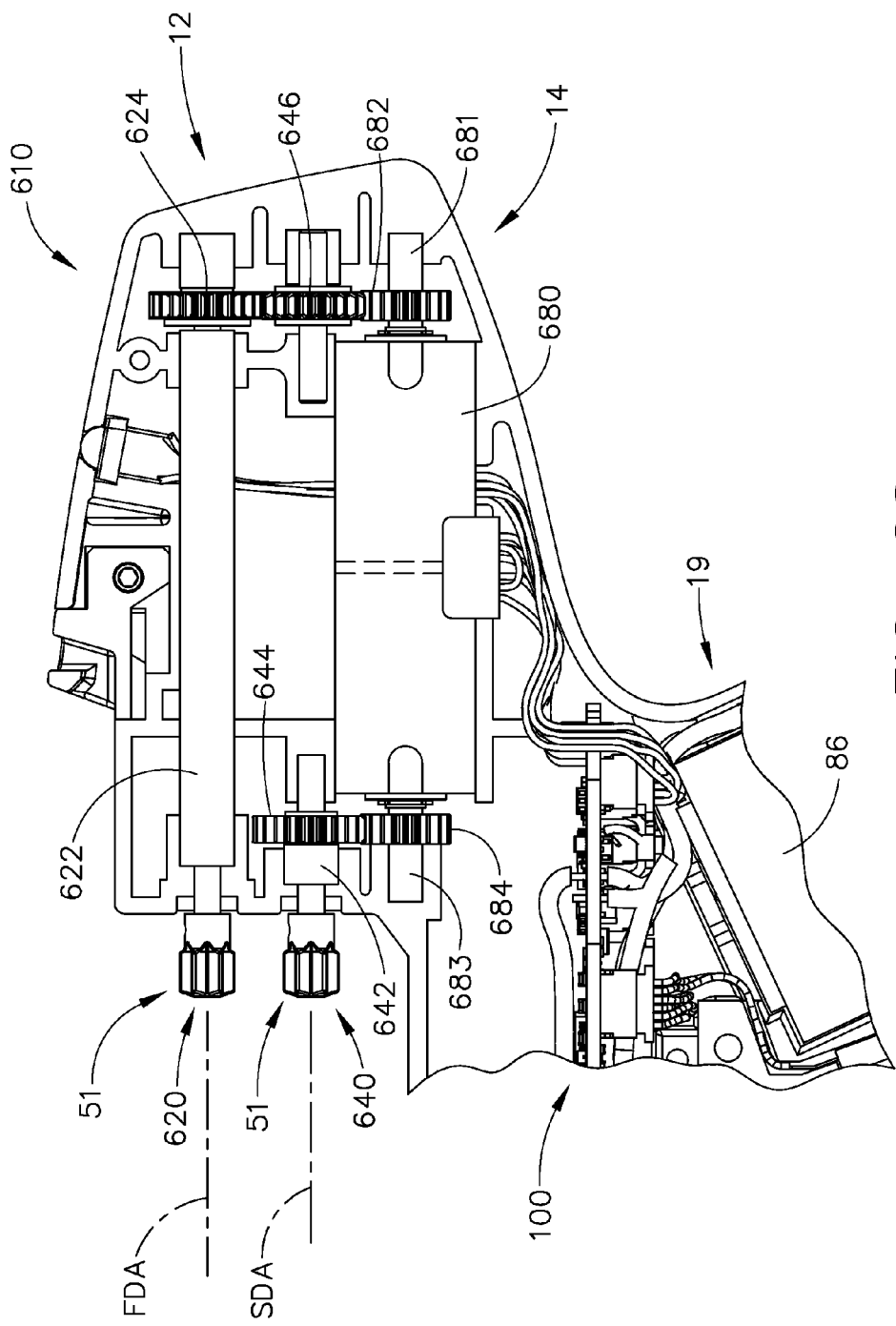
FIG. 28 is a side elevational view of a portion of another motor driven surgical instrument with a portion of the housing omitted for clarity.

FIG. 28 illustrates another form of motor driven surgical instrument 610 that may be identical to surgical instrument 10 except for the differences noted below. Those components of surgical instrument 610 that are the same as the components in the surgical instrument 10 described above will be designated with the same element numbers. As can be seen in FIG. 28, for example, the first drive shaft axis "FDA" is offset from and parallel with or is substantially parallel with the second drive shaft axis "SDA". This arrangement comprises a motor 680 that has dual, independently actuatable motor shafts 681, 683. The motor 680 may be controlled by a firing trigger arrangement of the various types described herein, such that actuation of the firing trigger in one manner causes the motor 680 to rotate the first motor shaft 681 and actuation of the firing trigger in another manner causes the motor 680 to rotate the second motor shaft 683. In this arrangement, a first motor gear 682 is mounted on the first motor shaft 681 and is supported in meshing engagement with an idler gear 646. Idler gear 646 is operably supported in meshing engagement with a first drive gear 624 that is mounted to a first drive shaft 622 of a first drive system 620. Thus, actuation of the first motor shaft 681 will result in actuation of the first drive system 620. Likewise, a second motor gear 684 is mounted on the second motor shaft 683 and is supported in meshing engagement with a second drive gear 644 that is mounted on a second drive shaft 642 of a second drive system 640. As such, actuation of the second motor shaft 683 will result in the actuation of the second drive system 640.

Figure 29:
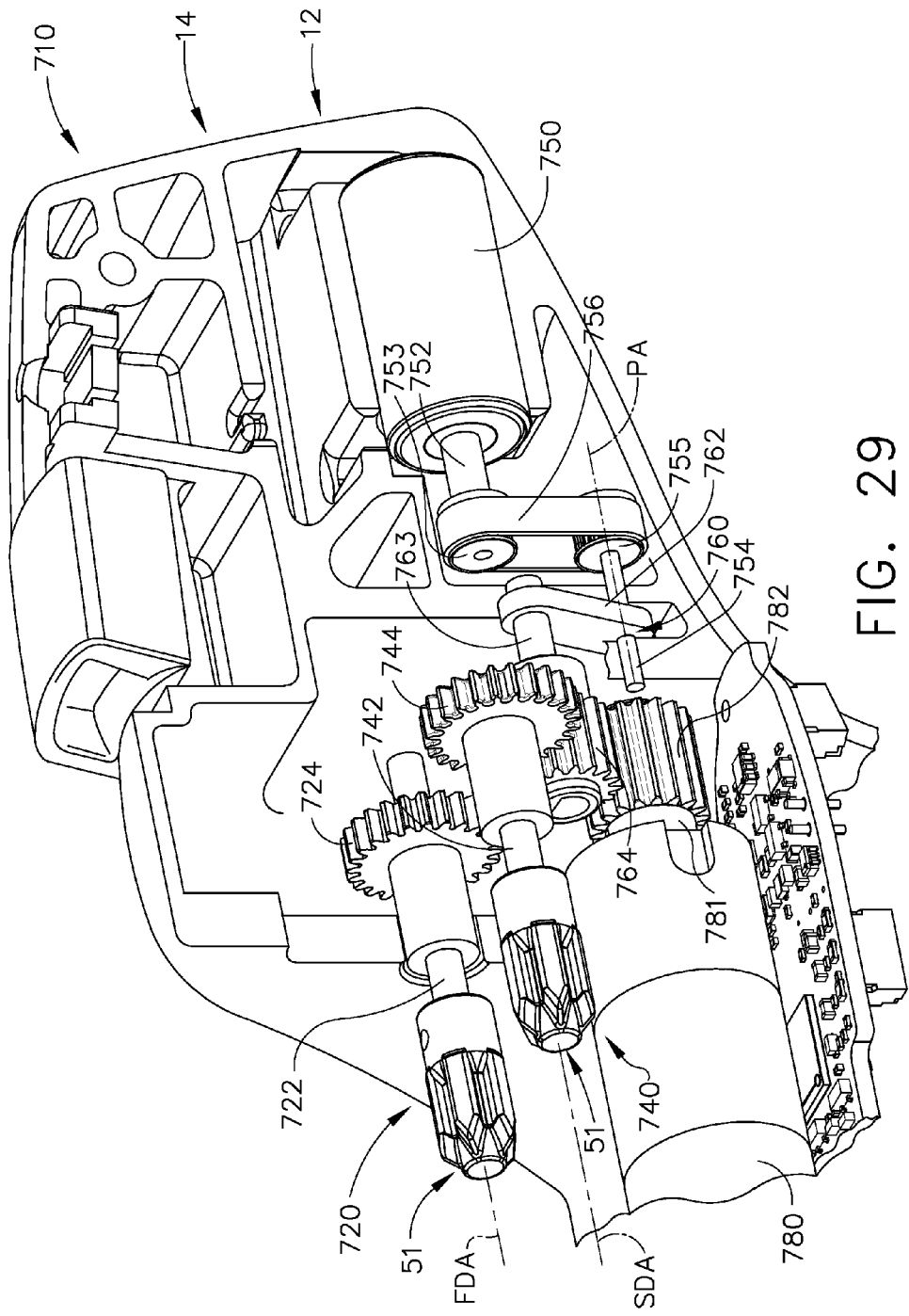
FIG. 29 is a perspective view of a portion of another motor driven surgical instrument with a portion of the housing omitted for clarity.

FIG. 29 illustrates another form of motor driven surgical instrument 710 that may be identical to surgical instrument 10 except for the differences noted below. Those components of surgical instrument 710 that are the same as the components in the surgical instrument 10 described above will be designated with the same element numbers. As can be seen in FIG. 29, for example, the first drive shaft axis "FDA" is offset from and parallel with or is substantially parallel with the second drive shaft axis "SDA". In this arrangement, first and second drive systems 720, 740 are powered by a motor 780 through a unique and novel "shiftable" transmission assembly 760. The first drive system 720 includes a first drive shaft 722 that has a first drive gear 724 keyed thereon or otherwise non-rotatably affixed thereto. Similarly, the second drive system 740 includes a second drive shaft 742 that has a second drive gear 744 keyed thereon or otherwise non-rotatably thereto. The motor 780 includes a motor gear 782 that is non-rotatably attached to the shaft 781 of the motor 780.

In the illustrated arrangement, a second motor 750 is employed to shift the transmission assembly 760 as will be discussed in further detail below. The second motor 750 may be controlled, for example, by the various firing trigger and switch arrangements disclosed herein. The second motor 750 can be controlled in a manner similar to the way that the motor 7038 is controlled as described hereinbelow in connection with FIGS. 61, 63, 64. As can be seen in FIG. 29, a first transfer pulley 753 is keyed onto or otherwise non-rotatably affixed to the motor shaft 752. A first pivot shaft 754 is rotatably supported within the housing 12 of the handle 14. The first pivot shaft 754 defines a pivot axis "PA". A second transfer pulley 755 is non-rotatably mounted on the first pivot shaft 754 and a transfer belt 756 is mounted on the first and second transfer pulleys 753, 755. In one form, the shiftable transmission assembly 760 includes a transfer link 762 that is attached to the first pivot shaft 754. In addition, an idler shaft 763 is attached to the transfer link 762 which operably supports an idler gear 764 thereon. The shiftable transmission assembly 760 is movable between a first drive position and a second drive position. To move the shiftable transmission assembly 760 to the first drive position, the clinician actuates the second motor 750 to rotate the pivot shaft 763 and idler gear 764 about pivot axis PA such that it is in meshing engagement with the motor gear 782 and the first drive gear 724. When in that position, actuation of the motor 780 will then result in actuation of the first drive system 720. When the clinician desires to actuate the second drive system 740, the second motor 750 is actuated to rotate the idler gear 764 about pivot axis PA into meshing engagement with the motor gear 782 and the second drive gear 744. When in that position, actuation of motor 780 results in actuation of the second drive system 740. One benefit that may be achieved with this arrangement is that precise gear orientation is not required. As the idler gear 764 swings into position, it may be rotating and automatically will find a mating tooth.

Figure 30:
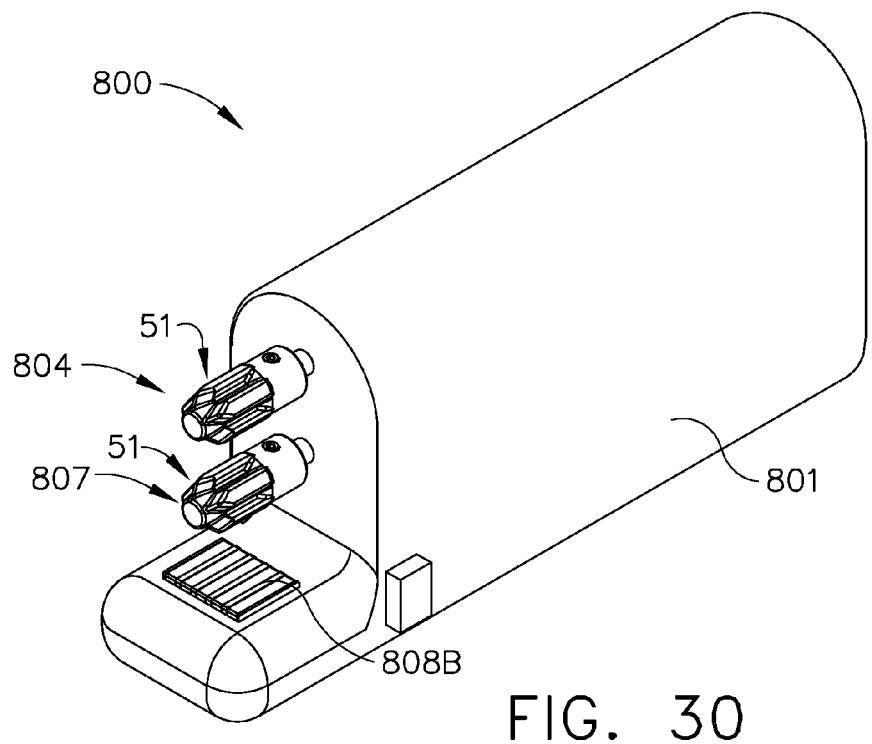
FIG. 30 is a front perspective view of a motor driven unit with first and second rotary drive systems.
Figure 31:
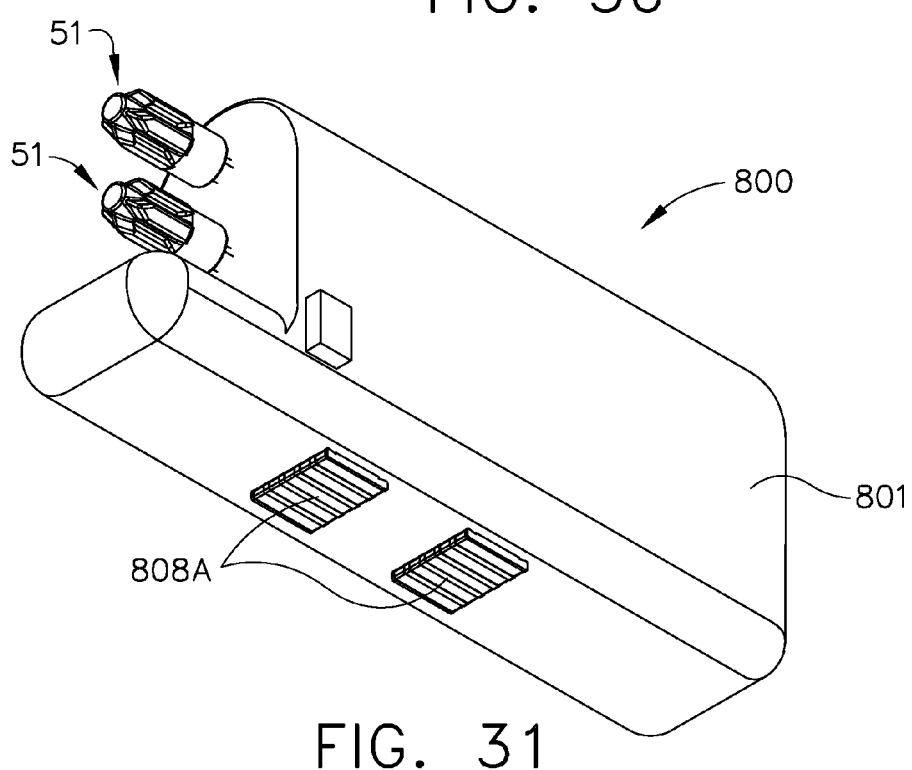
FIG. 31 is a bottom perspective view of the motor driven unit of FIG. 30.
Figure 32:
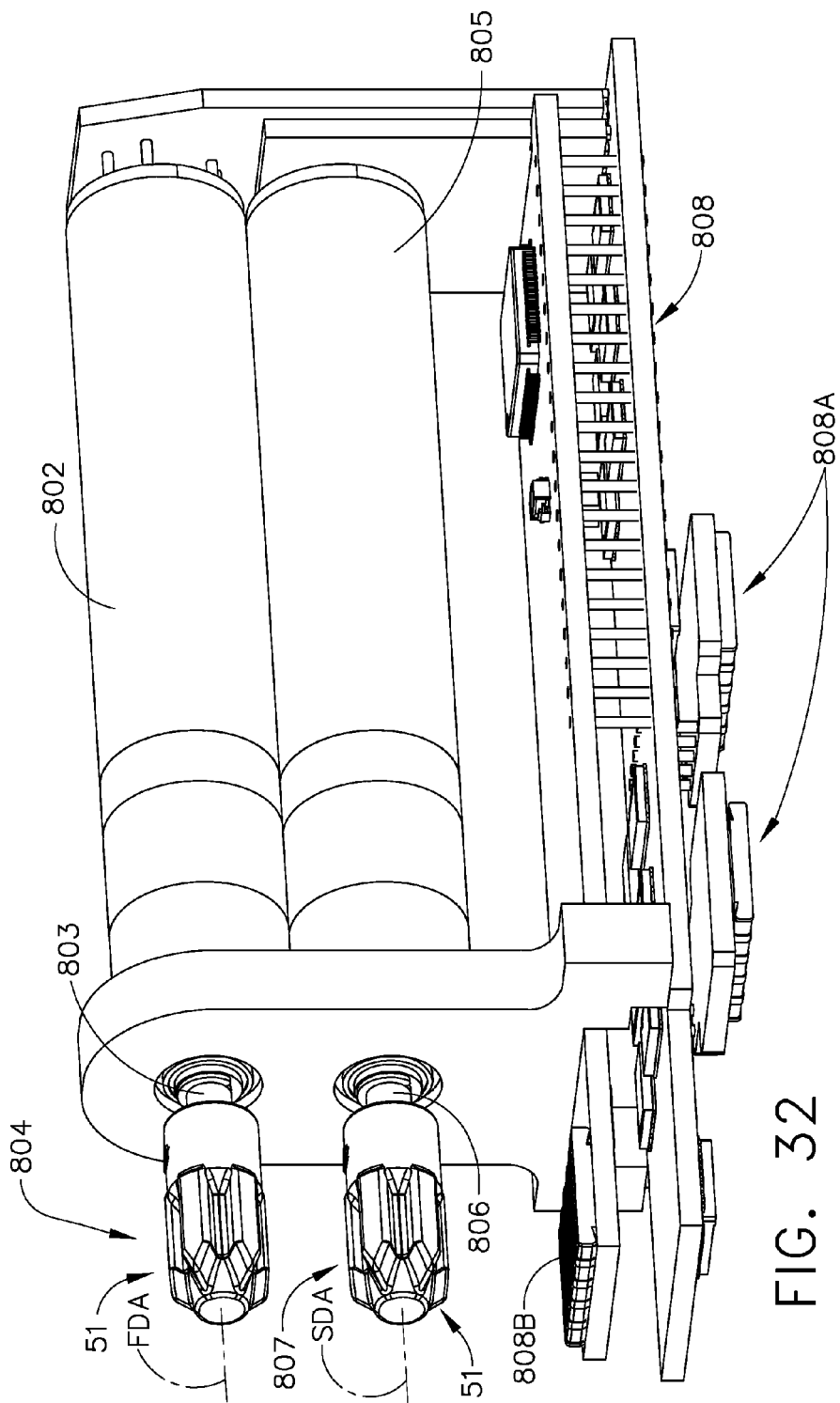
FIG. 32 is a perspective view of the motor driven unit of FIGS. 31 and 32 with the housing removed therefrom.

FIGS. 30-32 illustrate a unique and novel motor unit 800 that may be mounted within a housing of the types described herein. The motor unit 800 may include a separate housing structure 801 that operably supports a first motor 802 with a first motor shaft 803 that defines a first drive system 804. The motor unit 800 may include a second motor 805 with a second motor shaft 806 that defines a second drive system 807. As can be seen in FIG. 8, for example, the first drive shaft axis "FDA" is offset from and parallel with or is substantially parallel with the second drive shaft axis "SDA". The unit 800 may further include a control circuit board 808 which contacts 808A that operably interface with corresponding contacts on the circuit board mounted within the instrument housing or otherwise supported therein and communicating with the instrument's control system. The housing may further include electrical contacts 808B which are configured to operably interface with corresponding electrical contacts on an end effector tool that is coupled thereto.

As illustrated in FIG. 1, the modular surgical system 2 may include a variety of different surgical end effector arrangements 1000, 2000, and 3000 that may be used in connection with various surgical instruments described herein. As will be discussed in further detail below, each of the end effectors 1000, 2000, 3000 include dual, separate "first and second end effector drive systems" that are adapted to operably interface with the first and second drive systems in the surgical instrument to receive control motions therefrom. The end effector drive systems are each configured to linearly move corresponding end effector actuator components from first or beginning linear positions to second or ending linear positions in response to corresponding rotary motions applied to the end effector drive systems by the surgical instrument to which the end effector is operably attached. The end effector actuator components apply linear actuation motions to various end effector components located in the end effector tool head portion in order to perform various surgical procedures. As will be discussed in further detail below, the end effectors employ unique components and systems for assisting the clinician in coupling the first and second drive shafts of the surgical instrument with the corresponding drive shafts in the end effector. Because the four drive shafts are essentially simultaneously coupled together, various coupling arrangements and control techniques may be employed to ensure that the shafts are in the correct positions or "near correct positions" that will facilitate such simultaneous coupling of the drive systems.

Figure 33:
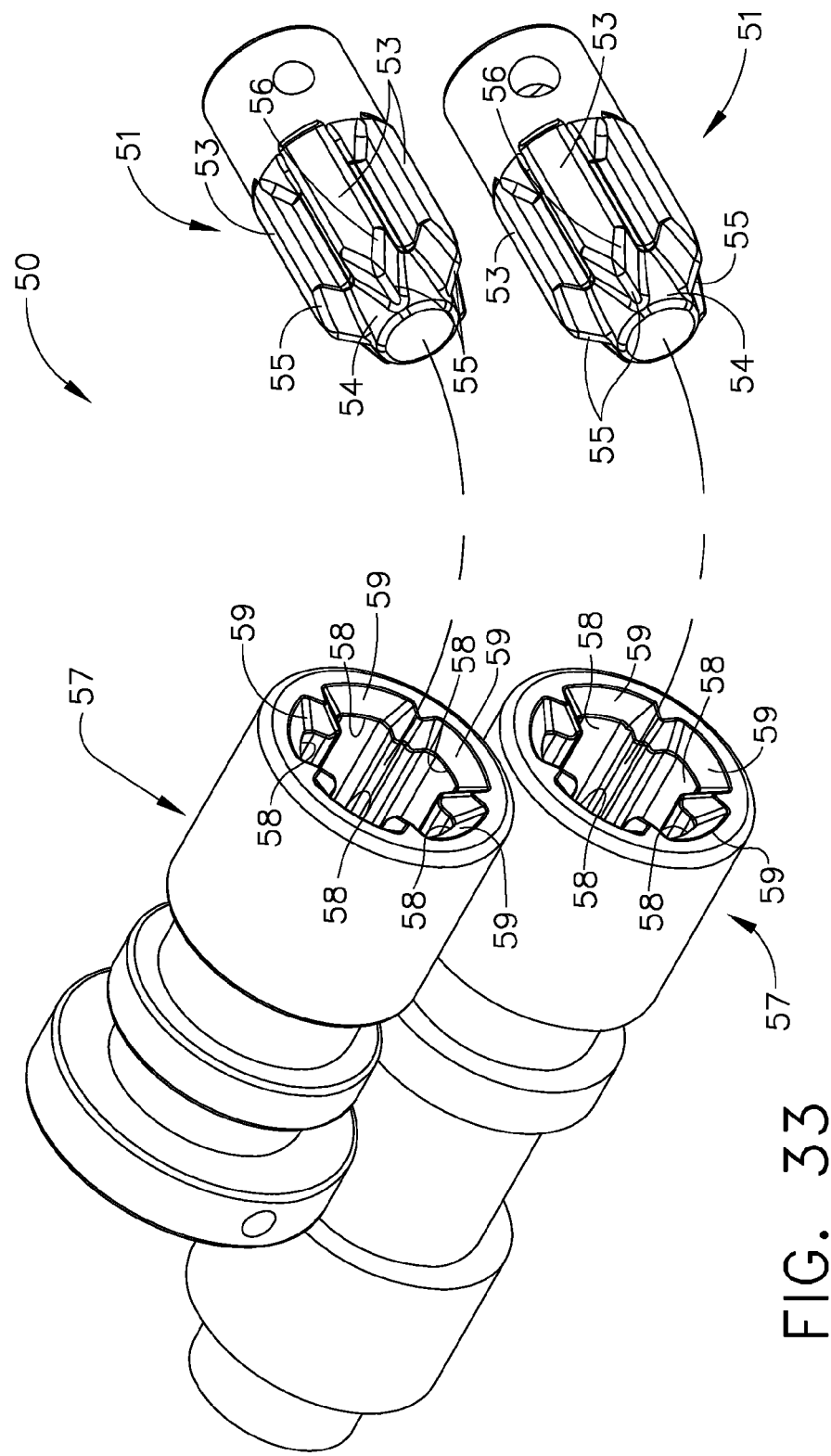
FIG. 33 is an exploded assembly view of a mechanical coupling system for operably coupling four rotary drive shafts together.

Referring now to FIG. 33, one form of mechanical coupling system 50 may be employed to facilitate the simultaneous removable and operable coupling of the two drive systems in the surgical instrument to the corresponding "driven" shafts in the end effectors. The coupling system 50 may comprise male couplers that may be attached to the drive shafts in the surgical instrument and corresponding female socket couplers that are attached to the driven shafts in the surgical end effector. For example, FIG. 9 illustrates male couplers 51 attached to the first and second drive shafts 22, 42 by set screws 52. Referring again to FIG. 33, each of the male couplers 51 are configured to be drivingly received within corresponding female socket couplers 57 that may also be attached to the driven shafts within the end effector. In one form, each male coupler 51 includes at least three drive ribs 53 that are equally spaced around a center portion 54 of the male coupler 51. In the illustrated embodiment, for example, five drive ribs 53 are equally spaced around the center portion 54. Each drive rib 53 has a pointed distal end 55. Each drive rib 53 may be formed with somewhat rounded edges 56 to facilitate easy insertion into corresponding socket grooves 58 within the female socket coupler 57. Each socket groove 58 has a tapered proximal entrance portion 59 to facilitate insertion of a corresponding drive rib 53 therein. The pointed distal end 55 of each drive rib 53 in conjunction with the tapered entrance 59 of each socket groove 58 will accommodate some misalignment between the male coupler 51 and its corresponding female socket coupler 57 during the coupling process. In addition, the rounded edges 57 on the pointed distal end 55 also assist in the slidable insertion of the male coupler 51 into the corresponding female socket coupler 58.

In one form, at least one of the male couplers 51 is movably attached to its corresponding first or second drive shaft of the surgical instrument or its corresponding first and second driven shaft of the surgical end effector. More specifically, the male coupler 51 may be attached for radial, or angular, travel on the shaft for a "first predetermined amount of radial travel" on the shaft. This may be accomplished for example, by key and keyway arrangements that are sized relative to each other to facilitate an amount of radial, or angular, travel of the male coupler 51 on the shaft. Stated another way, for example, the shaft may have a key formed thereon or otherwise mounted thereto that is smaller than a corresponding keyway formed in the male coupler 51 such that the key may move within the keyway and establish a first predetermined amount of radial travel. This first predetermined amount of radial travel is preferably sufficient enough to back drive or forward drive the coupler. For a male coupler 51 that has five ribs 53, for example, the first predetermined range of radial travel may be, for example, 5-37 degrees. Some embodiments may exist where the first predetermined range of radial travel may be less than 5° and preferably not more than 4°, for example. Such range of radial, or angular, travel may be sufficient if, for example, the corresponding female socket coupler 57 was rigidly affixed to its corresponding drive shaft and otherwise was incapable of any radial travel. However, if both the male and female couplers have the ability to radially, or angularly, adjust, such range of radial, or angular, travel may be reduced by 50% to provide each coupler (male coupler and corresponding female socket coupler) with a range of travel of about 3-16 degrees. The amount of radial, or angular, travel that a female socket coupler 57 may move on its corresponding shaft may be referred to herein as a "second predetermined amount of radial travel". The female socket couplers 57 may also be attached to their respective drive shafts with a key and keyway arrangement as described above that provides the desired second predetermined amount of radial travel. Some embodiments may exist where the second range of predetermined radial travel may be less than 5° and preferably not more than 4°, for example.

Various combinations and mounting arrangements of the male couplers and the female socket couplers are contemplated. For example, one or both of the male couplers may be movably mounted to their respective drive shafts of the surgical instrument (or driven shafts of the surgical end effector) in the various manners described herein. Likewise one or both of the female socket couplers may be movably mounted to their respective driven shafts on the end effector (or drive shafts of the surgical instrument) in the various manners described herein. For example, a male coupler on one of the first and second drive shafts may be movably mounted thereon. The other male coupler that is attached to the other drive shaft may be non-movably mounted thereto. The female socket coupler on the driven shaft that corresponds to the movably mounted male coupler may be non-movably attached to its driven shaft and the female socket coupler mounted on the other driven shaft that corresponds to the non-movably mounted coupler may be movably mounted to its driven shaft. Thus, one of a male coupler and a female coupler socket of a "coupler pair" is movable. The term "coupler pair" refers to the male coupler and corresponding female socket coupler that is configured to be coupled together to operably couple a drive shaft of the surgical instrument to its corresponding driven shaft of the end effector. In other arrangements both the male coupler and female coupler socket of a coupler pair may both be movably coupled to their respective shafts.

Such coupler arrangements serve to provide a small amount of angular slack, for example, between the coupler components so that the components may rotate slightly for sufficient alignment which will permit simultaneous alignment of the coupler components attached to the two separate rotary drive trains. In addition, there may be a sufficient amount of backlash or slack provided in the drive trains to accommodate the coupling process. Such backlash or slack may be provided by forming keys/keyways into the gears, couplers and or mating shafts to facilitate such slight rotation of components. In addition, a switch arrangement may be employed in connection with the various shiftable transmission assemblies which may activate the motor to cause a slight rotation of the drive shafts for coupling purposes.

This and other control techniques may be employed to ensure that the drive shafts in the surgical instruments are positioned in desired positions that facilitate their coupling with the corresponding drive shafts in the end effectors. The unique and novel mechanical coupling system 50 serves to provide some additional flexibility during the coupling process to enable the drive shafts to be coupled together in the event that there is some misalignment between the respective shafts. It will be understood that although the various embodiments described herein illustrate the male couplers 51 attached to the drive shafts within the surgical instrument and the female socket couplers 58 attached to the end effector drive shafts, the male couplers 51 could be attached to the end effector drive shafts and the female socket couplers 58 could be attached to the instrument drive shafts.

FIGS. 34-37 depict a surgical end effector 1000 that comprises a surgical cutting and fastening instrument of a type that is commonly referred to as an "open linear" stapler. Various forms of such open linear stapling devices are disclosed in, for example, U.S. Pat. No. 5,415,334, entitled SURGICAL STAPLER AND STAPLE CARTRIDGE and U.S. Pat. No. 8,561,870, entitled SURGICAL STAPLING INSTRUMENT, the entire disclosures of each being hereby incorporated by reference herein. The end effector 1000 comprises an end effector housing 1010 that may be fabricated from housing segments 1012, 1014 that are removably coupled together by screws, lugs, snap features, etc. Protruding from the end effector housing 1010 are a lower jaw 1020 and an upper jaw 1040 which may collectively form the end effector tool head 1004. The lower jaw 1020 comprises a lower jaw frame 1022 that is configured to operably support a surgical staple cartridge 1060 therein. Such surgical staple cartridges are well known in the art and will therefor not be described in great detail herein. Briefly, the surgical staple cartridge 1060 may comprise a cartridge body 1062 that has lines of staple pockets 1066 formed therein on each lateral side of an elongate slot 1068 that is centrally disposed within cartridge body 1062. The slot 1068 is configured to accommodate the longitudinal travel of a cutting member 1090 therethrough as will be discussed in further detail below. A surgical staple or staples (not shown) are supported in the staple pockets 1066 on staple drive members (not shown) that are configured to move upward within their respective pocket 1066 during a firing process. The staple cartridge 1060 may be configured to be removed from the lower jaw frame 1022 and replaced with another unspent cartridge making the end effector 1000 reusable. However, the end effector 1000 may also be disposable after a single use.

Figure 36:
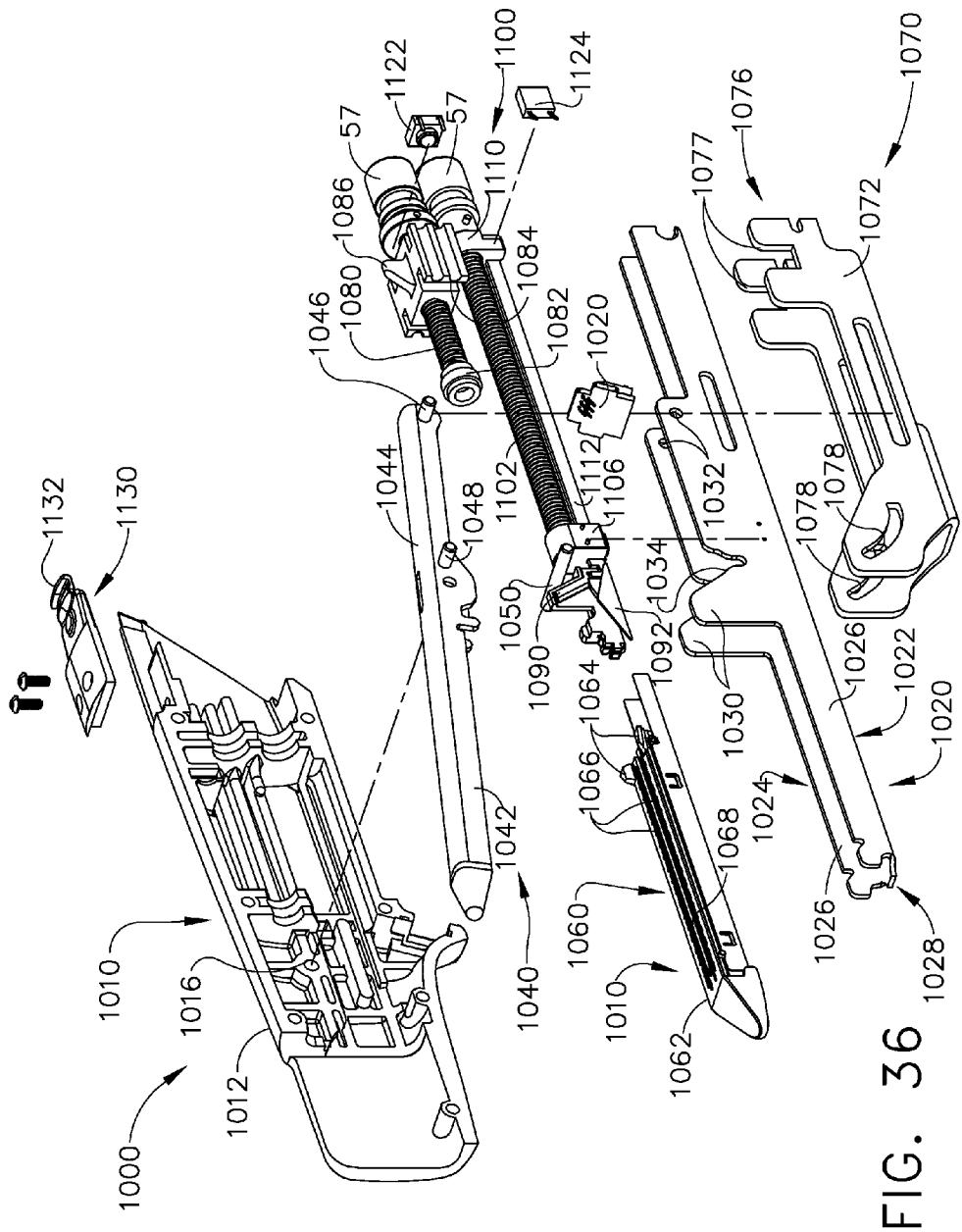
FIG. 36 is an exploded perspective assembly view of the surgical end effector of FIGS. 34 and 35.
Figure 37:
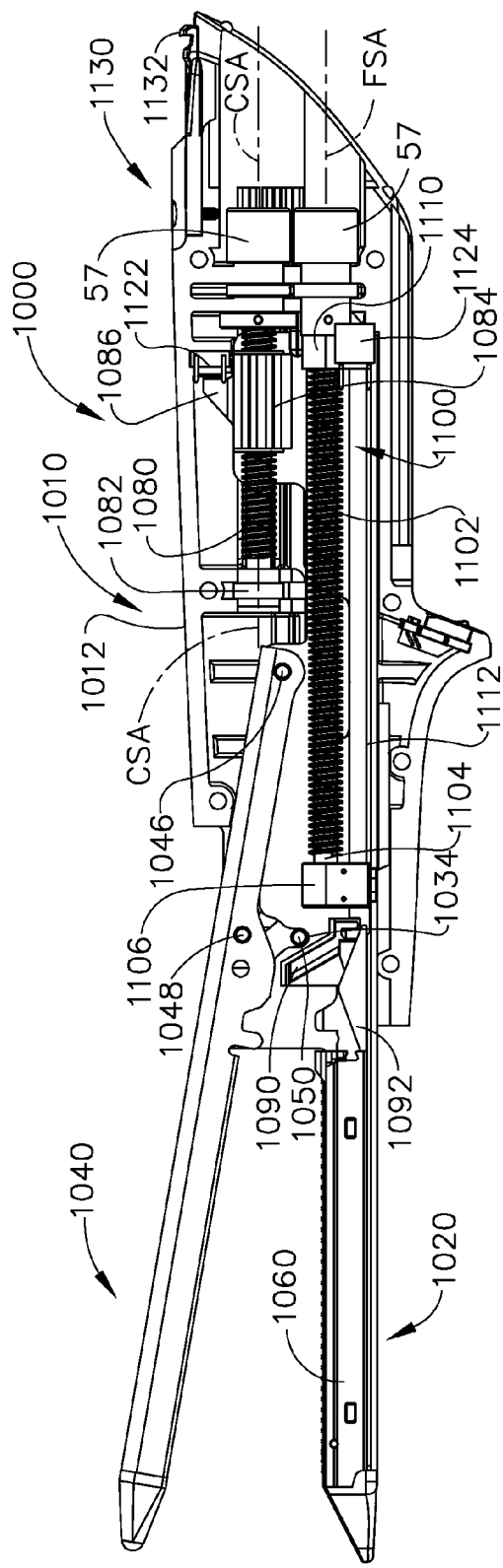
FIG. 37 is a side elevational view of the surgical end effector of FIGS. 33-36 with a portion of the housing omitted for clarity.
Figure 38:
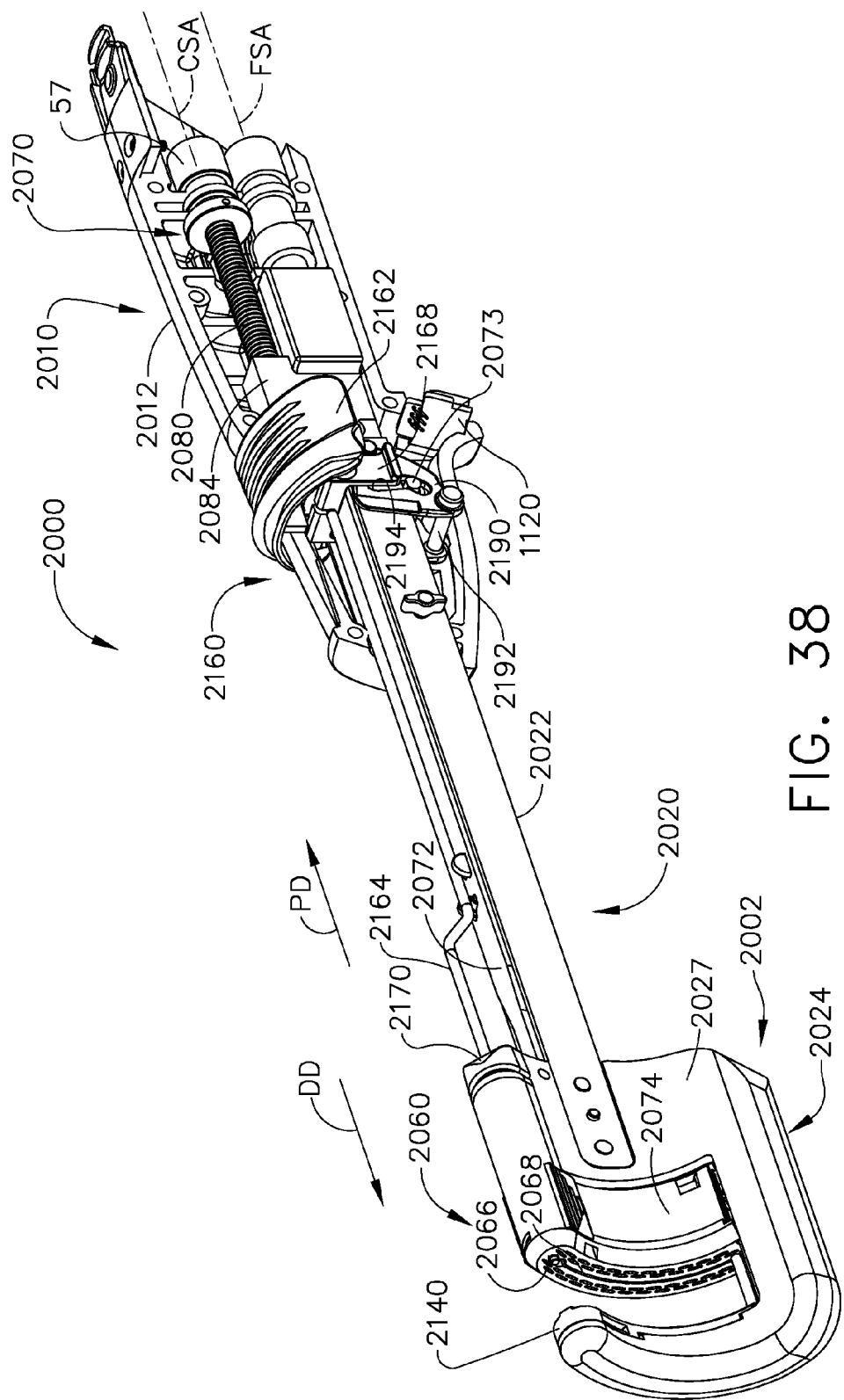
FIG. 38 is a left side perspective view of another end effector arrangement with a portion of the end effector housing omitted for clarity.

Referring to FIG. 36, the lower jaw frame 1022 may be formed from metal material and have a U-shaped distal portion 1024 that is configured to seatingly receive the surgical staple cartridge 1060 therein. The side walls 1026 of the U-shaped distal portion 1024 may have a distal end 1028 that is configured to releasably and retainingly engage a portion of the surgical cartridge 1060. The staple cartridge body 1062 may also have engagement features 1064 that are adapted to releasably engage upstanding wall portions 1030 of the lower jaw frame 1022. The end effector 1000 further comprises an upper jaw 1040 that includes an anvil portion 1042. The anvil portion 1042 may include an underside (not shown) that has a plurality of staple-forming pockets therein. The upper jaw 1040 further includes a proximal body portion 1044 that has a distal trunnion pin 1046 extending therethrough. The ends of the distal trunnion pin 1046 that protrude laterally from the proximal end of the proximal body portion 1044 are rotatably received within trunnion holes 1032 in the lower jaw 1020. The trunnion pin 1046 defines an attachment axis AA-AA about which the proximal end of the upper jaw 1040 pivots relative to the lower jaw 1020 such that the anvil portion 1042 is movable between an open position spaced from the staple cartridge 1060 mounted within the lower jaw 1020 and a closed position adjacent the staple cartridge 1060 and/or tissue that is located therebetween. The end effector 1000 may further include a transverse fulcrum pin 1050 that is received within cradles 1034 formed in the upstanding walls 1030 of the lower jaw 1020 and is mounted within holes 1016 in the housing segments 1012, 1014. The fulcrum pin 1050 may serve as a fulcrum axis or surface about which the anvil portion 1042 pivots.

The movement of the anvil portion 1042 between the open and closed positions is controlled by a first end effector drive system also referred to herein as the end effector closure system 1070. In one form, for example, the end effector closure system 1070 includes a closure shuttle 1072 that extends around the proximal body portion 1024 of the lower jaw 1020. The closure shuttle 1072 may also be referred to as a "first end effector actuator". The closure shuttle 1072 may include a U-shape portion that includes distal upstanding walls 1074 and proximal upstanding walls 1076. Each distal upstanding wall 1074 includes an arcuate cam slot 1078 that is adapted to receive a corresponding portion of a cam pin 1048 that is attached to the upper jaw 1040. Thus, axial or linear movement of the closure shuttle 1072 relative to the lower jaw 1020 will cause the upper jaw 1040 to pivot on the fulcrum pin 1050 and about the attachment axis AA-AA by virtue of the interaction of the cam pin 1048 within the cam slots 1078.

In various forms, the closure system 1070 includes a rotary end effector closure shaft 1080 that is threaded and includes a distal end portion 1082 that is rotatably supported within the end effector housing 1010. The end effector closure shaft 1080 defines a closure shaft axis CSA-CSA. See FIG. 37. A female socket coupler 57 is attached to the proximal end of the closure shaft 1080 to facilitate coupling of the closure shaft 1080 with a male coupler 51 attached to a first drive shaft in a surgical instrument. The closure system 1070 further includes a closure nut 1084 that is threadably received on the closure shaft 1080. The closure nut 1084 is configured to be seated within mounting slots 1077 in the upstanding walls 1076 of the closure shuttle 1072. Thus, rotation of the closure shaft 1080 in a first direction will cause the closure nut 1084 to drive the closure shuttle 1072 in the distal direction "DD". Movement of the closure shuttle 1072 in the distal direction "DD" results in the pivotal travel of the upper jaw 1040 from an open position to a closed position. Likewise, movement of the closure shuttle 1084 in the proximal direction "PD" will result in the movement of the upper jaw 1040 from a closed position back to an open position.

The end effector 1000 further includes a second end effector drive system also referred to herein as a firing system 1100 for driving a tissue cutting member 1090 and wedge sled assembly 1092 between starting and ending positions. When the wedge sled assembly 1092 is driven distally through the surgical staple cartridge 1060, the wedge sled assembly 1092 operably interacts with the drivers within the cartridge 1060 that have surgical staples supported thereon. As the wedge sled assembly 1092 is driven distally, the drivers are driven upward within their respective pockets to drive the staples supported thereon into forming engagement with the underside of the anvil portion 1042 of the upper jaw 1040. In one form, the firing system 1100 further includes a rotary threaded firing shaft 1102 that is rotatably supported in the end effector housing 1010. The firing shaft 1102 defines a firing shaft axis FSA-FSA that is parallel with or substantially parallel with the closure shaft axis CSA-CSA. See, e.g., FIG. 37. The firing shaft 1102 includes a distal end portion 1104 that is rotatably supported in a mounting unit 1106 that is mounted within the end effector housing 1010. A female socket coupler 57 is attached to the proximal end of the firing shaft 1102 to facilitate coupling of the firing shaft 1102 with a male closure coupler 51 that is attached to a second drive shaft in a surgical instrument. The firing system 1100 further includes a firing nut 1110 that is threadably received on the firing shaft 1102. Thus, rotation of the firing shaft 1102 results in the axial travel of the firing nut 1110 within the end effector housing 1010. In one form, the tissue cutting member 1090 and wedge sled assembly 1092 are coupled to the firing nut 1110 by a firing bar or firing bars 1112. The firing bar or bars may also be referred to herein as a "second end effector actuator" that is linearly or axially moved in response to actuation of the firing system. Thus, rotation of the firing shaft 1102 in a first direction will drive the firing nut 1110, firing bar(s) 1112, the tissue cutting member 1090 and the wedge sled assembly 1092 in the distal direction "DD" from, for example, a starting position (FIG. 35) to an ending position wherein the tissue cutting member 1090 and wedge sled assembly 1092 have been driven to the distal end of the surgical staple cartridge 1060. Rotation of the firing shaft 1102 in an opposite direction will drive the firing nut 1110, the firing bar(s) 1112, the tissue cutting member 1090 and the wedge sled assembly 1092 in a proximal direction "PD" from their respective ending positions back to their respective starting positions. In some embodiments, the wedge sled assembly may remain at the distal end of the surgical staple cartridge and not return with the tissue cutting member 1090 to the starting position. In still other embodiments, the tissue cutting member and the wedge sled assembly member may remain at the distal end of the staple cartridge member.

The end effector 1000 may also be equipped with various sensors that are coupled to an end effector contact board 1120 mounted within the end effector housing 1010. The contact board 1120 may be positioned with the end effector housing 1020 such that when the end effector 1000 is operably coupled to the surgical instrument, the end effector contact board 1120 is electrically coupled to a surgical instrument contact board 30 mounted in the surgical instrument housing 12. See, e.g., FIG. 1. Referring again to FIG. 34, a closure sensor 1122 may be mounted within the end effector housing 1010 and be electrically coupled to the end effector contact board 1120 such that when the end effector 1000 is operably coupled to the surgical instrument, the closure sensor 1122 is in communication with the surgical instrument's control system. The closure sensor 1122 may comprise a Hall effect sensor 7028 as shown hereinbelow, for example, in connection with FIGS. 61, 63 that is configured to detect the position of a switch lug 1086 on the closure nut 1084. In addition, a firing sensor 1124 may also be mounted within the end effector housing 1010 to detect the presence of a firing bar 1112. The firing sensor 1112 may comprise a Hall effect sensor 7028 as shown hereinbelow, for example, in connection with FIGS. 61, 63 and be electrically coupled to the end effector contact board 1120 for ultimate communication with the surgical instrument control system, such as the handle processor 7024 as will be discussed in further detail below in connection with FIGS. 61, 63, 64.

Use of the end effector 1000 will now be explained in connection with surgical instrument 10. It will be appreciated, however, that the end effector 1000 may be operably coupled to various other surgical instrument arrangements disclosed herein. Prior to use, the closure shaft 1080 and the firing shaft 1102 are "clocked" or positioned in their respective starting positions to facilitate attachment to the first and second drive shafts 22, 42, respectively. To couple the end effector 1000 to the surgical instrument 10, for example, the clinician moves the end effector 1000 into a position wherein the closure shaft axis CA-CA is in axial alignment with the first drive shaft axis FDA-FDA and wherein the firing shaft axis FSA-FSA is in axial alignment with the second drive shaft axis SDA-SDA. The female socket coupler 57 on the closure shaft 1080 is inserted into operable engagement with the male coupler 51 on the first drive shaft 22. Likewise, the female socket coupler 57 on the firing shaft 1102 is inserted into operable engagement with the male coupler 51 on the second drive shaft 42. Thus, when in that position, the closure shaft 1080 is operably coupled to the first drive shaft 22 and the firing shaft 1102 is operably coupled to the second drive shaft 42. The end effector contact board 1120 is operably coupled to the surgical instrument contact board 30 so that the sensors 1122, 1124 (and any other sensors within the end effector 1000) are in operable communication with the surgical instrument's control system. To retain the end effector 1000 in coupled operable engagement with the surgical instrument 10, the end effector 1000 includes a retainer latch 1130 that is attached to the end effector housing 1010 and configured to releasably engage a portion of the instrument housing 12. The retainer latch 1130 may include a retention lug 1132 that may releasable engage a retainer cavity 15 formed in the housing 12. See FIG. 1.

When coupled together, the closure sensor 1122 detects the position of the closure nut 1084 and the firing sensor 1124 detects the position of the firing bar 1112. That information is communicated to the surgical instrument control system. In addition, the clinician may confirm that the shiftable transmission assembly (or the transmission carriage 62 thereof) is in its first drive position. This may be confirmed by the actuation of the indicator light 77 on the housing 12 as discussed above. If the shiftable transmission assembly 60 is not in its first drive position, the clinician may actuate the firing trigger 92 to move the transmission carriage 62 into the first drive position, such that actuation of the rocker trigger 110 to actuate the motor 80 will result in actuation of the first drive system 20. Assuming that the closure system 1070 and firing system 1100 are each in their respective starting positions and the end effector 1000 has an unspent staple cartridge 1060 properly installed therein, the clinician can then position the jaws 1020, 1040 relative to the target tissue to be cut and stapled. The clinician may close the upper jaw 1040 by actuating the rocker trigger 110 to actuate the motor 80 and rotate the first drive shaft 22. Once the target tissue has been clamped between the upper jaw 1040 and the surgical staple cartridge 1060 in the lower jaw 1020, the clinician may then actuate the firing trigger 92 to move the transmission carriage 62 to its second drive position such that actuation of the motor 80 will result in the rotation of the second drive shaft 42. Once the transmission carriage 62 is moved to the second drive position, the clinician may once again actuate the rocker trigger 110 to actuate the second drive system 40 and the firing system 1100 in the end effector 1000 to drive the tissue cutting member 1090 and wedge sled assembly 1092 distally through the surgical staple cartridge 1060. As the tissue cutting member 1090 and wedge sled assembly 1092 are driven distally, the target tissue clamped between the jaws 1020, 1040 is cut and stapled. Once the tissue cutting member 1090 and wedge sled assembly 1092 have been driven to their distal-most positions in the surgical staple cartridge 1060, the clinician can actuate the rocker trigger 110 to reverse the motor rotation and return the firing system 1100 to its starting position.

Figure 119:
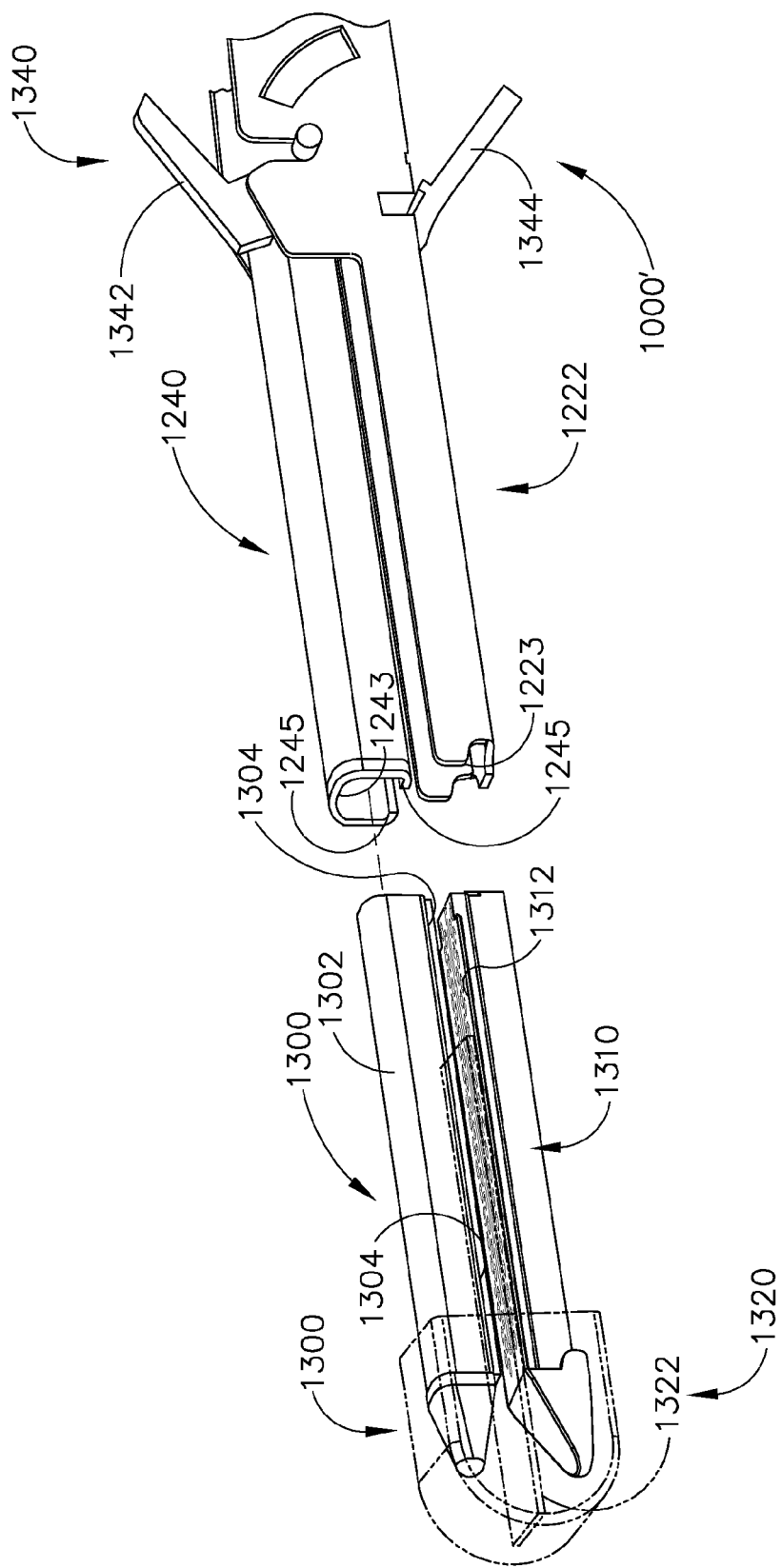
Figure 120:
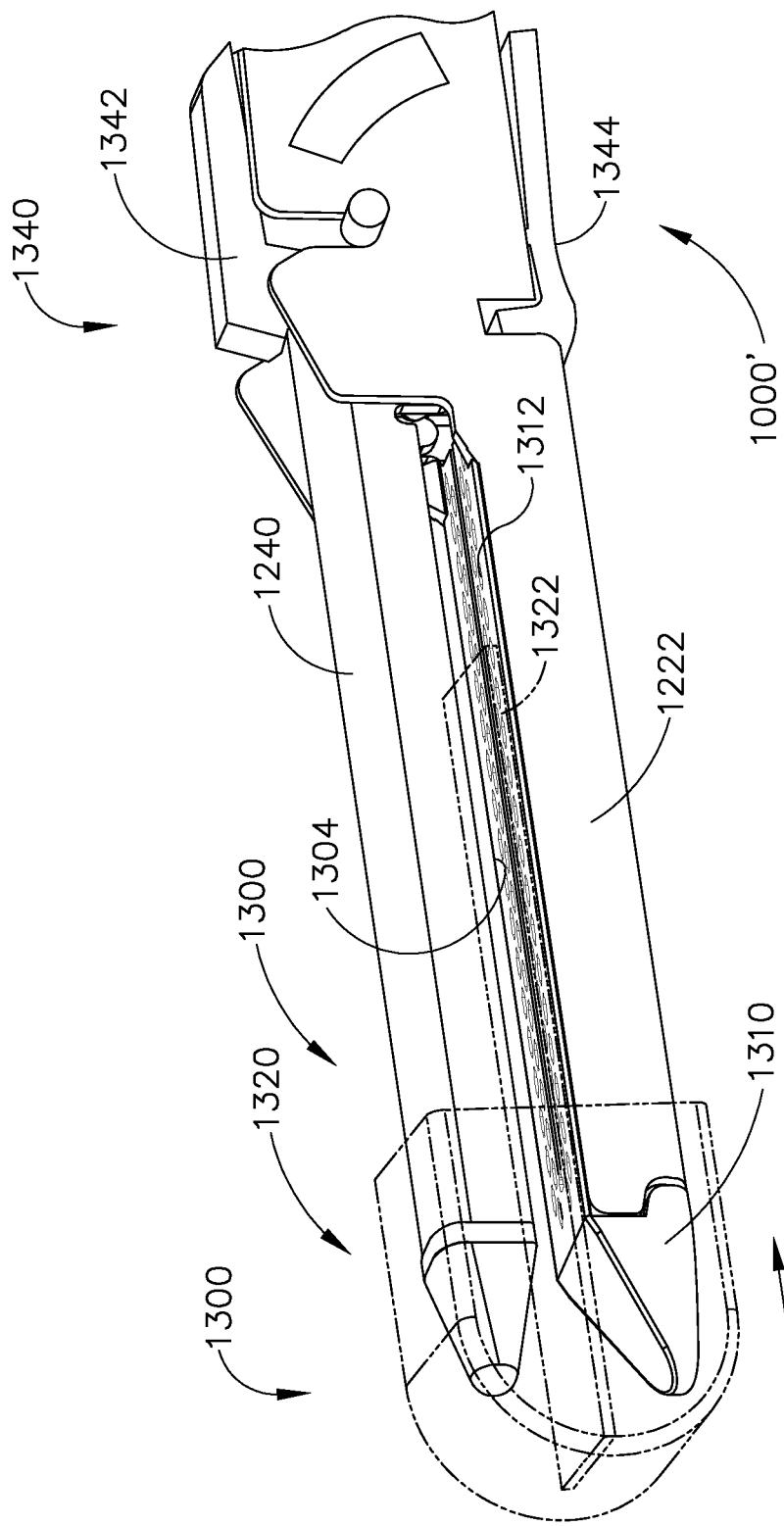
Figure 121:
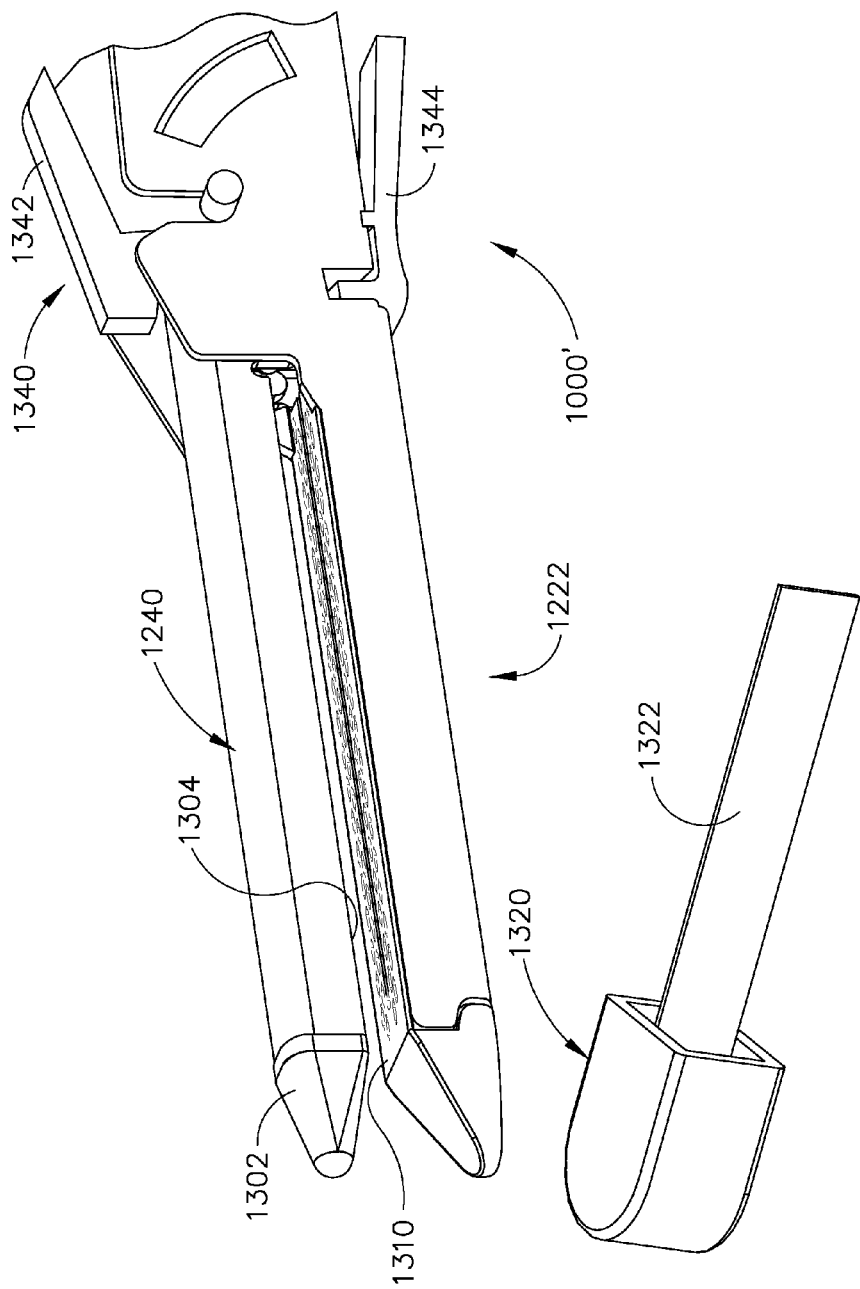

When employing end effector 1000 and other end effector and surgical instruments disclosed herein containing similar jaw arrangements it can be challenging to adequately clean the anvil pockets in the underside of the anvil. In addition, the anvil pockets can gall, scive or simply wear over time making them ill-suited for reuse. Furthermore, depending upon the application, loading and removing of the surgical staple cartridge may be difficult. FIGS. 119-121 illustrate a single-use "staple pack" 1300 that may address some, if not all, of these challenges.

FIG. 119 depicts a portion of an end effector 1000' that may be similar in construction and operation to, for example, end effector 1000 as well as other end effectors disclosed herein except for the specific differences discussed below. As can be seen in FIG. 119, the upper jaw 1240 includes an open distal end 1243. The upper jaw 1240 may be formed form metal material and have a U-shaped configuration when viewed from the distal end and include two-inwardly-extending, opposed retention lips 1245. The end effector 1000' further includes a lower jaw frame 1222 that is similar to, for example, lower jaw frame 1222 described herein. As can be seen in that Figure, the lower jaw frame 1222 also has an open distal end 1223.

Still referring to FIG. 119, one form of "single-use" staple pack 1300 includes an anvil 1302 that has a staple-forming surface 1304 that includes a plurality of staple-forming pockets (not shown) that are formed therein. The staple pack 1300 further includes a staple cartridge 1310 that has a cartridge deck 1312 that is configured for spaced confronting relationship to the staple-forming undersurface 1304 of the anvil 1302. The staple cartridge 1310 may be similar to other staple cartridges disclosed in further detail herein and operably support a plurality of surgical staples therein. The staple pack 1300 further includes a disposable keeper member 1320 that is sized and shaped to frictionally engage the anvil 1302 and staple cartridge 1310 in such a manner as to maintain alignment between the staple pockets in the staple-forming undersurface 1304 and the staples (not shown) within the staple cartridge 1310 prior to use. The keeper 1320 may also include a spacer strip 1322 that extends between the anvil 1302 and the staple cartridge 1310. The keeper may, for example, be molded from plastic or other suitable polymer material and the spacer strip 1322 may be fabricated from metal material. The spacer strip 1322 may be frictionally retained in a slot or other retention feature formed in the keeper 1320.

Referring now to FIG. 120, the staple pack 1300 is installed by aligning the anvil 1302 with the open distal end 1243 in the upper jaw 1240 and the staple cartridge 1310 is aligned with the open distal end 1245 in the lower jaw frame 1222. Thereafter, the staple pack 1300 is moved in the proximal direction "PD" to the position illustrated in FIG. 120. The retention lips 1245 serve to support the anvil 1302 within the upper jaw 1240. The end effector 1000' may also include a manually actuatable latch feature 1340 that may be moved from an unlatched position (FIG. 119) to a latched position (FIG. 121). When in the latched position, for example, the latch feature 1340 retains the anvil 1302 within the upper jaw 1240 and the staple cartridge 1310 within the lower jaw frame 1222. For example, the latch feature 1340 may include a movable upper latch arm 1342 that is configured to releasably engage a portion (e.g., lip, detent, ledge or other retention feature(s)) formed on the proximal end of the anvil 1302. Similarly the latch feature 1340 may include a movable lower latch arm 1344 that is configured to releasably engage a portion (e.g., lip, detent, ledge or other retention feature(s)) formed on the staple cartridge 1310. The upper and lower latch arms 1342, 1344 may be pivotally or otherwise movably supported on the end effector 1000' for selective movement between the latched and unlatched positions. In various forms the upper and lower latch arms 1342, 1344 may be normally biased into the latched position by a spring or springs (not shown). In such arrangements, the clinician may insert the staple pack 1300 into the upper jaw 1240 and lower jaw frame 1222. As the proximal end of the anvil 1302 contacts the upper latch arm 1342, the upper latch arm 1342 is pivoted or moved to permit the anvil 1302 to be seated into position. Once the anvil is seated in position, the upper latch arm 1342 is biased into latching engagement with the anvil 1302 (if a spring or biasing member is employed). In alternative arrangements, the upper latch arm 1342 may be manually moved into the latched position. Likewise, as the proximal end of the staple cartridge 1310 contacts the lower latch arm 1344, the lower latch arm 1344 is pivoted or moved to permit the staple cartridge 1310 to be seated into position. Once the staple cartridge 1310 is seated in position, the lower latch arm 1344 is biased into latching engagement with the staple cartridge 1310 to retain it in position (if a spring or biasing arrangement is employed). In alternative embodiments, the lower latch arm 1344 may be manually moved to the latched position. Once the staple pack 1300 has been installed and the anvil 1302 and staple cartridge 1310 have been latched or otherwise attached to the end effector 1000', the clinician may remove the keeper assembly 1320. See, e.g., FIG. 121. After the staple pack 1300 has been used, the clinician may then replace the keeper 1320 onto the distal ends of the anvil 1302 and the staple cartridge 1310. This may be accomplished by aligning the open end of the keeper member 1320 and then pressing the keeper member 1320 back into frictional engagement with the anvil 1302 and staple cartridge 1310. Once the distal ends of the anvil 1302 and staple cartridge 1310 have been seated into the keeper member 1320, the clinician may move the upper and lower latch arms 1342, 1344 to their an unlatched positions to enable the staple pack 1300 to be pulled out of the upper jaw 1240 and lower jaw frame 1222. Thereafter, the staple pack 1300 may be discarded as a unit. In other situations, the clinician may separately remove the anvil 1302 and staple cartridge 1310 from the end effector 1000' without first installing the keeper member 1320.

FIGS. 38-41 depict a surgical end effector 2000 that comprises a surgical cutting and fastening instrument of a type that may commonly be referred to as a "curved cutter stapler". Various forms of such stapling devices are disclosed in, for example, U.S. Pat. No. 6,988,650, entitled RETAINING PIN LEVER ADVANCEMENT MECHANISM FOR A CURVED CUTTER STAPLER and U.S. Pat. No. 7,134,587, entitled KNIFE RETRACTION ARM FOR A CURVED CUTTER STAPLER the entire disclosures of each being hereby incorporated by reference herein. The end effector 2000 comprises an end effector housing 2010 that may be fabricated from housing segments 2012, 2014 that are removably coupled together by screws, lugs, snap features, etc. Protruding from the end effector housing 2010 is an elongated frame assembly 2020 that terminates in an end effector tool head 2002. In one form, the frame assembly 2020 comprises a pair of spaced frame struts or plates 2022 that are fixedly attached to the housing 2010 and protrude distally therefrom. A C-shaped supporting structure 2024 is attached to the distal end of the frame plates 2022. The term "C-shaped" is used throughout the specification to describe the concave nature of the supporting structure 2024 and a surgical cartridge module 2060. The C-shaped construction facilitates enhanced functionality and the use of the term C-shaped in the present specification should be construed to include a variety of concave shapes which would similarly enhance the functionality of surgical stapling and cutting instruments. The supporting structure 2024 is attached to the frame plates 2022 by a shoulder rivet 2023 and posts 2026 which extend from the supporting structure 2024 into receiving holes in the frame plates 2022. In various forms, the supporting structure 2024 may be formed via a single piece construction. More specifically, the supporting structure 2024 may be formed from extruded aluminum material. By forming the supporting structure 2024 in this manner, multiple parts are not required and the associated cost of manufacture and assembly is substantially reduced. In addition, it is believed the unitary structure of the supporting structure 2024 enhances the overall stability of the end effector 2000. Furthermore, the unitary extruded structure of the supporting structure 2024 provides for a reduction in weight, easier sterilization since cobalt irradiation will effectively penetrate the extruded aluminum and less trauma to tissue based upon the smooth outer surface achieved via extrusion.

The end effector 2000 further includes a first end effector drive system also referred to as end effector closure system 2070 and a second end effector drive system also referred to herein as a firing system 2100. In one form, for example, the end effector closure system 2070 includes a closure beam assembly 2072 that is sized to be slidably received between the frame struts 2022 for axial travel therebetween. The closure beam assembly 2072 may also be referred to as a first end effector actuator and has an open bottom configured to slidably receive a firing bar assembly 2112 of the firing system 2100 as will be discussed in further detail below. In one form, for example, the closure beam assembly 2072 is a molded plastic member shaped for movement and functionality as will be further discussed below. By manufacturing the closure beam assembly 2072 from plastic, manufacturing costs may be reduced and the weight of the end effector 2000 may also be reduced. In addition, the end effector 2000 may be easier to sterilize with cobalt irradiation as plastic is easier to penetrate than stainless steel. In accordance with an alternate arrangement, the closure beam assembly 2072 may be made from extruded aluminum with the final features machined into place. While an extruded aluminum closure beam assembly might not be as easy to manufacture as the plastic component, it would still have the same advantages (i.e., elimination of components, easier to assemble, lower weight, easier to sterilize).

The closure beam assembly 2072 includes a curved distal end 2074 that is sized to be received between the side walls 2027 of the supporting structure 2024. The curved distal end 2074 is sized and shaped to receive and retain a cartridge housing 2062 of the cartridge module 2060. In various forms, the proximal end of the closure beam assembly 2072 is coupled to a closure nut 2084 that is threadably received on a threaded closure shaft 2080. The closure shaft 2080 defines a closure shaft axis CSA-CSA and has a female socket coupler 57 is attached to its proximal end to facilitate coupling of the closure shaft 2080 with a male coupler 51 attached to a first drive shaft in a surgical instrument. Rotation of the closure shaft 2080 in a first direction will cause the closure nut 2084 to drive the closure beam assembly 2072 in the distal direction "DD". Rotation of the closure shaft 2080 in an opposite direction will likewise result in the proximal travel of the closure nut 2084 and the closure beam assembly 2072.

As indicated above, the distal end 2074 of the closure beam assembly 2072 is configured to operably support the cartridge housing 2062 of a cartridge module 2060 therein. The cartridge module 2060 includes a plurality of surgical staples (not shown) on a staple driver (not shown) that, when axially advanced, drives the surgical staples out of their respective pockets 2066 positioned on each side of a slot 1068 that is configured to accommodate the passage of a knife member 2115 therethrough. The cartridge module 2060 may, for example, be somewhat similar to the cartridge modules disclosed in, for example, U.S. Pat. Nos. 6,988,650 and 7,134,587, which have both been incorporated by reference in their respective entireties herein excepted for any noted differences. The end effector 2000 may be disposed of after a single use or the end effector 2000 may be reusable by replacing the spent cartridge module during an ongoing procedure or for a new procedure after being resterilized.

The end effector 2000 further includes a firing system 2100 which includes a firing bar assembly 2112 that is configured to be slidably received within the open bottom of the closure beam assembly 2072. See FIG. 39. In one form, the firing system 2100 further includes a firing shaft 2102 that has a threaded distal end 2104 and a proximal portion 2106 that has a square cross-sectional shape. The threaded distal end 2104 is threadably received within a threaded firing nut 2110 that is attached to the proximal end of the firing bar assembly 2112. The threaded firing nut 2110 is sized to be slidably received within an axial cavity 2085 within the closure nut assembly 2084. See FIG. 41. Such arrangement permits the firing nut 2110 to be axially advanced with the closure nut assembly 2084 when the end effector 2000 is moved to a closed position and then move axially relative to the closure nut 2084 and closure beam assembly 2072 when the firing system 2100 is actuated. The firing shaft 2102 defines a firing shaft axis FSA-FSA that is parallel with or substantially parallel with the closure shaft axis CSA-CSA. See, e.g., FIG. 41. As can also be seen in FIGS. 39 and 41, the proximal portion 2106 of the firing shaft 2102 is slidably received within an elongated passage 2105 within a female socket coupler 57' that is otherwise identical to the female socket couplers described herein. The elongated passage 2105 has a square cross-sectional shape that is sized to slidably receive the proximal portion 2106 of the firing shaft 2102 therein. Such arrangement permits the firing shaft 2102 to move axially relative to the female socket coupler 57' while being rotatable with the female socket coupler 57'. Thus, when the closure beam assembly 2072 is advanced in the distal direction "DD" upon actuation of the first drive system in the surgical instrument, the firing nut 2110 will be carried in the distal direction "DD" within the closure nut assembly 2084. The proximal portion 2106 of the firing shaft 2102 will move axially within the passage 2105 in the female socket coupler 57' while remaining engaged therewith. Thereafter, activation of the second drive system in one rotary direction in the surgical instrument which is operably coupled to the female socket coupler 57' will rotate the firing shaft 2102 which will cause the firing bar assembly 2112 to move in the distal direction "DD". As the firing bar assembly 2112 moves in the distal direction, the knife bar 2115 is advanced distally through the cartridge module 2060. Actuation of the second drive system in a second rotary direction will cause the firing bar assembly 2112 to move in the proximal direction "PD".

Figure 39:
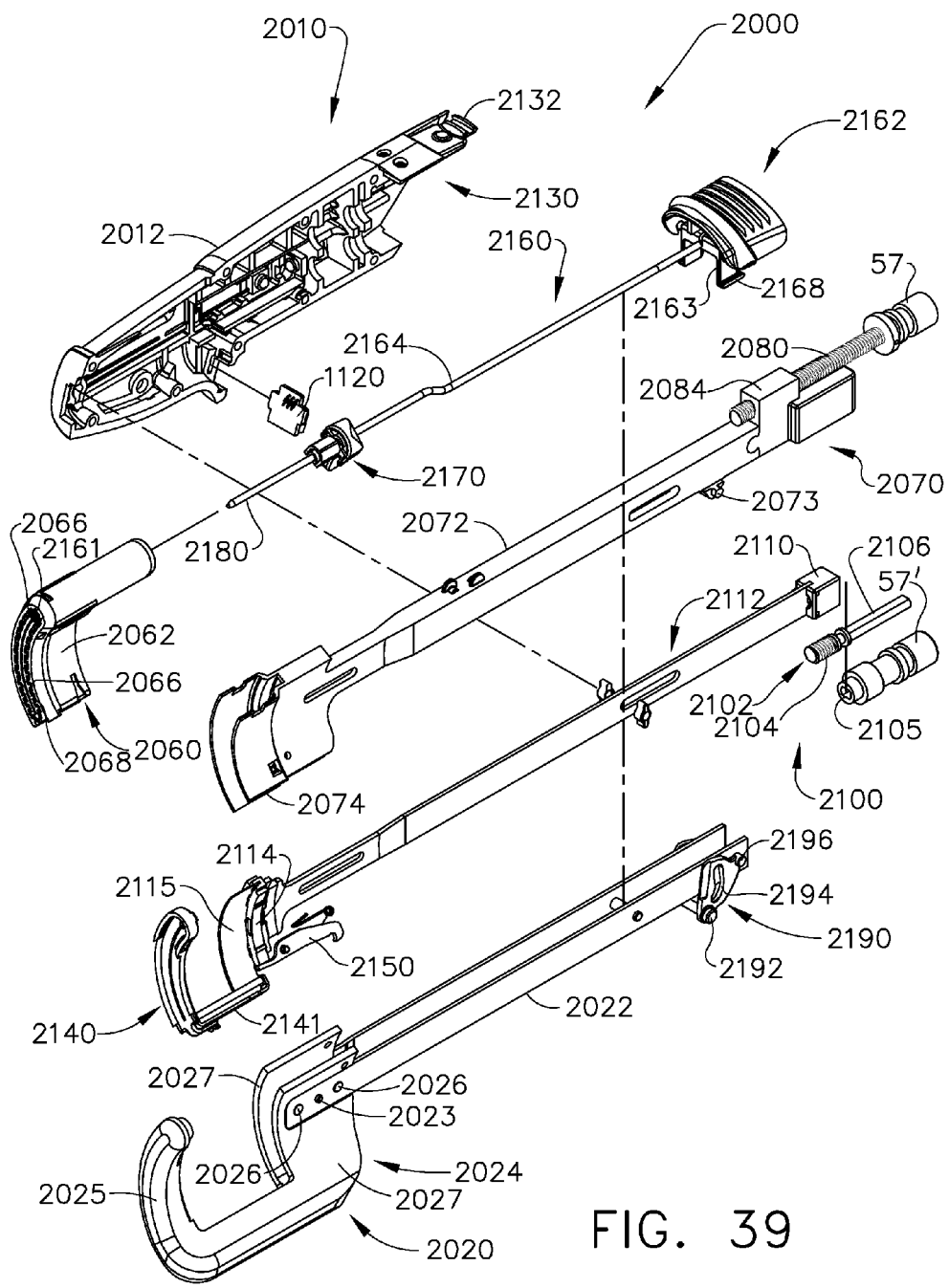
FIG. 39 is an exploded assembly view of the end effector of FIG. 38.
Figure 40:
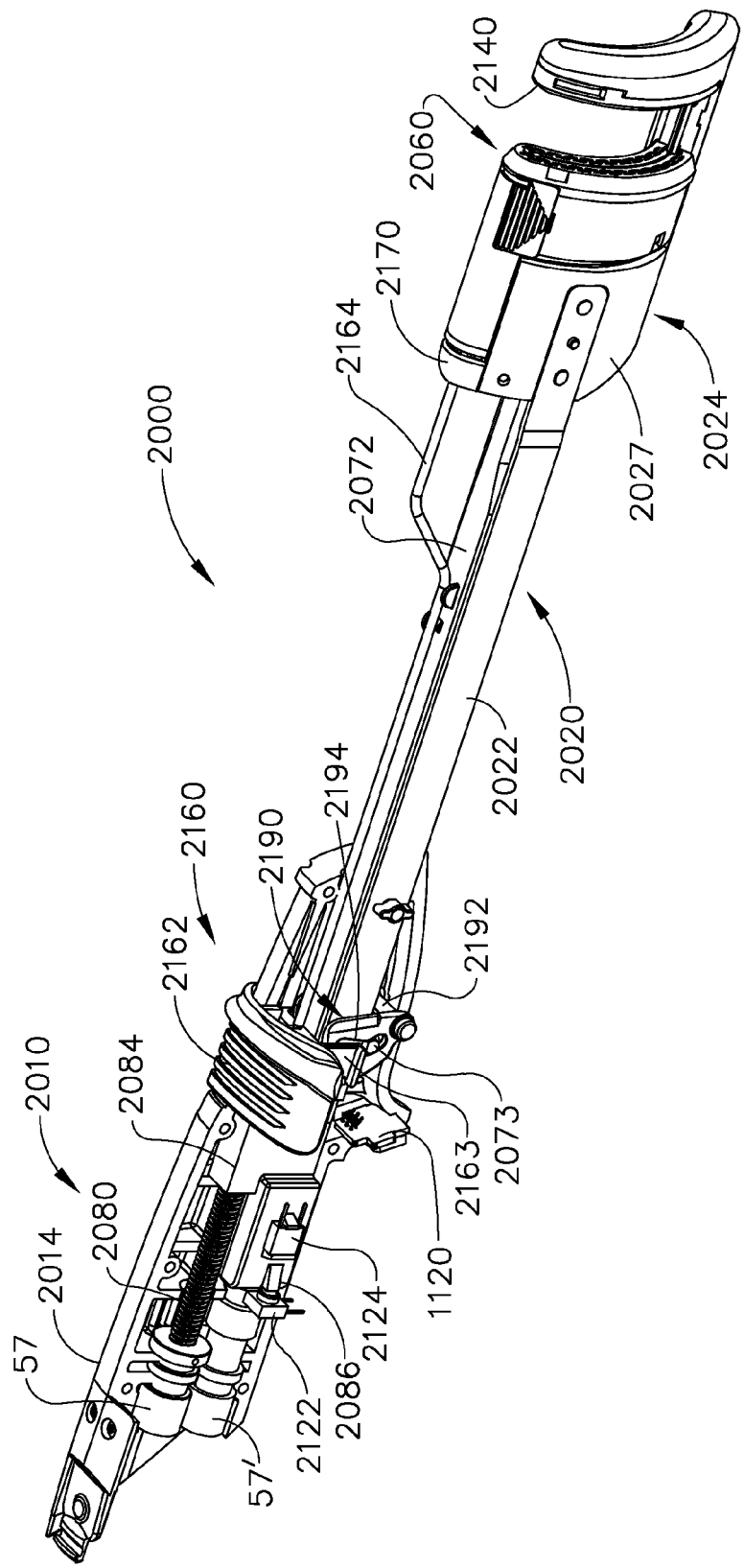
FIG. 40 is a right side perspective view of the end effector arrangement of FIGS. 37 and 38 with another portion of the end effector housing omitted for clarity.
Figure 41:
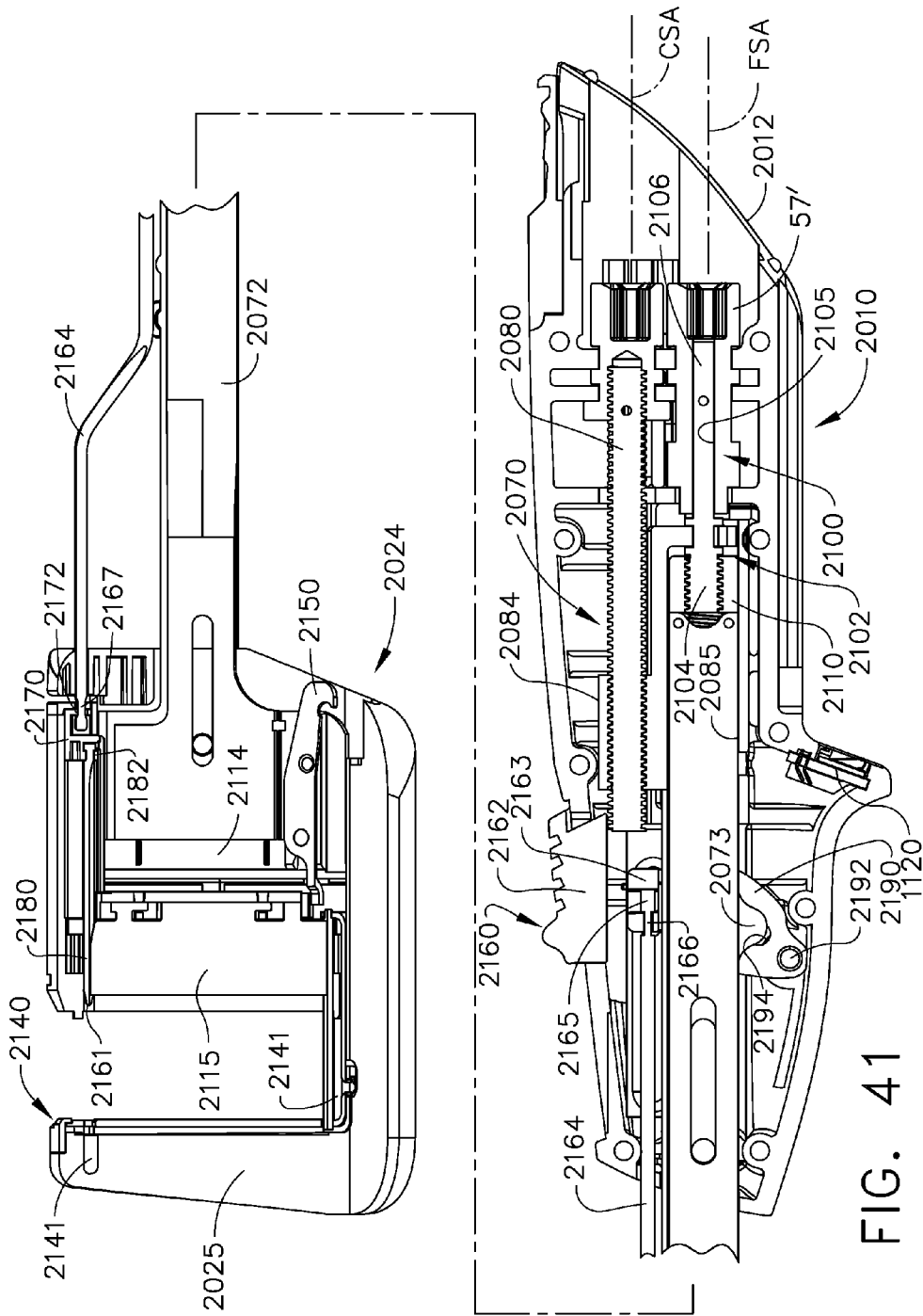
FIG. 41 is a cross-sectional view of the surgical end effector arrangement of FIGS. 38-40.

The distal end of the firing bar assembly 2112 includes a drive member 2114 and the knife member 2115 that protrudes distally therefrom. As can be seen in FIG. 39, the knife member 2115 is slidably received within an anvil arm portion 2142 of an anvil assembly 2140 that is configured to be seated within a curved anvil support portion 2025 of the support structure 2024. Further details regarding the anvil assembly 2140 may be found in U.S. Pat. Nos. 6,988,650 and 7,134,587. The end effector 2000 may also include a safety lockout mechanism 2150 (FIG. 39) for preventing the firing of a previously fired cartridge module 2060. Details regarding the interaction between the cartridge module 2060 and the safety lockout mechanism may be found in U.S. Pat. Nos. 6,988,650 and 7,134,587.

The end effector 2000 also includes a tissue retaining pin actuation mechanism 2160. The tissue retaining pin actuation mechanism 2160 includes a saddle shaped slide 2162 that is positioned on a top portion of the housing 2010. The slide 2162 is pivotally connected to a push rod driver 2163 that is slidably supported within the housing 2010. The push rod driver 2163 is restrained for longitudinal movement along the long axis of the end effector 2000. The push rod driver 2163 is connected to a push rod 2164 by a circumferential groove 2165 on the push rod 2164 that snaps into a slot 2166 of the push rod driver 2163. See FIG. 41. The distal end of the push rod 2164 contains a circumferential groove 2167 that interconnects with a groove 2172 in a proximal end of a coupler 2170 that is attached to the cartridge module 2160 (best seen in FIG. 41). The distal end of the coupler 2170 contains a groove 2174 for interconnecting with a circumferential slot 2182 on a retaining pin 2180. Manual movement of the slide 2162 results in movement of the push rod 2164. The distal movement or proximal retraction of the push rod 2164 results in corresponding movement of the retaining pin 2180. The retaining pin 2180 actuation mechanism 2160 also operably interacts with the closure beam assembly 2072 such that actuation of the closure system 2070 will result in automatic distal movement of the retaining pin 2180 if it has not already been manually moved to its most proximal position. When the retaining pin 2180 is advanced, it extends through the cartridge housing 2062 and into the anvil assembly 2140 to thereby capture tissue between the cartridge module 2060 and the anvil assembly 2140.

In one form, the retaining pin actuation mechanism 2160 includes a yoke 2190 rotationally or pivotally supported within the housing 2010 via a pivot pin 2192. The closure beam assembly 2072 further includes posts or lugs 2073 which extend laterally on both sides of the closure beam assembly 2072 inside the housing 2010. These posts 2073 are slidably received within corresponding arcuate slots 2194 in the yoke 2190. The yoke 2190 contains cam pins 2196 positioned to push camming surfaces 2168 on the push rod driver 2163. The yoke 2190 is not directly attached to the retaining pin 2180 so the surgeon, if they chose, can advance the retaining pin 2180 manually. The retaining pin 2180 will advance automatically if the surgeon chooses to leave the retaining pin 2180 alone when the closure beam assembly 2072 is advanced distally to a closed position. The surgeon must retract the retaining pin 2180 manually. By constructing the retaining pin actuation mechanism 2160 in this manner, manual closing and retracting of the retaining pin 2180 is permitted. If the surgeon does not manually close the retaining pin 21280, the present retaining pin actuation mechanism 2160 will do it automatically during instrument clamping. Further details regarding actuation and use of the retaining pin may be found in U.S. Pat. Nos. 6,988,650 and 7,134,587.

The end effector 2000 may also be equipped with various sensors that are coupled to an end effector contact board 2120 mounted within the end effector housing 2010. For example, the end effector 2000 may include a closure sensor 2122 that is mounted within the end effector housing 2010 and is electrically coupled to the end effector contact board 2120 such that when the end effector 2000 is operably coupled to the surgical instrument, the closure sensor 2122 is in communication with the surgical instrument's control system. The closure sensor 2122 may comprise a Hall effect sensor 7028 as shown hereinbelow in connection with FIGS. 61, 63 that is configured to detect the position of a switch lug 2086 on the closure nut 21084. See FIG. 40. In addition, a firing sensor 2124 may also be mounted within the end effector housing 2010 and be arranged to detect the location of the firing nut 2110 within the closure nut 2084. The firing sensor 2124 may comprise a Hall effect sensor 7028 as described hereinbelow in connection with FIGS. 61, 63 and be electrically coupled to the end effector contact board 2120 for ultimate communication with the surgical instrument control system as discussed herein. The contact board 2120 may be positioned with the end effector housing 2020 such that when the end effector 2000 is operably coupled to the surgical instrument, the end effector contact board 2120 is electrically coupled to a surgical instrument contact board 30 mounted in the surgical instrument housing 12 as was discussed above.

Use of the end effector 2000 will now be explained in connection with surgical instrument 10. It will be appreciated, however, that the end effector 2000 may be operably coupled to various other surgical instrument arrangements disclosed herein. Prior to use, the closure shaft 2080 and the firing shaft 2102 are "clocked" or positioned in their starting positions to facilitate attachment to the first and second drive shafts 22, 42, respectively. To couple the end effector 2000 to the surgical instrument 10, for example, the clinician moves the end effector 2000 into a position wherein the closure shaft axis CSA-CSA is in axial alignment with the first drive shaft axis FDA-FDA and wherein the firing shaft axis FSA-FSA is in axial alignment with the second drive shaft axis SDA-SDA. The female socket coupler 57 on the closure shaft 2080 is inserted into operable engagement with the male coupler 51 on the first drive shaft 22. Likewise, the female socket coupler 57' on the firing shaft 2102 is inserted into operable engagement with the male coupler 51 on the second drive shaft 42. Thus, when in that position, the closure shaft 2080 is operably coupled to the first drive shaft 22 and the firing shaft 2102 is operably coupled to the second drive shaft 42. The end effector contact board 1120 is operably coupled to the surgical instrument contact board 30 so that the sensors within the end effector 2000 are in operable communication with the surgical instrument's control system. To retain the end effector 2000 in coupled operable engagement with the surgical instrument 10, the end effector 2000 includes a retainer latch 2130 that is attached to the end effector housing 2010 and is configured to releasably engage a portion of the instrument housing 12. The retainer latch 2130 may include a retention lug 2132 that may releasable engage a retainer cavity 15 formed in the housing 12. See FIG. 1. When coupled together, the closure sensor 2122 detects the position of the closure nut 2084 and the firing sensor 2124 detects the position of the firing nut 2110. That information is communicated to the surgical instrument control system. In addition, the clinician may confirm that the shiftable transmission assembly (or the transmission carriage 62 thereof) is in its first drive position. This may be confirmed by the actuation of the indicator light 77 on the housing 12 as was discussed above. If the shiftable transmission assembly 60 is not in its first drive position, the clinician may actuate the firing trigger 92 to move the transmission carriage 62 into the first drive position, such that actuation of the rocker trigger 110 to actuate the motor 80 will result in actuation of the first drive system 20. Assuming that the closure system 2070 and firing system 2100 are each in their respective starting positions and the end effector 2000 has an unspent staple cartridge module 2060 properly installed therein, the clinician can then actuate the closure system 2070 to capture the target tissue between the cartridge module 2060 and the anvil assembly 2140.

The clinician may move the closure beam assembly 2072 distally by actuating the rocker trigger 110 to actuate the motor 80 and rotate the first drive shaft 22. This actuation moves the cartridge module 2060 toward the anvil assembly 2140 to clamp the target tissue therebetween. As the closure beam 2072 moves distally, the interaction of the posts 2073 and the yoke 2190 will cause actuation of the tissue retaining actuation mechanism 2160 to drive the retaining pin 2180 distally through the deck portion 2161 and through the anvil assembly 2140 into a pin pocket 2141 (See FIG. 41) therein. The retaining pin 2180 serves to trap the target tissue between the anvil assembly 2140 and the cartridge module 2060. Once the target tissue has been clamped between the anvil assembly 2140 and the cartridge module 2060, the clinician may then actuate the firing trigger 92 to move the transmission carriage 62 to its second drive position such that actuation of the motor 80 will result in the rotation of the second drive shaft 42. Once the transmission carriage 62 is moved to the second drive position, the clinician may once again actuate the rocker trigger 110 to actuate the second drive system 40 and the firing system 2100 in the end effector 2000 to drive the firing bar assembly 2112 distally which also drives the knife member 2115 distally through the cartridge module 2060 cutting the target tissue clamped between the anvil assembly 2140 and the cartridge module 2060. As the firing bar assembly 2112 moves distally, the drive member 2114 also drives the surgical staples supported in the cartridge module 2060 out of the cartridge module 2060 through the target tissue and into forming contact with the anvil assembly 2140. Once the cutting and stapling action is completed, the clinician can actuate the rocker trigger 110 to reverse the motor rotation and return the firing system 2100 to its starting position. The clinician may then return the transmission carriage 62 to its first drive position by means of the firing trigger 92 such that actuation of the rocker trigger 110 in the opposite direction will cause the motor 80 to rotate in a reverse direction to return the closure beam assembly 2073 to its starting position. As the closure beam assembly 2073 moves in the proximal direction, the yoke 2190 may interact with the tissue retaining pin actuation mechanism 2160 to withdraw the retaining pin 2180 to its starting position. In the alternative, the clinician may manually retract the retention pin 2180 to its starting position using the saddle shaped slide 2162. The clinician may retract the retention pin 2180 to its starting position prior to actuating the closure system 2070 to return the closure beam 2072 to its starting position. Further details regarding use of curved staple cutters may be found in U.S. Pat. Nos. 6,988,650 and 7,134,587.

FIGS. 42-45 depict a surgical end effector 3000 that comprises a surgical cutting and fastening instrument of a type that may commonly be referred to as a "circular surgical stapler". In certain types of surgical procedures, the use of surgical staples has become the preferred method of joining tissue and, as such, specially configured surgical staplers have been developed for these applications. For example, intra-luminal or circular staplers have been developed for use in surgical procedures involving the lower colon wherein sections of the lower colon are joined together after a diseased portion has been excised. Circular staplers useful for performing such procedures are disclosed, for example, in U.S. Pat. Nos. 5,104,025; 5,205,459; 5,285,945; 5,309,927; 8,353,439; and 8,360,297 which are each herein incorporated by reference in their respective entireties.

Figure 42:
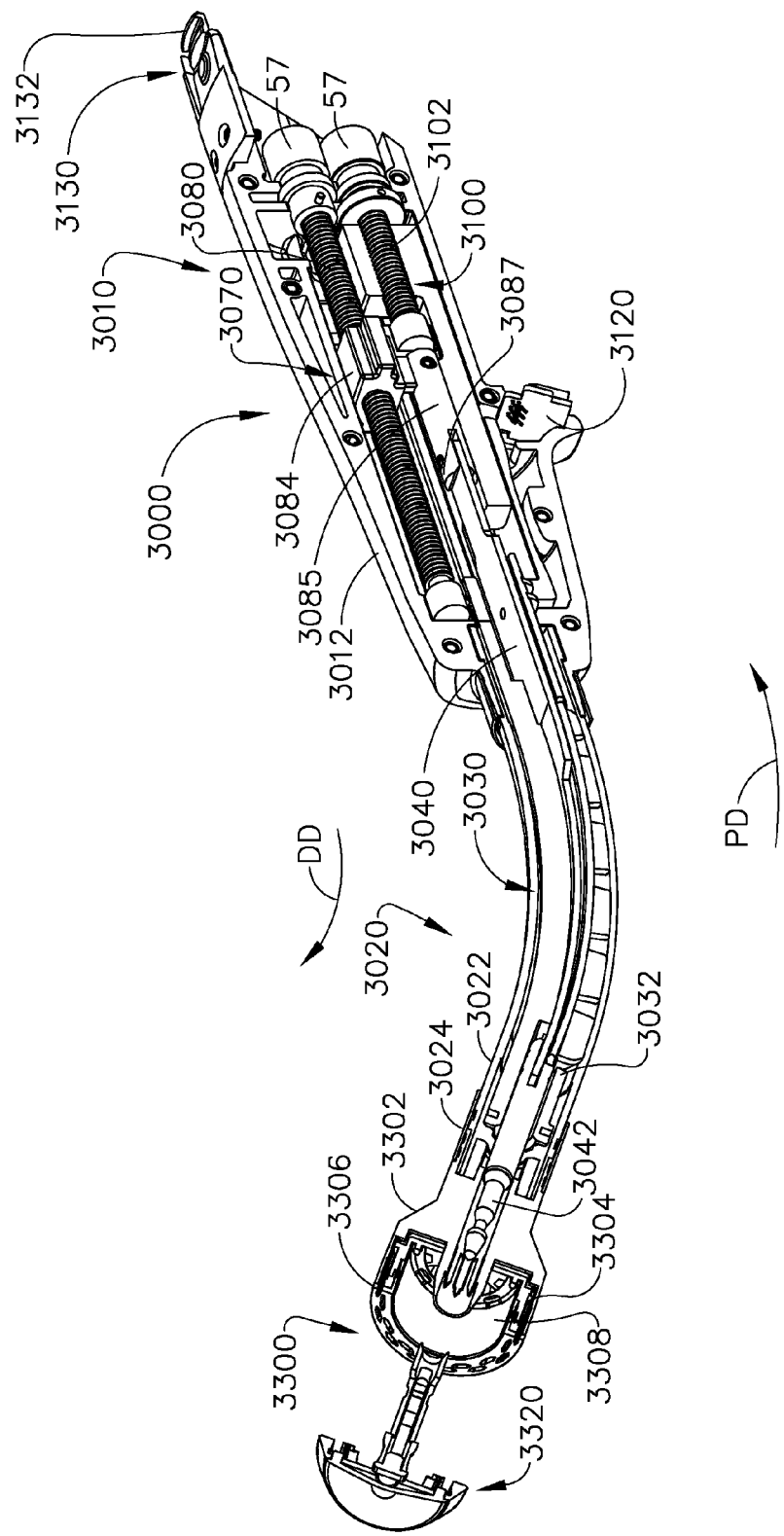
FIG. 42 is a cross-sectional perspective view of another surgical end effector.
Figure 43:
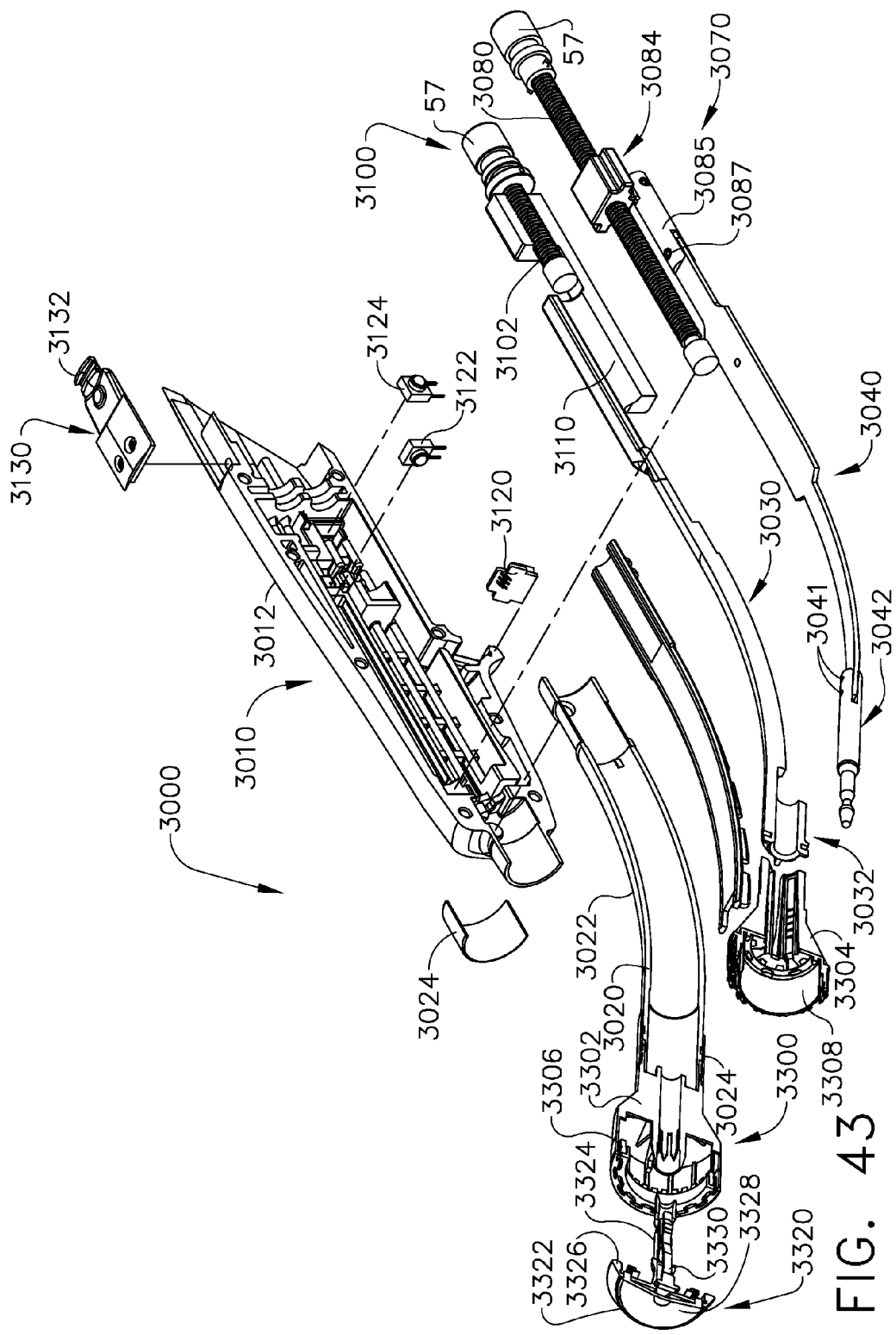
FIG. 43 is a partial exploded assembly view of the surgical end effector of FIG. 42.
Figure 44:
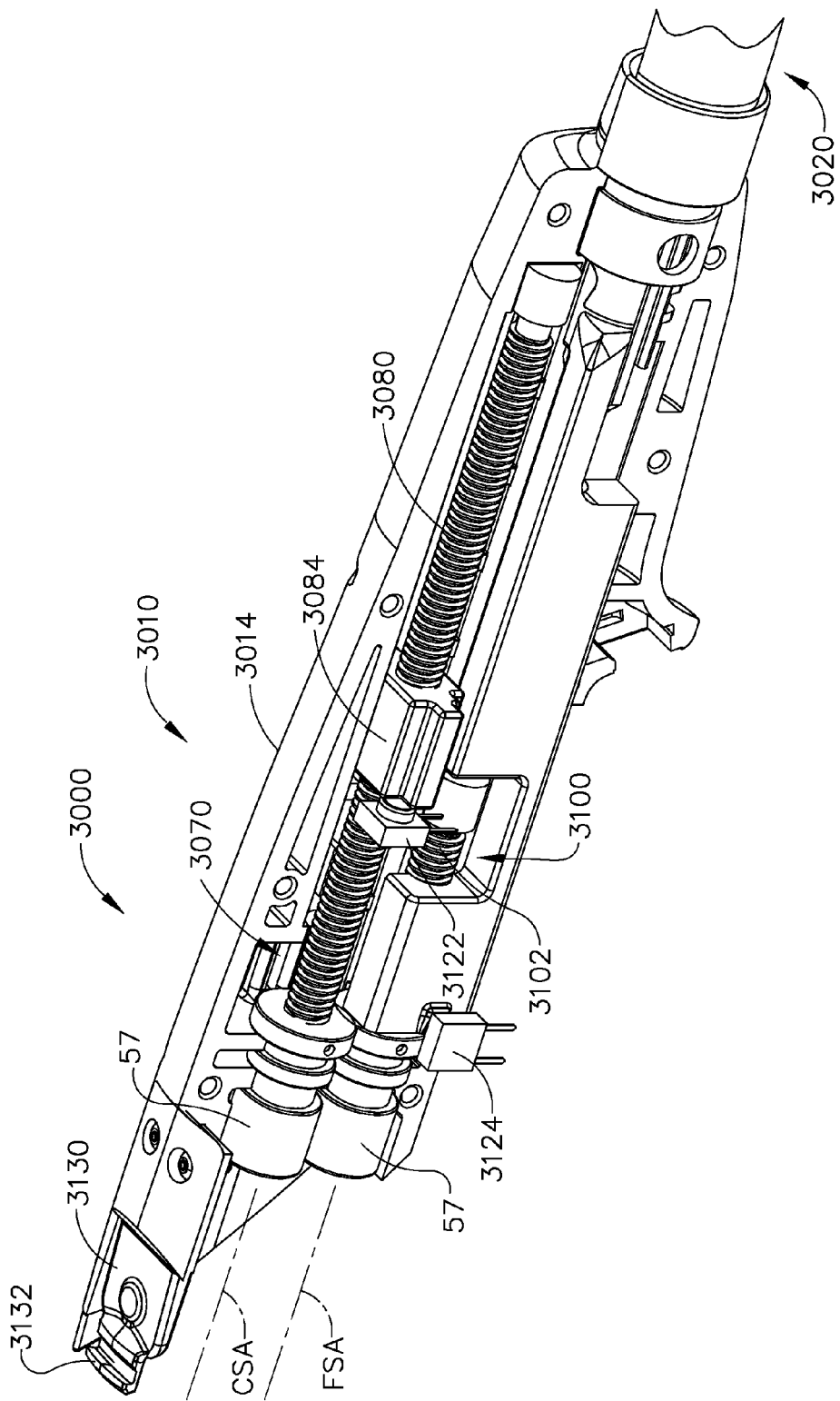
FIG. 44 is another partial perspective view of a portion of the surgical end effector of FIGS. 42 and 43.
Figure 45:
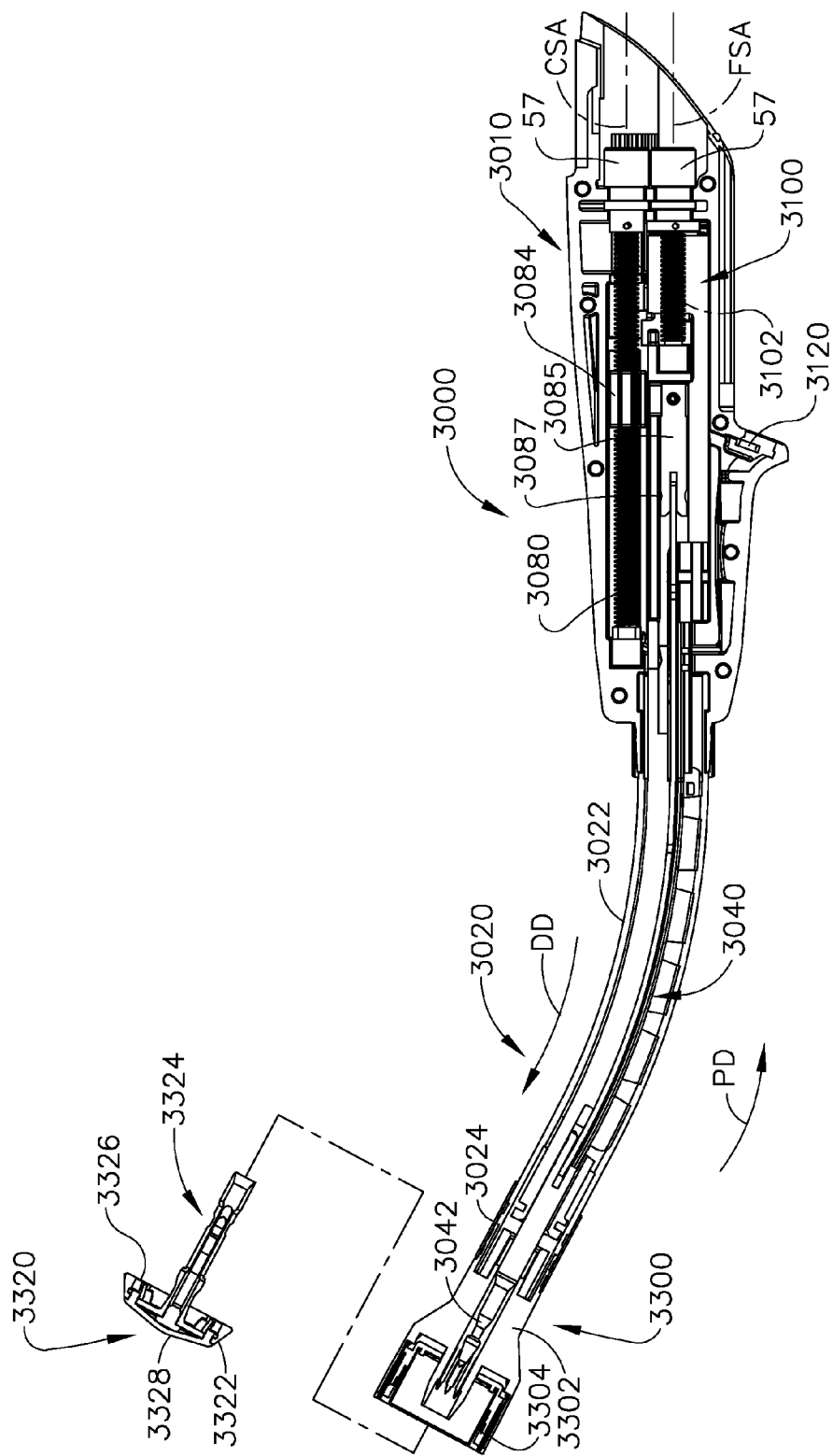
FIG. 45 is another cross-sectional view of the surgical end effector of FIGS. 42-44.

As shown in FIG. 42, the end effector 3000 comprises an end effector housing 3010 that may be fabricated from housing segments 3012, 3014 that are removably coupled together by screws, lugs, snap features, etc. Protruding from the end effector housing 3010 is an elongated shaft assembly 3020. The elongated shaft assembly 3020 is configured to operably support and interact with a circular tool head 3300 and an anvil 3320. As evidenced by the exemplary U.S. Patents referenced above, a variety of different circular staple cartridge and anvil arrangements are known in the art. As shown in FIG. 43, for example, the circular stapler head 3300 may include a casing member 3302 that supports a cartridge supporting assembly in the form of a circular staple driver assembly 3304 therein that is adapted to interface with a circular staple cartridge 3306 and drive staples supported therein into forming contact with the staple forming undersurface 3326 of the anvil 3320. A circular knife member 3308 is also centrally disposed within the staple driver assembly 3304. The proximal end of the casing member 3302 may be coupled to an outer tubular shroud 3022 of the arcuate shaft assembly 3020 by a distal ferrule member 3024. The anvil 3320 includes a circular body portion 3322 that has an anvil shaft 3324 for attaching a trocar thereto. The anvil body 3322 has a staple forming undersurface 3326 thereon and may also have a shroud 3328 attached to the distal end thereof. The anvil shaft 3324 may be further provided with a pair of trocar retaining clips or leaf-type springs 3330 that serve to releasably retain a trocar 3042 in retaining engagement with the anvil shaft 3324 as will be discussed in further detail below.

In one form, the shaft assembly 3020 includes a compression shaft 3030, a distal compression shaft portion 3032, and a tension band assembly 3040 that are operably supported within the outer tubular shroud 3022. A trocar tip 3042 is attached to a distal end of the tension band assembly 3040 by fasteners 3041. As is known, the trocar tip 3042 may be inserted into the anvil shaft 3324 of the anvil 3320 and retained in engagement by trocar retaining clips 3330.

The surgical end effector 3000 further includes a closure system 3070 and a firing system 3100. In at least one form, the closure system 3070 includes a closure nut assembly 3084 that is attached to the proximal end of the tension band 3040. As can be seen in FIGS. 42 and 43, the closure nut assembly 3084 includes a proximal coupler member 3085 that is attached to the proximal end of the tension band 3040 by a fastener 3087. The closure system 3070 further includes a threaded closure shaft 3080 that is in threaded engagement with the closure nut 3084. The closure shaft 3080 defines a closure shaft axis CSA-CSA and has a female socket coupler 57 attached to its proximal end to facilitate coupling of the closure shaft 3080 with a male coupler 51 that is attached to a first drive shaft in a surgical instrument. Rotation of the closure shaft 3080 in a first direction will cause the closure nut 3084 to drive the tension band assembly 3040 in the distal direction "DD". Rotation of the closure shaft 3080 in an opposite direction will likewise result in the proximal travel of the closure nut 3084 and the tension band assembly 3040.

As can be seen in FIG. 43, the distal compression shaft portion 3032 is coupled to the staple driver assembly 3304. Thus, axial movement of the compression shaft 3030 within the outer tubular shroud 3022 causes the staple driver assembly 3304 to move axially within the casing member 3302. The axial travel of the compression shaft 3030 is controlled by the firing system 3100. In one form, the firing system 3100 includes a threaded firing shaft 3102 that is in threaded engagement with a threaded firing nut 3110 that is attached to the proximal end of the compression shaft 3030. The firing shaft 3102 defines a firing shaft axis FSA-FSA that is parallel with or substantially parallel with the closure shaft axis CSA-CSA. See, e.g., FIGS. 44 and 45. The proximal end of the firing shaft 3102 has a female socket coupler 57 attached thereto to facilitate coupling of the firing shaft 3102 with a male coupler 51 that is attached to a second drive shaft in a surgical instrument. Activation of the second drive system of the surgical instrument in one rotary direction will rotate the firing shaft 3102 in a first direction to thereby drive the compression shaft 3030 in the distal direction "DD". As the compression shaft 3030 moves in the distal direction "DD", the circular staple driver assembly 3304 is driven distally to drive the surgical staples in the staple cartridge 3306 into forming contact with the underside 3326 of the anvil body 3322. In addition, the circular knife member 3308 is driven through the tissue clamped between the anvil body 3322 and the staple cartridge 3306. Actuation of the second drive system in a second rotary direction will cause the compression shaft 3030 to move in the proximal direction "PD".

The end effector 3000 may also be equipped with various sensors that are coupled to an end effector contact board 3120 mounted within the end effector housing 3010. For example, the end effector 3000 may include closure sensor(s) 3122 that are mounted within the end effector housing 3010 and are electrically coupled to the end effector contact board 3120 such that when the end effector 3000 is operably coupled to the surgical instrument, the closure sensor(s) 3122 are in communication with the surgical instrument's control system. The closure sensor(s) 3122 may comprise Hall effect sensors 7028 as described hereinbelow in connection with FIGS. 61, 63 that are configured to detect the position of the closure nut 3084. See FIG. 44. In addition, firing sensor(s) 3124 may also be mounted within the end effector housing 3010 and be arranged to detect the location of the firing nut 3110 within the closure nut 3084. The firing sensor(s) 3124 also may comprise Hall effect sensors 7028 as described hereinbelow in connection with FIGS. 61, 63 and be electrically coupled to the end effector contact board 3120 for ultimate communication with the surgical instrument control system, such as the handle processor 7024, for example, as described in further below in connection with FIGS. 61, 63, 64. The contact board 3120 may be positioned with the end effector housing 3020 such that when the end effector 3000 is operably coupled to the surgical instrument, the end effector contact board 3120 is electrically coupled to a surgical instrument contact board 30 mounted in the surgical instrument housing 12 as was discussed above.

Use of the end effector 3000 will now be explained in connection with surgical instrument 10. It will be appreciated, however, that the end effector 3000 may be operably coupled to various other surgical instrument arrangements disclosed herein. Prior to use, the closure shaft 3080 and the firing shaft 3102 are "clocked" or positioned in their starting positions to facilitate attachment to the first and second drive shafts 22, 42, respectively. To couple the end effector 3000 to the surgical instrument 10, for example, the clinician moves the end effector 3000 into a position wherein the closure shaft axis CSA-CSA is in axial alignment with the first drive shaft axis FDA-FDA and wherein the firing shaft axis FSA-FSA is in axial alignment with the second drive shaft axis SDA-SDA. The female socket coupler 57 on the closure shaft 3080 is inserted into operable engagement with the male coupler 51 on the first drive shaft 22. Likewise, the female socket coupler 57 on the firing shaft 3102 is inserted into operable engagement with the male coupler 51 on the second drive shaft 42. Thus, when in that position, the closure shaft 3080 is operably coupled to the first drive shaft 22 and the firing shaft 3102 is operably coupled to the second drive shaft 42. The end effector contact board 3120 is operably coupled to the surgical instrument contact board 30 so that the sensors 3122, 3124 within the end effector 3000 are in operable communication with the surgical instrument's control system. To retain the end effector 3000 in coupled operable engagement with the surgical instrument 10, the end effector 3000 includes a retainer latch 3130 that is attached to the end effector housing 3010 and configured to releasably engage a portion of the instrument housing 12. The retainer latch 3130 may include a retention lug 3132 that may releasable engage a retainer cavity 15 formed in the housing 12. See FIG. 1. When coupled together, the closure sensor 3122 detects the position of the closure nut 3084 and the firing sensor 3124 detects the position of the firing nut 3110. That information is communicated to the surgical instrument control system. In addition, the clinician may confirm that the shiftable transmission assembly (or the transmission carriage 62 thereof) is in its first drive position. This may be confirmed by the actuation of the indicator light 77 on the housing 12 as was discussed above. If the shiftable transmission assembly 60 is not in its first drive position, the clinician may actuate the firing trigger 92 to move the transmission carriage 62 into the first drive position, such that actuation of the rocker trigger 110 to actuate the motor 80 will result in actuation of the first drive system 20. Assuming that the closure system 3070 and firing system 3100 are each in their respective starting positions and the end effector 3000 has an unspent staple cartridge module properly installed therein, the end effector 3000 is ready for use.

As is known, when performing an anastomosis using a circular stapler, the intestine may be stapled using a conventional surgical stapler with multiple rows of staples being emplaced on either side of a target section (i.e., specimen) of the intestine. The target section is typically simultaneously cut as the section is stapled. After removing the target specimen, the clinician inserts the anvil 3320 into the proximal portion of the intestine, proximal of the staple line. This may be done by inserting the anvil body 3322 into an entry port cut into the proximal intestine portion or the anvil 3320 can be placed trans-anally, by placing the anvil 3320 on the distal end of the end effector 3000 and inserting the instrument through the rectum. Next, the clinician attaches the anvil shaft 3324 to the trocar tip 3042 of the end effector 3000 and inserts the anvil 3320 into the distal portion of the intestine. The clinician may then tie the distal end of the proximal section of the intestine to the anvil shaft 3324 using a suture or other conventional tying device and also tie the proximal end of the distal intestine portion around the anvil shaft 3324 using another suture.

The clinician may then move the tension band assembly 3040, trocar tip 3042 and anvil 3320 attached thereto proximally by actuating the rocker trigger 110 to actuate the motor 80 and rotate the first drive shaft 22. This actuation moves the anvil 3320 toward the cartridge 3306 supported in the casing member 3302 of the stapler head 3300 to close the gap therebetween and thereby engages the proximal end of the distal intestine portion with the distal end of the proximal intestine portion in the gap therebetween. The clinician continues to actuate the first drive system 20 until a desired amount of tissue compression is attained. Once the intestine portions have been clamped between the anvil assembly 3320 and the stapler head 3300, the clinician may then actuate the firing trigger 92 to move the transmission carriage 62 to its second drive position such that actuation of the motor 80 will result in the rotation of the second drive shaft 42. Once the transmission carriage 62 is moved to the second drive position, the clinician may once again actuate the rocker trigger 110 to actuate the second drive system 40 and the firing system 3100 in the end effector 3000 to drive the compression shaft 3030 distally which also drives the circular staple driver assembly 3304 and the circular knife member 3308 distally. Such action serves to cut the clamped pieces of intestine and drive the surgical staples through both clamped ends of the intestine, thereby joining the portions of intestine and forming a tubular pathway. Simultaneously, as the staples are driven and formed, the circular knife 3308 is driven through the intestinal tissue ends, cutting the ends adjacent to the inner row of staples. The clinician may then withdraw the end effector 3000 from the intestine and the anastomosis is complete.

FIGS. 46-49 illustrate another surgical end effector 3000' that may be identical to the surgical end effector 3000 described above except for the differences noted below. Those components of the surgical end effector 3000' that are the same as the components in the surgical end effector 3000 described above will be designated with the same element numbers. Those components of surgical end effector 3000' that may be similar in operation, but not identical to corresponding components of the surgical end effector 3000, will be designated with the same component numbers along with a "'". As can be seen in FIGS. 46-49, the surgical end effector 3000' includes a drive disengagement assembly, generally designated as 3090, that is advantageously configured to enable the clinician to disengage a distal portion of a drive train from a proximal portion of a drive train.

Figure 46:
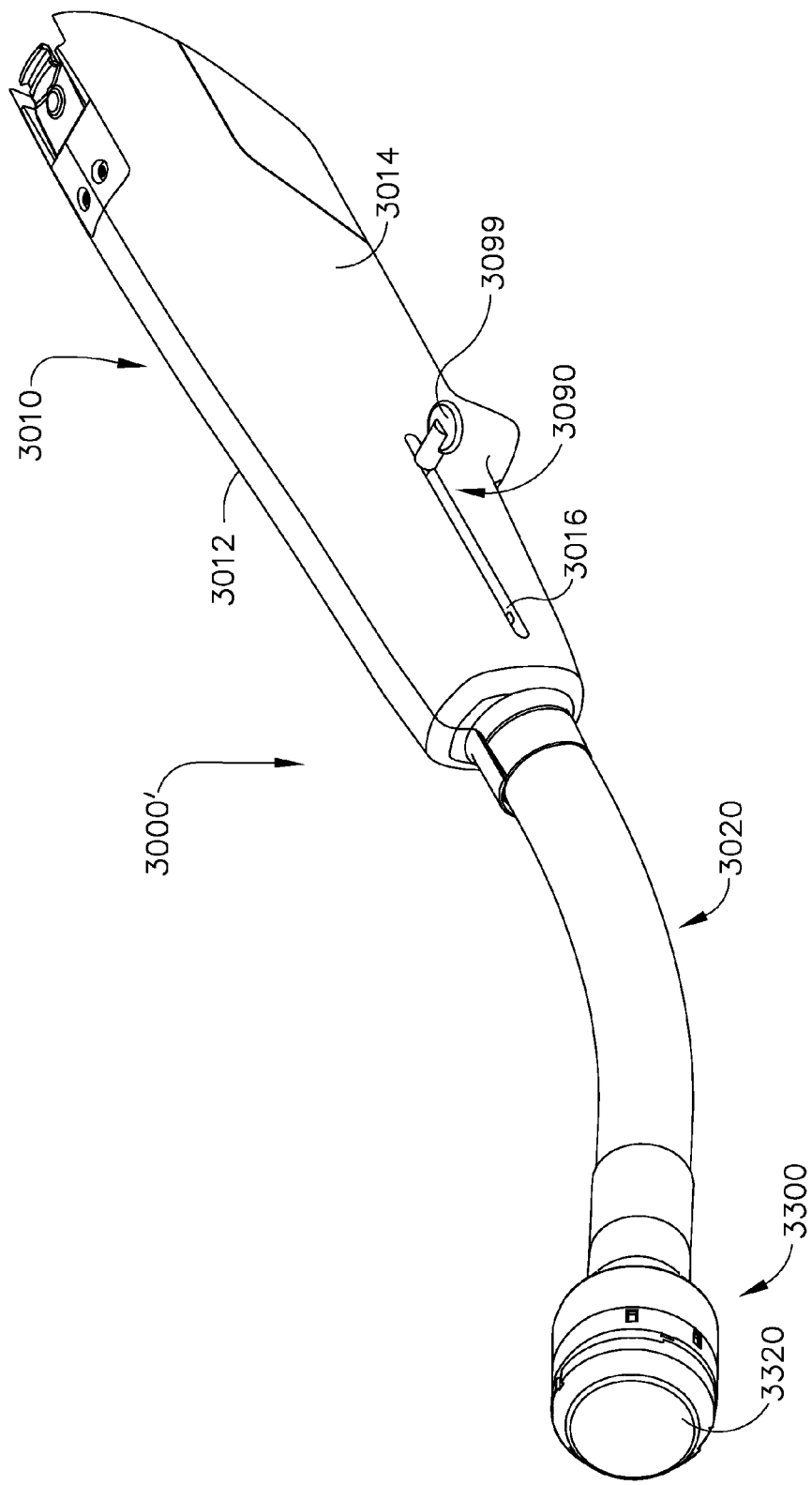
FIG. 46 is a perspective view of an end effector arrangement with a drive disengagement assembly.
Figure 47:
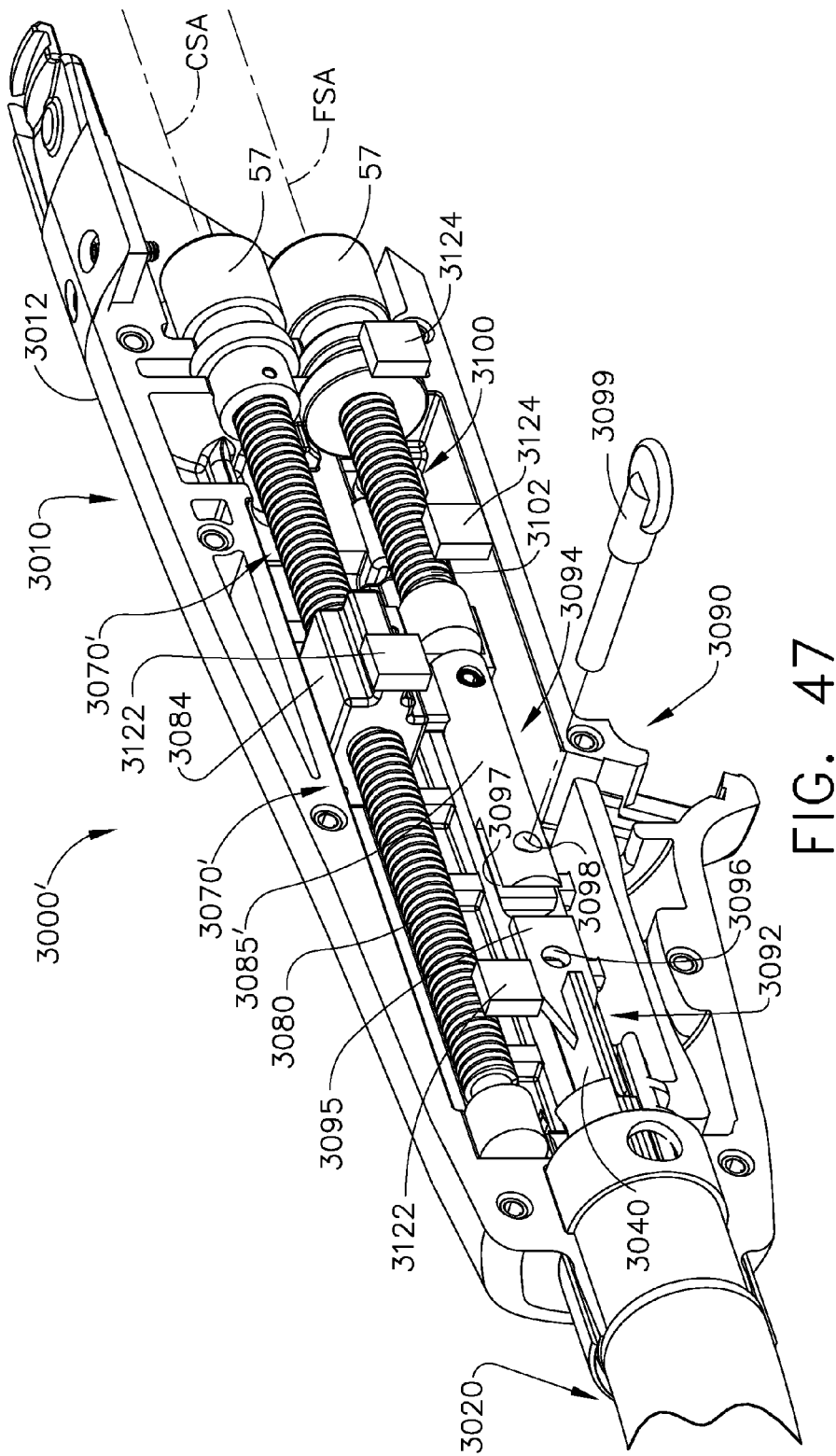
FIG. 47 is a partial perspective view of the surgical end effector of FIG. 46 with portions thereof omitted for clarity and with the proximal drive train portion of the closure system detached from the distal drive train portion of the closure system.
Figure 48:
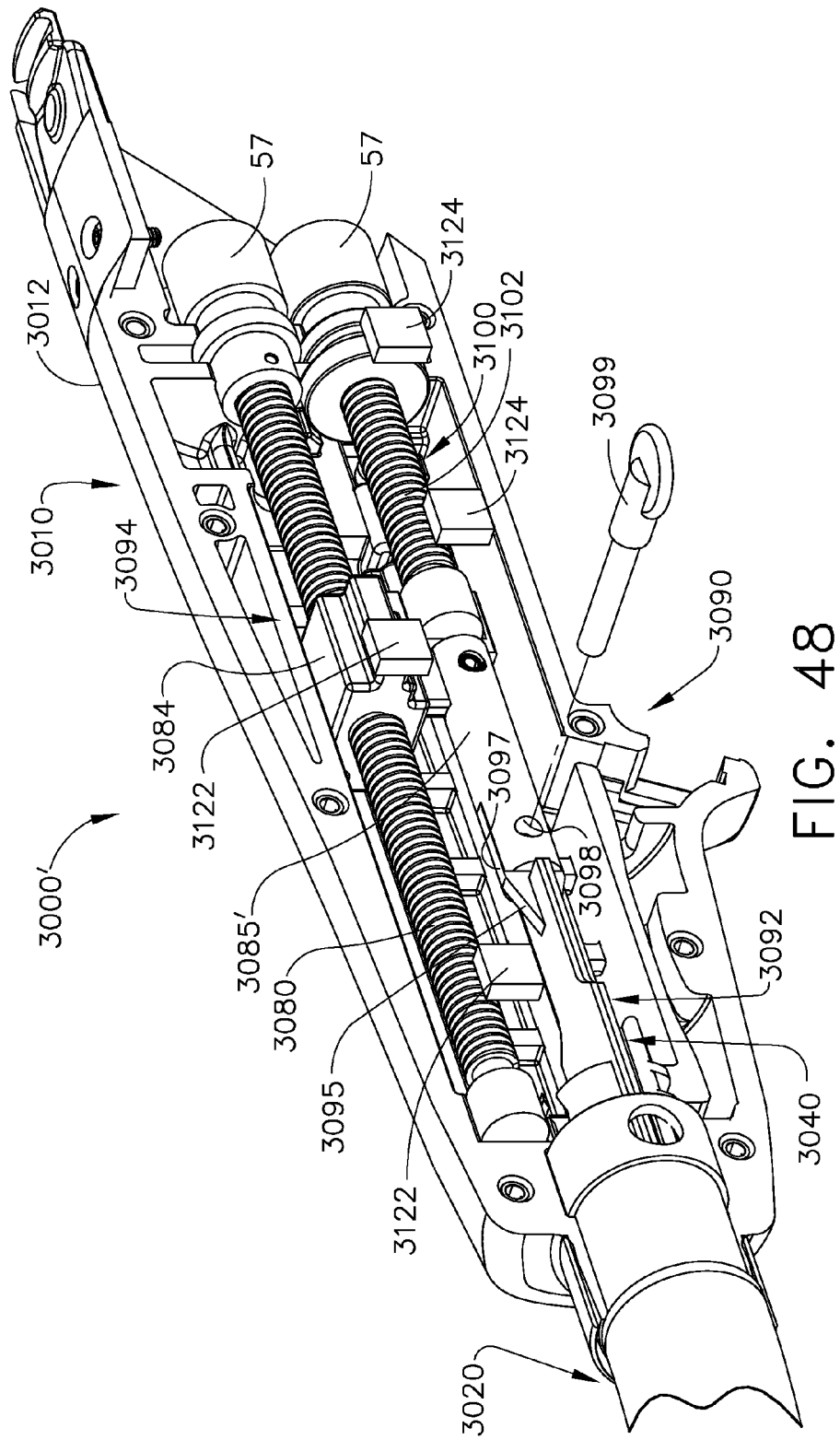
FIG. 48 is a partial perspective view of the surgical end effector of FIGS. 46 and 47 with portions thereof omitted for clarity and with the distal coupler member seated within the slot in the proximal coupler member and the drive coupler pin removed therefrom.
Figure 49:
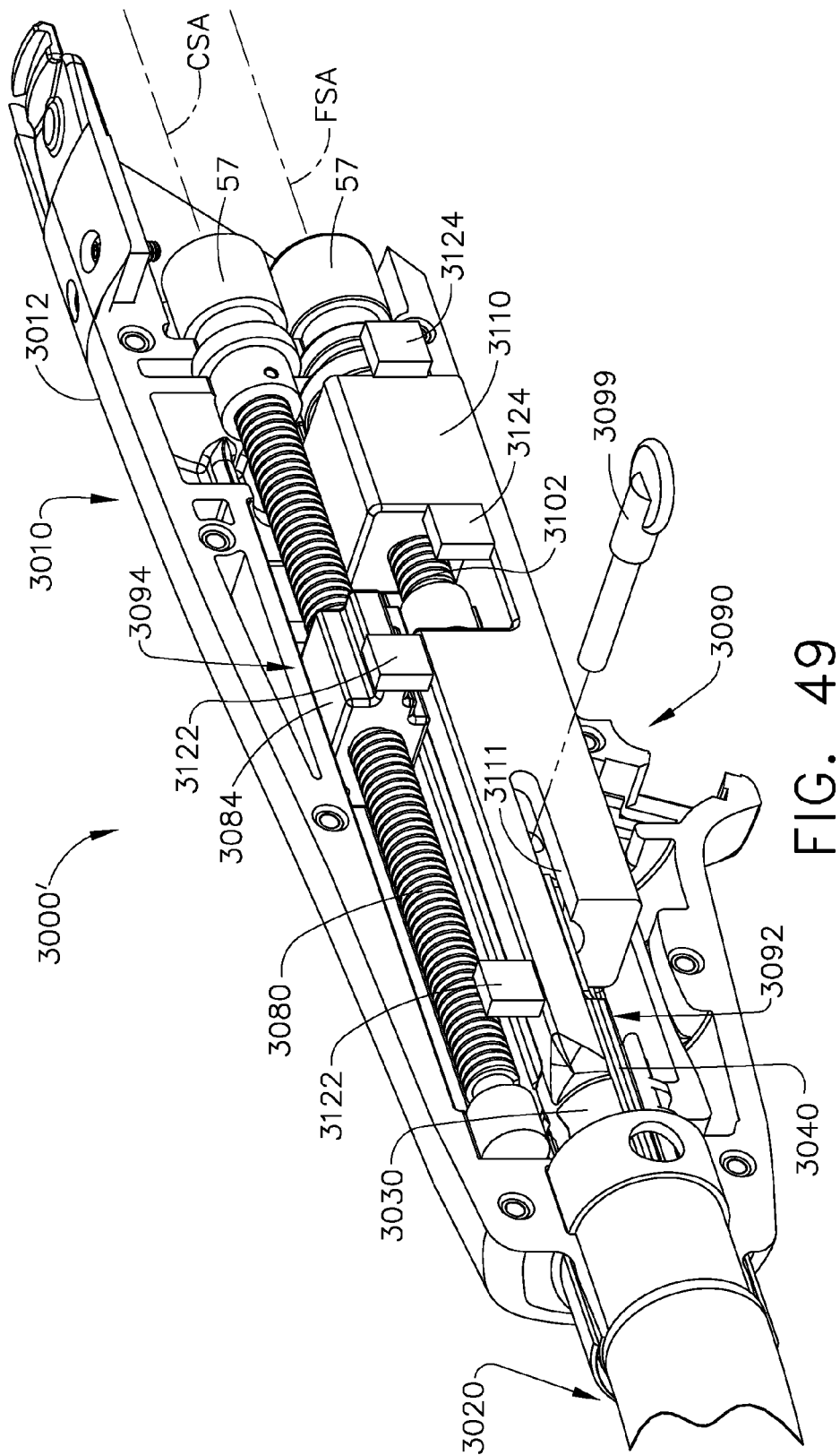
FIG. 49 is another partial perspective view of the surgical end effector of FIG. 48 showing portions of the end effector firing system.
Figure 50:
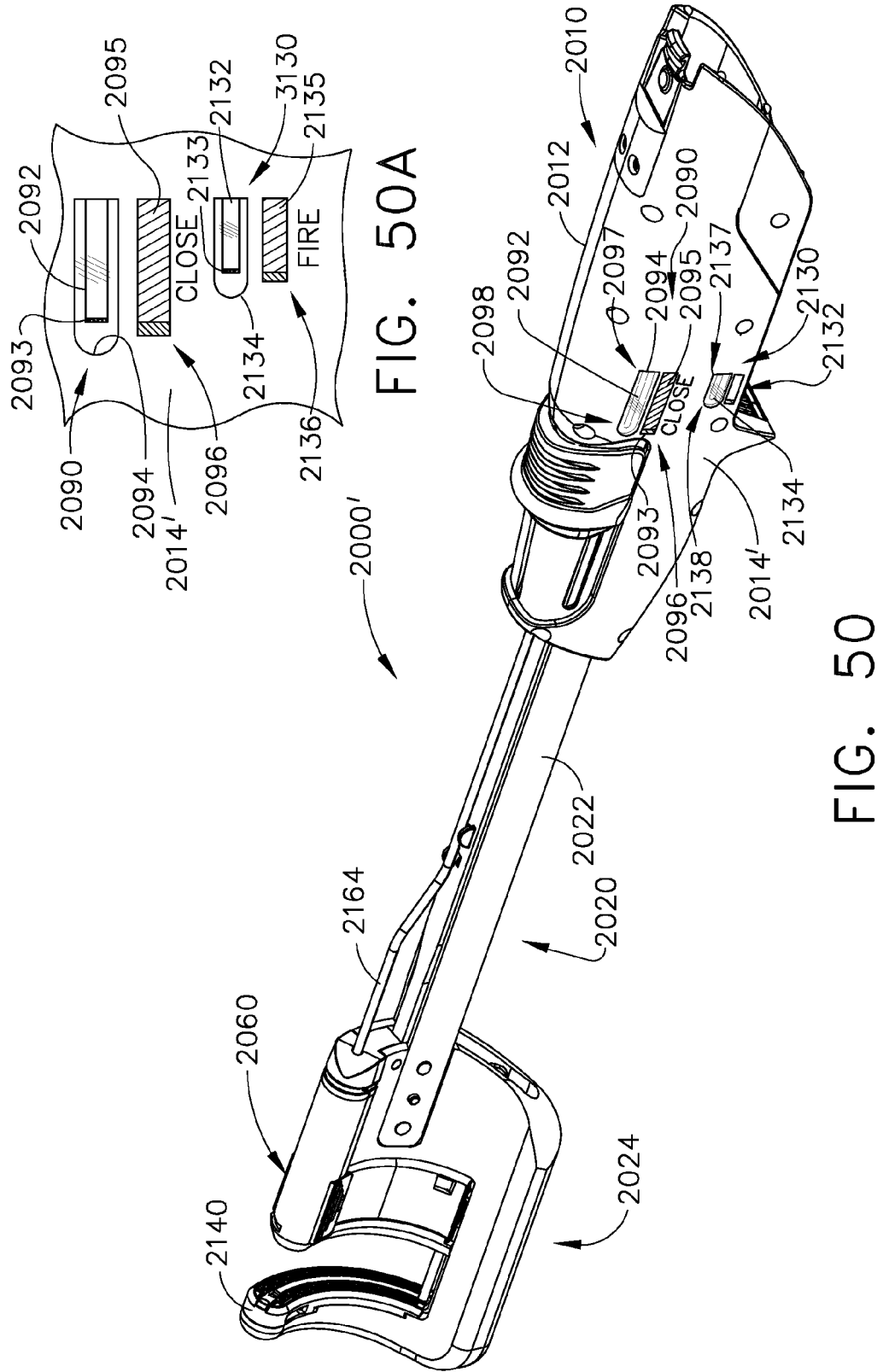
FIG. 50 is a perspective view of another surgical end effector arrangement.

In the depicted embodiment, the drive disengagement assembly 3090 is used in connection with the closure system 3070' so that in the event that the distal portion of the closure system becomes inadvertently jammed or otherwise disabled, the clinician may quickly mechanically separate the distal drive train portion from the proximal drive train portion of the closure system. More specifically and with reference to FIG. 47, the tension band assembly 3040 and the trocar tip 3042 (See FIGS. 42, 43 and 45) may also be referred to as the "distal drive train portion" 3092 of the closure system 3070' and the closure shaft 3080 and closure nut assembly 3084 may, for example, be referred to as the "proximal drive train portion" 3094 of the closure system 3070'. As can be seen in FIG. 47, one form of the drive disengagement assembly 3090 includes a distal coupler member 3095 that is attached to a proximal end of the tension band assembly 3040. The distal coupler member 3095 may be attached to the tension band assembly 3040 by press fit, adhesive, solder, welding, etc. or any combination of such attachment arrangements. The distal coupler member 3095 is sized to be slidable received within a slot 3097 in the proximal coupler member 3085' that is attached to the closure nut assembly 3084. The distal coupler member 3095 includes a distal hole 3096 therethrough that is configured to axially register with a proximal hole 3098 in the proximal coupler member 3085' when the distal coupler member 3095 is seated within the slot 3097. See FIG. 48. The drive disengagement assembly 3090 further comprises a drive coupler pin 3099 that is sized to be received within the axially aligned holes 3096, 3098 to retainingly couple the distal coupler member 3095 to the proximal coupler member 3085'. Stated another way, the drive coupler pin 3099 serves to mechanically and releasably couple the distal drive train portion 3092 to the proximal drive train portion 3094. The drive coupler pin 3099 extends along a coupling axis CA-CA that is transverse to the closure shaft axis CSA. To provide clearance for the drive coupler pin 3099 to move axially relative to the firing nut 3110, an axial slot 3111 is provided in the firing nut 3110. As can be seen in FIG. 46, the end effector housing portion 3014' is provided with an axially extending clearance slot 3016 to facilitate axial travel of the drive coupler pin 3099 during the actuation of the closure system 3070'. Such arrangement enables the clinician to quickly decouple the distal drive train portion 3092 from the proximal drive train portion 3094 at any time during use of the end effector 3000' simply by removing or pulling the drive coupler pin 3099 transversely out of the holes 3096, 3098 to permit the distal coupler member 3095 to be disengaged from the proximal coupler member 3085'.

While the drive disengagement assembly 3090 has been described in connection with the closure system 3070' of the end effector 3000', the drive disengagement assembly could, in the alternative, be employed in connection with the firing system 3100 of the end effector 3000'. In other arrangements, a drive disengagement assembly 3090 could be associated with the closure system and a second drive disengagement assembly may be associated with the firing system. Thus, one or both of the proximal drive train portions may be selectively mechanically separated from their respective distal drive train portions. Further, such drive disengagement assembly may be effectively employed in connection with the closure and/or firing systems of at least some of other surgical end effectors disclosed herein including but not necessarily limited to, for example, end effector 1000 and end effector 2000 and their respective equivalent arrangements.

Figure 51:
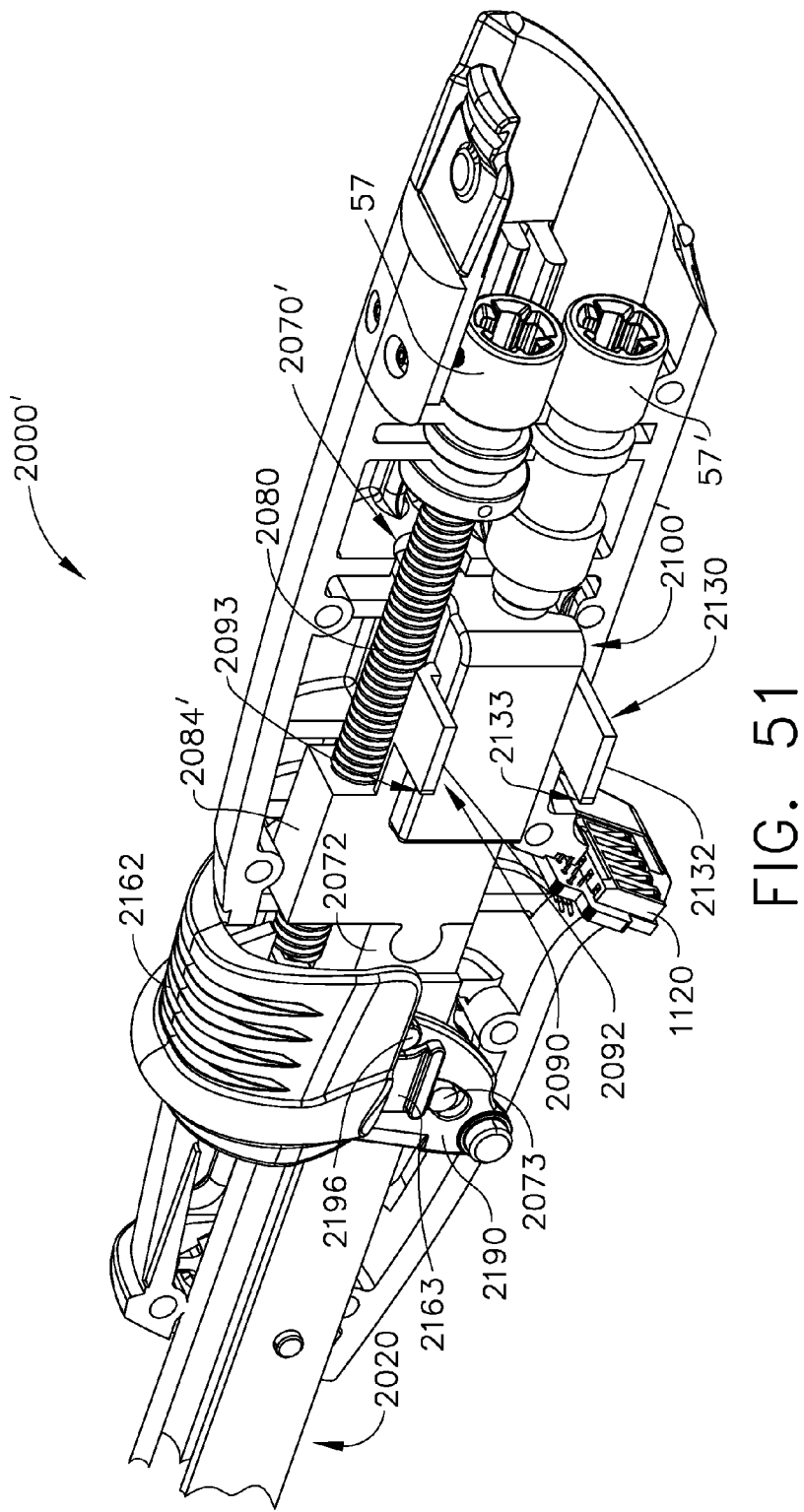
FIG. 51 is a perspective view of a portion of the end effector of FIG. 50 with a portion of the housing omitted for clarity.
Figure 52:
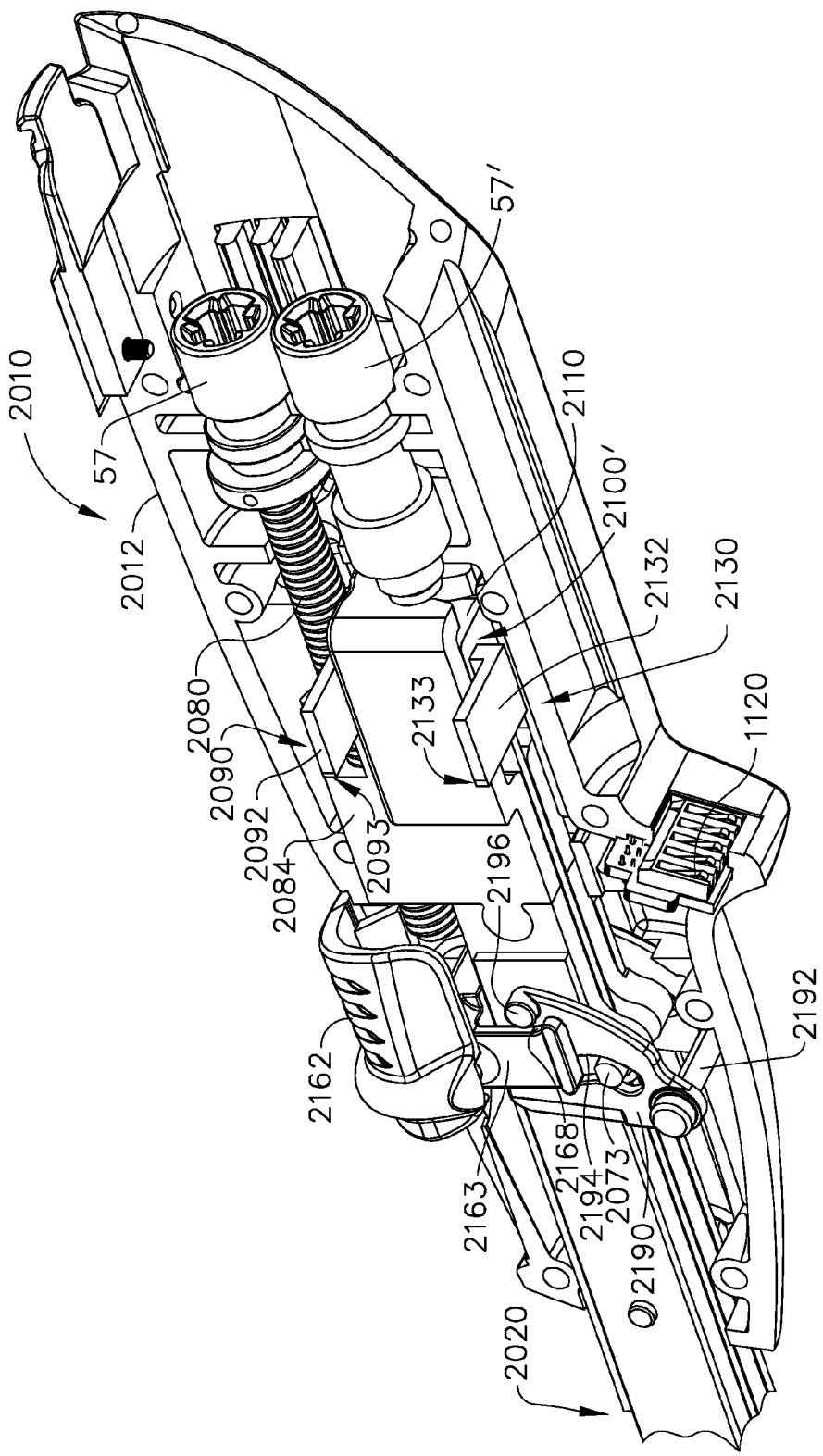
FIG. 52 is another perspective view of the end effector of FIGS. 50 and 51 with portions of the housing and closure system omitted for clarity.
Figure 53:
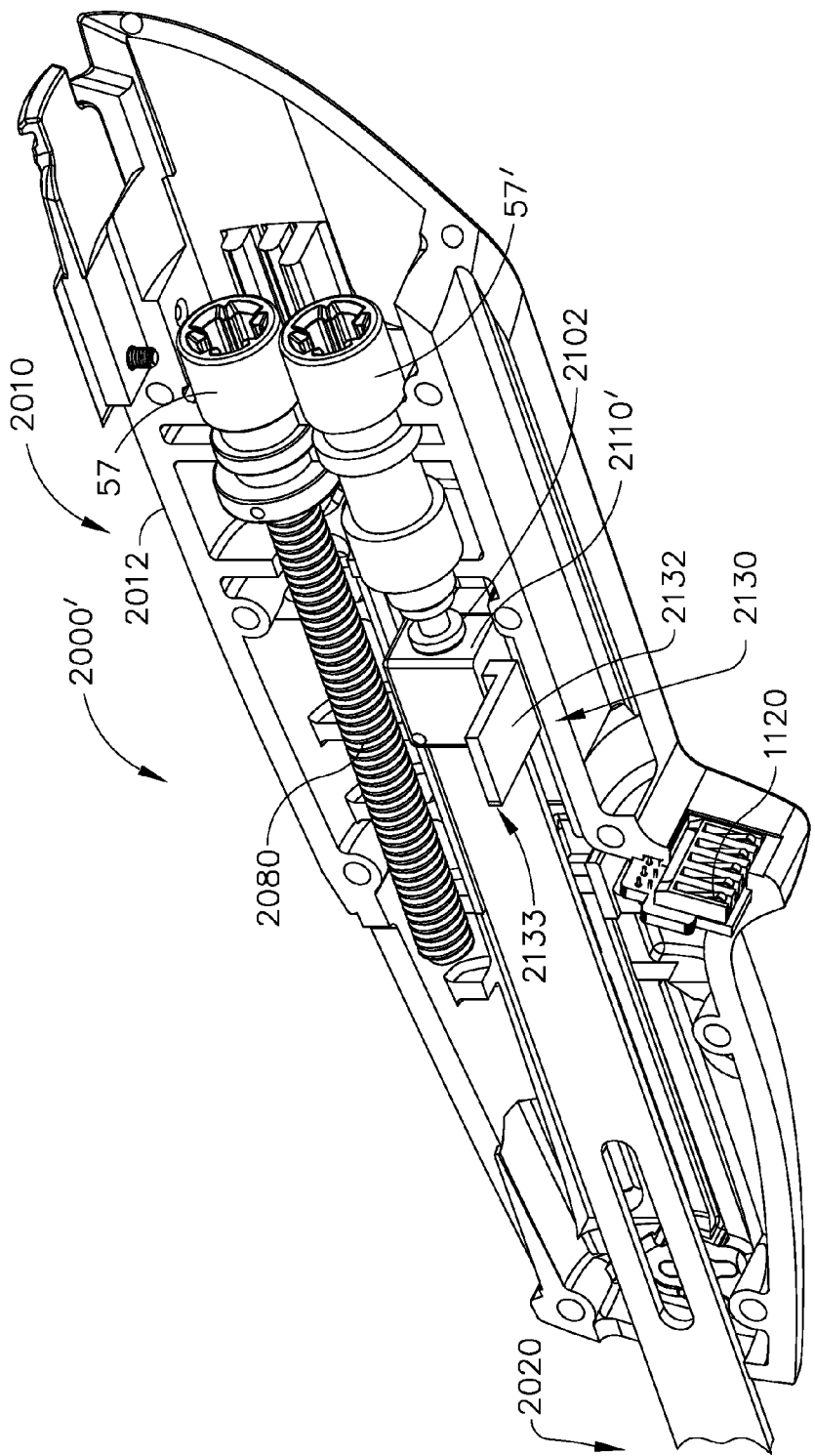
FIG. 53 is another perspective view of the end effector of FIGS. 50-52 with portions of the closure system and a portion of the housing omitted for clarity.

FIGS. 50-53 illustrate another surgical end effector 2000' that may be identical to the surgical end effector 2000 described above except for the differences noted below. Those components of the surgical end effector 2000' that are the same as the components in the surgical end effector 2000 described above will be designated with the same element numbers. Those components of surgical end effector 2000' that may be similar in operation, but not identical to corresponding components of the surgical end effector 2000, will be designated with the same component numbers along with a "'". As can be seen in FIGS. 51-53, the surgical end effector 2000' may be provided with indicator arrangements for providing a visual indication as to the firing status of the closure and firing systems.

More particularly and with reference to FIGS. 51 and 52, the closure system 2070 includes a closure system status assembly, generally designated as 2090. In one form, for example, the closure system status assembly 2090 includes a closure indicator member 2092 that is attached to or otherwise extends from the closure nut 2084'. The closure system status assembly 2090 further includes a closure indicator window 2094 or opening in the end effector housing 2010 such that the position of the closure indicator member 2092 may be assessed by the clinician by viewing the closure indicator member 2092 through the closure indicator window 2094. Similarly, the firing system 2100' may include a firing system status assembly, generally designated as 2130. In one form, for example, the firing system status assembly 2130 includes a firing indicator member 2132 that is attached to or otherwise extends from the firing nut 2110'. The firing system status assembly 2130 further includes a firing indicator window or opening 2134 in the end effector housing 2010 such that the position of the firing indicator member 2132 may be assessed by the clinician by viewing the firing indicator member 2132 through the firing indicator window 2134.

The closure system status assembly 2090 and the firing system status assembly 2130 reveal the mechanical state of the closure system 2070 and the firing system 2100. The mechanical state of the distal end of the end effector can generally be observed by the clinician, but it sometimes is covered or obstructed by tissue. The mechanical state of the proximal portion of the end effector cannot be seen without a window arrangement or protruding indicator. Color coding on the exterior of the shaft arrangement and or on the indicator may also be employed to provide the clinician confirmation that the end effector has been fully closed or fired (e.g., indicator on green for fully closed). For example, the closure indicator member 2092 may have a closure mark 2093 thereon that is viewable through the closure indicator window 2094. In addition, the housing 2010 may have a first closure indicia 2095 and a second closure indicia 2096 adjacent to the closure indicator window 2094 to assess the position of the closure indicator 2092. For example, the first closure indicia 2095 may comprise a first bar that has a first color (e.g., range, red, etc.) and the second closure indicia may comprise a bar or section of a second color that differs from the first color (e.g., green). When the closure mark 2093 on the closure indicator member 2092 is aligned on the proximal-most end of the first closure indicia bar 2095 (this position is represented by element number 2097 in FIG. 50), the clinician can observe that the closure system 2070 is in its unactuated position. When the closure mark 2093 is aligned within the first closure indicia bar 2095, the clinician can observe that the closure system 2070 is partially actuated—but not fully actuated or fully closed. When the closure mark 2093 is aligned with the second closure indicia 2096 (represented by element number 2098 in FIG. 50), the clinician can observe that the closure system 2070 is in its fully actuated or fully closed position.

Similarly, the firing indicator member 2132 may have a firing mark 2133 thereon that is viewable through the firing indicator window 2134. In addition, the housing segment 2014' may have a first firing indicia 2135 and a second firing indicia 2136 adjacent to the firing indicator window 2134 to assess the position of the firing indicator 2132. For example, the first firing indicia 2135 may comprise a first firing bar that has a first firing color (e.g., orange, red, etc.) and the second firing indicia may comprise a second firing bar or section of a second firing color that differs from the first firing color (e.g., green). When the firing mark 2133 on the firing indicator member 2132 is aligned on the proximal-most end of the first firing indicia bar 2135 (this position is represented by element number 2137 in FIG. 50), the clinician can observe that the firing system 2100 is in its unactuated position. When the firing mark 2133 is aligned within the first firing indicia bar 2135, the clinician can observe that the firing system 2100 is partially actuated—but not fully actuated or fully fired. When the firing mark 2133 is aligned with the second firing indicia 2136 (represented by element number 2138 in FIG. 50), the clinician can observe that the firing system 2170 is in its fully actuated or fully fired position. Thus, the clinician may determine the extent to which the closure and firing systems have been actuated by observing the position of the indicators within their respective windows.

In alternative arrangement, the indicator windows 2094 and 2134 may be provided in the end effector housing 2010' such that when the closure system 2070 and firing system 2100' are in their starting or unactuated positions, their respective indicators 2092, 2132 may be in full view in the indicator windows 2094, 2134, respectively. As the closure system 2070 and firing system 2100' are actuated, their indicators 2092, 2132 will move out of their indicator windows 2094, 2134. The clinician may then assess how far each of the systems 2070, 2100' have been actuated by observing how much of the indicators 2092, 2132 are viewable through the windows 2094, 2134.

The closure system status assembly 2090 and the firing system status assembly 2130 reveal the mechanical state of the closure system 2070 and the firing system 2100 whether the end effector 2000' is attached to the surgical instrument handle or housing or not. When the end effector 2000 is attached to the handle or housing, the closure system status assembly 2090 and the firing system status assembly 2130 will afford the clinician with the opportunity to determine the mechanical states of those systems as a primary or secondary check to the state shown on the surgical instrument handle or housing. The closure system status assembly 2090 and the firing system status assembly 2130 also serve as a primary check when the end effector 2000' is detached from the surgical instrument handle or housing. Further, such closure system and firing system status assemblies may be effectively employed in connection with the closure and/or firing systems of at least some of other surgical end effectors disclosed herein including but not necessarily limited to, for example, end effector 1000 and end effector 3000 and their respective equivalent arrangements.

FIGS. 54-60 illustrate another surgical end effector 2000" that may be identical to the surgical end effector 2000' described above except for the differences noted below. Those components of the surgical end effector 2000" that are the same as the components in the surgical end effector 2000' and/or end effector 2000 described above will be designated with the same element numbers. Those components of surgical end effector 2000" that may be similar in operation, but not identical to corresponding components of the surgical end effector 2000' and/or 2000, will be designated with the same component numbers along with a """. As can be seen in FIGS. 54-60, the surgical end effector 2000" includes a drive disengagement assembly, generally designated as 2200, that is advantageously configured to enable the clinician to disengage a distal portion of a drive train from a proximal portion of a drive train.

Figure 59:
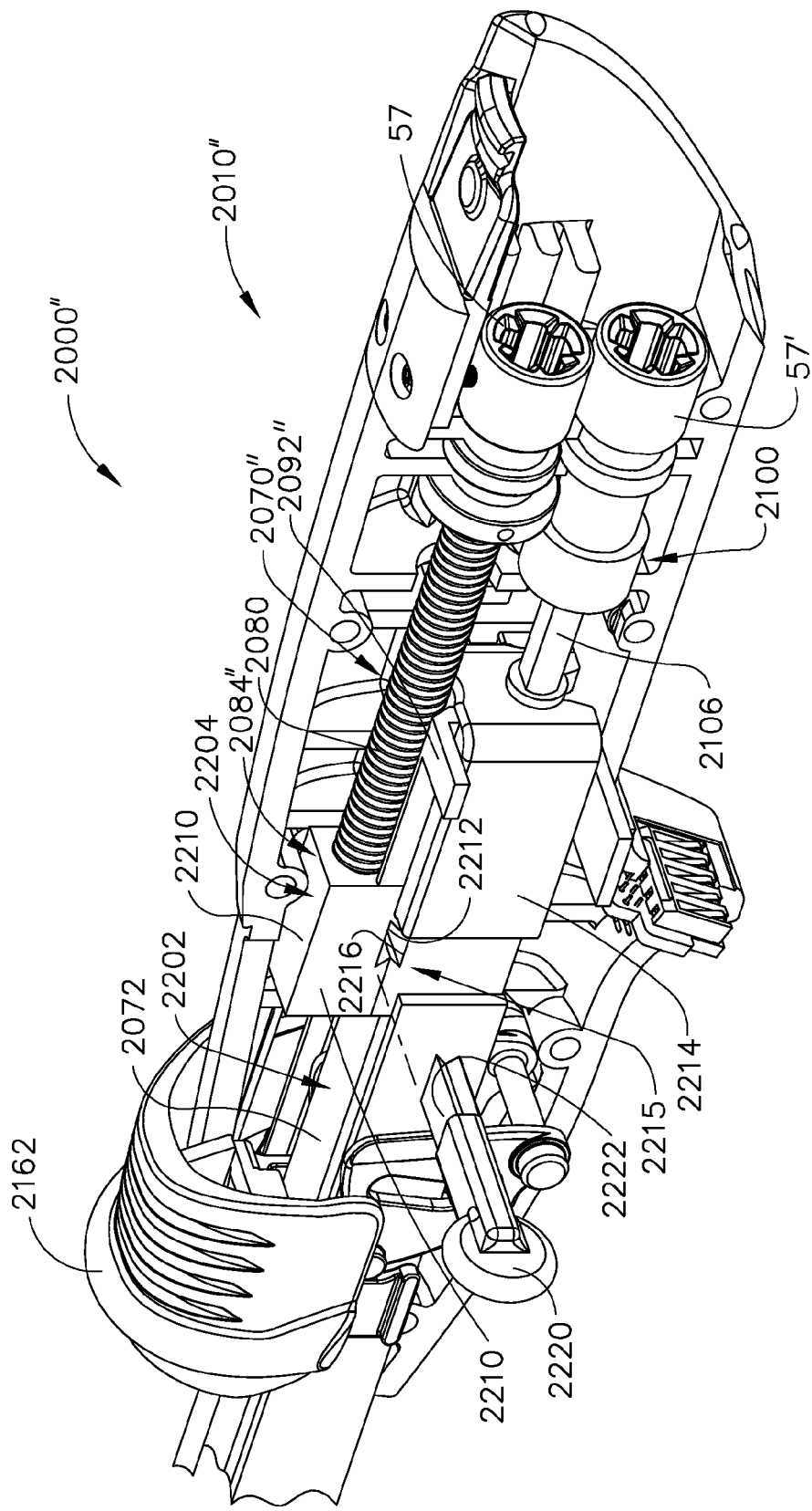
FIG. 59 is another perspective view of the end effector of FIG. 58 with the drive coupler pin removed.
Figure 60:
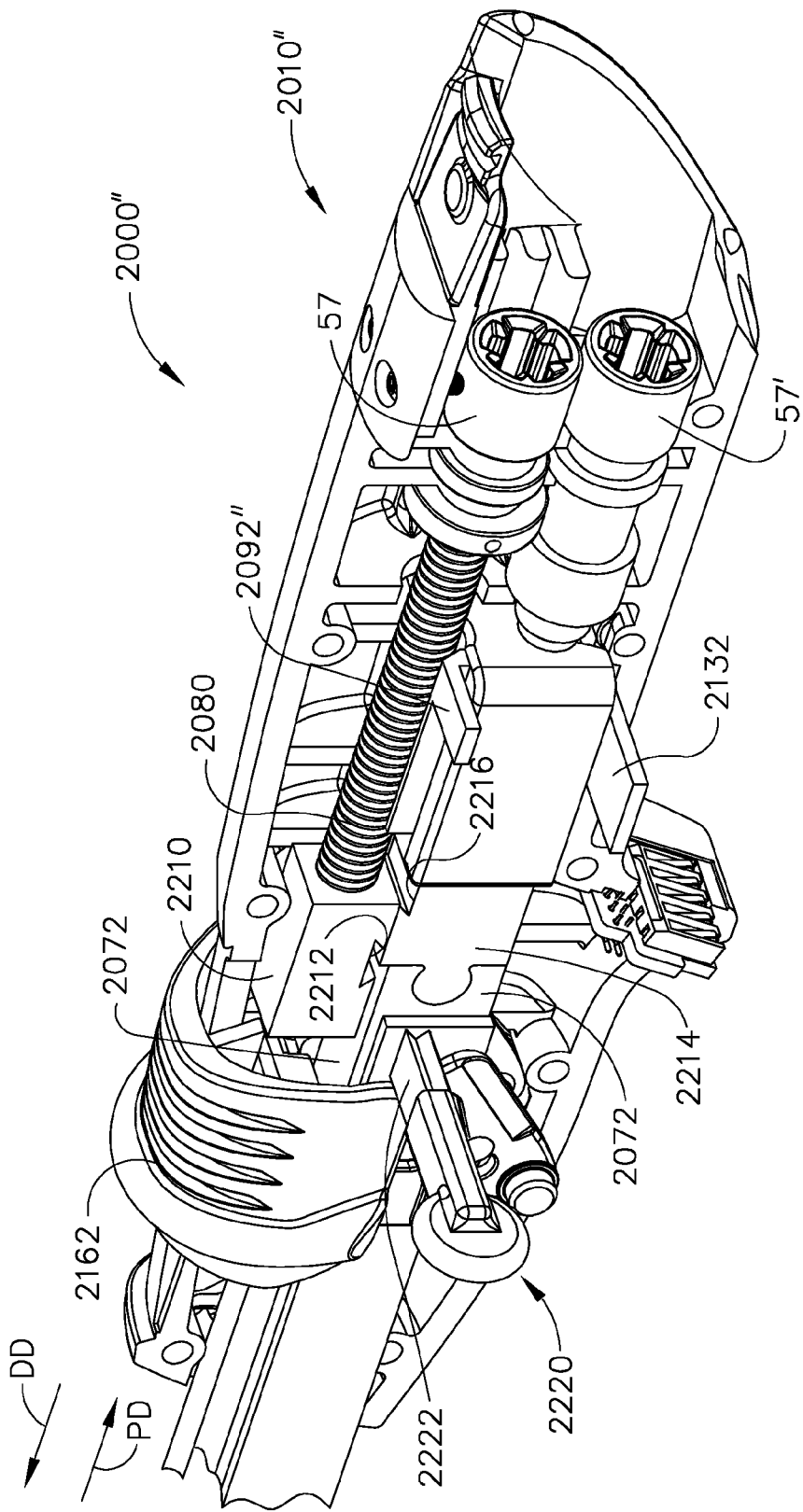
FIG. 60 is another perspective view of the end effector of FIG. 59 with the drive coupler pin removed and the closure drive beam assembly moved proximally to open the tool head.

In the depicted embodiment, the drive disengagement assembly 2200 is used in connection with the closure system 2070" of the end effector 2000" so that in the event that the distal portion of the closure system becomes inadvertently jammed or otherwise disabled, the clinician may quickly mechanically separate the distal drive train portion from the proximal drive train portion of the closure system. More specifically and with reference to FIG. 56, the closure beam assembly 2072 may also be referred to as the "distal drive train portion" 2202 of the closure system 2070" and the closure shaft 2080 and closure nut assembly 2084" may, for example, be referred to as the "proximal drive train portion" 2204 of the closure system 2070". As can be seen in FIG. 59, the closure nut assembly 2084", while substantially identical to closure nut assemblies 2084, 2084' described above, is provided in two parts. More specifically, closure nut assembly 2084" includes an upper threaded portion 2210 that is in threaded engagement with the closure shaft 2080 and a lower portion 2214 that supports the firing nut 2110 for axial movement therein in the manner discussed above. The lower portion 2214 of the closure nut assembly 2084" is directly attached to the closure beam assembly 2072 and includes the closure indicator member 2092" that functions in the same manner as closure indicator 2092 discussed above.

Figure 56:
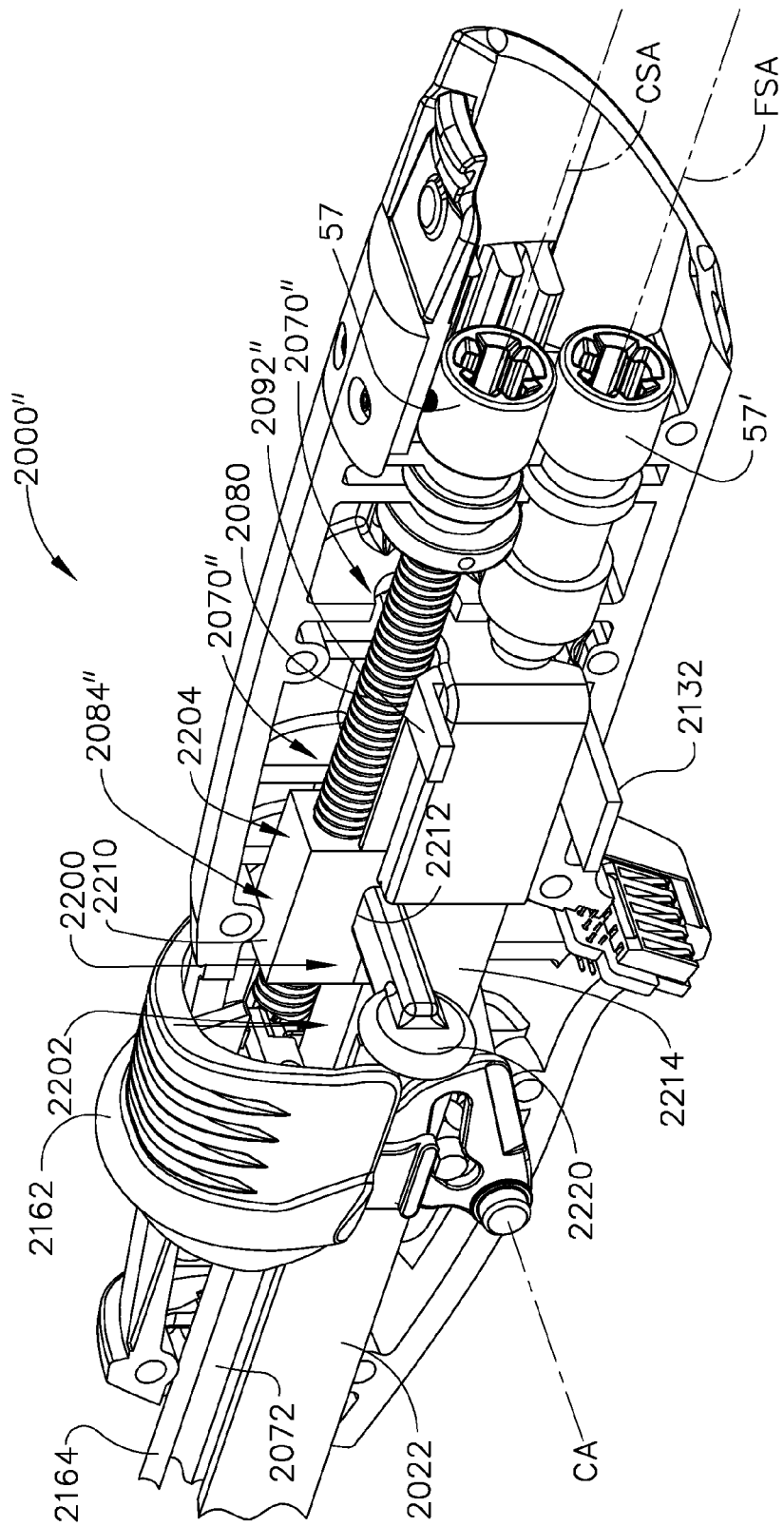
FIG. 56 is a perspective view of a portion of the end effector of FIGS. 54 and 55 with a portion of the end effector housing omitted for clarity.

In at least one form, the drive disengagement assembly 2200 includes a drive coupler pin 2220 that serves to couple the lower portion 2214 of the closure nut assembly 2084" to the upper portion 2210. As can be seen in FIG. 59, for example, the upper portion 2210 of the closure nut assembly 2084" includes a first dovetail slot segment 2212 that is configured for alignment with a second dovetail slot segment 2216 in the lower portion 2214 of the closure nut assembly 2084". When the first and second dovetail slot segments 2212, 2216 are aligned as shown in FIG. 59, they form hole 2215 into which the barrel portion 2222 of the drive coupler pin 2220 may be inserted to couple the upper and lower portions 2010 and 2014 together as shown in FIG. 56. Stated another way, the drive coupler pin 2220 serves to mechanically and releasably couple the distal drive train portion 2202 to the proximal drive train portion 2204 of the closure system 2070". The drive coupler pin 2220 extends along a coupling axis CA-CA that is transverse to the closure shaft axis CSA. See FIG. 56. To provide clearance for the drive coupler pin 2220 to move axially with the closure nut assembly 2084", the housing segment 2014" of the end effector housing 2010" is provided with an axially extending clearance slot 2224. Such arrangement enables the clinician to quickly decouple the distal drive train portion 2202 from the proximal drive train portion 2204 at any time during use of the end effector 2000" simply by removing or pulling the drive coupler pin 2220 transversely out of the hole 2215 formed by the dovetail slot segments 2212, 2216. Once the drive coupler pin 2220 has been removed from the hole 2215, the lower portion 2214 of the closure assembly 2084" can be moved relative to the upper portion 2212 to thereby enable the tissue to be released from between the cartridge module 2060 and the anvil assembly 2140.

Figure 54:
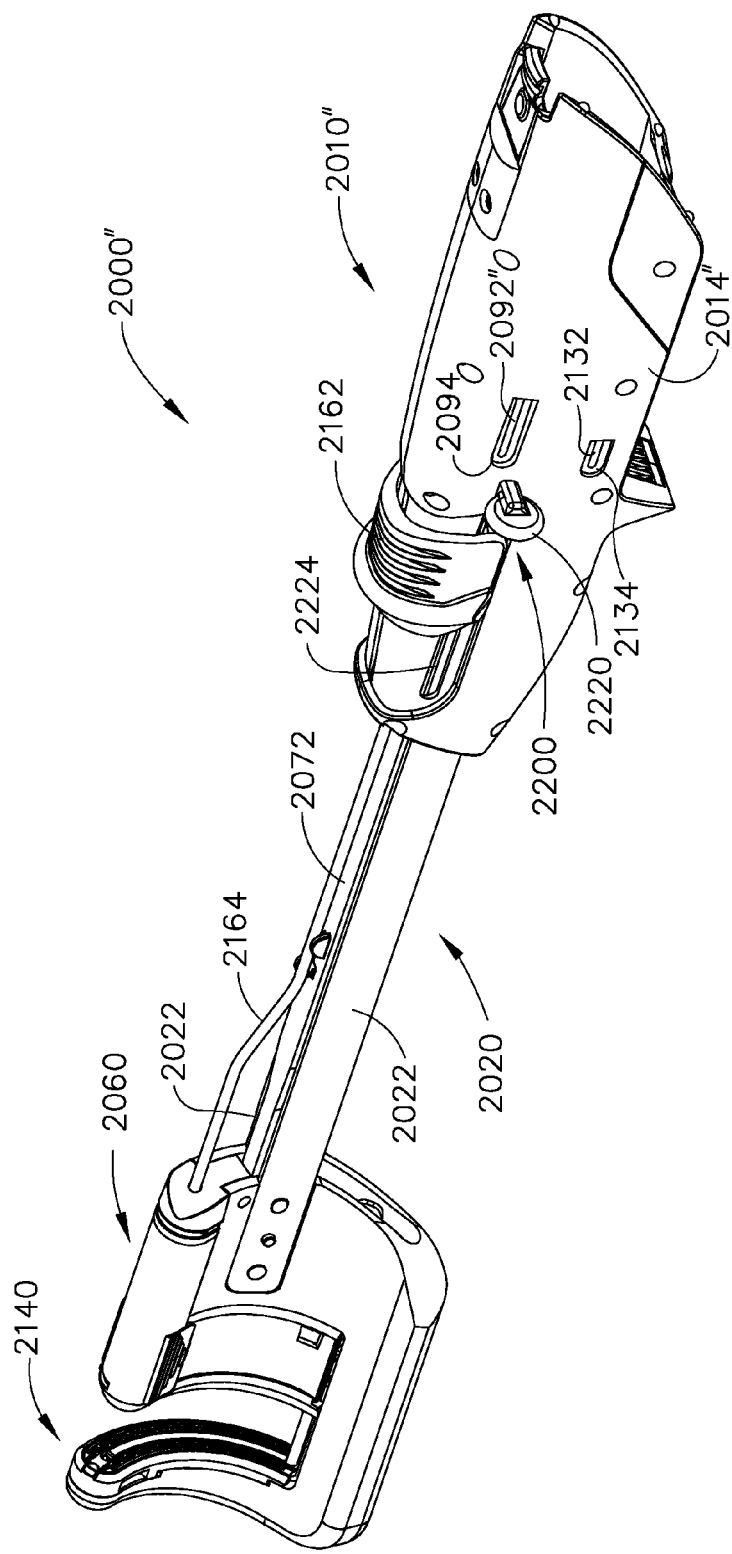
FIG. 54 is a perspective view of another end effector that is equipped with a drive disengagement assembly.
Figure 55:
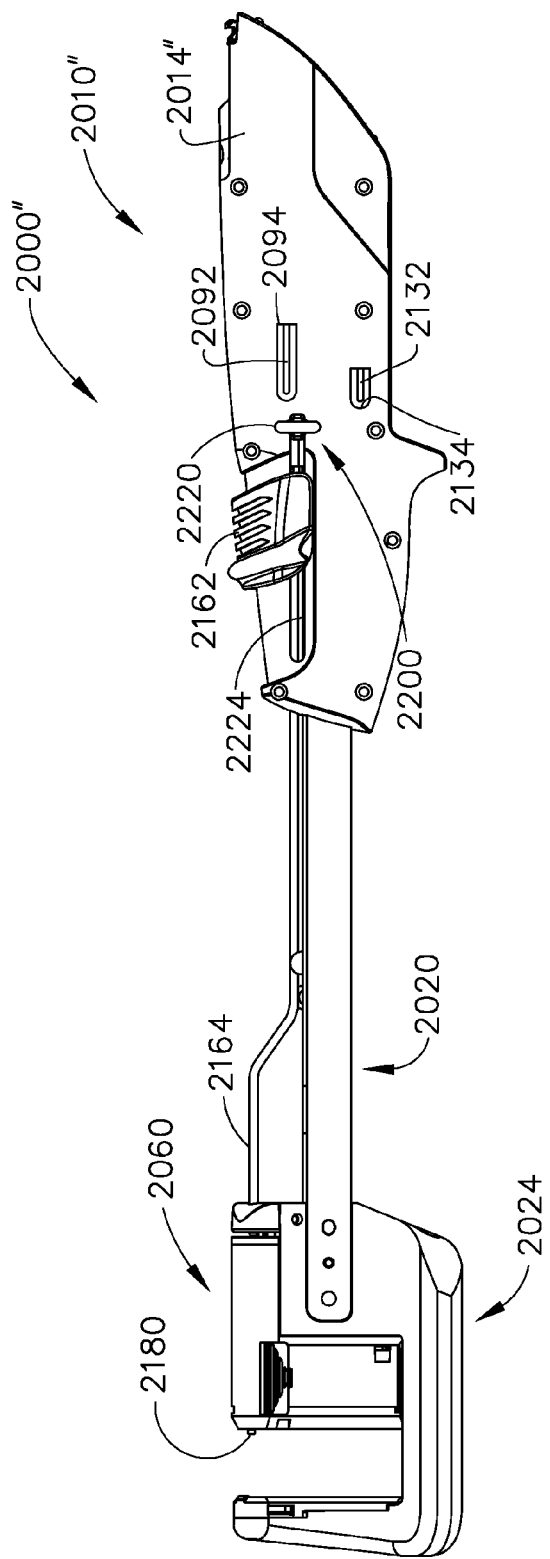
FIG. 55 is a side elevational view of the end effector of FIG. 54.
Figure 57:
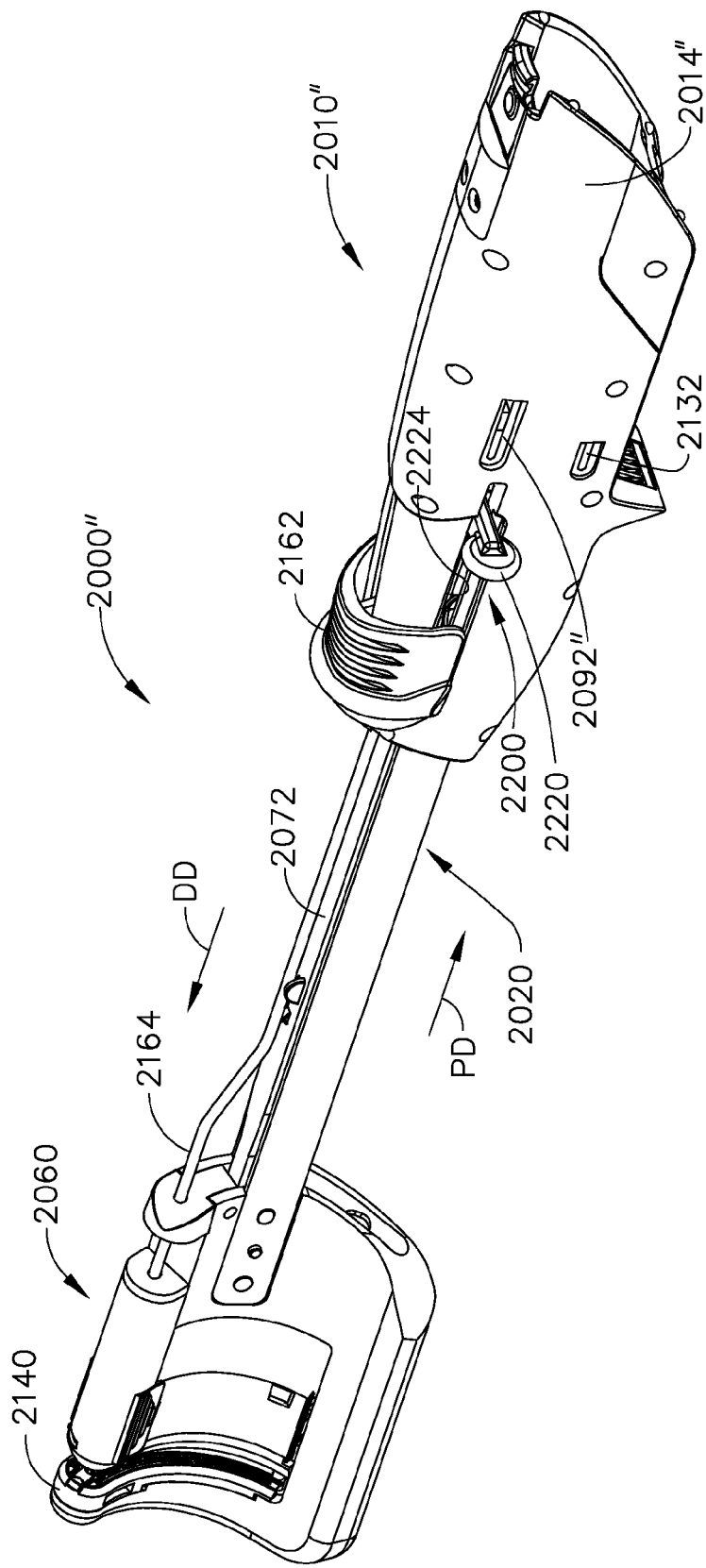
FIG. 57 is another perspective view of the end effector of FIGS. 54-56 with the tool head thereof in a closed position.
Figure 58:
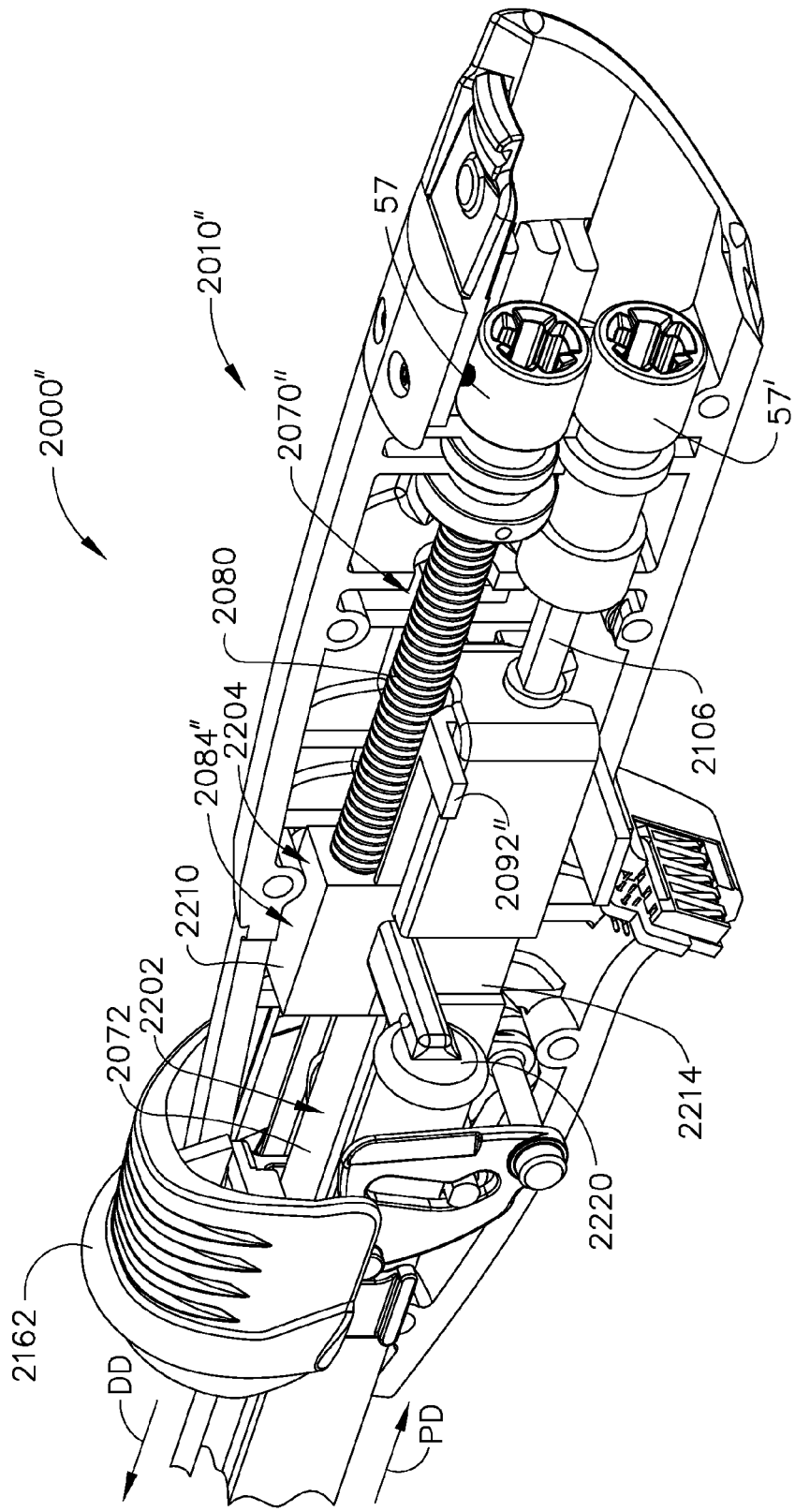
FIG. 58 is a another partial perspective view of the end effector of FIG. 57 with a portion of the end effector housing omitted for clarity.

FIGS. 54-56 depict the end effector 2000" in an "open" position prior to use. As can be seen in those Figures, for example, a cartridge module 2060 is installed and ready for use. FIGS. 57 and 58 depict the end effector 2000 in its closed state. That is, the closure beam 2080 has been rotated to drive the closure nut assembly 2084" in the distal direction "DD". Because the lower portion 2214 of the closure nut assembly 2084" is attached to the upper portion 2210 by the drive coupler pin 2220, the closure beam assembly 2072 (because it is attached to the lower portion 2214) is also moved distally to its closed position to clamp target tissue between the cartridge module 2260 and the anvil assembly 2140. As was also discussed above, the saddle shaped slide button 2162 on the housing 2010" is moved distally to cause the retaining pin to extend through the cartridge housing and into the anvil assembly 2140 to thereby capture the tissue between the cartridge module 2060 and the anvil assembly 2140. As was discussed in detail above, when the closure nut assembly 2084" moves distally, the firing nut 2110 also moves distally which draws the proximal portion 2106 of the firing shaft 2102 out of the elongated passage within the female socket coupler 57'. See FIG. 58. FIG. 59 illustrates the drive coupler pin 2220 removed from the hole 2215 formed by the dovetail slot segments 2212, 2216. Once the drive coupler pin 2220 has been removed from the hole 2215, the proximal drive train portion 2202 (closure beam assembly 2072) may be moved in the proximal direction "PD" by moving the saddle shaped slide button 2162 proximally. Such movement of the button 2162 will move the closure beam assembly 2072, the lower portion 2014 of the closure nut assembly 2084", the firing nut 2110 and firing bar assembly 2112, as well as the retaining pin proximally. Such movement will enable the tissue to be released from between the cartridge module 2060 and the anvil assembly 2140.

Figure 61:
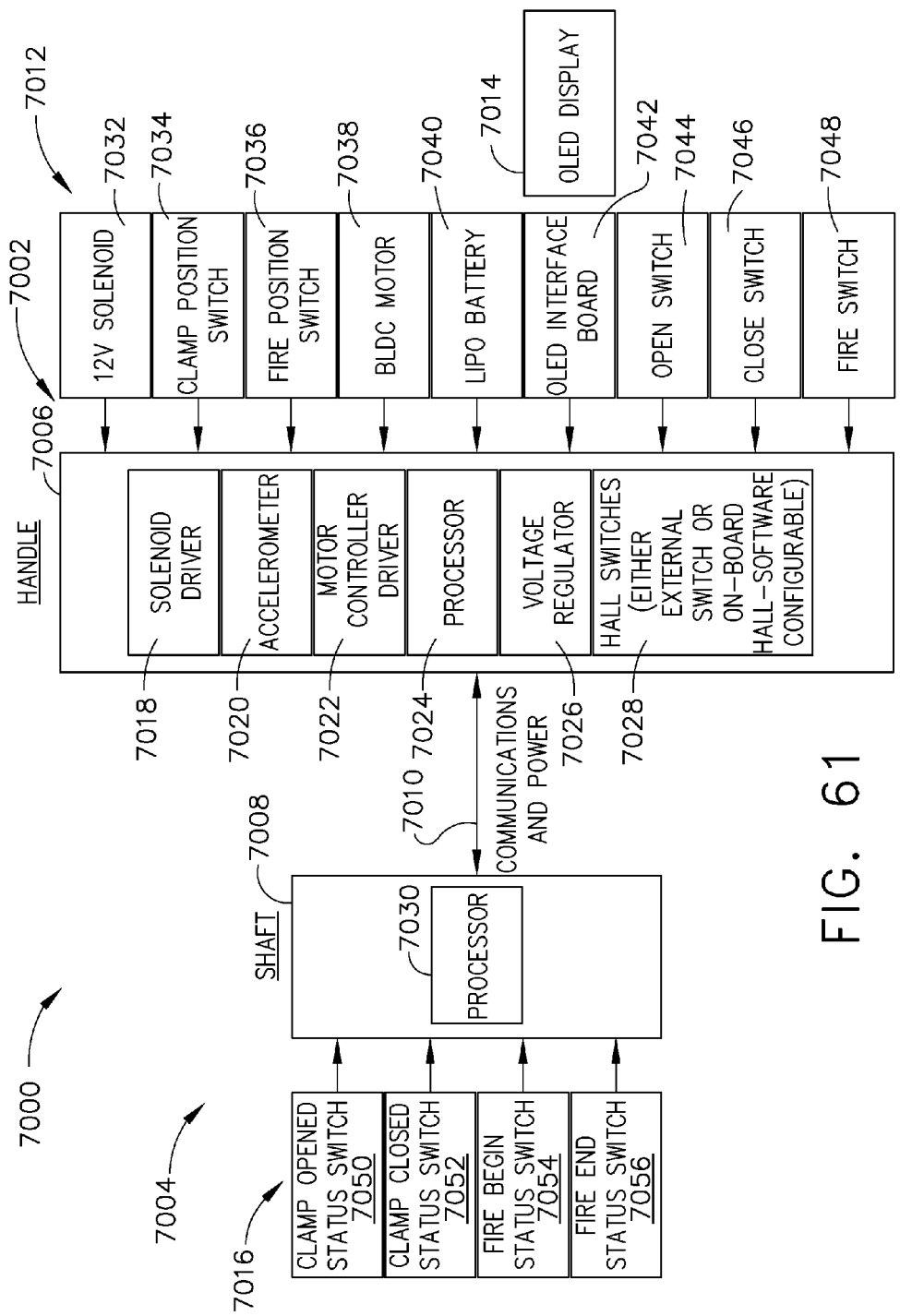
FIG. 61 is a block diagram of a modular motor driven surgical instrument comprising a handle portion and a shaft portion.

FIG. 61 is a block diagram of a modular motor driven surgical instrument 7000 comprising a handle portion 7002 and a shaft portion 7004. The modular motor driven surgical instrument 7000 is representative of the modular surgical instrument system generally designated as 2 that, in one form, includes a motor driven surgical instrument 10 that may be used in connection with a variety of surgical end effectors such as, for example, end effectors 1000, 2000 and 3000 as shown in FIG. 1. Having described various functional and operational aspects of the modular motor driven surgical instrument 10 in detail hereinabove, for conciseness and clarity of disclosure such details will not be repeated in the following description associated with FIGS. 61-64. Rather, the description of FIGS. 61-64 that follows will focus primarily on the functional and operational aspects of the electrical systems and subsystems of the modular motor driven surgical instrument 7000, which can be applied in whole or in part to the modular motor driven surgical instrument described hereinabove.

Accordingly, turning now to FIG. 61 the modular motor driven surgical instrument 7000 comprises a handle portion 7002 and a shaft portion 7004. The handle and shaft portions 7002, 7004 comprise respective electrical subsystems 7006, 7008 electrically coupled by a communications and power interface 7010. The components of the electrical subsystem 7006 of the handle portion 7002 are supported by the previously described control board 100. The communications and power interface 7010 is configured such that electrical signals and power can be readily exchanged between the handle portion 7002 and the shaft portion 7004.

In the illustrated example, the electrical subsystem 7006 of the handle portion 7002 is electrically coupled to various electrical elements 7012 and a display 7014. In one instance, the display 7014 is an organic light emitting diode (OLED) display, although the display 7014 should not be limited in this context. The electrical subsystem 7008 of the shaft portion 7004 is electrically coupled to various electrical elements 7016, which will be described in detail hereinbelow.

In one aspect, the electrical subsystem 7006 of the handle portion 7002 comprises a solenoid driver 7018, an accelerometer 7020, a motor controller/driver 7022, a handle processor 7024, a voltage regulator 7026, and is configured to receive inputs from a plurality of switches 7028. Although, in the illustrated embodiment, the switches 7028 are designated as Hall switches, the switches 7028 are not limited in this context. In various aspects, the Hall effect sensors or switches 7028 may be located either in the end effector portion of the instrument, the shaft, and/or the handle.

In one aspect, the electrical subsystem 7006 of the handle portion 7002 is configured to receive signals from a solenoid 7032, a clamp position switch 7034, a fire position switch 7036, a motor 7038, a battery 7040, an OLED interface board 7042, and open switch 7044, close switch 7046, and fire switch 7048. In one aspect, the motor 7038 is a brushless DC motor, although in various aspects the motor is not limited in this context. Nevertheless, the description of the motor 7038 may be applicable to the motors 80, 480, 580, 680, 750, and 780 previously described. The solenoid 7032 is representative example of the previously described shifter solenoid 71.

In one aspect, the electrical subsystem 7008 of the shaft portion 7004 comprises a shaft processor 7030. The electrical subsystem 7008 of the shaft is configured to receive signals from various switches and sensors located in the end effector portion of the instrument that are indicative of the status of the clamp jaws and cutting element in the end effector. As illustrated in FIG. 61, the electrical subsystem 7008 of the shaft is configured to receive signals from a clamp opened status switch 7050, a clamp closed status switch 7052, a fire begin status switch 7054, and a fire end status switch 7056, which are indicative of the states of the clamp and cutting element.

In one aspect, the handle processor 7024 may be a general purpose microcontroller suitable for medical and surgical instrument applications and including motion control. In one instance, the handle processor 7024 may be a TM4C123BH6ZRB microcontroller provided by Texas Instruments. The handle processor 7024 may comprise a 32-bit ARM® Cortex™-M4 80-MHz processor core with System Timer (SysTick), integrated nested vectored interrupt controller (NVIC), wake-up interrupt controller (WIC) with clock gating, memory protection unit (MPU), IEEE754-compliant single-precision floating-point unit (FPU), embedded trace macro and trace port, system control block (SCB) and thumb-2 instruction set, among other features. The handle processor 7024 may comprise on-chip memory, such as 256 KB single-cycle Flash up to 40 MHz. A prefetch buffer can be provided to improve performance above 40 MHz. Additional memory includes a 32 KB single-cycle SRAM, internal ROM loaded with TivaWare™ for C Series software, 2 KB EEPROM, among other features, such as two Controller Area Network (CAN) modules, using CAN protocol version 2.0 part A/B and with bit rates up to 1 Mbps.

In one aspect, the handle processor 7024 also may comprise advanced serial integration including eight universal asynchronous receiver/transmitters (UARTs) with IrDA, 9-bit, and ISO 7816 support (one UART with modem status and modem flow control). Four Synchronous Serial Interface (SSI) modules are provided to support operation for Freescale SPI, MICROWIRE or Texas Instruments synchronous serial interfaces. Additionally, six Inter-Integrated Circuit (I2C) modules provide Standard (100 Kbps) and Fast (400 Kbps) transmission and support for sending and receiving data as either a master or a slave, for example.

In one aspect, the handle processor 7024 also comprises an ARM PrimeCell® 32-channel configurable μDMA controller, providing a way to offload data transfer tasks from the Cortex™-M4 processor, allowing for more efficient use of the processor and the available bus bandwidth. Analog support functionality includes two 12-bit Analog-to-Digital Converters (ADC) with 24 analog input channels and a sample rate of one million samples/second, three analog comparators, 16 digital comparators, and an on-chip voltage regulator, for example.

In one aspect, the handle processor 7024 also comprises advanced motion control functionality such as eight Pulse Width Modulation (PWM) generator blocks, each with one 16-bit counter, two PWM comparators, a PWM signal generator, a dead-band generator, and an interrupt/ADC-trigger selector. Eight PWM fault inputs are provided to promote low-latency shutdown. Two quadrature encoder interface (QEI) modules are provided, with a position integrator to track encoder position and velocity capture using built-in timer.

In one aspect, two ARM FiRM-compliant watchdog timers are provided along with six 32-bit general-purpose timers (up to twelve 16-bit). Six wide 64-bit general-purpose timers (up to twelve 32-bit) are provided as well as 12 16/32-bit and 12 32/64-bit capture compare PWM (CCP) pins, for example. Up to 120 general purpose input/outputs (GPIOs) can be provided depending on configuration, with programmable control for GPIO interrupts and pad configuration, and highly flexible pin multiplexing. The handle processor 7024 also comprises lower-power battery-backed hibernation module with real-time clock. Multiple clock sources are provided for the microcontroller system clock and include a precision oscillator (PIOSC), main oscillator (MOSC), 32.768-kHz external oscillator for the hibernation module, and an internal 30-kHz oscillator.

In one aspect, the accelerometer 7020 portion of the electrical subsystem 7006 of the handle portion 7002 may be a micro-electromechanical system (MEMS) based motion sensor. As is well known, MEMS technology combines computers with tiny mechanical devices such as sensors, valves, gears, mirrors, and actuators embedded in semiconductor chips. In one example, the MEMS based accelerometer 7020 may comprise an ultra low power 8 bit 3-axis digital accelerometer such as the LIS331DLM provided by STMicroelectronics, for example.

In one aspect, the accelerometer 7020, such as the LIS331DLM, may be an ultra low-power high performance three axes linear accelerometer belonging to the "nano" family, with digital I2C/SPI serial interface standard output, with is suitable for communicating with the handle processor 7024. The accelerometer 7020 may feature ultra low-power operational modes that allow advanced power saving and smart sleep to wake-up functions. The accelerometer 7020 may include dynamically user selectable full scales of ±2 g/±4 g/±8 g and it is capable of measuring accelerations with output data rates from 0.5 Hz to 400 Hz, for example.

In one aspect, the accelerometer 7020 may include self-test capability to allow the user to check the functioning of the sensor in the final application. The accelerometer 7020 may be configured to generate an interrupt signal by inertial wake-up/free-fall events as well as by the position of the instrument itself. Thresholds and timing of interrupt generators may be programmable on the fly.

In one aspect, the motor controller/driver 7022 may comprise a three phase brushless DC (BLDC) controller and MOSFET driver, such as the A3930 motor controller/driver provided by Allegro, for example. The 3-phase brushless DC motor controller/driver 7022 may be employed with N-channel external power MOSFETs to drive the BLDC motor 7038, for example. In one instance, the motor controller/driver 7022 may incorporate circuitry required for an effective three-phase motor drive system. In one instance, the motor controller/driver 7022 comprises a charge pump regulator to provide adequate (>10 V) gate drive for battery voltages down to 7 V, and enables the motor controller/driver 7022 to operate with a reduced gate drive at battery voltages down to 5.5 V. Power dissipation in the charge pump can be minimized by switching from a voltage doubling mode at low supply voltage to a dropout mode at the nominal running voltage of 14 V. In one aspect, a bootstrap capacitor is used to provide the above-battery supply voltage required for N-channel MOSFETs. An internal charge pump for the high-side drive allows for dc (100% duty cycle) operation.

An internal fixed-frequency PWM current control circuitry regulates the maximum load current. The peak load current limit may be set by the selection of an input reference voltage and external sensing resistor. The PWM frequency can be set by a user-selected external RC timing network. For added flexibility, the PWM input can be used to provide speed and torque control, allowing the internal current control circuit to set the maximum current limit.

The efficiency of the motor controller/driver 7022 may be enhanced by using synchronous rectification. The power MOSFETs are protected from shoot-through by integrated crossover control with dead time. The dead time can be set by a single external resistor.

In one aspect, the motor controller/driver 7022 indicates a logic fault in response to the all-zero combination on the Hall inputs. Additional features of the motor controller/driver 7022 include high current 3-phase gate drive for N-channel MOSFETs, synchronous rectification, cross-conduction protection, charge pump and top-off charge pump for 100% PWM, integrated commutation decoder logic, operation over 5.5 to 50 V supply voltage range, diagnostics output, provides +5 V Hall sensor power, and has a low-current sleep mode.

In one aspect, the modular motor driven surgical instrument 7000 is equipped with a brushless DC electric motor 7038 (BLDC motors, BL motors) also known as electronically commutated motors (ECMs, EC motors). One such motor is the BLDC Motor B0610H4314 provided by Portescap. The BLDC Motor B0610H4314 can be autoclavable. The BLDC motor 7038 is a synchronous motor that is powered by a DC electric source via an integrated inverter/switching power supply, which produces an AC electric signal to drive the motor such as the motor controller/driver 7022 described in the immediately foregoing paragraphs. In this context, AC, alternating current, does not imply a sinusoidal waveform, but rather a bi-directional current with no restriction on waveform. Additional sensors and electronics control the inverter output amplitude and waveform (and therefore percent of DC bus usage/efficiency) and frequency (i.e., rotor speed).

The rotor part of the BLDC motor 7038 is a permanent magnet synchronous motor, but in other aspects, BLDC motors can also be switched reluctance motors, or induction motors. Although some brushless DC motors may be described as stepper motors, the term stepper motor tends to be used for motors that are designed specifically to be operated in a mode where they are frequently stopped with the rotor in a defined angular position.

In one aspect, the BLDC motor controller/driver 7022 must direct the rotation of the rotor. Accordingly, the BLDC motor controller/driver 7022 requires some means of determining the rotor's orientation/position (relative to the stator coils.) In one instance, the rotor part of the BLDC motor 7038 is configured with Hall effect sensors or a rotary encoder to directly measure the position of the rotor. Others measure the back electromotive force (EMF) in the undriven coils to infer the rotor position, eliminating the need for separate Hall effect sensors, and therefore are often called sensorless controllers.

In one aspect, the BLDC motor controller/driver 7022 contains 3 bi-directional outputs (i.e., frequency controlled three phase output), which are controlled by a logic circuit. Other, simpler controllers may employ comparators to determine when the output phase should be advanced, while more advanced controllers employ a microcontroller to manage acceleration, control speed and fine-tune efficiency.

Actuators that produce linear motion are called linear motors. The advantage of linear motors is that they can produce linear motion without the need of a transmission system, such as a ball-and-lead screw, rack-and-pinion, cam, gears or belts that would be necessary for rotary motors. Transmission systems are known to introduce less responsiveness and reduced accuracy. The direct drive, BLDC motor 7038 may comprise a slotted stator with magnetic teeth and a moving actuator, which has permanent magnets and coil windings. To obtain linear motion, the BLDC motor controller/driver 7022 excites the coil windings in the actuator causing an interaction of the magnetic fields resulting in linear motion.

In one aspect, the BLDC motor 7038 is a Portescap BO610 brushless DC motor that provides a combination of durability, efficiency, torque, and speed in a package suitable for use in the modular motor driven surgical instrument 7000. Such BLDC motors 7038 provide suitable torque density, speed, position control, and long life. The slotless BLDC motor 7038 uses a cylindrical ironless coil made in the same winding technique as ironless DC motors. The slotted BLDC motors 7038 also are autoclavable. The slotted BLDC motor 7038 may include a stator that consists of stacked steel laminations with windings placed in the slots that are axially cut along the inner periphery. The brushless DC slotted BLDC motor 7038 provides high torque density and heat dissipation, along with high acceleration. The three-phase configuration of the BLDC motor 7038 includes Wye connections, Hall effect sensors, supply voltage of 4.5-24V. The housing of the BLDC motor 7038 may be made of a 303SS material and the shaft may be made of a 17-4ph material.

In one aspect, the Hall switches 7028 may be Hall effect sensors known under the trade name BU520245G and are unipolar integrated circuit type Hall effect sensors. These sensors operate over a supply voltage range of 2.4V to 3.6V.

In one aspect, the voltage regulator 7026 replaces the usual PNP pass transistor with a PMOS pass element. Because the PMOS pass element behaves as a low-value resistor, the low dropout voltage, typically 415 mV at 50 A of load current, is directly proportional to the load current. The low quiescent current (3.2 µA typically) is stable over the entire range of output load current (0 mA to 50 mA).

In one aspect, the voltage regulator 7026 is a low-dropout (LDO) voltage regulator such as the TPS71533 LDO voltage regulator provided by Texas Instruments. Such LDO voltage regulators 7026 provide the benefits of high input voltage, low-dropout voltage, low-power operation, and miniaturized packaging. The voltage regulator 7026 can operate over an input range of 2.5 V to 24 V, are stable with any capacitor (≥0.47 µF). The LDO voltage and low quiescent current allow operations at extremely low power levels and thus the voltage regulator 7026 is suitable for powering battery management integrated circuits. Specifically, the voltage regulator 7026 is enabled as soon as the applied voltage reaches the minimum input voltage and the output is quickly available to power continuously operating battery charging integrated circuits of the handle portion 7002.

In one aspect, the battery 7040 is a lithium-ion polymer (LIPO) battery, polymer lithium ion or more commonly lithium polymer batteries (abbreviated Li-poly, Li-Pol, LiPo, LIP, PLI or LiP) are rechargeable (secondary cell) batteries. The LIPO battery 7040 may comprise several identical secondary cells in parallel to increase the discharge current capability, and are often available in series "packs" to increase the total available voltage.

Additional power for the modular motor driven surgical instrument 7000 may be provided by a synchronous step down DC-DC converter 7058 (FIG. 63-A) optimized for applications with high power density such as the TPS6217X family provided by Texas Instruments. A high switching frequency of typically 2.25 MHz may be employed to allow the use of small inductors and provides fast transient response as well as high output voltage accuracy by utilization of the DCS-Control™ topology.

With a wide operating input voltage range of 3V to 17V, the synchronous step down DC-DC converter 7058 (FIG. 63-A) is well suited for modular motor driven surgical instrument 7000 systems powered from either a Li-Ion or other battery as well as from 12V intermediate power rails. In one aspect, a synchronous step down DC-DC converter 7058 supports up to 0.5 A continuous output current at output voltages between 0.9V and 6V (with 100% duty cycle mode).

Power sequencing is also possible by configuring the Enable and open-drain Power Good pins. In Power Save Mode, the synchronous step down DC-DC converter 7058 (FIG. 63-A) show quiescent current of about 17 µA from VIN. Power Save Mode is entered automatically and seamlessly if load is small and maintains high efficiency over the entire load range. In Shutdown Mode, the synchronous step down DC-DC converter 7058 is turned off and shutdown current consumption is less than 2 µA.

In one aspect, the OLED interface 7042 is an interface to the OLED display 7014. The OLED display 7014 comprises organic light-emitting diodes in which the emissive electroluminescent layer is a film of organic compound which emits light in response to an electric current. This layer of organic semiconductor is situated between two electrodes, where in general at least one of these electrodes is transparent. The OLED display 7014 may include OLEDs from two main families. Those based on small molecules and those employing polymers. Adding mobile ions to an OLED creates a light-emitting electrochemical cell or LEC, which has a slightly different mode of operation. The OLED display 7014 can use either passive-matrix (PMOLED) or active-matrix addressing schemes. Active-matrix OLEDs (AMOLED) require a thin-film transistor backplane to switch each individual pixel on or off, but allow for higher resolution and larger display sizes. In one instance, the OLED display 7014 works without a backlight. Thus, it can display deep black levels and can be thinner and lighter than a liquid crystal display (LCD), making it ideally suitable for use on the handle portion 7002 of the modular motor driven surgical instrument 7000.

In one aspect, the shaft processor 7030 of the electrical subsystem 7008 of the shaft portion 7004 may be implemented as an ultra-low power 16-bit mixed signal MCU, such as the MSP430FR5738 Ultra-low Power MCU provided by Texas Instruments. The shaft processor 7030 is an ultra-low power microcontroller consisting of multiple devices featuring embedded FRAM nonvolatile memory, ultra-low power 16-bit MSP430 CPU, and additional peripherals targeted for various applications. The architecture, FRAM, and peripherals, combined with seven low-power modes, are optimized to achieve extended battery life in portable and wireless sensing applications. FRAM is a new nonvolatile memory that combines the speed, flexibility, and endurance of SRAM with the stability and reliability of flash, all at lower total power consumption. Peripherals include 10-bit A/D converter, 16-channel comparator with voltage reference generation and hysteresis capabilities, three enhanced serial channels capable of I2C, SPI, or UART protocols, internal DMA, hardware multiplier, real-time clock, five 16-bit timers, among other features.

The shaft processor 7030 includes a 16-bit RISC architecture up to 24 MHz clock and operates over a wide supply voltage range of 2 V to 3.6 V and is optimized for ultra-low power modes. The shaft processor 7030 also includes intelligent digital peripherals, an ultra-low power ferroelectric RAM, and up to 16 KB of nonvolatile memory. The embedded microcontroller provides ultra-low power writes, a fast write cycle of 125 ns per word, 16 KB in 1 ms, and includes built in Error Coding and Correction (ECC) and Memory Protection Unit (MPU).

Having described the electrical system, subsystems, and components of the handle and shaft portions 7002, 7004 of the modular motor driven surgical instrument 7000, the functional aspects of the control system will now be described. Accordingly, in operation, the electrical subsystem 7006 of the handle portion 7002 is configured to receive signals from the open switch 7044, close switch 7046, and fire switch 7048 supported on a housing of the handle portion 7002. When a signal is received from the close switch 7046 the handle processor 7024 operates the motor 7038 to initiate closing the clamp arm. Once the clamp is closed, the clamp closed status switch 7052 in the end effector sends a signal to the shaft processor 7030, which communicates the status of the clamp arm to the handle processor 7024 through the communications and power interface 7010.

Once the target tissue has been clamped, the fire switch 7048 may be actuated to generate a signal, which is received by the handle processor 7024. In response, the handle processor 7024 actuates the transmission carriage to its second drive position such that actuation of the motor 7038 will result in the rotation of a second drive shaft, as described in detail above in connection with FIGS. 1-8. Once the cutting member is positioned, the fire begin status switch 7054 located in the end effector sends a signal indicative of the position of the cutting member to the shaft processor 7030, which communicates the position back to the handle processor 7024 through the communications and power interface 7010.

Actuating the first switch 7048 once again sends a signal to the handle processor 7038, which in response actuates the second drive system and the firing system in the end effector to drive the tissue cutting member and wedge sled assembly distally through the surgical staple cartridge. Once the tissue cutting member and wedge sled assembly have been driven to their distal-most positions in the surgical staple cartridge, the fire end switch 7056 sends a signal to the shaft processor 7030 which communicates the position back to the handle processor 7024 through the interface 7010. Now the fire switch 7048 may be activated to send a signal to the handle processor 7024, which operated the motor 7038 in reverse rotation to return the firing system to its starting position.

Actuating the open switch 7044 once again sends a signal to the handle processor 7024, which operates the motor 7038 to open the clamp. Once open, the clamp opened status switch 7050 located in the end effector sends a signal to the shaft processor 7030, which communicates the position of the clamp to the handle processor 7024. The clamp position switch 7034 and the fire position switch 7036 provide signals to the handle processor 7024 that indicate the respective positions of the clamp arm and the cutting member.

FIG. 62 is a table 7060 depicting the total time it takes to complete a stroke and the load current requirements for various operations of various device shafts. The first column 7062 from the left lists circular, contour, and TLC devices/shafts. These devices/shafts are compared over three different operations closing, opening, and firing as shown in the second column 7064. The third column 7066 depicts the total time in seconds required for the device/shaft listed in the first column 7063 to complete one stroke. The fourth column 7068 lists the load current requirements in amperes for the devices/shafts listed in the first column 7062 to complete the operation in the second column 7064 for a complete stroke as indicated in the third column 7066. As indicated in the chart, closing and opening the clamp arm takes about the same time for each of the device/shafts listed in the first column 7062. For the firing operation, the circular device/shaft requires the most load current at 15.69 A and the TLC device/shaft requires the least amount load current at 0.69 A.

Figure 63A:
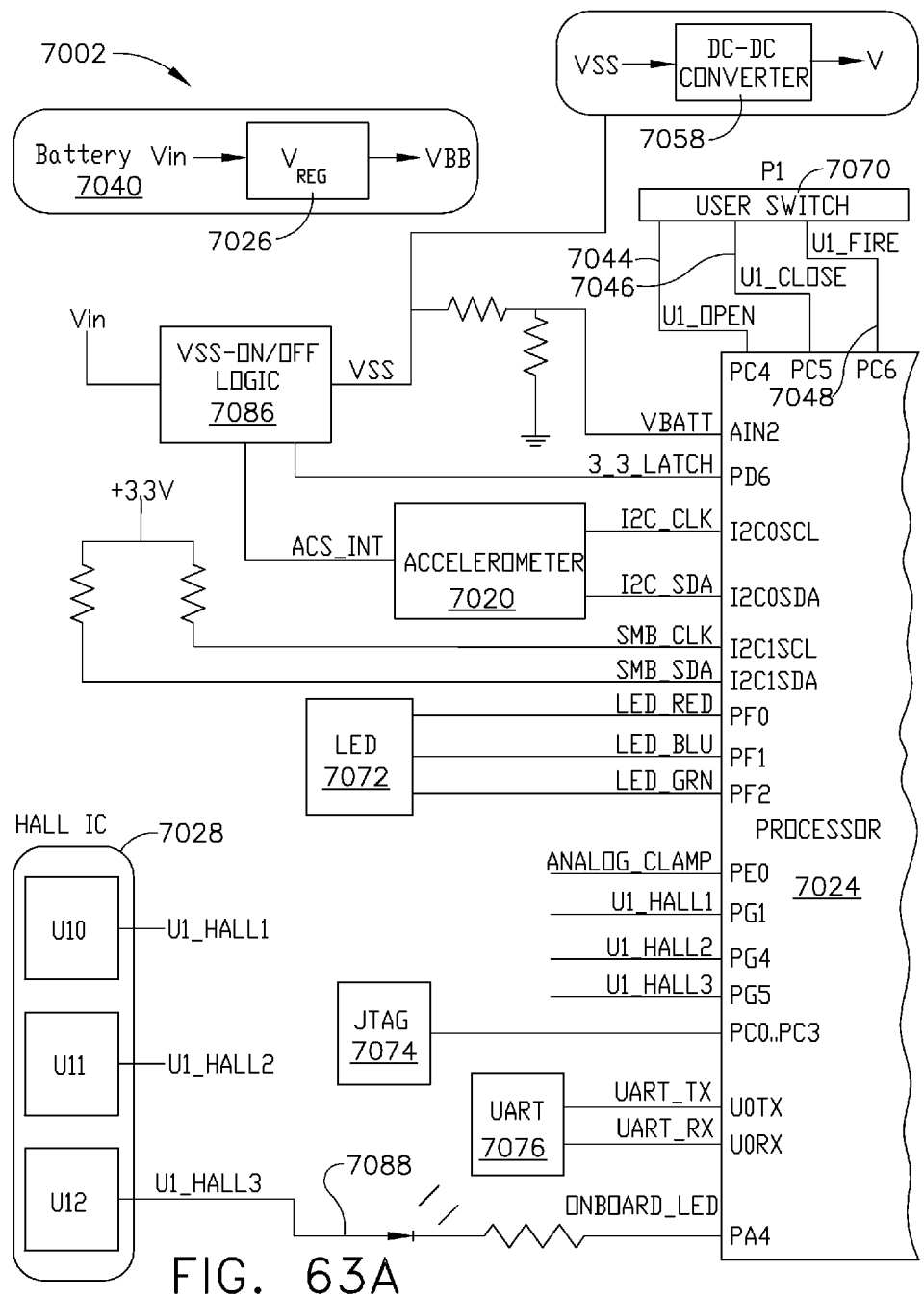
FIG. 63, which is divided into FIGS. 63-A and 63-B, is a detail diagram of the electrical system in the handle portion of the modular motor driven surgical instrument.
Figure 63B:
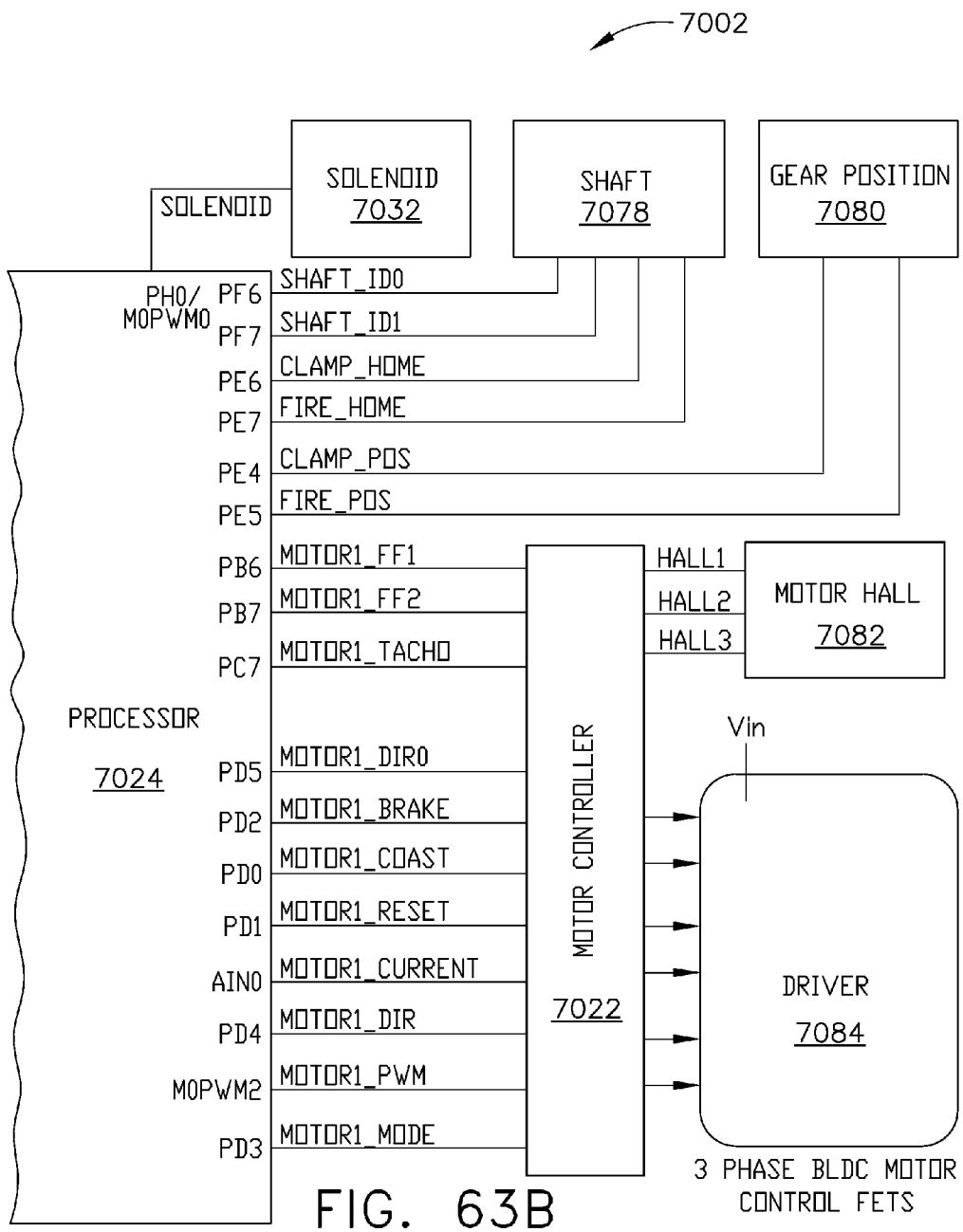

FIG. 63-A is a detail diagram of the electrical system in the handle portion 7002 of the modular motor driven surgical instrument 7000. As shown in FIG. 63-A, the voltage regulator 7026 and DC-DC converter 7058 provide the operating voltages for the electrical system. The voltage regulator 7026 regulates the battery 7040 voltage. The handle processor 7024 receives inputs from the accelerometer 7020. The VSS-ON/OFF Logic supply 7086 provides the input voltage to the handle processor 7024 and the VSS input to the DC-DC converter 7058.

A tri-color LED 7072 is electrically coupled to the handle processor 7024. The handle processor 7024 energizes either the red, blue, or green LED 7072 to provide visual feedback.

Three Hall effect sensor 7028 U10, U11, U12 provide three separate Hall effect outputs U1_Hall1, U1_Hall2, U1_Hall3 which are coupled to the handle processor 7024 as shown. The U1_Hall3 output drives an onboard LED 7088. In one aspect, the Hall effect sensor outputs U1_Hall1, U1_Hall2, U1_Hall3, and the ANALOG_CLAMP signal are coupled to the handle processor 7024 to determine the position of the clamp arm and the cutting member at the end effector portion of the modular motor driven surgical instrument 7000, or the positions of other elements of the instrument 7000.

The user switch 7070 is a representative example of the previously described "rocker-trigger" 110 that is pivotally mounted to a pistol grip portion of the handle. The user switch 7070 is operable to actuate a first motor switch 7044 that is operably coupled to the handle processor 7024. The first motor switch 7044 may comprise a pressure switch which is actuated by pivoting the user switch 7070 into contact therewith. Actuation of the first motor switch 7044 will result in actuation of the motor 7038 such that the drive gear rotates in a first rotary direction. A second motor switch 7046 is also coupled to the handle processor 7024 and mounted for selective contact by the user switch 7070. Actuation of the second motor switch 7046 will result in actuation of the motor 7038 such that the drive gear is rotated in a second direction. A fire switch 7048 is coupled to handle processor 7024. Actuation of the fire switch 7048 results in the axial movement of the transmission carriage to advance the cutting element as was described above.

A Joint Test Action Group (JTAG) 7074 input is also coupled to the handle processor 7024. The JTAG 7074 input is the IEEE 1149.1 Standard Test Access Port and Boundary-Scan Architecture devised for integrated circuit (IC) debug ports. The handle processor 7024 implements the JTAG 7074 to perform debugging operations like single stepping and breakpointing.

A UART 7076 is coupled to the handle processor 7024. The UART 7076 translates data between parallel and serial forms. The UART 7076 is commonly used in conjunction with communication standards such as EIA, RS-232, RS-422 or RS-485. The universal designation indicates that the data format and transmission speeds are configurable. The electric signaling levels and methods (such as differential signaling etc.) are handled by a driver circuit external to the UART 7076. The UART 7076 may be an individual (or part of an) integrated circuit used for serial communications over the serial port of the handle processor 1024. The UART 7076 can be included in the handle processor 1024.

A description of the remaining functional and operational aspects of the electrical subsystem 7006 of the handle portion 7002 of the modular motor driven surgical instrument 7000 will now be provided in connection with FIG. 63-B. As shown, the handle processor 7024 provides a signal to drive the solenoid 7032. A shaft module 7078 provides position signals SHAFT_ID0, SHAFT_ID1, CLAMP_HOME, and FIRE_HOME to the handle processor 7024. A gear position module 7080 provides the position of the clamp and the cutting element to the handle processor 7024. The positional information provided by the shaft module 7078 and the gear position module 7080 enable the handle processor 7024 to properly activate the motor 7038 when the user switch 7070 signals are received to open the clamp, close the clamp, and/or fire the cutting element.

The motor controller 7022 receives commands from the handle processor 7024 and provides commands to the MOS-FET driver 7084, which drives the 3-phase BLDC motor 7038 (FIG. 61). As previously described, the BLDC motor controller 7022 must direct the rotation of the rotor. Accordingly, the BLDC motor controller/driver 7022 determines the position/orientation of the rotor relative to the stator coils. Accordingly, the rotor part of the BLDC motor 7038 is configured with Hall effect sensors 7028 to directly measure the position of the rotor. The BLDC motor controller 7022 contains 3 bi-directional outputs (i.e., frequency controlled three phase output), which are controlled by a logic circuit.

Accordingly, as described in FIGS. 61, 63-A, 63-B, and 64 a motor control system comprising the motor controller 7022, the motor driver 7084, the motor Hall effect sensors 7028 in combination with the gear position module 7080 and/or the shaft module 7078 is operable to synchronize the gears such that the male couplers in the handle portion smoothly couple with the female couplers in the shaft portion of the surgical instruments described herein. In one instance, for example, although some tolerances may be provided for ease of shifting or keying, the motor control system is configured to track the position of the gears to ensure that the gears do not stop in a position that would prohibit shifting from one to the other or installing the two rotary keyings. In another instance, the motor may be configured to be slowly indexed during installation or shifting to resolve any minor out of synchronization conditions. These same issues may be encountered with the example described in connection with FIG. 6 when the instrument shifts between two drives and not just when installing new end-effectors. This situation may be resolved by proper synchronization of the gears employing the motor control system described in connection with FIGS. 61, 63-A, 63-B, and 64. In other instances, encoders may be provided to track the rotations of the gears/gear shafts.

Figure 64:
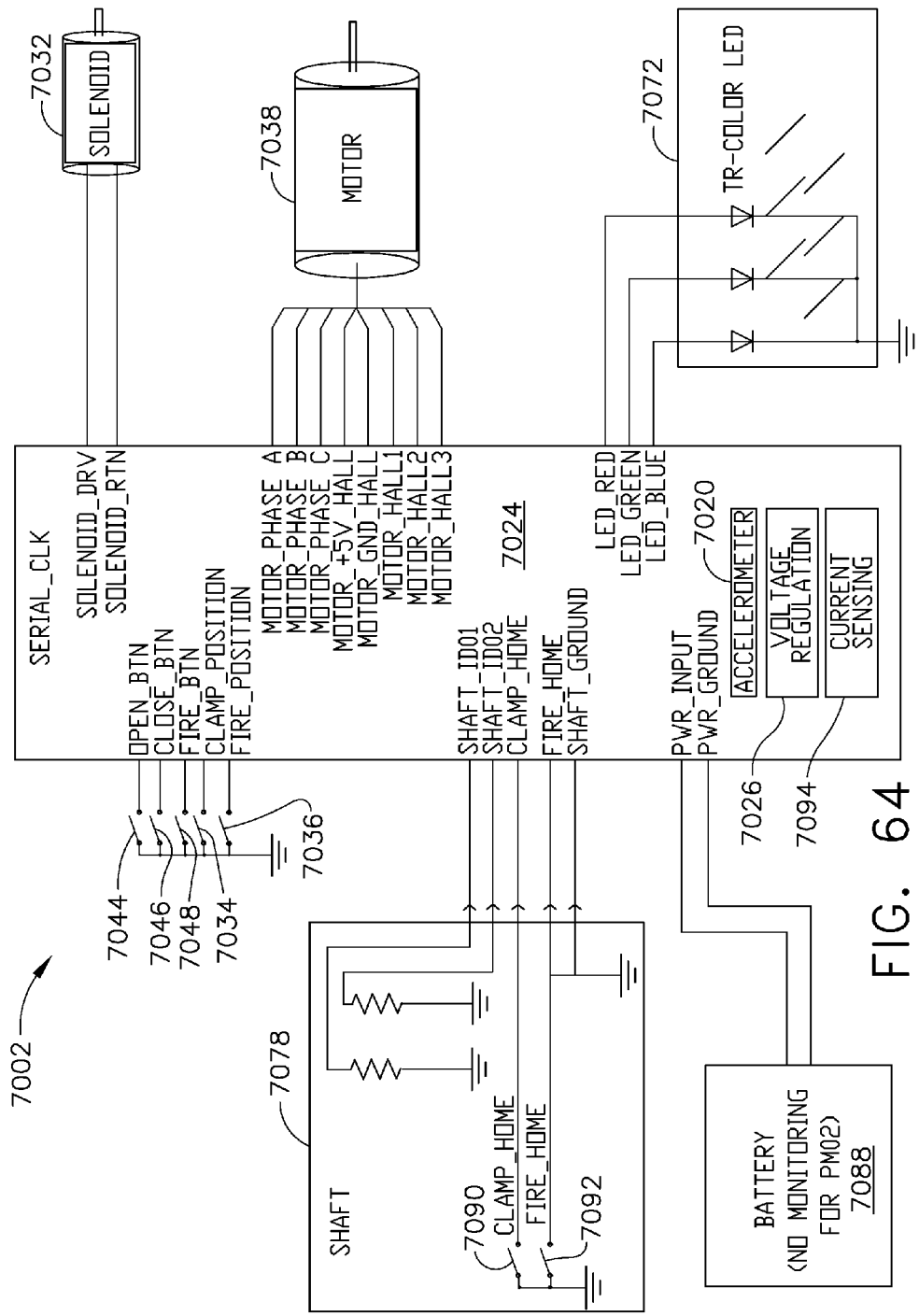
FIG. 64 is block diagram of the electrical system of the handle and shaft portions of the modular motor driven surgical instrument.

FIG. 64 is block diagram of the electrical system of the handle and shaft portions of the modular motor driven surgical instrument. As shown in FIG. 64, the handle processor 7024 receives inputs from the open switch 7044, close switch 7046, fire switch 7048, clamp position switch 7034, and fire position switch 7036. In addition, the handle processor 7024 receives inputs from a clamp home switch 7090 and a fire home switch 7092 from the shaft module 7078. Using various combinations of these switch inputs, the handle processor 7024 provides the proper commands to the motor 7038 and the solenoid 7032. A battery monitoring circuit 7088 monitors the power input to the handle processor 7024 relative to ground. The handle processor 7024 drives the tri-color LED 7072. The accelerometer 7020 provides three-axis orientation inputs to the handle processor 7024 to determine various parameters such as orientation of the instrument 7000 and whether the instrument 7000 has been dropped. The voltage regulator 7026 provides the regulated power supply for the system. A current sensing module 7094 is provided to sense the current drawn from the power supply.

Figure 65:
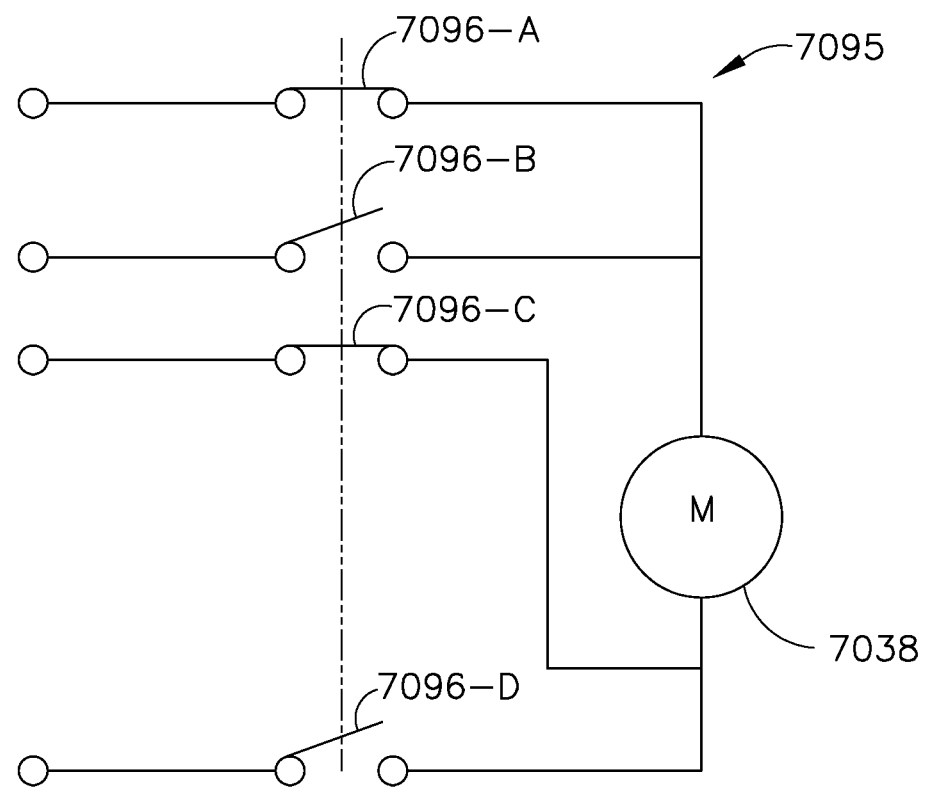
FIG. 65 illustrates a mechanical switching motion control system to eliminate microprocessor control of motor functions.

FIG. 65 illustrates a mechanical switching motion control system 7095 to eliminate microprocessor control of motor functions. In the system described in connection with FIGS. 61-64, a microprocessor such as the handle processor 7024 is employed to control the function of the motor 7038. The handle processor 7024 executes a control algorithm based on the various states of the switches deployed throughout the instrument 7000. This requires the use of the handle processor 7024 and associated identification functions to provide control for different end effectors.

As shown in FIG. 65, however, an alternative technique may be employed to control the motor 7038 that eliminates the need for the handle processor 7024 by placing motion related switched 7096A, 7096B, 7096C, 7096D in the end effector shaft. The switches 7096A-D are then configured to turn on and off specific functions of the motor 7038 or to reverse the direction of the motor 7038 based on where specific end effector components are positioned. In one instance, a switch that indicates full deployment of the cutting member could be employed to switch the functions of the motor 7038 to reverse direction and withdraw the cutting member. In another instance, the switches 7096A-D could be configured to detect pressure or force such that a simple closure of the anvil down on the tissue would provide an on/off signal back to the closure motor 7038 to stop the closure motion.

In various instances, a surgical instrument can include a handle, an electric motor positioned within the handle, a shaft attachable to the handle, and an end effector extending from the shaft, wherein the electric motor is configured to motivate an end effector function at the end effector. In some instances, the surgical instrument can include a control system comprising one or more sensors and a microprocessor which can receive input signals from the sensors, monitor the operation of the surgical instrument, and operate the electric motor to perform the end effector function in view of the sensor input signals. In at least one such instance, the handle of the surgical instrument can be usable with more than one shaft. For instance, a linear stapling shaft or a circular stapling shaft could be assembled to the handle. The handle can include at least one sensor configured to detect the type of shaft that has been assembled thereto and communicate this information to the microprocessor. The microprocessor may operate the electric motor differently in response to the sensor input signals depending on the type of the shaft that has been assembled to the handle. For instance, if the electric motor is configured to operate a closing system of the end effector, the microprocessor will rotate the electric motor in a first direction to close an anvil of the circular stapler shaft and a second, or opposite, direction to close an anvil of the linear stapler shaft. Other control systems are envisioned in which the same operational control of the electric motor can be achieved without the use of a microprocessor. In at least one such instance, the shafts and/or the handle of the surgical instrument can include switches which can operate the surgical instrument differently depending on the type of the shaft that has been assembled to the handle.

In various instances, a surgical instrument system can include a power source, a first motor configured to perform a first end effector function, a second motor configured to perform a second end effector function, and a control system of switches configured to selectively place the power source in communication with the first motor and the second motor in response to the control system of switches. In various instances, such a surgical instrument system may not include a microprocessor. The first motor can comprise a closing motor of a closing system configured to close an anvil of the end effector and the second motor can comprise a firing motor of a firing system configured to fire staples from a staple cartridge of the end effector. The control system of switches can include a closure trigger switch which, when closed, can close a closure power circuit which couples the power source to the closing motor. The control system can further include a closure end-of-stroke switch which can be opened by the closure system when the anvil is in a fully closed position and open the closure power circuit to stop the closing motor and the closure drive. The control system of switches can also include a firing trigger switch which can be part of a firing power circuit which couples the power source to the firing motor. In various circumstances, the default condition of the firing power circuit can be open which can prevent the firing motor from being operated prior to firing power circuit being closed. Thus, closing the firing switch alone may not close the firing power circuit and operate the firing motor. The firing power circuit can further include a second closure end-of-stroke switch which can be closed by the closure system when the anvil is in a fully closed position. Closing the firing switch and the second closure end-of-stroke switch may close the firing power circuit and operate the firing motor. The control system can further include a firing end-of-stroke switch can be opened by the firing drive when the firing drive reaches the end of its firing stroke. The opening of the firing end-of-stroke switch can open the firing power circuit and stop the firing motor. The control system can further include a second firing end-of-stroke switch witch can be closed by the firing drive to close a reverse firing power circuit which reverses the polarity of the power applied to the firing motor and operates the firing motor in an opposite direction and retracts the firing drive. Closing the reverse firing power circuit may also require the firing trigger switch to be in a closed condition. When the firing drive reaches its fully-retracted position, it can close a proximal firing switch. The closure of the proximal firing switch can close a reverse closing power circuit which can reverse the polarity of the power applied to the closing motor and operate the closing motor in an opposite direction and open the anvil. Closing the reverse closure power circuit may also require the closure trigger switch to be in a closed condition. When the anvil reaches its fully-open position, the anvil can open a proximal closure switch which can open the reverse closing power circuit and stop the closing motor. This is but one example.

In various instances, as described herein, a handle of a surgical instrument can be used with several different shaft assemblies which can be selectively attached to the handle. In some instances, as also described herein, the handle can be configured to detect the type of shaft that has been assembled to the handle and operate the handle in accordance with a control system contained within the handle. For instance, a handle can include a microprocessor and at least one memory unit which can store and execute a plurality of operating programs, each of which are configured to operate a specific shaft assembly. Other embodiments are envisioned in which the handle does not include a control system; rather, the shaft assemblies can each comprise their own control system. For instance, a first shaft assembly can comprise a first control system and a second shaft assembly can comprise a second control system, and so forth. In various instances, the handle may comprise an electrical motor, a power source, such as a battery and/or an input cable, for example, and an electrical circuit configured to operate the electrical motor based on control inputs from the attached shaft assembly. The handle may further comprise an actuator which, in conjunction with the shaft control system, may control the electrical motor. In various instances, the handle may not comprise additional control logic and/or a microprocessor, for example, for controlling the electrical motor. With the exception of the handle actuator, the control system of the shaft assembly attached to the handle would include the control logic needed to operate the electrical motor. In various instances, the control system of the shaft assembly may include a microprocessor while, in other instances, it may not. In some instances, the first control system of a first shaft assembly can include a first microprocessor and the second control system of a second shaft assembly can include a second microprocessor, and so forth. In various instances, a handle can include a first electrical motor, such as a closing motor, for example, and a second electrical motor, such as a firing motor, for example, wherein the control system of the attached shaft assembly can operate the closing motor and the firing motor. In certain instances, the handle can comprise a closing actuator and a firing actuator. With the exception of the closing actuator and the firing actuator, the control system of the shaft assembly attached to the handle would include the control logic needed to operate the closing motor and the firing motor. In various instances, a handle can include a shaft interface and each shaft assembly can include a handle interface configured to engage the shaft interface. The shaft interface can include an electrical connector configured to engage an electrical connector of the handle interface when a shaft assembly is assembled to the handle. In at least one instance, each connector may comprise only one electrical contact which are mated together such that only one control path is present between the handle and the shaft assembly. In other instances, each connector may comprise only two electrical contacts which form two mated pairs when the shaft assembly is attached to the handle. In such instances, only two control paths may be present between the handle and the shaft assembly. Other embodiments are envisioned in which more than two control paths are present between the handle and the shaft assembly.

Figures 73, 74:
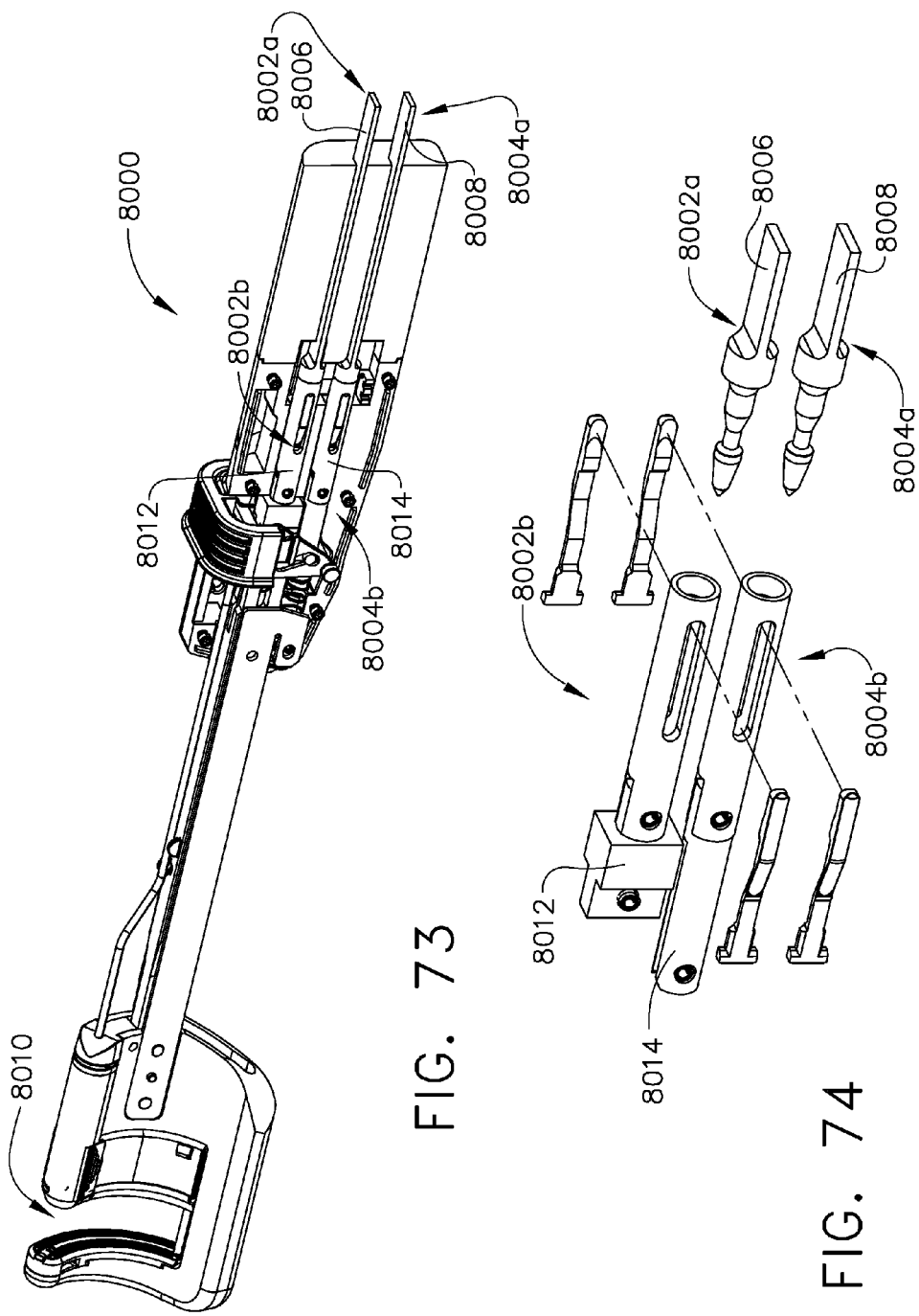
FIG. 73 is a cross-sectional, perspective view of a surgical end effector attachment for use with a surgical instrument handle, according to various embodiments of the present disclosure.
FIG. 74 is an exploded, perspective view of drive systems of the surgical end effector attachment of FIG. 73, according to various embodiments of the present disclosure.
Figure 75:
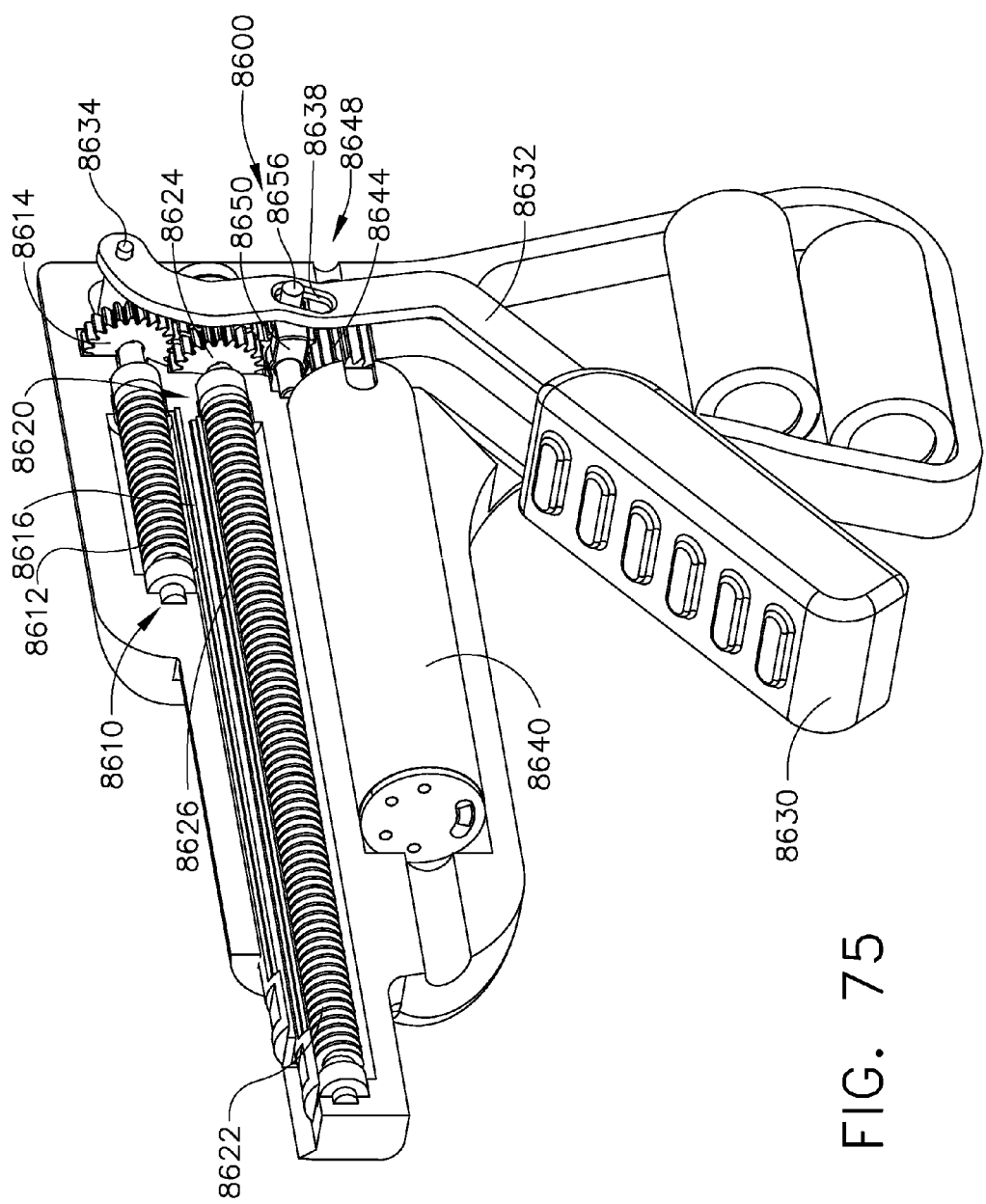
FIG. 75 is a perspective view of a handle for a surgical instrument, wherein the handle comprises a drive system having a first output drive assembly and a second output drive assembly, according to various embodiments of the present disclosure.
Figure 76:
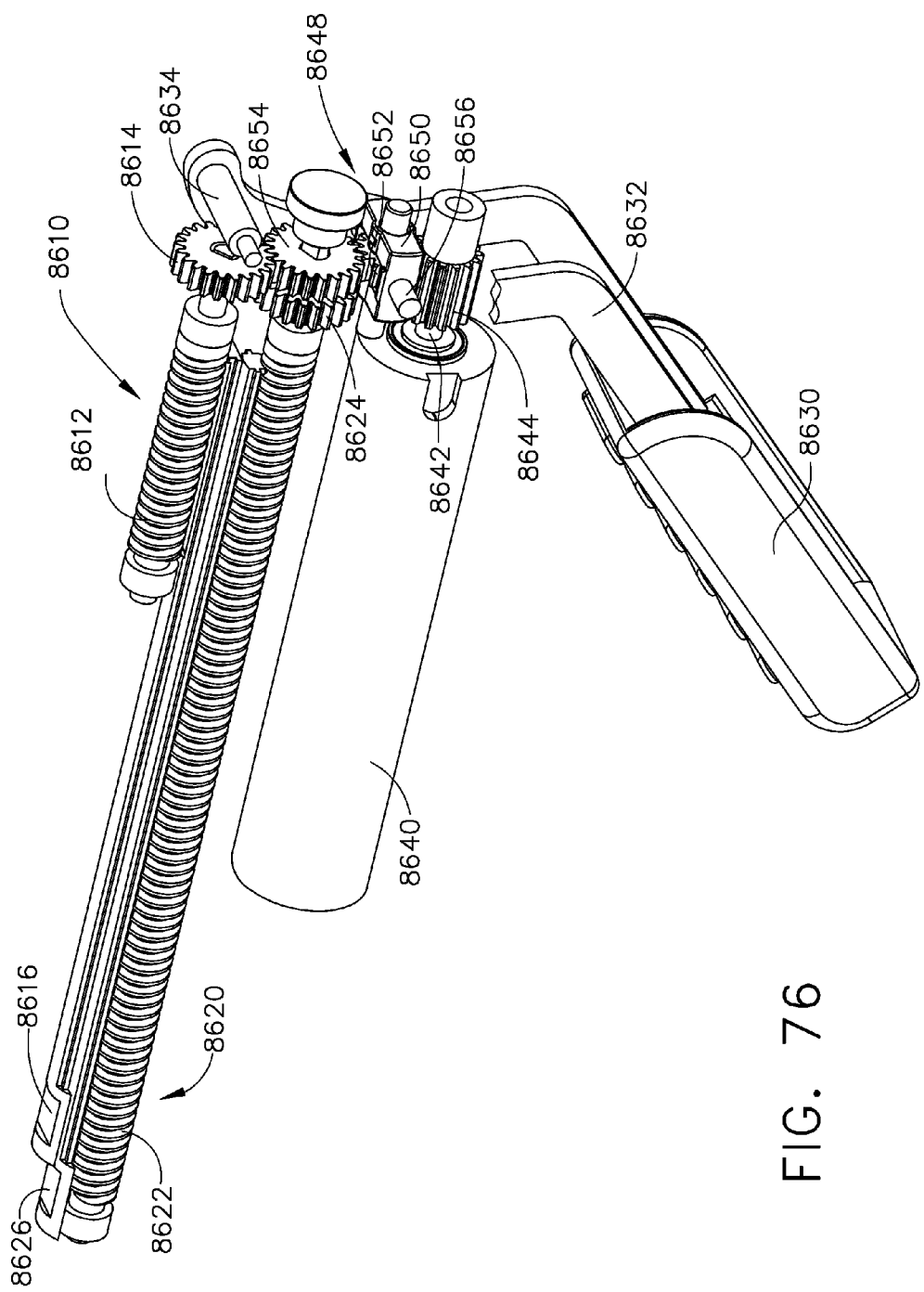
FIG. 76 is a perspective view of the drive system of FIG. 75, according to various embodiments of the present disclosure.
Figure 77:
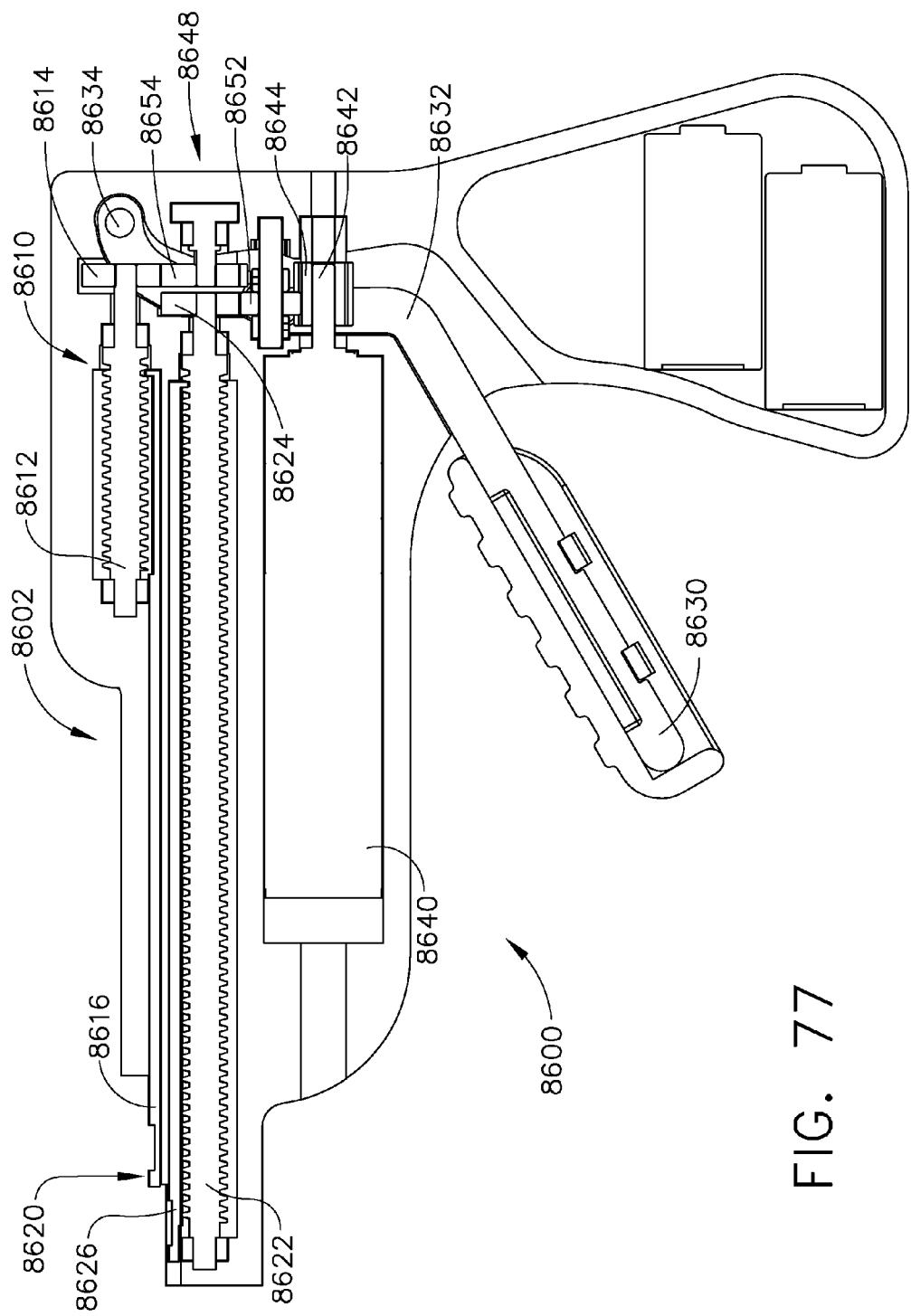
FIG. 77 is a cross-sectional, elevation view of the handle of FIG. 75, depicting the drive system engaged with the first output drive assembly and disengaged from the second output drive assembly, according to various embodiments of the present disclosure.
Figure 78:
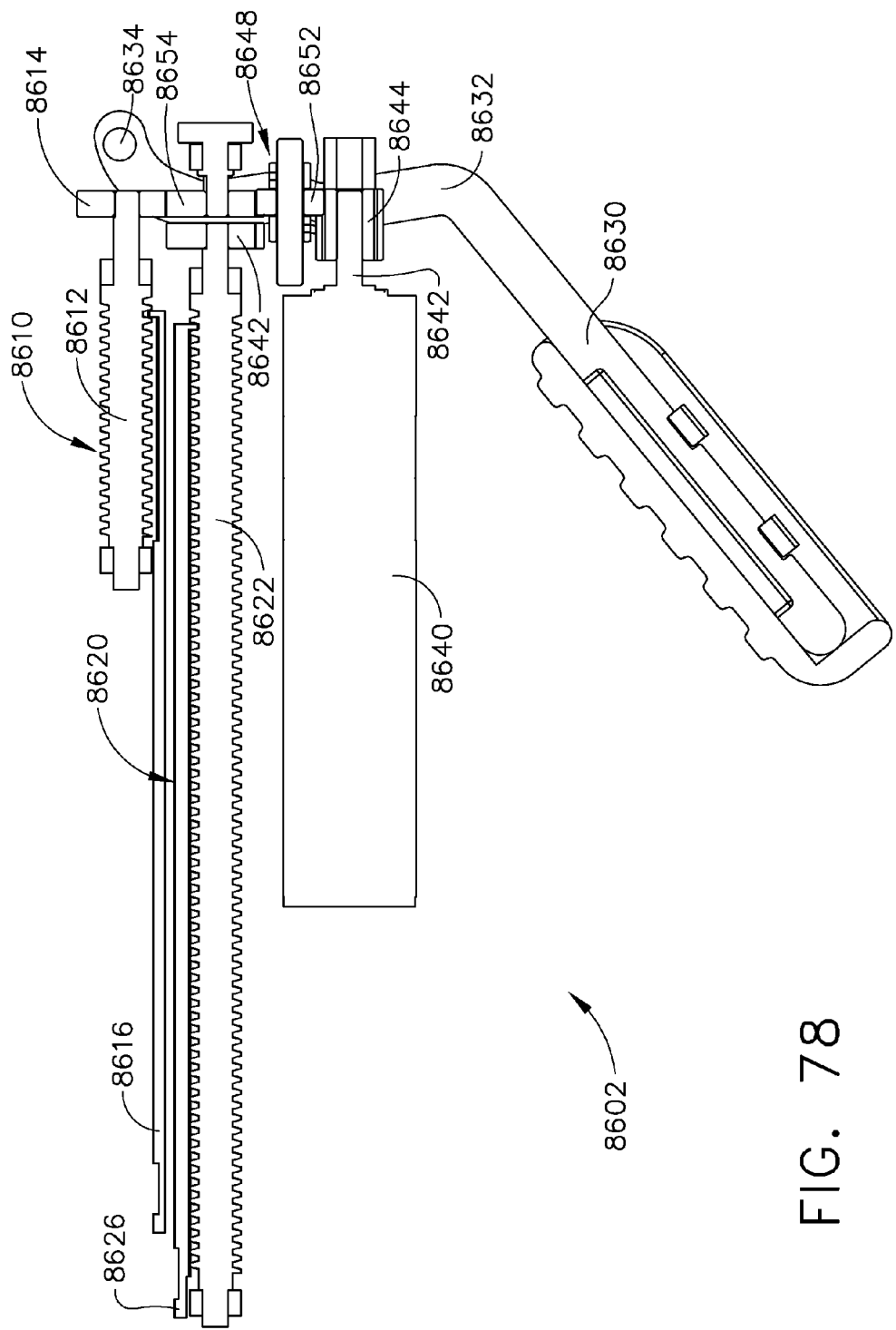
FIG. 78 is a cross-sectional, elevation view of the drive system of FIG. 75, depicting the drive system engaged with the second output drive assembly and disengaged from the first output drive assembly, according to various embodiments of the present disclosure.

In various instances, surgical end effector attachments can be compatible with a surgical instrument handle. For example, a surgical end effector can be coupled to the handle of a surgical instrument and can deliver and/or implement a drive motion that was initiated in the handle of the surgical instrument. Referring to FIGS. 73 and 74, the surgical end effector 8010 can be one of the several surgical end effectors that can be compatible with the handle 8000 of a surgical instrument. Various different surgical end effectors are described throughout the present disclosure and are depicted throughout the associated figures. The reader will appreciate that these various, different surgical end effectors described and depicted herein may be compatible with the same surgical instrument handle and/or can be compatible with more than one type of surgical instrument handle, for example.

The handle 8000 can include drive systems, for example, which can be configured to transfer a drive motion from the handle 8000 of the surgical instrument to a component, assembly and/or system of the end effector 8010. For example, the handle 8000 can include a first drive system 8002a and a second drive system 8004a. In certain instances, one of the drive systems 8002a, 8004a can be configured to deliver a closing drive motion to the jaw assembly of the end effector 8010 (FIG. 73), for example, and one of the drive systems 8002a, 8004a can be configured to deliver a firing drive motion to a firing element in the end effector 8010, for example. The drive systems 8002a, 8004a can be configured to transfer a linear motion, displacement, and/or translation from the handle 8000 to the end effector 8010. In various instances, the first drive system 8002a can include a drive bar 8006, which can be configured to translate and/or be linearly displaced upon activation of the first drive system 8002a. Similarly, the second drive system 8004a can include a drive bar 8008, which can be configured to translate and/or be linearly displaced upon activation of the second drive system 8004a.

In various instances, the end effector assembly 8010 can include a first drive system 8002b, which can correspond to the first drive system 8002a of the handle 8000, for example, and can also include a second drive system 8004b, which can correspond to the second drive system 8004a of the handle 8000, for example. In various instances, the first drive system 8002b in the end effector 8010 can include a drive element 8012, which can be operably and releasably coupled to the drive bar 8006 of the first drive system 8002a of the handle 8000, for example, and can be configured to receive a linear motion from the drive bar 8006, for example. Additionally, the second drive system 8004b of the end effector 8010 can include a drive element 8014, which can be operably and releasably coupled to the drive bar 8008 of the second drive system 8004a of the handle 8000, for example, and can be configured to receive a linear motion from the drive bar 8008, for example.

In various instances, the handle 8000 and/or the end effector 8010 can include a coupling arrangement, which can be configured to releasably couple the drive bar 8006 to the drive element 8012, for example, and/or the drive bar 8008 to the drive element 8014, for example. In other words, the coupling arrangement can couple the first drive system 8002a of the handle 8000 to the first drive system 8002b of the end effector 8010 and the second drive system 8004a of the handle 8000 to the second drive system 8004b of the end effector 8010 such that a drive force initiated in the handle 8000 of the surgical instrument can be transferred to the appropriate drive system 8002b, 8004b of the attached surgical end effector 8010. Though the surgical system depicted in FIGS. 73 and 74 includes a pair of drive systems 8002a, 8004a in the handle 8000 and a corresponding pair of drive system 8002b, 8004b in the end effector 8010, the reader will appreciate that the various coupling arrangements disclosed herein can also be used in a surgical end effector and/or handle comprising a single drive system or more than two drive systems, for example.

In various instances, a coupling arrangement for coupling a drive system in the handle of a surgical instrument to a drive system in an attached end effector can include a latch, which can be configured to retain and secure the connection between the corresponding handle and end effector drive systems. As described in greater detail herein, the latch can be spring-loaded, and can be coupled to a trigger, for example, which can be configured to operably overcome the bias of a spring to unlock, open, and/or release the coupling arrangement, for example. In various instances, the coupling arrangement can include independent and/or discrete coupling mechanisms and/or joints for each drive system 8002b, 8004b in the surgical end effector 8010. In such instances, one of the drive systems 8002b, 8004b can be activated without activating the other drive system 8002b, 8004b. In other instances, the drive systems 8002b, 8004b can be activated simultaneously and/or concurrently, for example.

Referring now to FIGS. 66-72, a coupling arrangement 8100 for use with a surgical end effector is depicted. For example, a surgical end effector can be attached to a handle 8170 (FIGS. 67-69) of a surgical instrument via the coupling arrangement 8100, for example. In various instances, the coupling arrangement 8100 can include a coupler housing or frame 8102, for example. The coupler housing 8102 can be positioned within a proximal attachment portion of the end effector, for example. Additionally, the coupler housing 8102 can include a carriage 8104, for example, which can be configured to move relative to the coupler housing 8102, for example. For example, the coupler housing 8102 can include a channel 8103, which can be dimensioned and structured to receive the slidable and/or shiftable carriage 8104. For example, the carriage 8104 can be restrained by the coupler housing 8102, such that the carriage 8104 is movably held in the channel 8103 and is configured to move and/or slide within the channel 8103. The channel 8103 can guide and/or restrain movement of the carriage 8014 relative to the housing 8102, for example. In certain instances, the carriage 8104 can have a ramped surface, such as a ramp or wedge 8106, for example, which can further guide and/or facilitate movement of the carriage 8104, for example.

In various instances, the coupling arrangement 8100 can include a trigger 8120 in sliding engagement with the ramp 8106 of the carriage 8104. For example, the trigger 8120 can include an inclined surface 8122 that is configured to slide along the ramp 8106 of the carriage 8104 when the trigger 8120 is moved between a first, or unactuated, position (FIG. 68) and a second, or actuated, position (FIGS. 67 and 69), for example. In certain instances, the coupling arrangement 8100 can include a guide, such as guide rails 8110, for example, which can be positioned and structured to guide the trigger 8120 between the first, unactuated position and the second, actuated position, for example. For example, the coupler housing 8102 can include a pair of guide rails 8110, which can define an actuation path for the trigger 8120.

In various instances, when the trigger 8120 is moved along the actuation path defined by at least one guide rail 8110 in a direction $D_1$ (FIGS. 67 and 69) from the unactuated position (FIG. 68) to the actuated position (FIGS. 67 and 69), for example, the carriage 8104 can be shifted downward or in a direction $D_3$ (FIGS. 67 and 69) within the channel 8103 via the inclined surface 8122 of the trigger 8120 and the ramp 8106 of the carriage 8104. Accordingly, activation of the trigger 8120 can shift the carriage 8104 relative to the coupler housing 8102, trigger 8120 and/or various other components, assemblies, and/or systems of the coupling arrangement 8100, for example.

In various instances, when the trigger 8120 is moved along at least one guide rail 8110 in a direction $D_2$ (FIG. 68) from the actuated position (FIGS. 67 and 69) to the unactuated position (FIG. 68), for example, the carriage 8104 can be shifted upward or in a direction $D_4$ (FIG. 68) within the channel 8103 via the inclined surface 8122 of the trigger 8120 and the ramp 8106 of the carriage 8104. Accordingly, actuation of the trigger 8120 can affect movement of the carriage 8104 relative to the coupler housing 8102, for example. In certain instances, a spring and/or other biasing mechanism can be configured to bias the carriage 8104 and/or the trigger 8120 toward a predefined position relative to the channel 8103 and/or the coupler housing 8102, for example.

Figure 66:
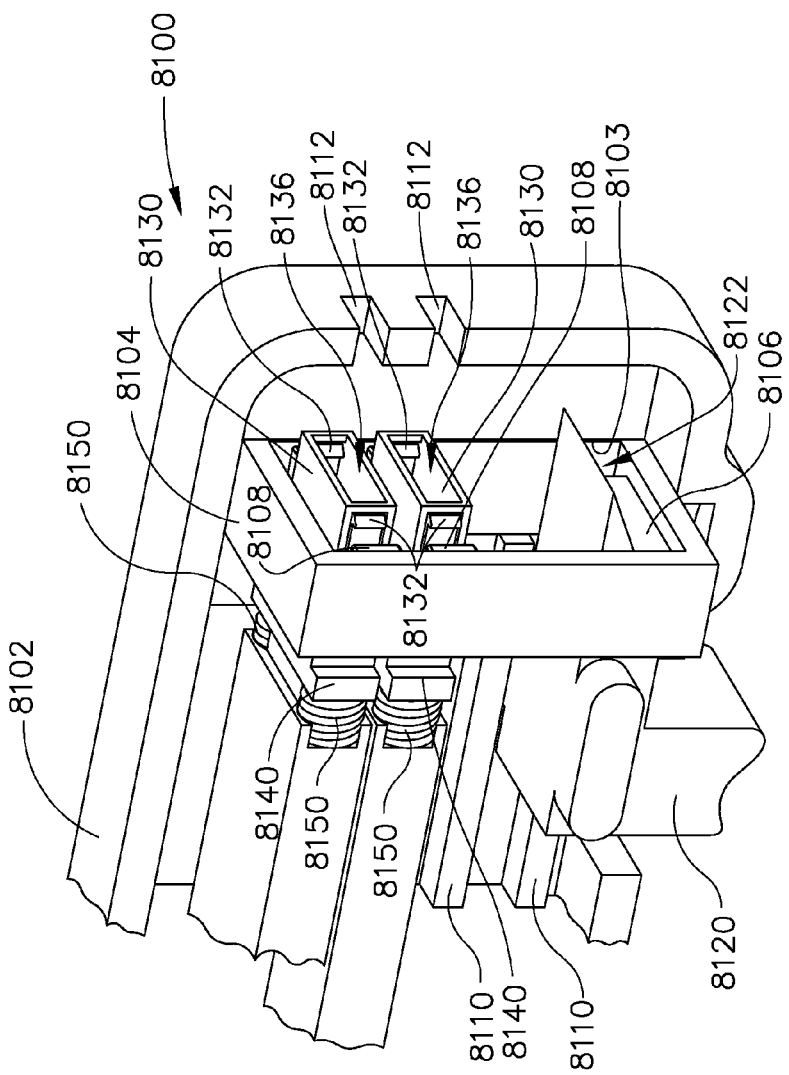
FIG. 66 is a perspective view of a coupling arrangement comprising a coupler housing and a pair of sockets positioned within the coupler housing, according to various embodiments of the present disclosure.

Referring now to FIG. 66, in various instances, a slot 8112 can be defined in the coupler housing 8102 and/or the end effector. The slot 8112 can be dimensioned to receive a drive member 8172 of the handle 8170 of a surgical instrument, for example. In certain instances, a pair of slots 8112 can be defined in the coupler housing 8102, and each slot 8112 can be configured to receive one of the drive members 8172 of the handle 8170, for example. As described in greater detail herein, the drive members 8172 can be coupled to and/or otherwise driven by a drive system in the handle 8170. For example, each drive member 8172 can be coupled to and/or otherwise driven by a linear actuator of a drive system in the handle 8170, which can be configured to translate and deliver a linear drive motion to the corresponding drive system in the end effector, for example.

Figure 71:
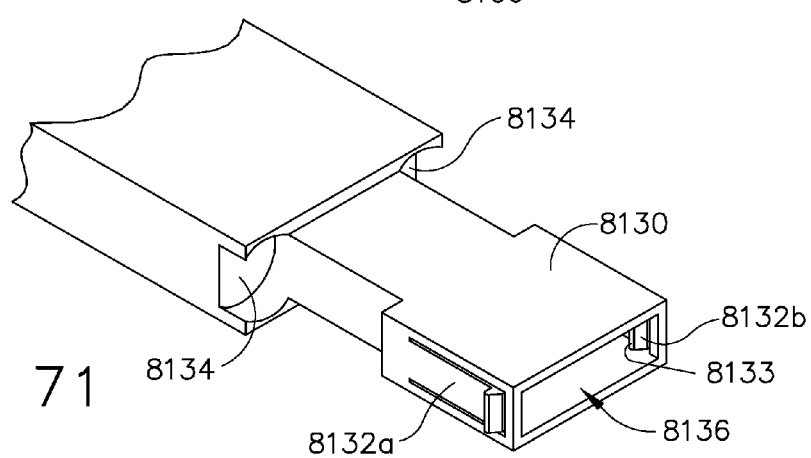
FIG. 71 is a perspective view of a socket of the coupling arrangement of FIG. 66, according to various embodiments of the present disclosure.
Figure 72:
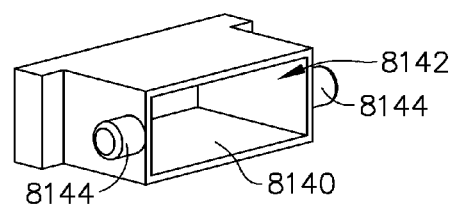
FIG. 72 is a perspective view of a latch of the coupling arrangement of FIG. 66, according to various embodiments of the present disclosure.

In various instances, the carriage 8104 can also be configured to move and/or shift relative to a drive member socket 8130 of the coupling arrangement 8100. The drive member socket 8130 can be configured to receive one of the drive members 8172 from the handle 8170, for example. Referring primarily to FIG. 71, the socket 8103 can include an opening 8136, which can be dimensioned and/or structured to receive a drive system component of the handle 8170. For example, referring primarily to FIG. 67, the opening 8136 can be configured to receive a distal portion of the drive bar 8172. In such instances, when the drive bar 8172 is secured within the opening 8136 in the socket 8130, as described in greater detail herein, the socket 8130 can be configured to transfer a drive force from the handle 8170 to the surgical end effector via the drive bar 8172 and socket 8130 engagement, for example.

Figure 67:
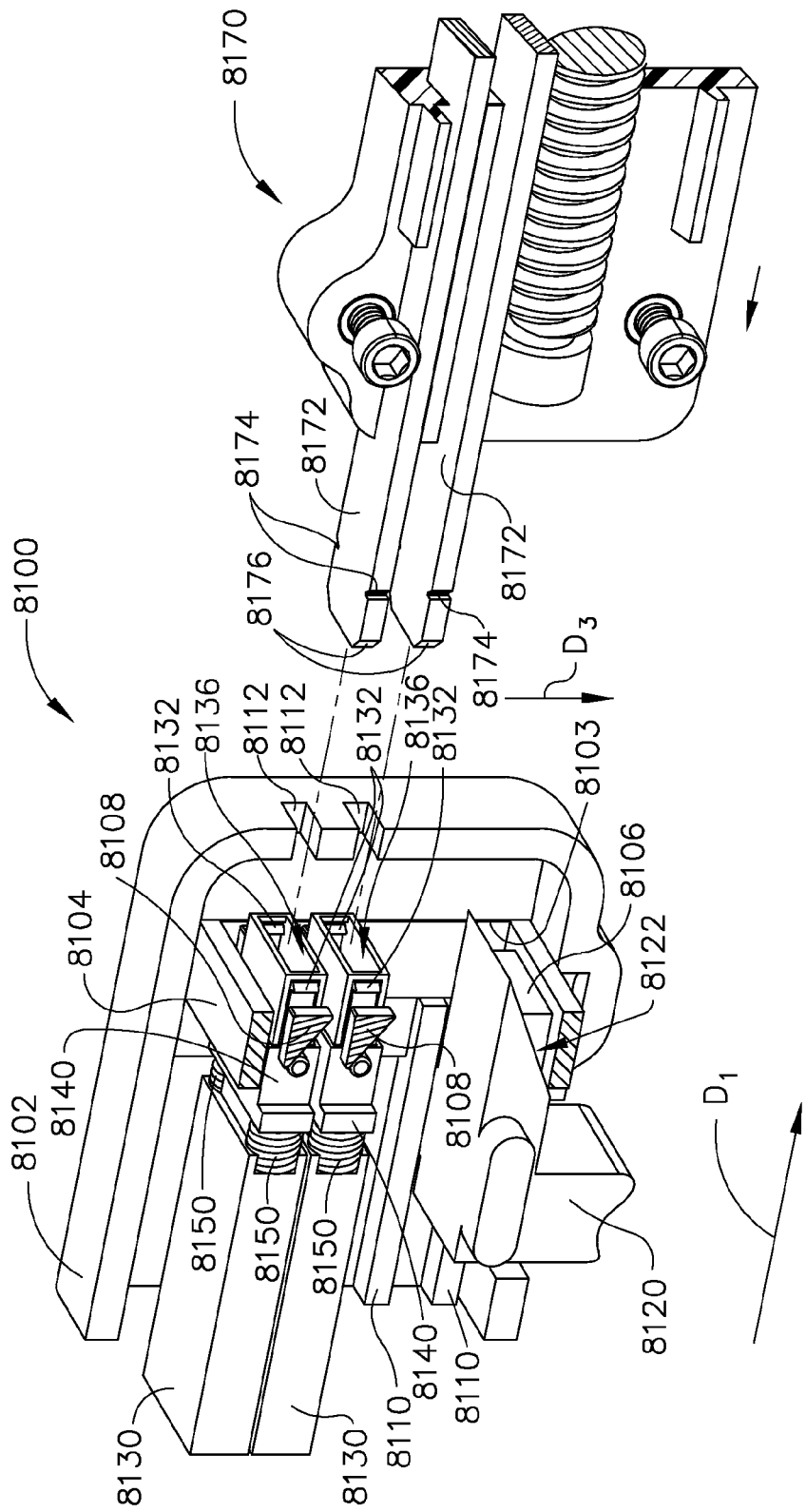
FIG. 67 is a cross-sectional, perspective view of the coupling arrangement of FIG. 66, depicting a pair of drive members uncoupled to the pair of sockets and further depicting the coupling arrangement in an unlocked configuration, according to various embodiments of the present disclosure.

Referring still to FIG. 67, the drive bar 8172 can include a bevel 8176 and a groove or divot 8174, for example, which can facilitate engagement and/or locking of the drive bar 8172 to the socket 8130. In various instances, the drive member socket 8130 can be secured and/or fixed within the end effector and/or within the coupler housing 8102, for example, and the carriage 8104 can be configured to move and/or shift relative to and/or around the socket 8130 when the carriage 8104 slides within the channel 8103 in the coupler housing 8102.

Referring primarily to FIG. 71, the socket 8130 can include at least one flexible tab 8132a, 8132b. The flexible tab 8132a, 8132b can be inwardly biased toward the opening 8136 and/or can include an inwardly-biased tooth, for example. In certain instances, the flexible tab 8132a, 8132b can include the tooth 8133, for example, which can be configured to engage the groove 8174 in the drive bar 8172 when the drive bar 8172 is inserted into the opening 8136 in the socket 8130. For example, the bevel 8176 of the drive bar 8172 can pass by the tooth 8133 within the socket opening 8136, and can flex or deflect the tab 8132 outward from the opening 8136. As the drive bar 8172 continues to enter the opening 8136 of the socket 8130, the tooth 8136 of the tab 8132*a*, 8132*b* can engage or catch the groove 8174 in the drive bar 8172. In such instances, the tooth 8136-groove 8174 engagement can releasably hold the drive bar 8172 within the socket 8130, for example.

In various instances, the socket 8130 can include a recess 8134, which can be configured to receive a spring 8150, for example. In other instances, the socket 8136 can include more than one recess 8134, and the coupling arrangement 8100 can include more than one spring 8150, for example. Moreover, in certain instances, the socket 8130 can include more than one flexible tab 8132*a*, 8132*b*. For example, the socket 8130 can include a pair of laterally-positioned tabs 8132*a*, 8132*b*. A first tab 8132*a* can be positioned on a first lateral side of the socket 8130, for example, and a second tab 8132*b* can be positioned on a second lateral side of the socket 8130, for example. In certain instances, the tabs 8132*a*, 8132*b* can be deflected outward from the opening 8136 to accommodate entry of the drive bar 8172, for example. In other instances, the socket 8130 may not include an inwardly-biased tab and/or can include more than two tabs, for example.

Figure 68:
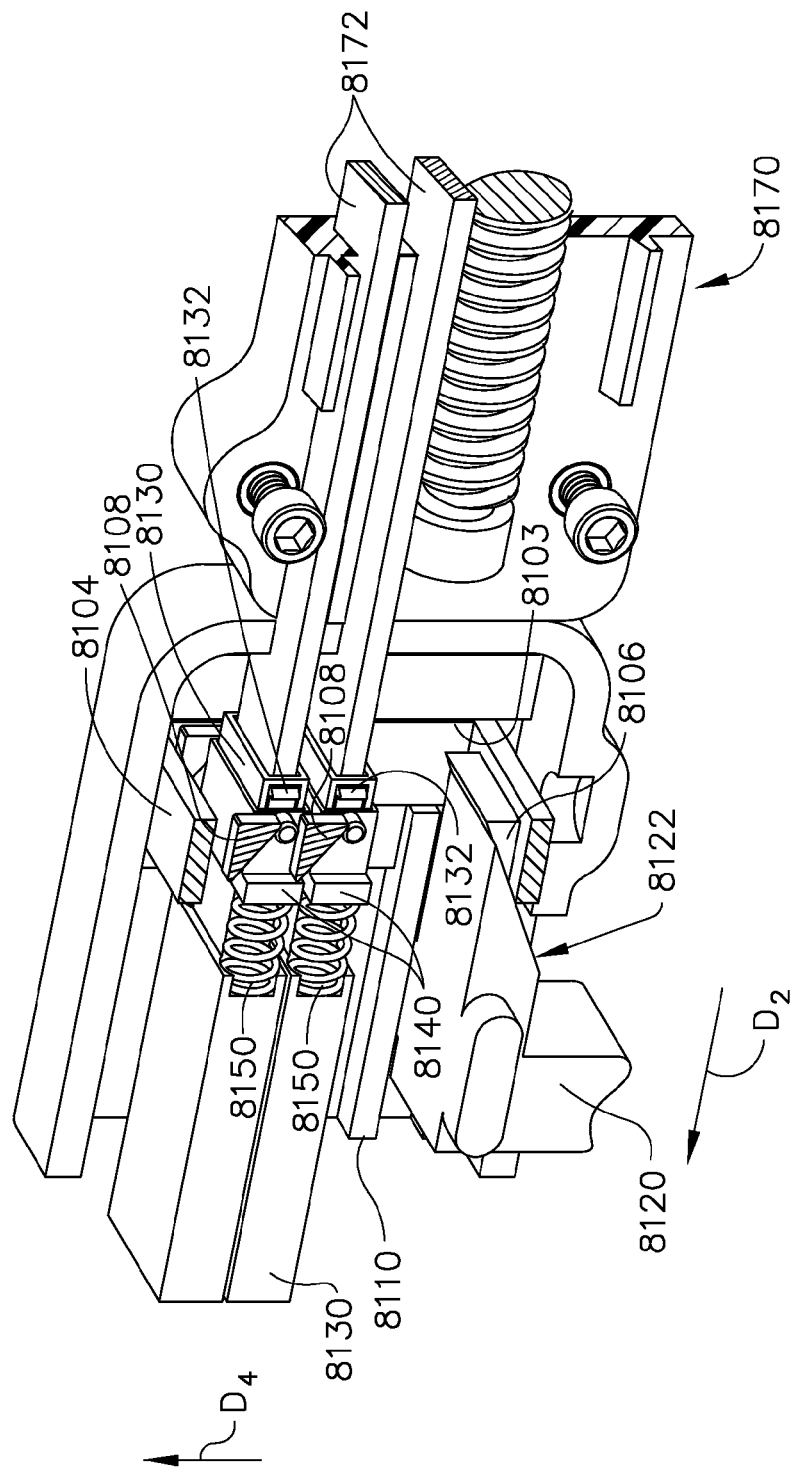
FIG. 68 is a cross-sectional, perspective view of the coupling arrangement of FIG. 66, depicting the pair of drive members coupled to the pair of sockets and further depicting the coupling arrangement in a locked configuration, according to various embodiments of the present disclosure.

In various instances, the coupling arrangement 8100 can also include a latch or sleeve 8140, which can be movably positioned relative to the socket 8130. For example, the latch 8140 can include an opening 8142 (FIG. 72), which can be dimensioned and structured to at least partially surround at least a portion of the socket 8130. For example, the latch 8140 can be positioned around the socket 8130, and can be movably positioned relative to the tabs 8132*a*, 8132*b* of the socket 8130, for example. In various instances, the spring 8150 can be positioned between a portion of the socket 8130 and a portion of the latch 8140, for example, such that the spring 8150 can bias the latch 8140 toward a socket-latching position (FIG. 68). For example, the spring 8150 can bias the latch 8140 into the socket-latching position (FIG. 68) in which the latch 8140 is positioned to surround and/or restrain outward deflection of the tab(s) 8132*a*, 8132*b*.

Figure 69:
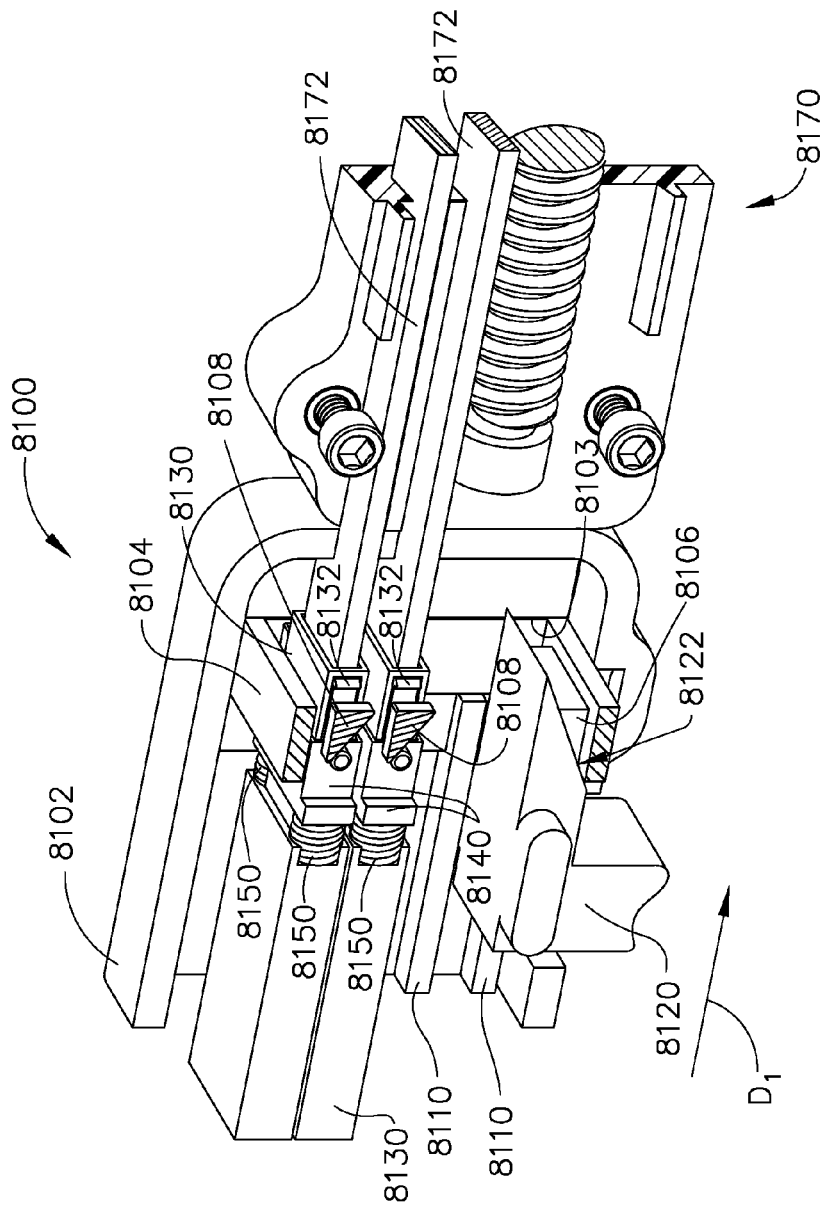
FIG. 69 is a cross-sectional, perspective view of the coupling arrangement of FIG. 66, depicting the pair of drive members coupled to the pair of sockets and further depicting the coupling arrangement in an unlocked configuration, according to various embodiments of the present disclosure.
Figure 70:
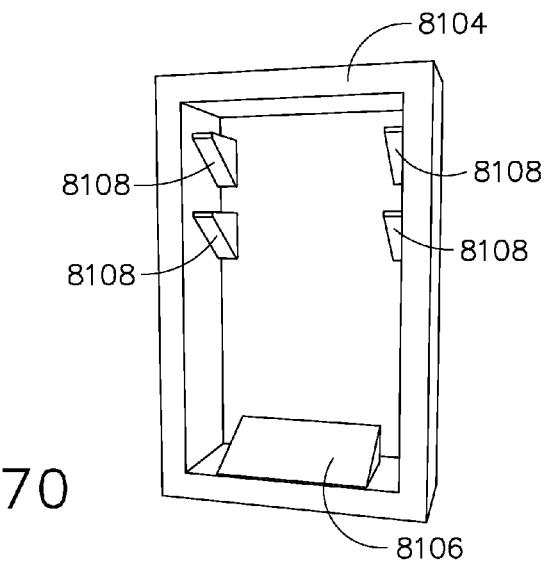
FIG. 70 is a perspective view of an insert of the coupling arrangement of FIG. 66, according to various embodiments of the present disclosure.

In various instances, when the latch 8140 is positioned to limit and/or prevent outward deflection of the tab(s) 8132*a*, 8132*b*, i.e., in the socket-latching position, outward movement of the tab(s) 8132*a*, 8132*b* away from the opening 8136 can be limited, such that the tab(s) 8132*a*, 8132*b* can block and/or otherwise prevent entry and/or release of the drive bar 8172 relative to the opening 8136 in the socket 8130, for example. Moreover, when the trigger 8120 moves from the unactuated position (FIG. 68) to the actuated position (FIGS. 67 and 69), the latch 8140 can overcome the bias of the spring(s) 8150, for example, and can be moved from the socket-latching position (FIG. 68) to an unlatched position (FIGS. 67 and 69). When in the unlatched position, the latch 8140 can be shifted away from the flexible tab(s) 8132*a*, 8132*b*, such that the flexible tab(s) 8132*a*, 8132*b* can be deflected outward, for example, and the socket 8130 can receive the drive bar 8172, for example.

In various instances, the latch 8140 can comprise a nub or protrusion 8144. Furthermore, referring primarily to FIG. 70, the carriage 8104 in the coupler housing 8102 can include a biasing member 8108. The biasing member 8108 can include a ramp or angled surface, for example, which can be configured to bias the nub 8144, and thus the latch 8140, between the first or socket-latching position (FIGS. 67 and 69) and the second, or latched, position (FIG. 68), for example. For example, when movement of the trigger 8120 causes the carriage 8104 to shift relative to the coupler housing 8102 and the socket 8130, as described herein, the nub 8144 can slide along the angled surface of the biasing member 8108, such that the latch 8140 moves relative to the flexible tab 8132 of the socket 8130. In such instances, the activation of the trigger 8120 can overcome the bias of the spring 8150 and retract the latch 8140 from the socket-latching position around the flexible tab(s) 8132 of the socket 8130 to the unlatched position. In such instances, when the latch 8140 is retracted, the flexible tab(s) 8132 can be permitted to deflect and/or engage a driving bar 8172. Moreover, when the trigger is unactuated, the spring 8150 can bias the latch 8140 relative to and/or around the flexible tab(s) 8132*a*, 8132*b*, such that deflection of the tab(s) 8132*a*, 8132*b*, and thus engagement with a drive bar 8172, is limited and/or prevented, for example.

In certain instances, the latch 8140 can include a pair of laterally-opposed nubs 8144, which can slidably engage laterally-opposed biasing members 8108 of the carriage 8104. Furthermore, in instances where the coupling arrangement 8100 couples more than one drive system between the handle 8170 and the surgical end effector, for example, the carriage 8104 can include multiple biasing members 8108, and/or multiple pairs of biasing members 8108. For example, each socket 8130 can include a pair of laterally positioned nubs 8144, and the carriage 8104 can include a biasing member 8108 for each nub 8144, for example.

Referring primarily to FIG. 68, prior to activation of the trigger 8120 and/or upon release of the trigger 8120, the trigger 8120 can be positioned in the distal, unactuated position, the carriage 8104 can be positioned in the lifted position relative to the coupler housing 8102, and the latch 8140 can be positioned in the socket-latching position. In such an arrangement, the latch 8140 can prevent entry and/or engagement of the drive bar 8172 with the socket 8130, for example. In various instances, spring(s) 8150 and/or a different spring and/or biasing member can bias the trigger 8120 into the unactuated position, the carriage 8104 into the lifted position, and/or the latch 8140 into the socket-latching position, for example. To connect and/or attach one of the drive bars 8172 to one of the sockets 8130, referring now to FIG. 67, the trigger 8120 can be moved to the proximal, actuated position, which can shift the carriage 8104 to the lowered position, which can shift the latch 8140 to the unlatched position, for example. In such an arrangement, a drive bar 8172 can be configured to enter and/or be received by the socket 8130, for example.

Thereafter, if the trigger 8120 is released, referring now to FIG. 68, for example, the spring(s) 8150 can bias the trigger 8120 back to the distal, unactuated position, can bias the carriage 8104 back to the lifted position, and can bias the latch 8140 back to a socket-latching position. Accordingly, the drive member 8172 can be locked into engagement with the socket 8130 because the latch 8140 can prevent outward deflection of the flexible tabs 8132*a*, 8132*b*, and thus, can secure the drive member 8172 within the socket 8130, for example. Accordingly, referring now to FIG. 69, to decouple the drive member 8172 from the socket 8130, the trigger 8120 can again be moved to the proximal, actuated position, which can shift the carriage 8104 to the lowered position, which can shift the latch 8140 to the unlatched position, for example. In such an arrangement, i.e., when the socket 8130 is unlatched, the drive member 8172 can be removed from the socket 8130, for example.

In various instances, a surgical instrument can include a drive system coupled to a motor. In certain instances, the motor and the drive system can affect various surgical functions. For example, the motor and the drive system can affect opening and/or closing of a surgical end effector, and can affect a cutting and/or firing stroke, for example. In certain instances, the motor and drive system can affect multiple distinct surgical functions. For example, opening and closing of the surgical end effector can be separate and distinct from cutting and/or firing of fasteners from the surgical end effector. In such instances, the drive system can include a transmission and/or clutch assembly, which can shift engagement of the drive system between different output systems, for example.

In various instances, a surgical instrument can include a drive system having multiple output shafts, and a clutch for shifting between the different output shafts. In certain instances, the output shafts can correspond to different surgical functions. For example, a first output shaft can correspond to an end effector closure motion, and a second output shaft can correspond to an end effector firing motion, for example. In various instances, the drive system can switch between engagement with the first output shaft and the second output shaft, for example, such that the surgical functions are separate and distinct and/or independent. For example, an end effector closure motion can be separate and distinct from an end effector firing motion. For example, it may be preferable to initiate a closure motion and, upon completion of the closure motion, initiate a separate firing motion. Moreover, it may be preferable to control and/or drive the independent closure motion and firing motion with a single drive system, which can be coupled to an electric motor, for example. In other instances, the first output shaft and the second output shaft can be operably coupled and the various surgical functions and/or surgical motions can occur simultaneously and/or at least partially simultaneously, for example.

Referring now to FIGS. 75-78, a handle 8600 for a surgical instrument can include a drive system 8602, which can include a first output drive system 8610 and a second output drive system 8620, for example. In various instances, when an end effector is attached to the handle 8600, the first output drive system 8610 can be coupled to a first drive system in the attached end effector, and the second output drive system 8620 can be coupled to a second drive system in the attached end effector. The first output drive system 8610 can affect a first surgical function, such as clamping of the end effector jaws, for example, and the second output drive system 8620 can affect a second surgical function, such as firing of a firing element through the end effector, for example. In other instances, the surgical functions with respect to the first output drive system 8610 and the second output drive system 8620 can be reversed and/or otherwise modified, for example.

In various instances, the drive system 8602 can include a motor assembly, which can include an electric motor 8640 and a motor shaft 8642. A drive gear 8644 can be mounted to the motor shaft 8642, for example, such that the electric motor 8640 drives and/or affects rotation of the drive gear 8644. In various instances, the first output drive system 8610 can include a first drive shaft 8612 and a first driven gear 8612. The first driven gear 8614 can be mounted to the first drive shaft 8612, for example, such that the rotation of the first driven gear 8614 affects the rotation of the first drive shaft 8612. In various instances, a linear actuator 8616 can be threadably positioned on the first drive shaft 8612, and rotation of the first drive shaft 8612 can affect linear displacement of the linear actuator 8616, for example. Moreover, in various instances, the second output drive system 8620 can include a second drive shaft 8622 and a second driven gear 8624. The second driven gear 8624 can be mounted to the second drive shaft 8622, for example, such that the rotation of the second driven gear 8624 affects the rotation of the second drive shaft 8622. In various instances, a linear actuator 8626 can be threadably positioned on the second drive shaft 8624, and rotation of the second drive shaft 8624 can affect linear displacement of the linear actuator 8626, for example.

In various instances, the drive system 8602 can further comprise a transmission or shifter assembly 8648. The shifter assembly 8648 can be configured to shift engagement of the drive gear 8644 between the first output drive system 8610 and the second output drive system 8620, for example. For certain instances, the shifter assembly 8648 can include a shifting gear 8652, which can be in meshing engagement with the drive gear 8644, for example. Additionally, the shifting gear 8652 can be configured to shift or move between a range of positions, for example, and can remain in meshing engagement with the drive gear 8644 as the shifting gear 8652 moves within the range of positions.

For example, the shifting gear 8652 can move into and/or out of engagement with at least one of the first driven gear 8614 and/or the second driven gear 8624. In various instances, the shifting gear 8652 can move into meshing engagement with the second driven gear 8624 of the second output drive system 8620. For example, when in a first position (FIG. 78) of the range of positions, the shifting gear 8652 can be disengaged from the second driven gear 8624, and when in a second position (FIG. 77) of the range of positions, the shifting gear 8652 can be engaged with the second driven gear 8624, for example. In instances when the shifting gear 8652 is engaged with the second driven gear 8624, the shifting gear 8652 can transfer a force from drive gear 8644 to the second driven gear 8624, such that the motor 8640 can affect a surgical function via the second output drive system 8620, for example. Moreover, in instances when the shifting gear 8652 is disengaged from the second driven gear 8624, rotation of the motor 8640 may not be transferred to the second output drive system 8620, for example.

In various instances, the shifter assembly 8648 can further comprise an intermediate and/or transfer gear 8654. The transfer gear 8642 can be configured to transfer a drive force from the shifting gear 8652 to the first driven gear 8614, for example. In various instances, the transfer gear 8654 can be in meshing engagement with the first drive gear 8614, for example, such that the rotation of the transfer gear 8654 is transferred to the first driven gear 8614, for example. Moreover, in various instances the shifting gear 8652 can move into and/or out of engagement with the transfer gear 8654. For example, when in the first position (FIG. 78) of the range of positions, the shifting gear 8652 can be engaged with the transfer gear 8654, and when in the second position (FIG. 77) of the range of positions, the shifting gear 8652 can be disengaged from the transfer gear 8654, for example. In instances when the shifting gear 8652 is engaged with the transfer gear 8654, the shifting gear 8652 can transfer a force from the drive gear 8644 to the first driven gear 8614 via the transfer gear 8654. In such instances, the motor 8640 can affect a surgical function via the first output drive system 8610, for example. Moreover, in instances when the shifting gear 8652 is disengaged from the transfer gear 8654, rotation of the motor 8640 may not be transferred to the first output drive system 8610, for example.

In various instances, the transfer gear 8654 can be rotatably mounted on the second drive shaft 8622 of the second output drive system 8620. For example, the transfer gear 8654 can be configured to rotate relative to the second drive shaft 8622 without affecting rotation of the second drive shaft 8622 and the second driven gear 8624 fixed thereto. In various instances, the shifter assembly 8648 can include a bracket or collar 8650, which can at least partially surround the shifting gear 8652. The bracket 8650 can be positioned around the shifting gear 8652, for example, such that movement of the bracket 8650 can move the shifting gear 8652.

In various instances, the handle 8600 and/or the shifting assembly 8648 can further include a trigger or clutch 8630. The clutch 8630 can be configured to shift the bracket 8650 and/or the shifting gear 8652 within the range of positions. For example, clutch 8630 can comprise a trigger extending from the handle 8600, and can be engaged with the bracket 8650 and/or the shifting gear 8652. In various instances, the bracket 8650 can include a pin 8656, which can extend from the bracket 8640 into an aperture 8638 (FIG. 75) in the clutch 8630. For example, the clutch 8630 can include an arm 8632 and/or a pair of arms 8632 coupled to a pivot point 8634 on the handle 8600. The clutch 8630 can pivot at the pivot point 8634, for example, and pivoting of the arm(s) 8632 can move the pin 8656 of the bracket 8560. Movement of the bracket 8650 can shift the shifting gear 8652 between the first position (FIG. 78) and the second position (FIG. 77), for example.

In various instances, the movement of the bracket 8650 can be constrained such that the shifting gear 8652 moves along a longitudinal axis through its range of positions. Moreover, the pivoting stroke and/or range of movement of the clutch 8630 can be restrained and/or limited, for example, such that the shifting gear 8652 remains within the range of positions as the clutch 8630 pivots. Furthermore, the aperture 8638 (FIG. 75) in the clutch 8630 can be configured and/or structured to maintain and/or hold the shifting gear 8652 within the range of positions and/or in alignment with one of the second driven gear 8624 and/or the transfer gear 8654, for example. In various instances, the handle 8600 can include a spring or other biasing mechanism, to bias the shifting gear 8652 into one of the first position or the second position. In some instances, the handle 8600 can include a bistable complaint mechanism configured to hold the shifting gear 8652 in its first position or its second position. To the extent that the shifting gear 8652 is between the first position and the second position, the bistable compliant mechanism can be dynamically unstable and act to place the shifting gear 8652 in its first position or its second position. Alternatively, the shifting gear 8652 can be biased into an intermediate position, wherein the shifting gear 8652 can be simultaneously engaged with the first output drive system 8610 and the second output drive system 8620, for example. Additionally or alternatively, the handle 8600 can include a lock and/or detent for holding the shifting gear 8652 in one of the first position or the second position, for example.

A surgical instrument can include a rotatable drive shaft configured to operate a closure drive and a firing drive of a surgical instrument. Referring to FIGS. 79-84, a surgical instrument 10000 can include a rotatable drive shaft 10020, a closure drive 10030, and a firing drive 10040. As will be described in greater detail below, the drive shaft 10020 can include a first thread 10024 configured to operate the closure drive 10030 and a second thread 10026 configured to operate the firing drive 10040. In various instances, the instrument 10000 can comprise a circular stapler, for example.

The surgical instrument 10000 can comprise a frame 10002 and means for generating a rotary motion. In certain instances, rotary motion can be created by a manually-driven hand crank, for example, while, in various instances, rotary motion can be created by an electric motor. In either event, the generated rotary motion can be transmitted to a rotary input shaft 10010. Input shaft 10010 can include a proximal bearing portion 10011 and a distal bearing portion 10013 which are rotatably supported by the frame 10002. In various instances, the proximal bearing portion 10011 and/or the distal bearing portion 10013 can be directly supported by the frame 10002 while, in certain instances, the proximal bearing portion 10011 and/or the distal bearing portion 10013 can include a bearing positioned between the input shaft 10010 and the frame 10002. The input shaft 10010 can further include a gear 10012 mounted to and/or keyed to the input shaft 10010 such that, when input shaft 10010 is rotated in direction A (FIG. 79), gear 10012 is also rotated in direction A. Correspondingly, when input shaft 10010 is rotated in an opposite direction, i.e., direction A' (FIG. 82), the gear 10012 is also rotated in direction A'.

Referring primarily to FIGS. 79 and 80, the drive shaft 10020 can include a proximal end 10021 and a distal end 10023. The proximal end 10021 and the distal end 10023 can be rotatably supported by the frame 10002. In various instances, the proximal end 10021 and/or the distal end 10023 can be directly supported by the frame 10002 while, in certain instances, the proximal end 10021 and/or the distal end 10023 can include a bearing positioned between the drive shaft 10020 and the frame 10002. A gear 10022 can be mounted to and/or keyed to the proximal end 10021 of the drive shaft 10020. The gear 10022 is meshingly engaged with the gear 10012 such that, when the input shaft 10010 is rotated in direction A, the drive shaft 10020 is rotated in direction B. Correspondingly, referring to FIG. 81, when the input shaft 10010 is rotated in direction A', the drive shaft 10020 is rotated in direction B'.

Referring again to FIG. 79, the closure drive system 10030 can include a closure pin 10032 engaged with the first thread 10024 of the drive shaft 10020. The closure drive system 10030 can further comprise a translatable closure member 10033. The closure pin 10032 is positioned within an aperture defined in the proximal end of the closure member 10033. The closure pin 10032 can include a first end positioned within the groove defined by the first thread 10024. When the drive shaft 10020 is rotated, a sidewall of the groove can contact the first end of the closure pin 10032 and displace the closure pin 10032 proximally or distally, depending on the direction in which the drive shaft 10020 is being rotated. For example, when the drive shaft 10020 is rotated in direction B (FIG. 79), the closure pin 10032 can be displaced, or translated, distally as indicated by direction D. Correspondingly, when the drive shaft 10020 is rotated in direction B' (FIG. 82), the closure pin 10032 can be displaced, or translated, proximally as indicated by direction P. The closure pin 10032 can be closely received within the aperture defined in the closure member 10033 such that the displacement, or translation, of the closure pin 10032 is transferred to the closure member 10033. As the reader will appreciate, the closure pin 10032 and the closure member 10033 are constrained from rotating relative to the frame 10002 such that the rotation of the drive shaft 10020 is converted to the translation of the closure pin 10032 and the closure member 10033.

Figure 81:
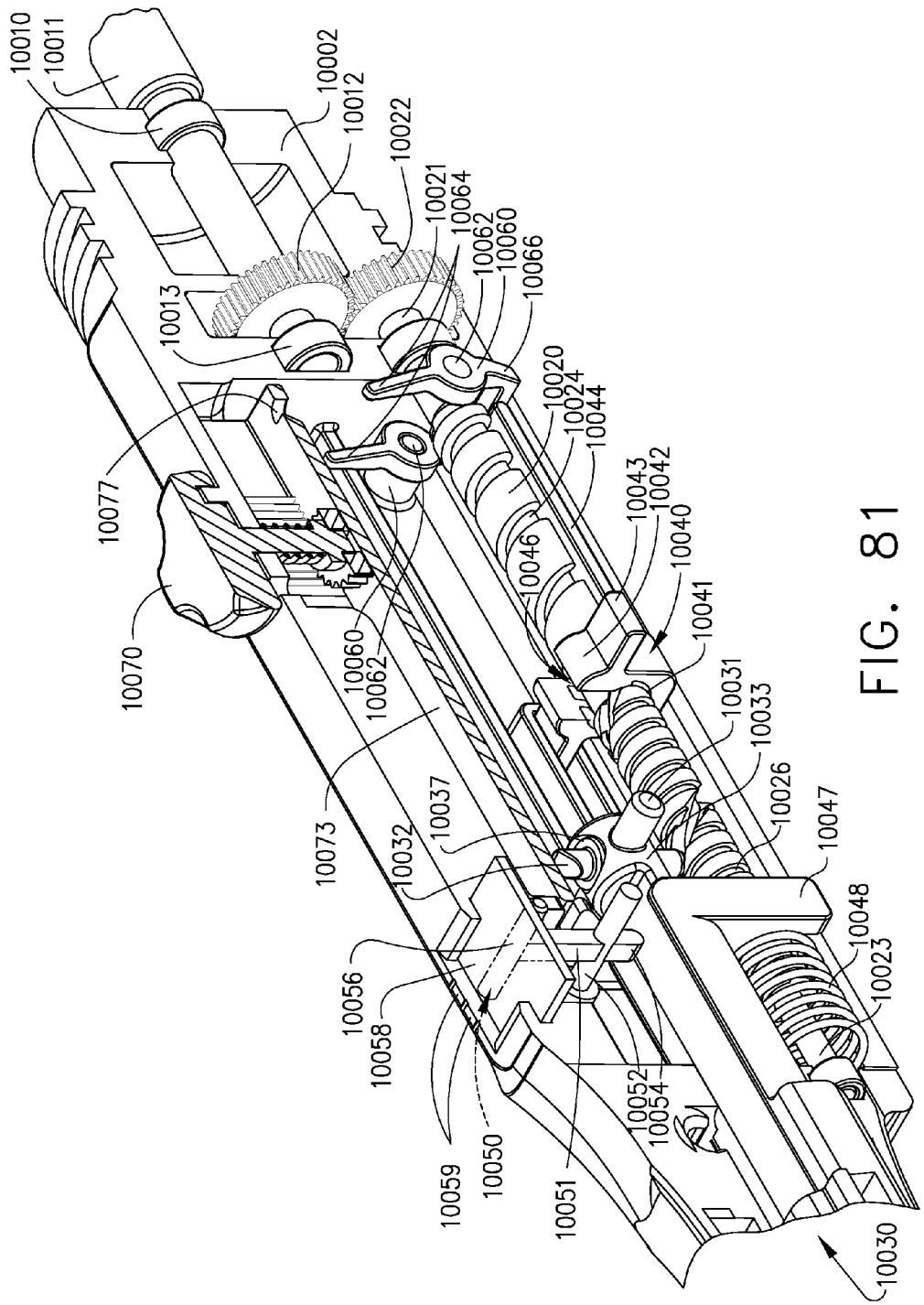
FIG. 81 is a partial cross-sectional perspective view of the surgical instrument of FIG. 79 illustrated with the closure drive in an open configuration and the firing drive in an unfired configuration.
Figure 82:
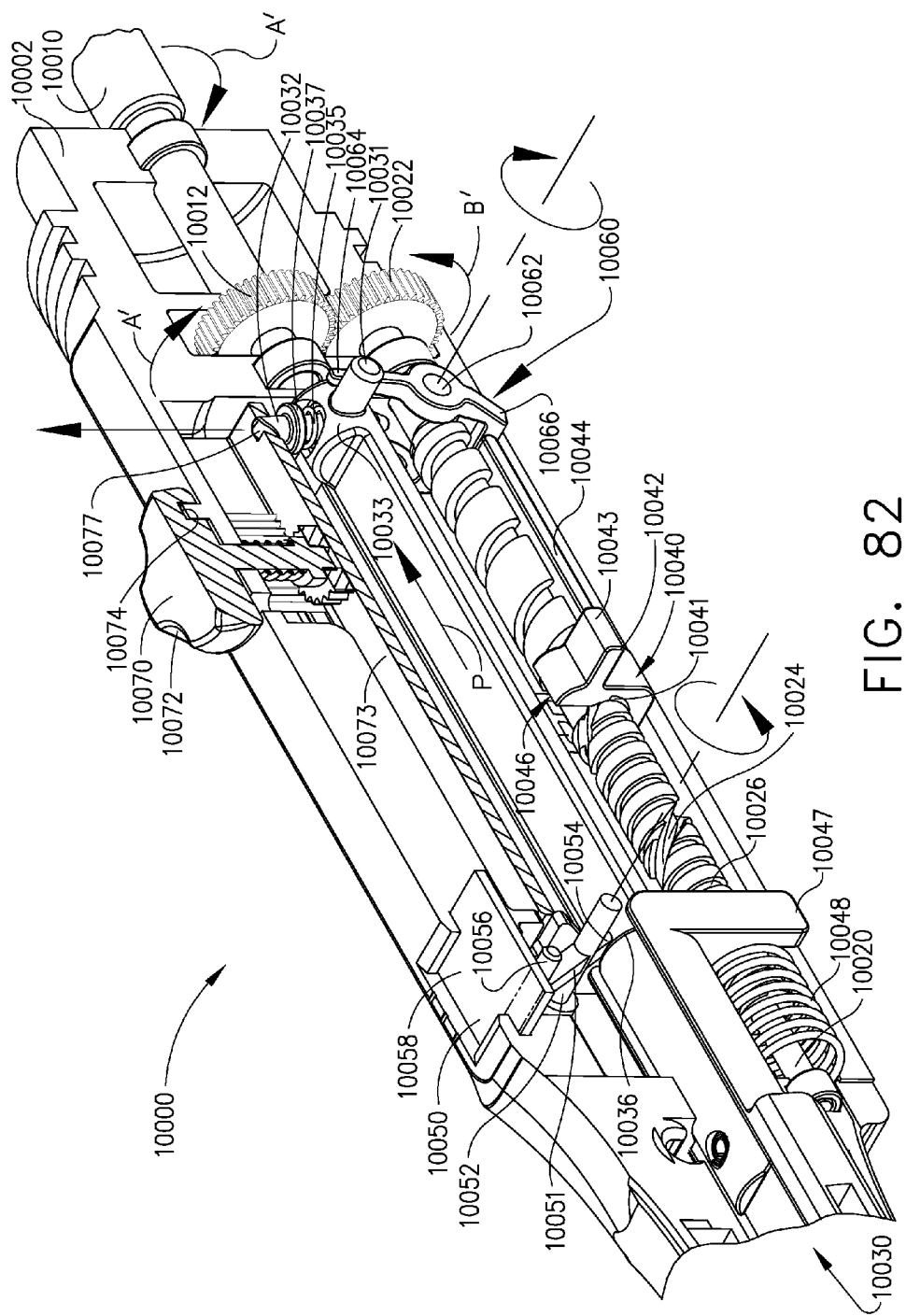
FIG. 82 is a partial cross-sectional perspective view of the surgical instrument of FIG. 79 illustrated with the closure drive in a closed configuration and the firing drive in an unfired configuration.

Referring primarily to FIG. 80, the first thread 10024 extends along a first length 10025 of the drive shaft 10020. In certain instances, the first thread 10024 may extend along the entire length of the drive shaft 10020 while, in other circumstances, the first thread 10024 may extend along less than the entire length of the drive shaft 10020. The first thread 10024 can include a proximal portion adjacent the proximal end 10021 of the drive shaft 10020 and a distal portion adjacent the distal end 10023 of the drive shaft 10020. When the closure pin 10032 is in the distal portion of the first thread 10024, as illustrated in FIG. 81, the closure member 10033 can position an anvil of the surgical instrument 10000 in an open position. As the drive shaft 10020 is rotated in direction B', the closure pin 10032 can translate proximally until the closure pin 10032 reaches the proximal portion of the first thread 10024, as illustrated in FIG. 82. As the closure pin 10032 moves proximally, the closure pin 10032 can pull the closure member 10033 and the anvil proximally. When the closure pin 10032 reaches the proximal portion of the first thread 10024, the anvil can be in a fully closed position.

Further to the above, the closure drive 10030 can be operated to move the anvil of the surgical instrument 10000 into a suitable position relative to a staple cartridge. In various instances, the surgical instrument 10000 can include an actuator which can be operated in a first direction to rotate the input shaft 10010 in direction A and the drive shaft 10020 in direction B and a second direction to rotate the input shaft 10010 in direction A' and the drive shaft 10020 in direction B'. In other instances, the surgical instrument 10000 can include a first actuator configured to rotate the input shaft 10010 in direction A and the drive shaft 10020 in direction B, when operated, and a second actuator configured to rotate the input shaft 10010 in direction A' and the drive shaft 10020 in direction B', when operated. In either event, an operator of the surgical instrument 10000 can move the anvil of the surgical instrument 10000 toward and away from the staple cartridge, as needed, in order to create a desired gap between the anvil and the staple cartridge. Such a desired gap may or may not be created when the anvil is in its fully closed position.

Further to the above, the surgical instrument 10000 can include a catch configured to receive and releasably hold the drive pin 10032 when the closure system 10030 has reached its fully closed configuration. Referring primarily to FIGS. 81 and 82, the surgical instrument 10000 can include a catch bar 10073 comprising a catch aperture 10077 defined therein. As the drive pin 10032 is advanced proximally, the drive pin 10032 can become aligned with, and then at least partially enter, the catch aperture 10077. The catch pin 10032 can be biased toward the catch bar 10073 by a spring 10035 positioned intermediate the closure member 10033 and a circumferential head 10037 extending around the catch pin 10032. When the catch pin 10032 is positioned distally with respect to the catch aperture 10077, the spring 10035 can bias the drive pin 10032 against the catch bar 10073. When the catch pin 10032 is moved proximally by the rotation of the drive screw 10020 and becomes aligned with the catch aperture 10077, the spring 10035 can move the drive pin 10032 upwardly into the catch aperture 10077. The drive pin 10032 can be moved upwardly by the spring 10035 until the head of the drive pin 10032 contacts the catch bar 10073. Notably, the movement of the drive pin 10032 toward the catch aperture 10077 can cause the drive pin 10032 to become operably disengaged from the first thread 10024. Thus, the closure system 10030 can become deactivated when the drive pin 10032 reaches the catch aperture 10077 such that subsequent rotation of the drive shaft 10020 does not move the drive pin 10032, the closure member 10033, and the anvil operably engaged therewith, at least until the drive pin 10032 is re-engaged with the first thread 10024 as described in greater detail further below.

As discussed above, the entry of the drive pin 10032 into the catch aperture 10077 of the catch bar 10073 can demarcate the end of the closing stroke of the closure system 10030 and the fully closed position of the anvil. In various instances, the catch bar 10073 may not be movable relative to the frame 10002 and the catch aperture 10077 may demarcate a fixed position. In other instances, the catch bar 10073 may be movable relative to the frame 10002. In such instances, the final, closed position of the anvil will depend on the position of the catch aperture 10077. As a result, the gap between the anvil and the staple cartridge of the surgical instrument 10000 will depend on the position of the catch aperture 10077. Referring generally to FIG. 79, the surgical instrument 10000 can further comprise a gap setting system 10070 configured to move the catch bar 10073. The gap setting system 10070 can comprise a rotatable knob 10072 and a drive gear 10071 engaged with the rotatable knob 10072. The catch bar 10073 can include a rack 10075 extending therefrom which comprises a plurality of teeth. The drive gear 10071 is meshingly engaged with the rack 10075 such that, when the knob 10072 is rotated in a first direction, the rack 10075 can drive the catch bar 10073 distally and, when the knob 10072 is rotated in a second direction opposite the first direction, the rack 10075 can drive the catch bar 10073 proximally. When the catch bar 10073 is moved distally, the catch aperture 10077 can be positioned such that a larger gap between the anvil and the staple cartridge may be present when the closure drive 10030 is in its fully closed position. When the catch bar 10073 is moved proximally, the catch aperture 10077 can be positioned such that a smaller gap between the anvil and the staple cartridge may be present when the closure drive 10030 is in its fully closed position. In various instances, the catch aperture 10077 can be positionable within a range of positions which can accommodate a range of distances between the anvil and the staple cartridge of the surgical instrument 10000.

In various instances, the gap setting system 10070 can comprise a knob lock configured to releasably hold the knob 10072 in position. For instance, the frame 10002 can include a lock projection 10004 extending therefrom which can be received within one or more lock apertures 10074 defined in the knob 10072. The lock apertures 10074 can be positioned along a circumferential path. Each lock aperture 10074 can correspond with a preset position of the closure drive 10030 and a preset gap distance between the anvil and the staple cartridge of the surgical instrument 10000. For instance, when the lock projection 10004 is positioned in a first lock aperture 10074, the closure drive 10030 can be held in a first preset position and, correspondingly, the anvil can be held a first preset distance from the staple cartridge. In order to move the knob 10072 into a second preset position, the knob 10072 can be lifted away from the frame 10002 such that lock projection 10004 is no longer positioned in the first lock aperture 10074, rotated to drive the rack 10075 and the catch bar 10073, and then moved toward the frame 10002 such that the lock projection 10004 enters into a second lock aperture 10074 defined in the knob 10072. When the lock projection 10004 is positioned in the second lock aperture 10074, the closure drive 10030 can be held in a second preset position and, correspondingly, the anvil can be held a second preset distance from the staple cartridge which is different than the first preset distance. In order to move the knob 10072 into a third preset position, the knob 10072 can be lifted away from the frame 10002 such that lock projection 10004 is no longer positioned in the first or second lock aperture 10074, rotated to drive the rack 10075 and the catch bar 10073, and then moved toward the frame 10002 such that the lock projection 10004 enters into a third lock aperture 10074 defined in the knob 10072. When the lock projection 10004 is positioned in the third lock aperture 10074, the closure drive 10030 can be held in a third preset position and, correspondingly, the anvil can be held a third preset distance from the staple cartridge which is different than the first and second preset distances. The gap setting system 10070 can further include a biasing element configured to bias the knob 10072 toward the frame 10002. For instance, the gap setting system 10070 can include a spring 10076 positioned intermediate the housing 10002 and the drive gear 10071, for example, configured to bias a lock aperture 10074 into engagement with the lock projection 10004.

In certain instances, an operator of the surgical instrument 10000 may be able to discern the position of the closure system 10030 by observing the position of the anvil. In some instances, however, the anvil may not be visible in a surgical field. Referring primarily to FIG. 79, the surgical instrument 10000 can further comprise an anvil position indicator system 10050 configured to indicate the position of the anvil. The anvil position indicator system 10050 can include a window 10058 defined in the frame 10002 and a pivotable member 10051 observable through the window 10058. The pivotable member 10051 can include a pivot 10052 rotatably mounted to the frame 10002, a drive end 10054, and a display end 10056. The pivotable member 10051 can be movable between a first position (FIG. 81) which indicates that the anvil is in a fully open position, a second position (FIG. 82) which indicates that the anvil is in a fully closed position, and a range of positions between the first position and the second position which represent a range of positions of the anvil. The closure system 10030 can be configured to contact the drive end 10054 of the pivotable member 10051 to move the pivotable member 10051. When the drive pin 10032 is moved proximally by the drive shaft 10020, referring primarily to FIG. 82, the drive pin 10032 can pull the closure member 10033 proximally such that a shoulder 10036 defined on the closure member 10033 can contact the drive end 10054 of the pivotable member 10051 and rotate the pivotable member 10051 about the pivot 10052. The rotation of the pivotable member 10051 can move the display end 10056 within the window 10058 to indicate the position of the anvil. To facilitate this observation, the frame 10002 and/or the window 10058 can include one or more demarcations 10059 which can indicate the position of the anvil. For instance, when the display end 10056 of the pivotable member 10051 is aligned with a proximal demarcation 10059 (FIG. 81), the operator can determine that the anvil is in an open position and, when the display end 10056 is aligned with a distal demarcation 10059 (FIG. 82), the operator can determine that the anvil is in a closed position. If the display end 10056 is positioned intermediate the proximal and distal demarcations 10059, the operator can assume that the anvil is in a position between its open position and its closed position. Additional demarcations 10059 between the proximal and distal demarcations 10059 can be utilized to indicate additional positions of the anvil. When the closure member 10033 is moved distally to open the anvil (FIG. 84), the pivotable member 10051 can rotate back into its first position and become aligned with the proximal demarcation 10059 once again. The position indicator system 10050 can further include a biasing member, such as a spring, for example, configured to bias the pivotable member 10051 into its first position.

As discussed above, the closure system 10030 of the surgical instrument 10000 can be operated to position the anvil of the surgical instrument 10000 relative to the staple cartridge. During the operation of the closure system 10030, the firing system 10040 may not be operated. The firing system 10040 may not be operably engaged with the drive shaft 10020 until after the closure drive 10030 has reached its fully closed position. The surgical instrument 10000 can include a switch, such as switch 10060, for example, configured to switch the surgical instrument between an anvil closure operating mode and a staple firing operating mode. The closure drive 10030 can further comprise a switch pin 10031 extending from the proximal end of the closure member 10033. Upon comparing FIGS. 81 and 82, the reader will appreciate that the switch pin 10031 comes into contact with the switch 10060 as the closure pin 10032 is being advanced proximally to close the anvil. The switch 10060 can be pivotably mounted to the frame 10002 about a pivot 10062 and can include one or more arms 10064 extending therefrom. The switch pin 10031 can contact the arms 10064 and rotate the switch 10060 about the pivot 10062 when the drive pin 10032 reaches its fully closed position. The switch 10060 can further comprise an arm 10066 extending therefrom which can be configured to push a firing nut 10042 of the firing drive 10040 into operative engagement with the drive shaft 10020 when the switch 10060 is rotated about pivot 10062. More particularly, in at least one circumstance, the arm 10066 can be configured to displace a push bar 10044 distally which can, in turn, push the firing nut 10042 onto the second thread 10026. At such point, the drive pin 10032 and the closure system 10030 may be disengaged from the first thread 10024, as a result of the catch aperture 10077 described above, and the firing nut 10042 and the firing system 10040 can be engaged with the second thread 10026.

Further to the above, the firing nut 10042 can comprise a threaded aperture 10041 defined therein which can be threadably engaged with the second thread 10026. When the closure drive 10030 is being operated, further to the above, the firing nut 10042 may be positioned proximally with respect to the second thread 10026 such that the threaded aperture 10041 is not threadably engaged with the second thread 10026. In such circumstances, the firing nut 10042 may sit idle while the drive shaft 10020 is rotated to operate the closure system 10030. When the firing nut 10042 is displaced distally, further to the above, the threaded aperture 10041 can become threadably engaged with the second thread 10026. Once the firing nut 10042 is threadably engaged with the second thread 10026, rotation of the drive shaft 10020 in direction B' (FIG. 82) will displace the firing nut 10042 distally. The firing nut 10042 can include one or more anti-rotation features, such as flanges 10043, for example, which can be slidably engaged with the frame 10002 to prevent the firing nut 10042 from rotating with the drive shaft 10020. The firing drive 10040 can further include a firing member coupled to the firing nut 10042 which can be pushed distally by the firing nut 10042. The firing member can be configured to eject staples from the staple cartridge. When the firing nut 10042 reaches the distal end of the second thread 10026, the firing nut 10042 may become threadably disengaged from the second thread 10026 wherein additional rotation of the drive shaft 10020 in direction B' may no longer advance the firing nut 10042.

Figure 83:
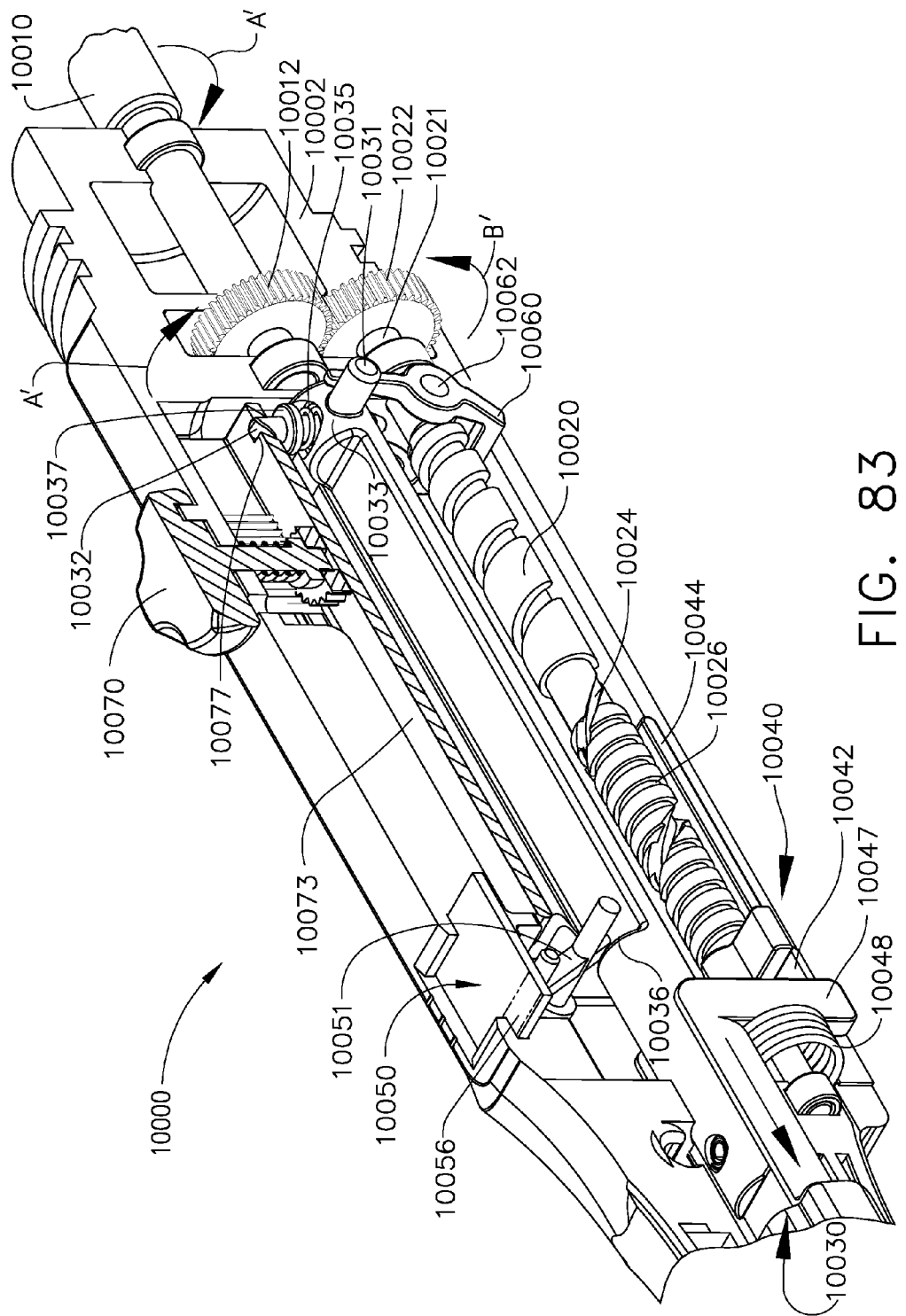
FIG. 83 is a partial cross-sectional perspective view of the surgical instrument of FIG. 79 illustrated with the closure drive in a closed configuration and the firing drive in a fired configuration.
Figure 84:
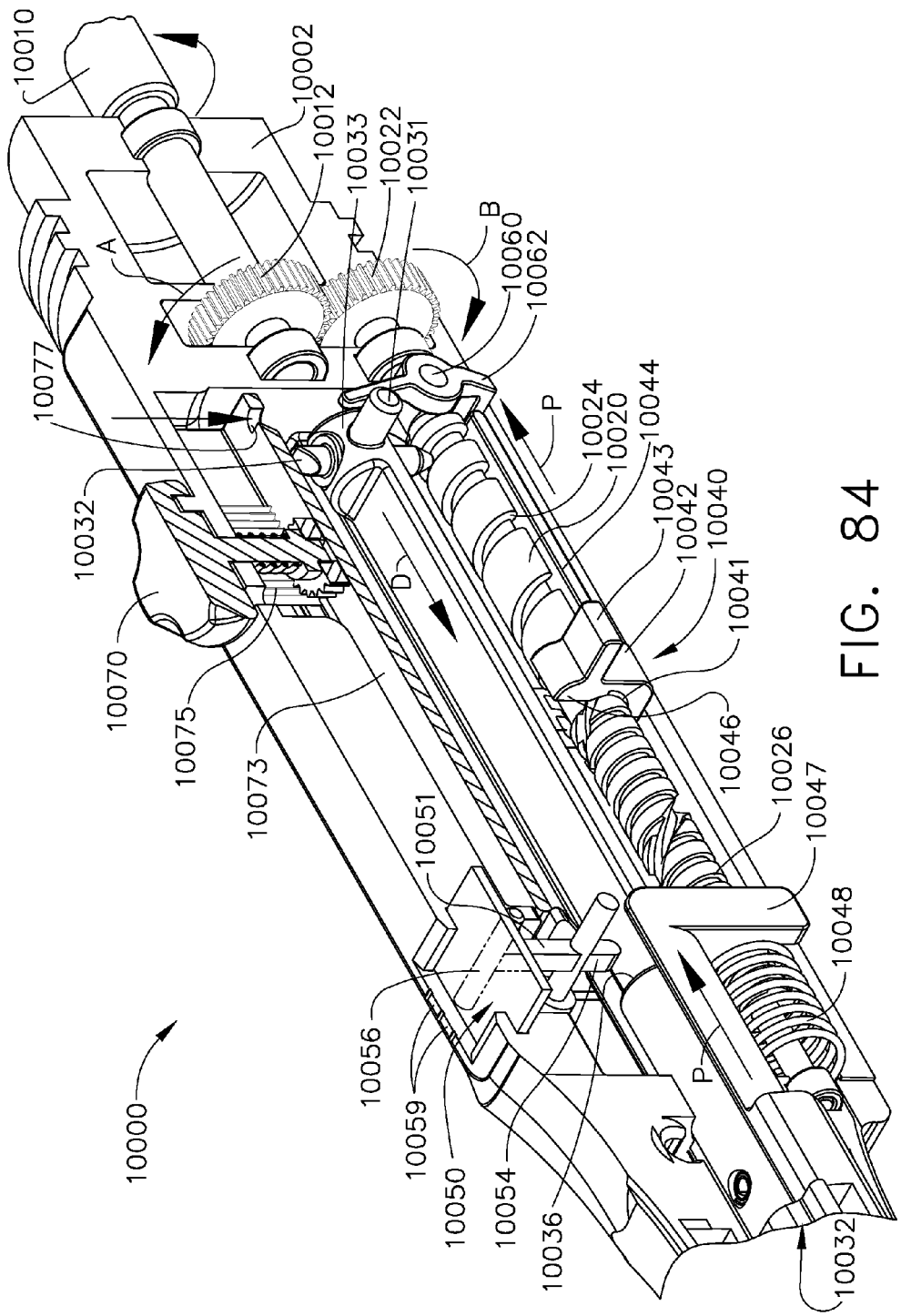
FIG. 84 is a partial cross-sectional perspective view of the surgical instrument of FIG. 79 illustrated with the firing drive in a retracted configuration and the closure drive in the process of being re-opened.

Referring primarily to FIGS. 82 and 83, the surgical instrument 10000 can further comprise a reverse activator 10047 positioned at the distal end of the second thread 10026. The firing nut 10042 can be configured to contact the reverse actuator 10047 and displace the reverse actuator 10047 distally when the firing nut 10042 reaches the distal end of the second thread 10026. A biasing member, such as spring 10048, for example, can be positioned intermediate the reverse actuator 10047 and the frame 10002 which can be configured to resist the distal movement of the reverse actuator 10047. The distal movement of the reverse actuator 10047 can compress the spring 10048, as illustrated in FIG. 83, and apply a proximal biasing force to the firing nut 10042. When the drive shaft 10020 is rotated in direction B, the proximal biasing force applied to firing nut 10042 can re-engage the threaded aperture 10041 of the firing nut 10042 with the second thread 10026 and the firing nut 10042 can be moved proximally, as illustrated in FIG. 84. The proximal movement of the firing nut 10042 can move the firing member proximally. When moving proximally, the firing nut 10042 can displace the push bar 10044 such that the push bar 10044 contacts the arm 10066 of the switch 10060 and rotates the switch 10060 in an opposite direction back into its unswitched position. At such point, the firing nut 10042 may become threadably disengaged from the second thread 10026 and further rotation of drive shaft 10020 in direction B may no longer displace the firing nut 10042 proximally. At such point, the firing nut 10042 will have resumed its idle position.

When the switch 10060 is rotated back into its original position, further to the above, the arms 10064 of the switch 10060 can push the switch pin 10031 and the closure member 10033 distally. The distal movement of the switch pin 10031 and the closure member 10033 can displace the drive pin 10032 from the catch aperture 10077 defined in the catch bar 10073. As the drive pin 10032 exits the catch aperture 10077, the drive pin 10032 can move downwardly against the biasing force of the spring 10035 in order to slide under the catch bar 10073. The downward movement of the drive pin 10032 can re-engage the drive pin 10032 with the first thread 10024. Further rotation of the drive shaft 10020 in direction B will displace the drive pin 10032 and the closure member 10033 distally to open the anvil of the surgical instrument 10000. At such point, the surgical instrument 10000 will have been reset for a subsequent use thereof. In various instances, the staple cartridge can be replaced and/or reloaded and the surgical instrument 10000 can be used once again.

As the reader will appreciate from the above, the drive screw 10020 can displace the drive pin 10032 to operate the closure drive 10030 and the firing nut 10042 to operate the firing drive 10040. Further to the above, the drive screw 10020 can displace the drive pin 10032 along a first length 10025 of the drive screw 10020. Similarly, the drive screw 10020 can displace the firing nut 10042 along a second length 10027 of the drive screw 10020. The first length 10025 can define a closure stroke of the closure system 10030 and the second length 10027 can define a firing stroke of the firing stroke 10040. The first length 10025 can be longer than the second length 10027, although the second length 10027 could be longer than the first length 10025 in certain circumstances. In use, the closure pin 10032 can pass by the firing nut 10042. For instance, when the closure pin 10032 is moved proximally to close the anvil, the closure pin 10032 can pass by the firing nut 10042 when the firing nut 10042 is in its idle position. Similarly, the closure pin 10032 can pass by the firing nut 10042 in its idle position when the closure pin 10032 is moved distally to open the anvil. In order to facilitate this relative movement, the firing nut 10042 can include an opening, such as slot 10046, for example, defined therein through which the closure pin 10032 can pass as the closure pin 10032 moves relative to the firing nut 10042. Such an opening defined in the firing nut 10042 could also permit the firing nut 10042 to slide by the closure pin 10032 in various other embodiments.

Further to the above, the first length 10025 and the second length 10027 can at least partially overlap. Moreover, the first thread 10024 and the second thread 10026 can at least partially overlap. The first thread 10024 and the second thread 10026 can be defined on the same portion of the drive screw 10020. The first thread 10024 and the second thread 10026 can be sufficiently dissimilar such that the closure pin 10032 does not follow the second thread 10026 and such that the firing nut 10042 does not follow the first thread 10024. For instance, the first thread 10024 can include a first thread pitch and the second thread 10026 can include a second thread pitch which is different than the first thread pitch. The first thread pitch of the first thread 10024 may or may not be constant. In the event that the first thread pitch is constant, the closure pin 10032 and the anvil operably engaged with the first thread 10024 will move at a constant speed throughout the closure stroke for a given rotational speed of the drive shaft 10020. In the event that the first thread pitch is not constant, the closure pin 10032 and the anvil will move at different speeds during the closure stroke for a given rotational speed of the drive shaft 10020. For instance, the distal portion of the first thread 10024 can include a thread pitch which is greater than the thread pitch of the proximal portion of the first thread 10024. In such circumstances, the anvil will move quickly away from its open position and move slower once it nears its closed position for a given rotational speed of the drive shaft 10020. Such an arrangement would permit the anvil to be moved quickly into position against tissue positioned intermediate the anvil and the staple cartridge and then slower once the anvil was engaged with the tissue in order to mitigate the possibility of over-compressing the tissue. In various other instances, the distal portion of the first thread 10024 can include a thread pitch which is less than the thread pitch of the proximal portion of the first thread 10024. In either event, the thread pitch can change between the ends of the first thread 10024. This change can be linear and/or non-linear.

Further to the above, the second thread pitch of the second thread 10026 may or may not be constant. In the event that the second thread pitch is constant, the firing nut 10042 and the firing member operably engaged with the second thread 10026 will move at a constant speed throughout the closure stroke for a given rotational speed of the drive shaft 10020. In the event that the second thread pitch is not constant, the firing nut 10042 and the firing member will move at different speeds during the firing stroke for a given rotational speed of the drive shaft 10020. For instance, the distal portion of the second thread 10026 can include a thread pitch which is less than the thread pitch of the proximal portion of the second thread 10026. In such circumstances, the firing member will move slower at the end of its firing stroke for a given rotational speed of the drive shaft 10020. Such an arrangement would slow the firing member down as it reached the end of the staple forming process. Moreover, such an arrangement could generate a larger amount of torque at the end of the firing stroke which correlates with the completion of the staple forming process. In various other instances, the distal portion of the second thread 10026 can include a thread pitch which is greater than the thread pitch of the proximal portion of the second thread 10026. In either event, the thread pitch can change between the ends of the second thread 10026. This change can be linear and/or non-linear.

Turning now to FIGS. 86-93, a surgical instrument 10500 can include a shaft 10504 and an end effector 10505. The end effector 10505 can include a staple cartridge 10506 and a movable anvil 10508. The surgical instrument 10500 can include a closure drive including a closure member operably engageable with the anvil 10504 and a firing drive including a firing member configured to deploy staples from the staple cartridge 10506. The surgical instrument 10500 can include means for generating a rotary motion such as a hand crank and/or an electric motor, for example. The rotary motion can be transmitted to an input shaft 10510. The surgical instrument 10500 can include a transmission 10502 which is configured to selectively transmit the rotation of the input shaft 10510 to the closure drive and to the firing drive, as discussed in greater detail further below.

Figure 87:
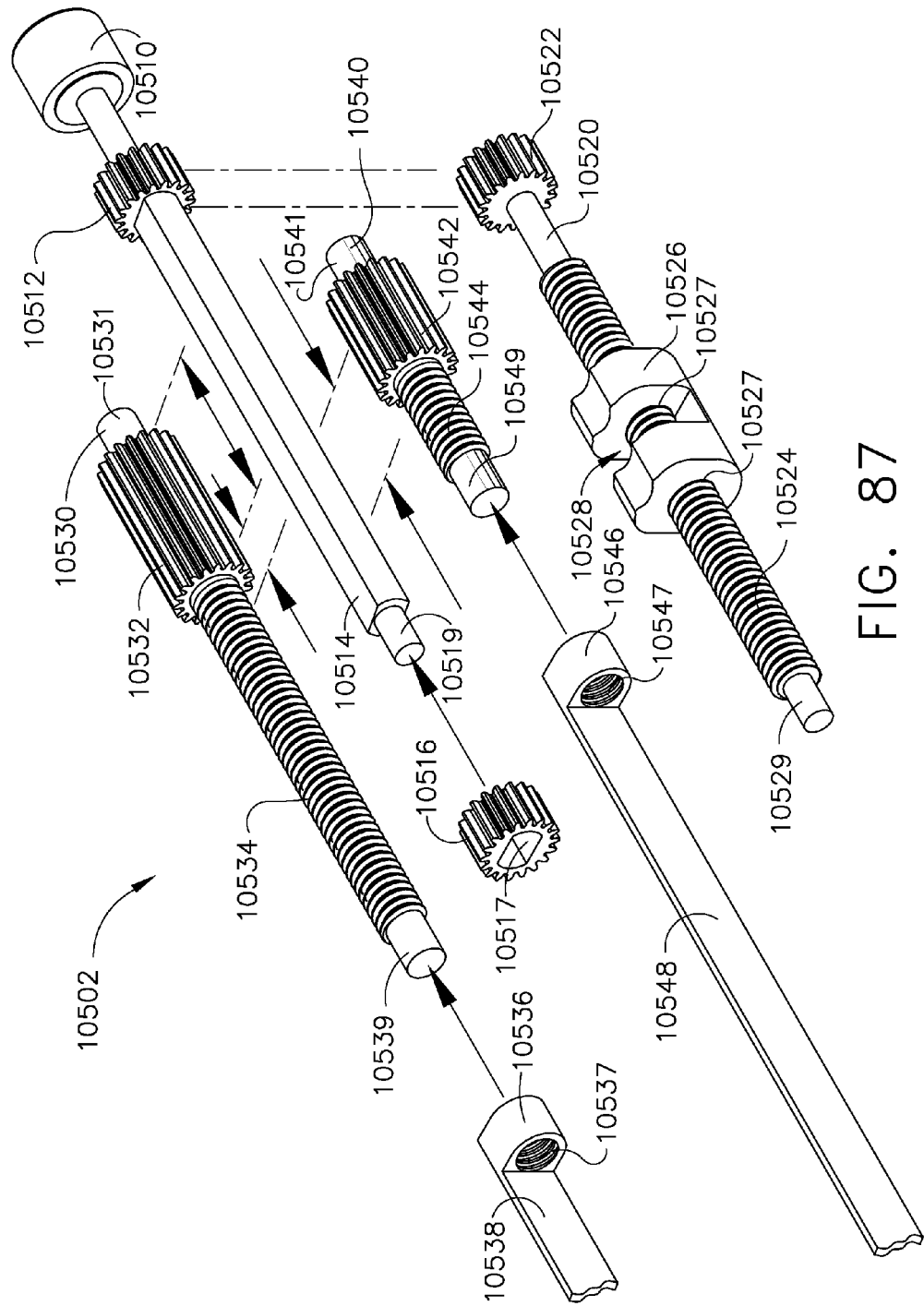
FIG. 87 is an exploded view of the transmission of FIG. 86.

The input shaft 10510 can include a input gear 10512 mounted and/or keyed thereto which rotates with the input shaft 10510. The input shaft 10510 can be rotatably supported by a frame of the surgical instrument 10500 by a proximal end 10511 and a distal end 10519. The input gear 10512 can be meshingly engaged with an intermediate gear 10522 mounted and/or keyed to an intermediate shaft 10520. Thus, when input shaft 10510 and input gear 10512 are rotated in direction A (FIG. 89), intermediate shaft 10520 and intermediate gear 10522 are rotated in direction B (FIG. 89). Similar to the above, the intermediate shaft 10520 can be rotatably supported by the surgical instrument frame by a proximal end 10521 and a distal end 10529. The intermediate shaft 10520 can further include a threaded portion 10524 which can be threadably engaged with a shifter block 10526. Referring primarily to FIG. 87, the shifter block 10526 can include one or more threaded apertures 10527 threadably engaged with the threaded portion 10524. When the intermediate shaft 10520 is rotated in direction B, referring primarily to FIG. 89, the intermediate shaft 10520 can displace the shifter block 10526 proximally.

Further to the above, the shifter block 10526 can include a gear slot 10528 defined therein. The input shaft 10510 can further include a slider gear 10516 slidably mounted thereto which is positioned in the gear slot 10528. When the shifter block 10526 is moved proximally by the intermediate shaft 10520, as discussed above, the shifter block 10526 can push the slider gear 10516 proximally along a keyed input shaft portion 10514. Referring primarily to FIG. 87, the slider gear 10516 can include an aperture 10517 defined therein including one or more flat surfaces, for example, which are aligned with corresponding flat surfaces on the keyed input shaft portion 10514. The flat surfaces of the aperture 10517 and the keyed input shaft portion 10514 can permit the slider gear 10516 to be slid longitudinally along the input shaft 10510 and, in addition, co-operate to transmit rotational motion between the slider gear 10516 and the input shaft 10510. As will be described in greater detail below, the shifter block 10526 can slide the slider gear 10516 through a first range of positions in which the slider gear 10516 is engaged with a closure shaft 10530, a second range of positions in which the slider gear 10516 is engaged with a firing shaft 10540, and a null position, or a range of null positions, intermediate the first range and the second range of positions in which the slider gear 10516 is not engaged with either the closure shaft 10530 or the firing shaft 10540.

Further to the above, FIG. 85 depicts the anvil 10508 of the end effector 10505 in a fully closed position and a firing driver 10548 in an unfired position. FIG. 86 depicts the transmission 10502 in a configuration which is consistent with the configuration of the end effector 10505 depicted in FIG. 85. More particularly, the slider gear 10516 is in its null, or idle, position and is not operably engaged with a closure shaft 10530 of the closure drive or a firing shaft 10540 of the firing drive. When the slider gear 10516 is in its idle position, the slider gear 10516 is positioned intermediate a closure gear 10532 mounted and/or keyed to the closure shaft 10530 and a firing gear 10542 mounted and/or keyed to the firing shaft 10540. Moreover, the slider gear 10516 is not engaged with the closure gear 10532 or the firing gear 10542 when the slider gear 10516 is in its idle position. In order to move the anvil 10508 into its open position, and/or detach the anvil 10508 from the end effector 10505, as illustrated in FIG. 88, the input shaft 10510 can be rotated in direction A, as illustrated in FIG. 89. As discussed above, the rotation of input shaft 10510 in direction A can rotate the intermediate shaft 10520 in direction B and move shifter block 10526 proximally. When the shifter block 10526 moves proximally, the shifter block 10526 can push the slider gear 10516 into operative engagement with the closure gear 10532. At such point, the continued rotation of input shaft 10510 in direction A can be transmitted to the closure shaft 10530 via the meshingly engaged slider gear 10516 and closure gear 10532. When the slider gear 10516 is meshingly engaged with the closure gear 10532, the rotation of the input shaft 10510 in direction A will rotate the output shaft 10530 in direction C, as illustrated in FIG. 89. The closure drive can further include a closure nut 10536 comprising a threaded aperture 10537 defined therein which is threadably engaged with a threaded portion 10534 of the closure shaft 10530. The closure nut 10536 can include one or more anti-rotation features slidably engaged with the frame of the surgical instrument, for example, which can prevent the closure nut 10536 from rotating with the closure shaft 10530 such that the rotational movement of the closure shaft 10530 can be converted to longitudinal movement of the closure nut 10536. The closure system can further include a closure member 10538 extending from the closure nut 10536 which can be engaged with the anvil 10508. When the closure shaft 10530 is rotated in direction C, referring again to FIG. 89, the closure nut 10536 and the closure member 10538 can be advanced distally to move the anvil 10508 into an open position.

Further to the above, FIG. 89 depicts the transmission 10502 in a closure configuration, i.e., a configuration in which the anvil 10508 can be opened and closed. When the slider gear 10516 is meshingly engaged with the closure gear 10532, the input shaft 10510 will directly drive the closure shaft 10530. Concurrently, the input shaft 10510 will directly drive the intermediate shaft 10520 owing to the meshing engagement between the input gear 10512 and the intermediate gear 10522. Also, when the slider gear 10516 is meshingly engaged with the closure gear 10532, the slider gear 10516 is not meshingly engaged with the firing gear 10542 and, as such, the input shaft 10510 will not drive the firing shaft 10540 when the transmission 10502 is in the closure configuration.

Once the anvil 10508 has been moved into an open position and/or detached from the closure member 10538, further to the above, tissue can be positioned intermediate the anvil 10508 and the staple cartridge 10506. Thereafter, referring to FIGS. 90 and 91, the anvil 10508 can be moved into its closed position by rotating the input shaft 10510 in an opposite direction, i.e., direction A', which will rotate the closure shaft 10530 in an opposite direction, i.e., direction C', in order to move the closure nut 10536, the closure member 10538, and the anvil 10508 proximally. The input shaft 10510 will also rotate intermediate shaft 10520 in an opposite direction, i.e., direction B', when the input shaft 10510 is rotated in direction A'. When the intermediate shaft 10520 is rotated in direction B', the intermediate shaft 10520 will displace the shifter block 10526 and the slider gear 10516 distally. The shifter block 10526 can push the slider gear 10516 distally until the slider gear 10516 is no longer meshingly engaged with the closure gear 10532 and the slider gear 10516 has been returned to its idle position. Additional rotation of the intermediate shaft 10520 in direction B' will cause the shifter block 10526 to displace the slider gear 10516 distally until the slider gear 10516 is meshingly engaged with the firing gear 10542. At such point, referring to FIGS. 92 and 93, the input shaft 10510 can directly drive the firing shaft 10540. Thereafter, the input shaft 10510 can rotate the firing shaft 10540 in direction D' when the input shaft 10510 is rotated in direction A'. The firing system can further comprise a firing nut 10546 including a threaded aperture 10547 which is threadably engaged with a threaded portion 10544 of the firing shaft 10540. When the firing shaft 10410 is rotated in direction A', the firing shaft 10540 can advance the firing nut 10546 distally. The firing nut 10546 can include one or more anti-rotation features which can be slidably engaged with the frame of the surgical instrument such that the firing nut 10546 does not rotate with the firing shaft 10540 and such that rotational movement of the firing shaft 10540 can be converted to longitudinal movement of the firing nut 10546. The firing drive can further include a firing member 10548 extending from the firing nut 10546 which is advanced distally to eject staples from the staple cartridge 10506. Throughout the firing stroke of the firing system, the shifter block 10526 can continue to advance the slider gear 10516 distally. The firing stroke can be completed when the shifter block 10526 advances slider gear 10516 distally to the point in which the slider gear 10516 is no longer threadably engaged with the firing gear 10542. At such point, the firing member 10548 may be in its fully fired position.

Further to the above, FIG. 93 depicts the transmission 10502 in a firing configuration, i.e., a configuration in which the firing member 10548 can be advanced or retracted. When the slider gear 10516 is meshingly engaged with the firing gear 10542, the input shaft 10510 will directly drive the firing shaft 10540. Concurrently, the input shaft 10510 will directly drive the intermediate shaft 10520 owing to the meshing engagement between the input gear 10512 and the intermediate gear 10522. Also, when the slider gear 10516 is meshingly engaged with the firing gear 10542, the slider gear 10516 is not meshingly engaged with the closure gear 10532 and, as such, the input shaft 10510 will not drive the closure shaft 10530 when the transmission 10502 is in the firing configuration.

In order to retract the firing member 10548, the input shaft 10510 can be rotated in direction A to rotate intermediate shaft 10520 in direction B, displace the shifter block 10526 proximally, and re-engage the slider gear 10516 with the firing gear 10542. At such point, the continued rotation of input shaft 10510 in direction A will rotate the firing shaft 10540 in an opposite direction to direction D', displace the firing nut 10546 proximally, and retract the firing member 10548. As the slider gear 10516 is rotating the firing gear 10542, the shifter block 10526 can continue to pull the slider gear 10516 proximally until the slider gear 10516 is no longer meshingly engaged with the firing gear 10542 and the slider gear 10516 reaches its idle position. At such point, the continued rotation of input shaft 10510 in direction A will continue to displace the shifter block 10526 and the slider gear 10516 proximally and re-engage the slider gear 10516 with the closure gear 10532 in order to re-open the anvil 10508.

Figure 94:
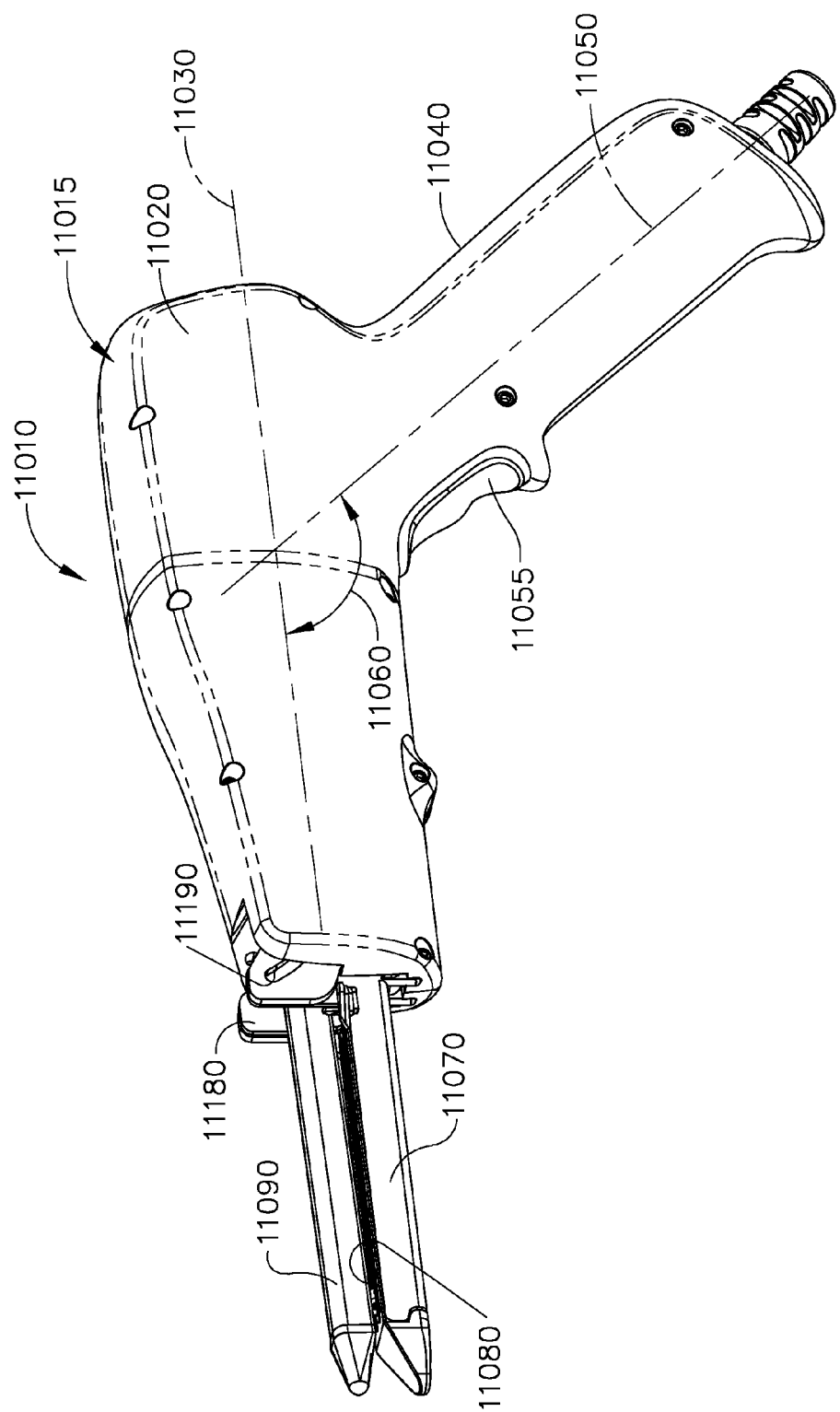
FIG. 94 is a perspective view of a surgical stapling instrument in accordance with at least one embodiment.
Figure 96:
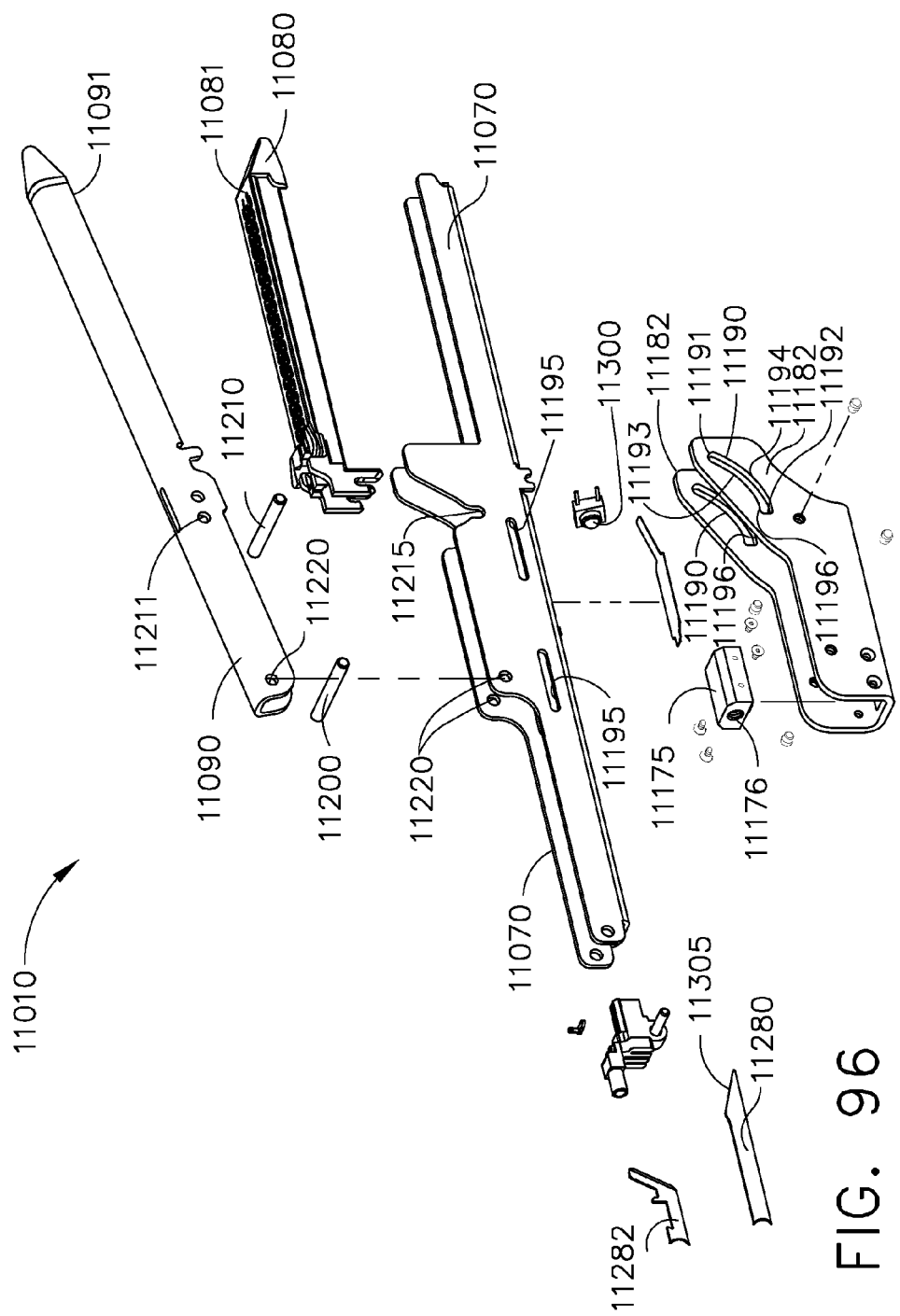
FIG. 96 is an exploded view of an end effector of the surgical stapling instrument of FIG. 94.
Figure 97:
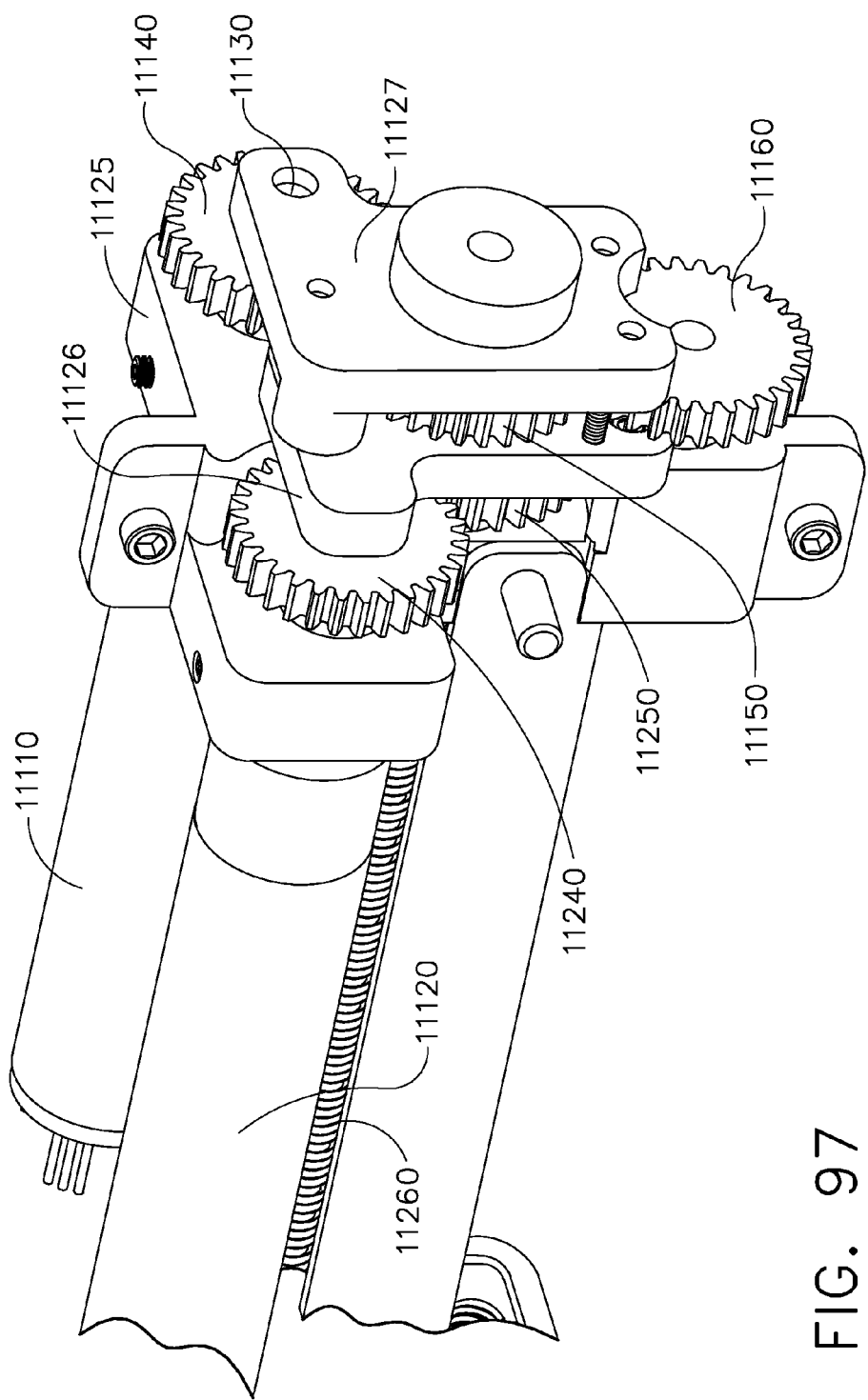
FIG. 97 is a partial perspective view of a motor and gear assembly of the surgical stapling instrument of FIG. 94.
Figure 98:
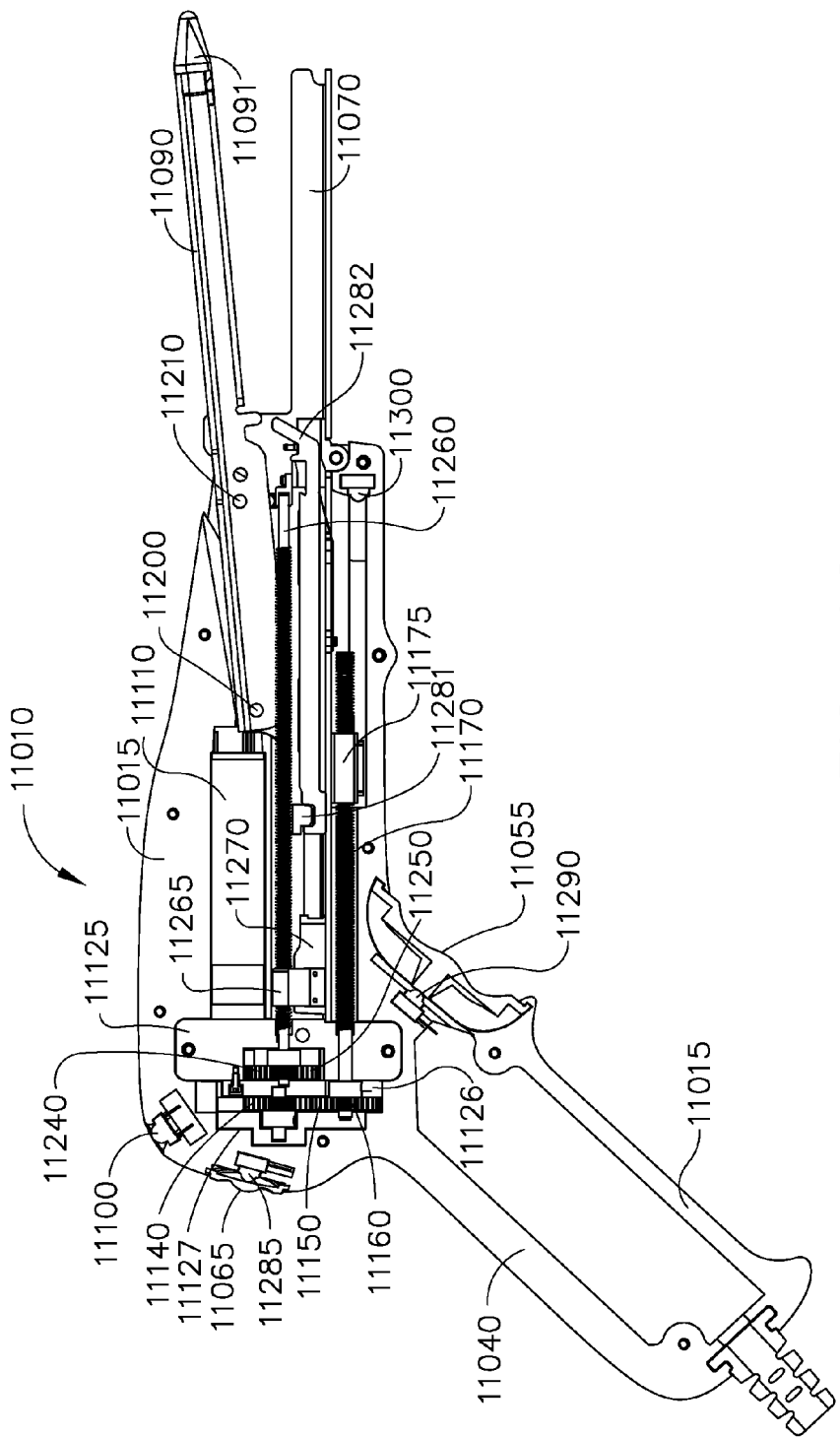
FIG. 98 is a cross-sectional elevational view of the surgical stapling instrument of FIG. 94.

FIGS. 94-98 illustrates a surgical instrument 11010 configured to staple and/or incise tissue. Surgical instrument 11010 can include a pistol-grip shaped handle 11015. Handle 11015 includes a first handle portion 11020 defining a longitudinal axis 11030 from which jaws 11070 and 11090 can extend. Handle 11015 includes a second handle portion, i.e., handle grip 11040, which defines a second portion axis 11050. Second portion axis 11050 defines an angle 11060 with longitudinal axis 11030. In various instances, angle 11060 can comprise any suitable angle, such as about 120 degrees, for example. The jaw 11070 can comprise a cartridge channel including an opening configured to removably receive a staple cartridge 11080. The staple cartridge 11080 can include a plurality of staples removably stored within staple cavities arranged in at least two longitudinal rows, one on either side of a channel in which a knife for transecting tissue can travel, as described in greater detail below. In at least on instance, three longitudinal rows of staple cavities can be arranged on a first side of the knife channel while three longitudinal rows of staple cavities can be arranged on a second side of the knife channel. The jaw 11090 can comprise an anvil rotatable to a position in opposition to and alignment with the staple cartridge 11080 so that anvil pockets defined in the anvil 11090 can receive and form staples ejected from the staple cartridge 11080. FIG. 98 depicts the anvil 11090 in an open position while FIG. 94 depicts the anvil 11090 in a closed position. Although not illustrated, other embodiments are envisioned in which the jaw including the staple cartridge 11080 is rotatable relative to the anvil 11090. In any event, as will be described in greater detail below, the handle 11015 can further include a closure button 11065 (FIG. 98) configured to operate a closure system which moves the anvil 11090 between its open and closed positions and a firing button 11055 configured to operate a firing system which ejects the staples from the staple cartridge 11080. The closure button 11065 can be positioned and arranged on the handle 11015 such that it can be easily accessed by the thumb of the operator's hand which is supporting the handle 11015, for example, while the firing button 11055 can be positioned and arranged such that it can be easily accessed by the index finger of the operator's handle which is supporting the handle 11015.

Figure 95:
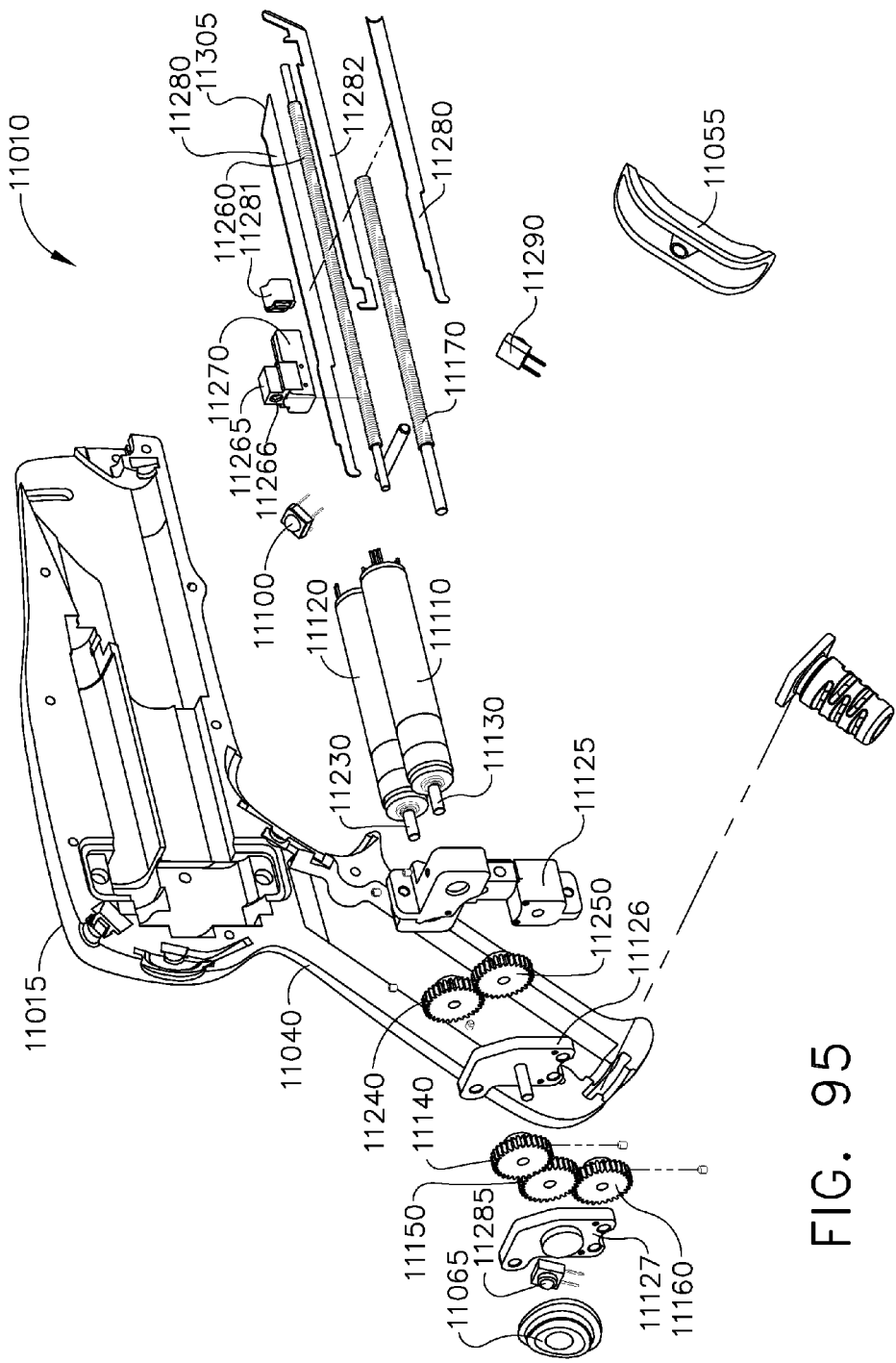
FIG. 95 is an exploded view of a handle of the surgical stapling instrument of FIG. 94.

Further to the above, the anvil 11090 can be moved toward and away from the staple cartridge 11080 during use. In various instances, the closure button 11065 can include a bi-directional switch. When the closure button 11065 is depressed in a first direction, the closure system of the surgical instrument 11010 can move the anvil 11090 toward the staple cartridge 11080 and, when the closure button 11065 is depressed in a second direction, the closure system can move the anvil 11090 away from the staple cartridge 11080. Referring primarily to FIGS. 95 and 97, the closure system can include a closure motor 11110 configured to move the anvil 11090. The closure motor 11110 can include a rotatable closure shaft 11130 extending therefrom to which a first closure gear 11140 can be affixed. The closure motor 11110 can rotate the closure shaft 11130 and the closure shaft 11130 can rotate the first closure gear 11140. The first closure gear 11140 can be meshingly engaged with an idler gear 11150 which, in turn, can be meshingly engaged with a closure lead screw drive gear 11160. Closure lead screw drive gear 11160 is affixed to a closure lead screw 11170. When the first closure gear 11140 is rotated by the closure shaft 11130, the first closure gear 11140 can rotate the idler gear 11150, the idler gear 11150 can rotate the closure lead screw drive gear 11160, and the closure lead screw drive gear 11160 can rotate the closure lead screw 11170.

Referring primarily to FIG. 97, the closure shaft 11130, the first closure gear 11140, the idler gear 11150, and the closure lead screw drive gear 11160 can be rotatably supported by a motor block 11125 supported within the handle portion 11120. The closure lead screw 11170 can include a first end which is also rotatably supported by the motor block 11125 and/or a second end which is rotatably supported by the housing of the handle 11015. The closure lead screw 11170 can further comprise a threaded portion intermediate the first end and the second end. The closure system can further comprise a closure block 11175 (FIG. 96) which can include a threaded aperture 11176 which is threadably engaged with the threaded portion of the closure lead screw 11170. The closure block 11175 can be constrained from rotating with the closure lead screw 11170 such that, when the closure lead screw 11170 is rotated, the closure lead screw 11170 can displace the closure block 11175 proximally or distally, depending on the direction in which the closure lead screw 11170 is being rotated. For instance, if the closure lead screw 11170 is rotated in a first direction, the closure lead screw 11170 can displace the closure block 11175 distally and, when the closure lead screw 11170 is rotated in a second, or opposite, direction, the closure lead screw 11170 can displace the closure block 11175 proximally. Referring primarily to FIG. 96, the closure block 11175 can be mounted to a latch member in the form of closure channel 11180, which translates along the outside of cartridge channel 11170. In various instances, the closure channel 11180 can be enclosed within the handle portion 11120 while, in some instances, the closure channel 11180 can protrude from the handle portion 11120. Closure channel 11180 can comprise an approximately "U" shaped channel when viewed from the end and can include opposing sidewalls 11182. Each sidewall 11182 can include a cam slot 11190 defined therein. As described in greater detail further below, the cam slots 11190 can be configured to engage the anvil 11090 and move the anvil 11090 relative to the staple cartridge 11080.

Further to the above, the closure channel 11180 fits around the cartridge channel 11070 so that cartridge channel 11070 nests inside the "U" shape of the closure channel 11180. Referring primarily to FIG. 96, the cartridge channel 11070 can include elongated slots 11195 defined therein and the closure channel 11180 can include pins which extend inwardly into the elongated slots 11195. The closure channel pins and the elongated slots 11195 can constrain the movement of the closure channel 11180 such that closure channel 11180 translates relative to the cartridge channel 11070 along a longitudinal path. The translational movement of the closure channel 11180 can rotate the anvil 11090. The anvil 11090 can be connected to the closure channel 11180 via a distal closure pin 11210 which extends through anvil cam holes 11211 defined in the anvil 11090 and the cam slots 11190 defined in the closure channel 11180. Each cam slot 11190 can include a first, or distal, end 11191 and a second, or proximal, end 11192. Each cam slot 11190 can further include a first, or proximal, drive surface 11193 and a second, or distal, drive surface 11194. When the closure system is in its open configuration and the anvil 11090 is in its open position, the closure channel 11180 can be in its first, or unadvanced, position and the distal closure pin 11210 can be in the first, or distal, ends 11191 of the cam slots 11190. When the closure channel 11180 is advanced distally to move the anvil 11090 toward the staple cartridge 11080, the first drive surface 11193 can contact the distal closure pin 11210 and push the distal closure pin 11210 downwardly toward the staple cartridge 11080. When the closure system is in its closed configuration and the anvil 11090 is in its closed position opposite the staple cartridge 11080, the closure channel 11180 can be in its second, or completely advanced, position and the distal closure pin 11210 can be in the second, proximal ends 11192 of the cam slots 11190.

Each cam slot 11190 can comprise a curved, or arcuate, path. The first drive surface 11193 can comprise a first arcuate surface and the second drive surface 11194 can comprise a second arcuate surface. In various instances, each cam slot 11190 can include at least one curved portion and at least linear portion. In at least one instance, each first drive surface 11193 can comprise a flat surface in a distal end 11191 of a cam slot 11190. The flat surface can comprise a vertical surface which is perpendicular to, or at least substantially perpendicular to, the longitudinal axis 11030 of the instrument 11010. Such a flat surface can act as a detent which would require an initial amount of force to displace the closure pin 11210 into the arcuate portion of the cam slot 11190. In certain instances, each first drive surface 11193 can comprise a flat surface 11196 in a proximal end 11192 of a cam slot 11190. Each flat surface 11196 can comprise a horizontal surface which is parallel to, or at least substantially parallel to, the longitudinal axis 11030. The flat surfaces 11196 can provide a large mechanical advantage between the closure channel 11180 and the anvil 11090. In various instances, the first drive surfaces 11193 can apply very little mechanical advantage to the closure pin 11210 when the closure pin 11210 is in the distal ends 11191 of the slots 11190; however, as the closure pin 11210 slides through the cam slots 11190 toward the proximal ends 11192, the mechanical advantage applied to the closure pin 11210 by the first drive surfaces 11193 can increase. When the closure pin 11210 enters into the proximal ends 11192, the mechanical advantage applied by the first drive surfaces 11193 can be at its greatest, and certainly larger than the mechanical advantage applied by the first drive surfaces 11193 when the closure pin 11210 is in the distal ends 11191 of the cam slots 11190. That said, where the distal ends 11191 may apply a lower mechanical advantage to the closure pin 11210, the distal ends 11191 may quickly displace the closure pin 11210 relative to the cartridge 11080. As the closure channel 11180 is advanced distally and the mechanical advantage applied to the closure pin 11210 increases, as discussed above, the first drive surfaces 11193 may move the anvil 11090 more slowly for a given speed of the closure channel 11180.

As illustrated in FIG. 96, the cartridge channel 11070 can further include distal closure slots 11215 defined therein which can be configured to receive the distal closure pin 11210 as the anvil 11090 approaches its closed position. Distal closure slots 11215 are substantially vertical and can include open ends at the top of the cartridge channel 11070 and closed ends at the opposite ends thereof. The slots 11215 may be wider at their open ends than their closed ends. In various instances, the closure pin 11210 can contact the closed ends of the closure slots 11215 when the anvil 11090 reaches its closed position. In such instances, the closed ends of the closure slots 11215 can stop the movement of the anvil 11090. In certain instances, the anvil 11090 can contact the staple cartridge 11080 when the anvil 11090 is in its closed position. In at least one instance, the anvil 11090 can be rotated about the pivot pin 11200 until a distal end 11091 of the anvil 11090 contacts a distal end 11081 of the staple cartridge 11080. As illustrated in FIG. 98, the distal closure pin 11210 which moves the anvil 11090 is positioned distally with respect to the pivot pin 11220. Thus, the closure force applied to the anvil 11090 by the closure drive is applied distally with respect to the pivot which rotatably connects the anvil 11090 to the cartridge channel 11070. Similarly, the opening force applied to the anvil 11090 by the closure drive is applied distally with respect to the pivot which rotatably connects the anvil 11090 to the cartridge channel 11070.

As discussed above, the handle 11015 can include a closure button 11065 configured to operate the closure system of the surgical instrument 11010. The movement of the closure button 11065 can be detected by a sensor or a switch, for example. When the closure button 11065 is pressed, a closure switch 11285 can be activated, or closed, which causes power to flow to the closure motor 11110. In such instances, the switch 11285 can close a power circuit which can supply electrical power to the closure motor 11110. In certain instances, the surgical instrument 11010 can include a microprocessor, for example. In such instances, the closure switch 11285 can be in signal communication with the microprocessor and, when the closure switch 11285 has been closed, the microprocessor can operably connect a power supply to the closure motor 11110. In any event, a first voltage polarity can be applied to the closure motor 11110 to rotate the closure output shaft 11130 in a first direction and close the anvil 11090 and, in addition, a second, or opposite, voltage polarity can be applied to closure motor 11110 to rotate the closure output shaft 11130 in a second, or opposite, direction and open the anvil 11090.

In various instances, the surgical instrument 11010 may be configured such that the operator of the surgical instrument 11010 is required to hold the closure button 11065 in a depressed state until the closure drive has reached its fully closed configuration. In the event that the closure button 11065 is released, the microprocessor can stop the closure motor 11110. Alternatively, the microprocessor can reverse the direction of the closure motor 11110 if the closure button 11065 is released prior to the closure drive reaching its fully closed configuration. After the closure drive has reached its fully closed configuration, the microprocessor may stop the closure motor 11110. In various instances, as described in greater detail below, the surgical instrument 11010 can comprise a closure sensor 11300 (FIGS. 96 and 98) configured to detect when the closure system has reached its fully closed configuration. The closure sensor 11300 can be in signal communication with the microprocessor which can disconnect the power supply from the closure motor 11110 when the microprocessor receives a signal from the closure sensor 11300 that the anvil 11090 has been closed. In various instances, re-pressing the closure button 11065 after the closure system has been placed in its closed configuration, but before the firing system has been operated, can cause the microprocessor to reverse the direction of the closure motor 11110 and re-open the anvil 11090. In certain instances, the microprocessor can re-open the anvil 11090 to its fully open position while, in other instances, the microprocessor can re-open the anvil 11090 to a partially open position.

Once the anvil 11090 has been sufficiently closed, the firing system of the surgical instrument 11010 can be operated. Referring primarily to FIGS. 95 and 97, the firing system can include a firing motor 11120. The firing motor 11120 can be positioned adjacent to the closure motor 11110. The closure motor 11110 can extend along a first longitudinal motor axis and the firing motor 11120 can extend along a second longitudinal motor axis which is parallel, or at least substantially parallel to the first motor axis. The first longitudinal motor axis and the second longitudinal motor axis can be parallel to the longitudinal axis 11030 of the surgical instrument 11010. The closure motor 11110 can be positioned on a first side of the longitudinal axis 11030 and the firing motor 11120 can be positioned on a second side of the longitudinal axis 11030. In such instances, the first longitudinal motor axis can extend along a first side of the longitudinal axis 11030 and the second longitudinal motor axis can extend along a second side of the longitudinal axis 11030. In various instances, the first longitudinal motor axis can extend through the center of the closure shaft 11130. Similar to the above, the firing motor 11120 can include a rotatable firing shaft 11230 extending therefrom. Also similar to the above, the second longitudinal motor axis can extend through the center of the firing shaft 11230.

Further to the above, a first firing gear 11240 can be mounted to the firing shaft 11230. The first firing gear 11240 is meshingly engaged with a firing lead screw drive gear 11250 which is mounted to a firing lead screw 11260. When the firing shaft 11230 is rotated by the motor 11120, the firing shaft 11230 can rotate the first firing gear 11240, the first firing gear 11240 can rotate the firing lead screw drive gear 11250, and the firing lead screw drive gear 11250 can rotate the firing lead screw 11260. Referring primarily to FIG. 97, the firing shaft 11230, the first firing gear 11240, the firing lead screw drive gear 11250, and/or the firing lead screw 11260 can be rotatably supported by the motor block 11125. The first firing gear 11240 and the firing lead screw drive gear 11250 can be positioned intermediate the motor block 11125 and a first block plate 11126. The first block plate 11126 can be mounted to the motor block 11125 and can also rotatably support the firing shaft 11230, the first firing gear 11240, the firing lead screw drive gear 11250, and/or the firing lead screw 11260. In various instances, the surgical instrument 11010 can further comprise a second block plate 11127 which can be mounted to the first block plate 11126. Similar to the above, the first closure gear 11140, the idler gear 11150, and the closure lead screw drive gear 11160 can be positioned intermediate the first block plate 11126 and the second block plate 11127. In various instances, the first block plate 11126 and/or the second block plate 11127 can rotatably support the closure shaft 11130, the first closure gear 11140, the idler gear 11150, the closure lead screw drive gear 11160, and/or the closure lead screw 11170.

The motor and gear arrangement described above can aid in conserving space within the handle 11015 of surgical instrument 11010. As described above, and referring primarily to FIG. 97, the closure motor 11110 and the firing motor 11120 are located on the motor block 11125. The closure motor 11110 is located on one side and slightly proximally of the firing motor 11120. Offsetting one motor proximally from another creates space for two gear trains with one gear train behind the other. For example, the closure gear train comprising the first closure gear 11140, the closure idler gear 11150, and the closure lead screw drive gear 11160 is proximal to the firing gear train comprising the first firing gear 11240 and the firing lead screw drive gear 11250. Having motor shafts extend proximally away from the jaws, with the main body of the motor extending distally toward the jaws, creates room in the handle 11015 and allows a shorter handle 11015 by having the main body of the motors 11110 and 11120 aligned parallel alongside other parts within the handle 11015.

Further to the above, the closure and firing gear trains are designed for space conservation. In the embodiment depicted in FIG. 97, the closure motor 11110 drives three gears, while the firing motor 11120 drives two gears; however, the closure gear train and the firing gear train can include any suitable number of gears. The addition of a third gear, i.e., the closure idler gear 11150, to the closure gear train permits the closure lead screw 11170 to be shifted downwardly with respect to the firing lead screw 11260 so that the separate lead screws can rotate about different axes. Moreover, the third gear eliminates the need for larger diameter gears to shift the axes of the lead screws so that the overall diameter of the space required by the gear trains, and the volume of the handle 11015, can be reduced.

Referring primarily to FIG. 98, the closure lead screw 11170 can extend along a first longitudinal shaft axis and the firing lead screw 11260 can extend along a second longitudinal shaft axis. The first longitudinal shaft axis and the second longitudinal shaft axis can be parallel to the longitudinal axis 11030 of the surgical instrument 11010. The first longitudinal shaft axis or the second longitudinal shaft axis can be collinear with the longitudinal axis 11030. In various instances, the firing lead screw 11260 can extend along the longitudinal axis 11030 and the second longitudinal shaft axis can be collinear with the longitudinal axis 11030. In such instances, the closing lead screw 11170 and the first longitudinal shaft axis can be offset with respect to the longitudinal axis 11030.

Further to the above, the firing lead screw 11260 can include a first end rotatably supported by the motor block 11125, for example, a second end rotatably supported by the handle 11015, and a threaded portion extending between the first end and the second end. The firing lead screw 11260 can reside within the "U" shape of the cartridge channel 11070 and above the closure lead screw 11170. Referring primarily to FIG. 95, the firing drive can further comprise a firing block 11265 which can include a threaded aperture 11266 threadably engaged with the threaded portion of the firing lead screw 11260. The firing block 11265 can be constrained from rotating with the firing lead screw 11260 such that the rotation of the firing lead screw 11260 can translate the firing block 11265 proximally or distally depending on the direction that the firing lead screw 11260 is rotated by the firing motor 11120. For instance, when the firing lead screw 11260 is rotated in a first direction, the firing lead screw 11260 can displace the firing block 11265 distally and, when the firing lead screw 11260 is rotated in a second direction, the firing lead screw 11260 can displace the firing block 11265 proximally. As described in greater detail below, the firing block 11265 can be advanced distally to deploy staples removably stored in the staple cartridge 11080 and/or incise tissue captured between the staple cartridge 11080 and the anvil 11090.

Further to the above, the firing block 11265 can be affixed to a pusher block 11270 such that the pusher block 11270 translates with the firing block 11265. The firing system can further include firing wedges 11280 which are attached to and extend distally from the pusher block 11270. The firing wedges 11280 can each include at least one cam surface at a distal end thereof which can be configured to eject staples from the staple cartridge 11080. The firing system can further comprise a knife block 11281 slidably disposed along the firing wedges 11280. In various instances, the initial distal movement of the firing block 11265 may not be transferred to the knife block 11281; however, as the firing block 11265 is advanced distally, the pusher block 11270, for example, can contact the knife block 11281 and push the knife block 11281 and a knife 11282 mounted thereto distally. In other instances, the knife block 11281 can be mounted to the firing wedges 11280 such that the knife block 11281 and the knife 11282 move with the firing wedges 11280 throughout the movement of the firing wedges 11280. The firing block 11265, the pusher block 11270, the firing wedges 11280, the knife block 11281, and the knife 11282 can form a pusher block and knife assembly. In any event, the firing wedges 11280 and the knife 11282 can be moved distally to simultaneously fire the staples stored within the staple cartridge 11080 and incise the tissue captured between the staple cartridge 11080 and the anvil 11090. The cam surfaces of the firing wedges 11280 can be positioned distally with respect to the cutting surface of the knife 11282 such that the tissue captured between the staple cartridge 11080 and the anvil 11090 can be stapled before it's incised.

As discussed above, the closure button 11065, when pushed, contacts the closure switch 11285 to energize closure motor 11110. Similarly, the firing button 11055, when pushed, contacts a firing switch 11290 to energize the firing motor 11120. In various instances, the firing switch 11290 can close a power circuit which can supply electrical power to the firing motor 11120. In certain instances, the firing switch 11290 can be in signal communication with the microprocessor of the surgical instrument 11010 and, when the firing switch 11290 has been closed, the microprocessor can operably connect a power supply to the firing motor 11120. In either event, a first voltage polarity can be applied to the firing motor 11120 to rotate the firing output shaft 11230 in a first direction and advance the firing assembly distally and a second, or opposite, voltage polarity can be applied to firing motor 11120 to rotate the firing output shaft 11230 in a second, or opposite, direction and retract the firing assembly. In various instances, the firing button 11055 can include a bi-directional switch configured to operate the firing motor 11120 in its first direction when the firing button 11055 is pushed in a first direction and in its second direction when the firing button 11055 is pushed in a second direction.

As discussed above, the firing system can be actuated after the closure system has sufficiently closed the anvil 11090. In various instances, the anvil 11090 may be sufficiently closed when it has reached its fully closed position. The surgical instrument 11010 can be configured to detect when the anvil 11090 has reached its fully closed position. Referring primarily to FIG. 98, the surgical instrument 11010 can include a closure sensor 11300 configured to detect when the closure channel 11180 has reached the end of its closure stroke and, thus, detect when the anvil 11090 is in its closed position. The closure sensor 11300 can be positioned at or adjacent to the distal end of the closure lead screw 11170. In at least one instance, the closure sensor 11300 can comprise a proximity sensor configured to sense when the closure channel 11180 is adjacent to and/or in contact with the closure sensor 11300. Similar to the above, the closure sensor 11300 can be in signal communication with the microprocessor of the surgical instrument 11010. When the microprocessor receives a signal from the closure sensor 11300 that the closure channel 11180 has reached its fully advanced position and the anvil 11090 is in a closed position, the microprocessor can permit the firing system to be actuated. Moreover, the microprocessor can prevent the firing system from being actuated until the microprocessor receives such a signal from the closure sensor 11300. In such instances, the microprocessor can selectively apply power from a power source to the firing motor 11120, or selectively control the power being applied to the firing motor 11120, based on the input from the closure sensor 11300. Ultimately, in these embodiments, the firing switch 11290 cannot initiate the firing stroke until the instrument is closed.

Certain embodiments are envisioned in which the firing system of the surgical instrument 11010 can be operated even though the closure system is in a partially closed configuration and the anvil 11090 is in a partial closed position. In at least one embodiment, the firing assembly of the surgical instrument 11010 can be configured to contact the anvil 11090 and move the anvil 11090 into its fully closed position as the firing assembly is advanced distally to fire the staples stored in the staple cartridge 11080. For instance, the knife 11282 can include a camming member configured to engage the anvil 11090 as the knife 11282 is advanced distally which can move the anvil 11090 into its fully closed position. The knife 11282 can also include a second camming member configured to engage the cartridge channel 11070. The camming members can be configured to position the anvil 11090 relative to the staple cartridge 11080 and set a tissue gap distance therebetween. In at least one instance, the knife 11282 can comprise an I-beam which is displaced distally to set the tissue gap, eject the staples from the staple cartridge 11080, and incise the tissue.

The surgical instrument 11010 can a sensor configured to detect when the firing system has completed its firing stroke. In at least one instance, the surgical instrument 11010 can include a sensor, such as an encoder, for example, which can be configured to detect and count the rotations of the firing lead screw 11260. Such a sensor can be in signal communication with the microprocessor of the surgical instrument 11010. The microprocessor can be configured to count the rotations of the firing lead screw 11260 and, after the firing lead screw 11260 has been rotated a sufficient number of times to fire all of the staples from the staple cartridge 11080, the microprocessor can interrupt the power supplied to the firing motor 11120 to stop the firing lead screw 11260. In certain instances, the microprocessor can reverse the voltage polarity applied to the firing motor 11120 to automatically retract the firing assembly once the firing assembly has fired all of the staples.

As discussed above, the surgical instrument 11010 can include a power supply. The power supply can include a power supply located external to the handle 11015 and a cable which can extend into the handle 11015, for example. The power supply can include at least one battery contained within handle 11015. A battery can be positioned in the first handle portion 11020 and/or the handle grip 11040. It is envisioned that the batteries, gears, motors, and rotating shafts may all be combined in one unit separable from the rest of handle 11015. Such a unit may be cleanable and sterilizable.

In various instances, the surgical instrument 11010 can include one or more indicators configured to indicate the state of the surgical instrument 11010. In at least one embodiment, the surgical instrument 11010 can include an LED 11100, for example. To communicate the state of the surgical instrument to the user, the LED 11100 can glow in different colors during different operating states of surgical instrument 11010. For example, the LED 11100 can glow a first color when the surgical instrument 11010 is powered and an unspent staple cartridge 11080 is not positioned in the cartridge channel 11070. The surgical instrument 11010 can include one or more sensors which can be configured to detect whether a staple cartridge 11080 is present in the cartridge channel 11070 and whether staples have been ejected from the staple cartridge 11080. The LED 11100 can glow a second color when the surgical instrument 11010 is powered and an unspent staple cartridge 11080 is positioned in the cartridge channel 11070. The LED 11010 can glow a third color when the instrument 11010 is powered, an unspent staple cartridge 11080 is loaded into the cartridge channel 11070, and the anvil 11090 is in a closed position. Such a third color can indicate that the surgical instrument 11010 is ready to fire the staples from the staple cartridge 11080. The LED 11100 can glow a fourth color after the firing process has begun. The LED can glow a fifth color after the firing process has been completed. This is but one exemplary embodiment. Any suitable number of colors could be utilized to indicate any suitable number of states of the surgical instrument 11010. While one or more LEDs may be utilized to communicate the state of the surgical instrument, other indicators could be utilized.

In use, a user of the surgical instrument 11010 may first load the surgical instrument 11010 with a staple cartridge 11080 by placing the staple cartridge 11080 into the cartridge channel 11070. Loading the cartridge 11080 into the cartridge channel 11070 may cause the LED 11100 to change from a first color to a second color. The user may grasp the handle grip 11040 and use the thumb activated closure switch 11065 to open the anvil 11090 of the surgical instrument 11010 in order to place the staple cartridge 11080 within the cartridge channel 11070. The user could then position the staple cartridge 11080 on one side of the tissue to be stapled and transected and the anvil 11090 on the opposite side of the tissue. Holding closure button 11065 with their thumb, the user may close surgical instrument 11010. Release of the closure button 11065 before the closing stroke is completed can reopen the anvil 11090 and allow the user to reposition the surgical instrument 11010, if necessary. The user may enjoy the advantage of being able to use an open linear cutter with pivotable jaws without the necessity of assembling linear cutter portions. The user may further enjoy the advantage of a pistol-grip feel.

As the anvil 11090 is being moved into its fully closed position, the closure channel 11080 can contact the closure sensor 11300, and the closure sensor 11300 can signal the microprocessor to arm firing switch 11290. At such point, the LED 11100 may glow a third color to show a loaded, closed, and ready-to-fire surgical instrument 11010. The user can then press the firing button 11055 which contacts the firing switch 11290 and causes the firing switch 11290 to energize the firing motor 11120. Energizing the firing motor 11120 rotates the firing shaft 11230 which, in turn, rotates the first firing gear 11240 and the firing lead screw drive gear 11250. The firing lead screw drive gear 11250 rotates the firing lead screw 11260. Threads of the firing lead screw 11260 engage and apply a force against internal threads defined in the firing block 11265 to move the firing block 11265 distally. The firing block 11265 moves pusher block 11270 distally, carrying firing wedges 11280 distally. The cam surfaces 11305 at the distal end of the firing wedges 11280 cam staples stored within the staple cartridge 11080 toward the anvil 11090, and the anvil 11090 can form the staples to fasten the tissue. The pusher block 11270 engages the knife block 11281 to push the knife block 11281 and the knife 11282 distally to transect the stapled tissue. After the firing stroke has been completed, the firing motor 11120 can be reversed to return the pusher block 11270, the knife block 11281, the firing wedges 11280, and the knife 11282. The surgical instrument 11010 can include a button and/or switch which automatically instructs the microprocessor to retract the firing assembly even though the firing stroke has not yet been completed. In some instances, the firing assembly may not need to be retracted. In any event, the user can open the surgical instrument 11010 by pressing the closure button 11065. The closure button 11065 can contact the closure switch 11285 and energize the closure motor 11110. The closure motor 11110 can be operated in a reverse direction to retract the closure channel 11180 proximally to reopen the anvil 11090 of the surgical instrument 11010. The LED 11100 may glow a fourth color designating a fired cartridge, and a complete procedure.

Figure 99:
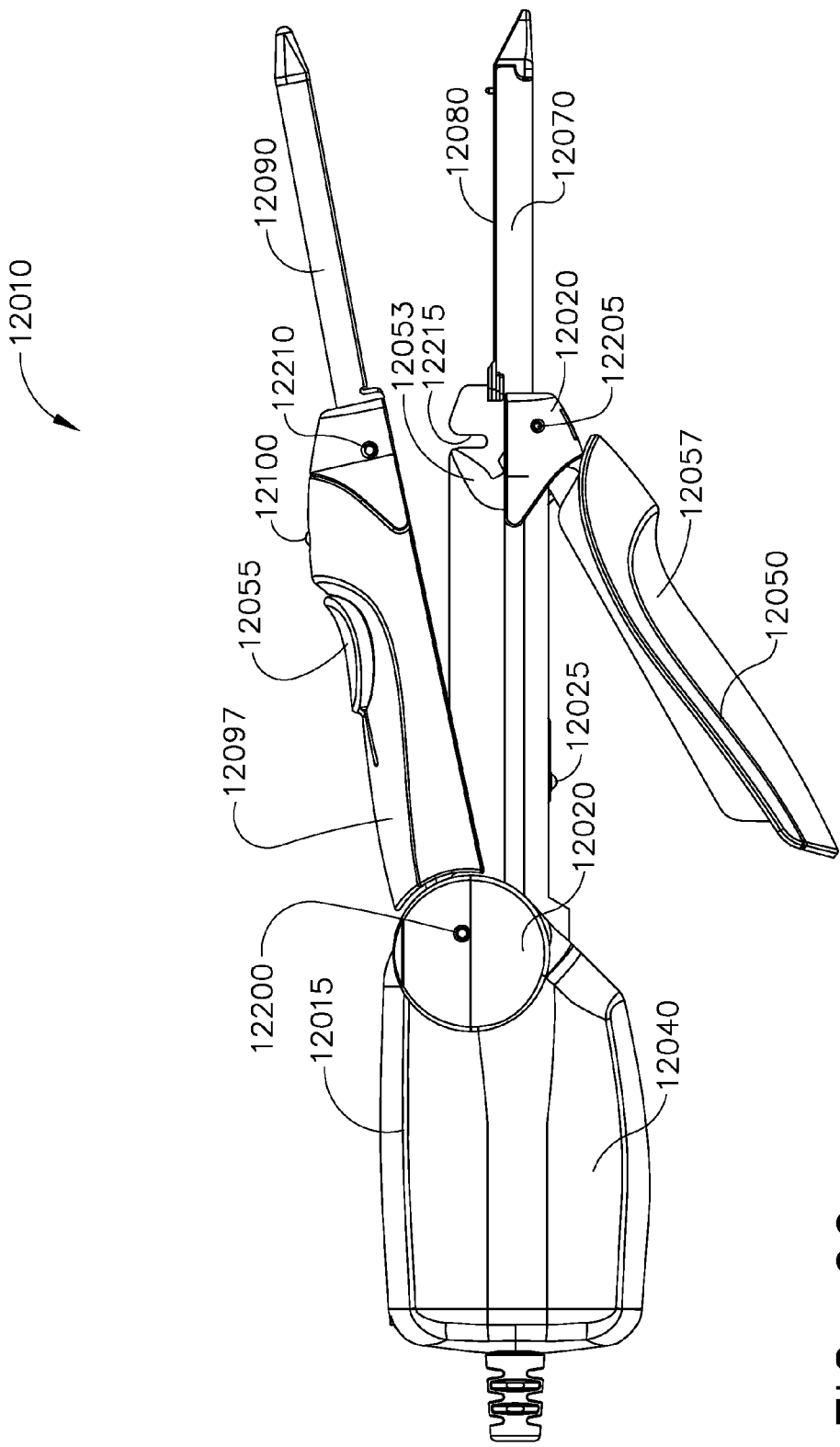
FIG. 99 is a perspective view of a surgical stapling instrument in accordance with at least one embodiment illustrated in an open, unlatched condition.
Figure 100:
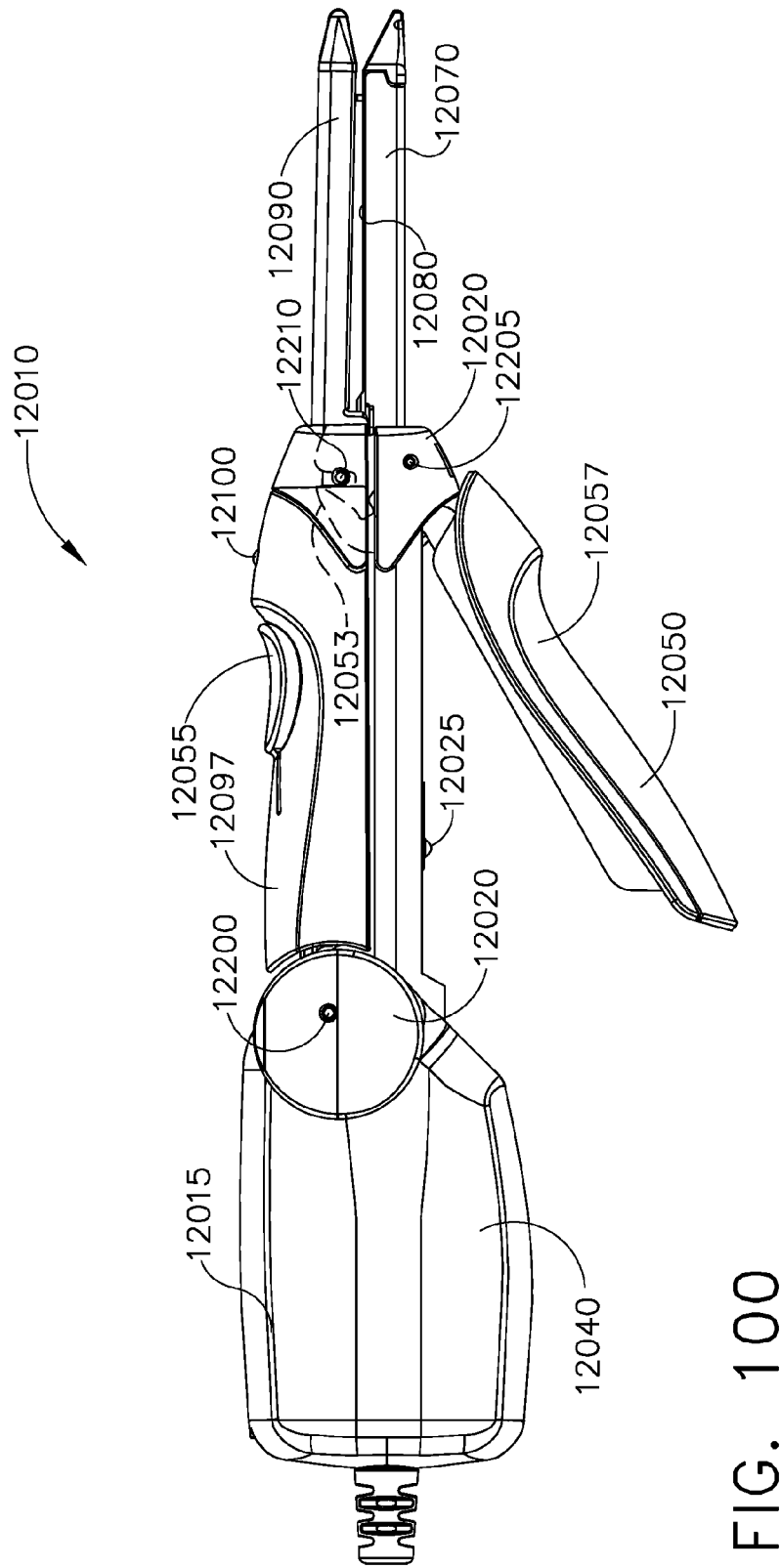
FIG. 100 is a perspective view of the surgical stapling instrument of FIG. 99 illustrated in a closed, unlatched condition.
Figure 101:
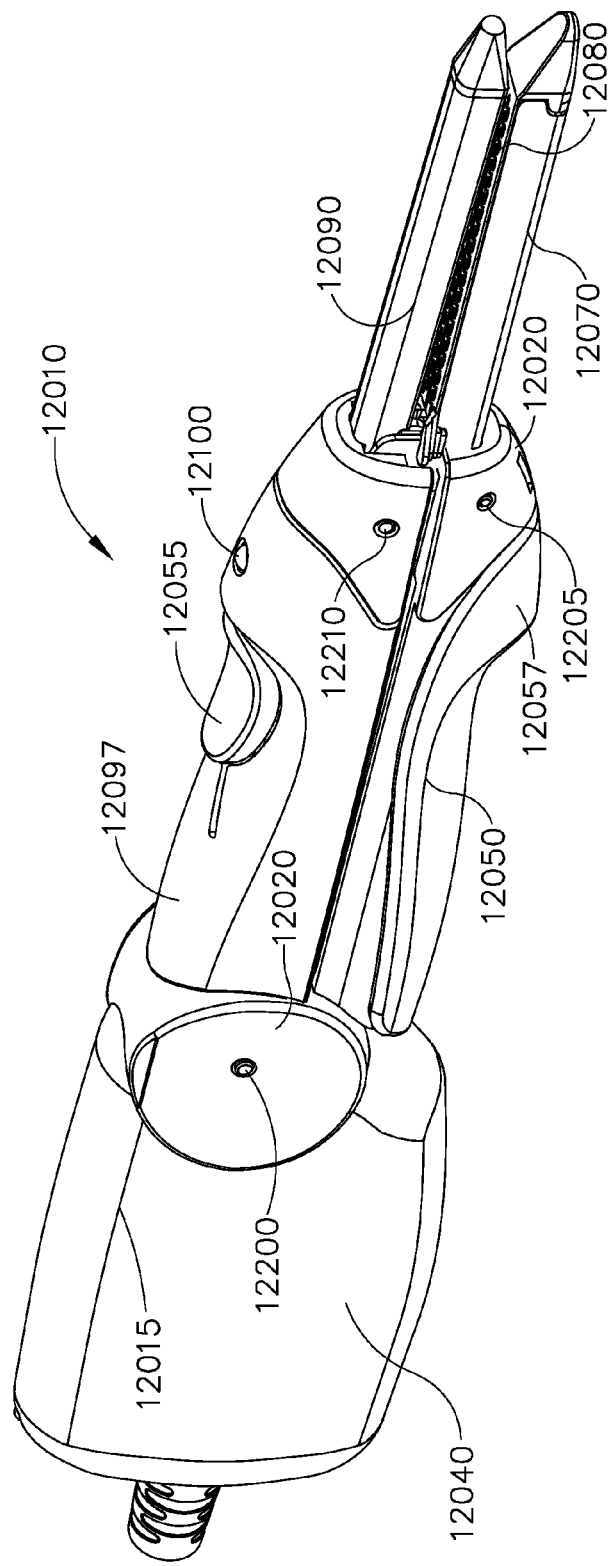
FIG. 101 is a perspective view of the surgical stapling instrument of FIG. 99 illustrated in a closed, latched condition.
Figure 102:
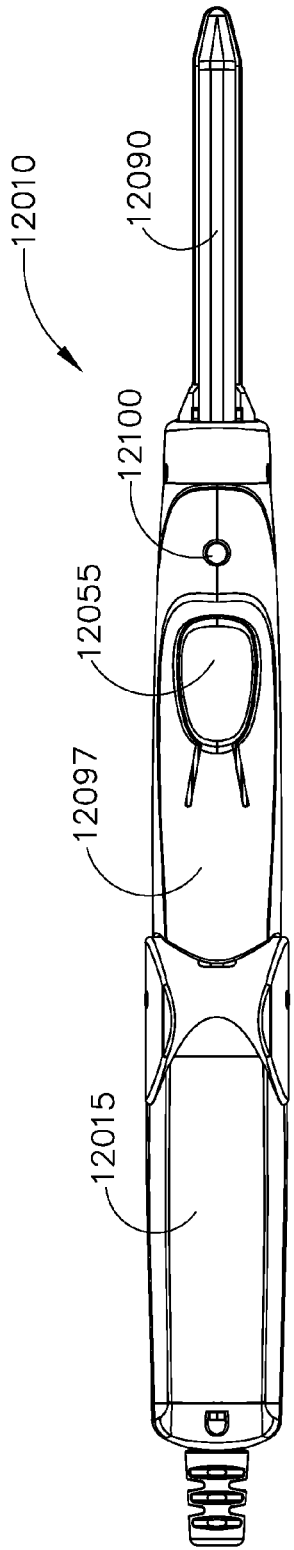
FIG. 102 is a plan view of the surgical stapling instrument of FIG. 99.
Figure 103:
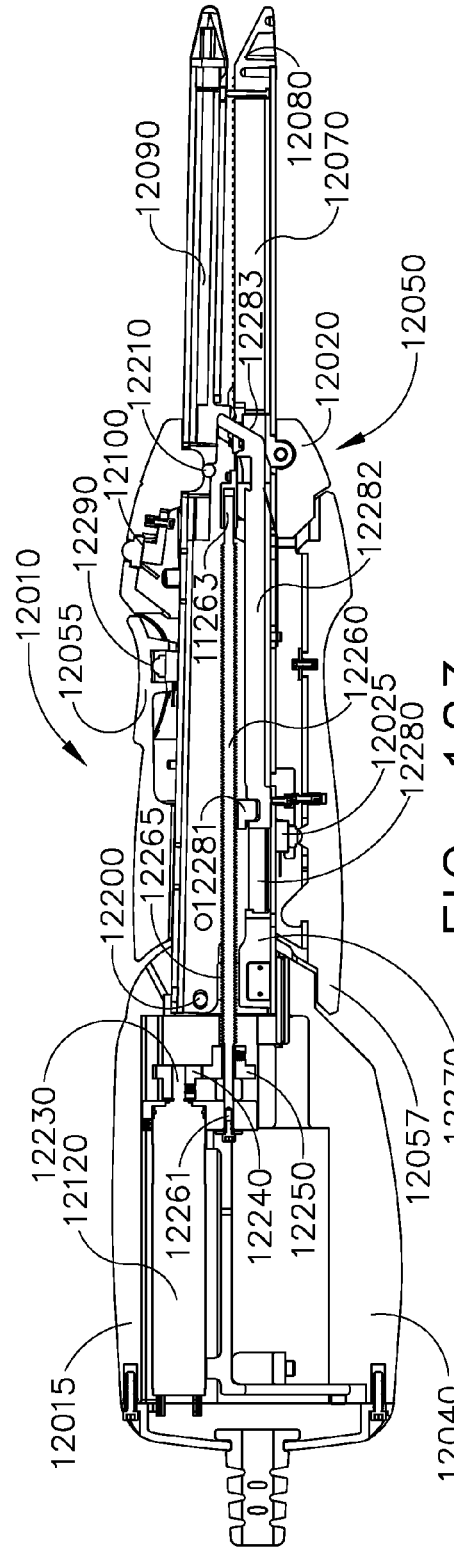
FIG. 103 is a cross-sectional view of the surgical stapling instrument of FIG. 99.

A surgical stapling instrument 12010 is depicted in FIGS. 99-106. The instrument 12010 can include a handle 12015, a closure drive including a closure latch 12050 configured to compress tissue between a staple cartridge 12080 and an anvil 12090, and a firing drive configured to eject staples from the staple cartridge 12080 and incise the tissue. FIG. 99 depicts the instrument 12010 in an open, unlatched condition. When the instrument 12010 is in its open, unlatched condition, the anvil 12090 is pivoted away from the staple cartridge 12080. In various instances, the anvil 12090 can be pivoted relative to the staple cartridge 12080 through a wide angle so that the anvil 12090 and the staple cartridge 12080 may be easily positioned on opposite sides of the tissue. FIG. 100 depicts the instrument 12010 in a closed, unlatched condition. When the instrument 12010 is in its closed, unlatched condition, the anvil 12090 has been rotated toward the staple cartridge 12080 into a closed position opposite the staple cartridge 12080. In various instances, the closed position of the anvil 12090 may depend on the thickness of the tissue positioned intermediate the anvil 12090 and the staple cartridge 12080. For instance, the anvil 12090 may reach a closed position which is further away from the staple cartridge 12080 when the tissue positioned intermediate the anvil 12090 and the staple cartridge 12080 is thicker as compared to when the tissue is thinner. FIG. 101 depicts the instrument 12010 in a closed, latched condition. When the instrument 12010 is in its closed, latched condition, the closure latch 12050 has been rotated to engage the anvil 12090 and position the anvil 12090 relative to the staple cartridge 12080. At such point, as described in greater detail further below, the firing drive of the surgical instrument 12010 can be actuated to fire the staples from the staple cartridge 12080 and incise the tissue.

Figure 106:
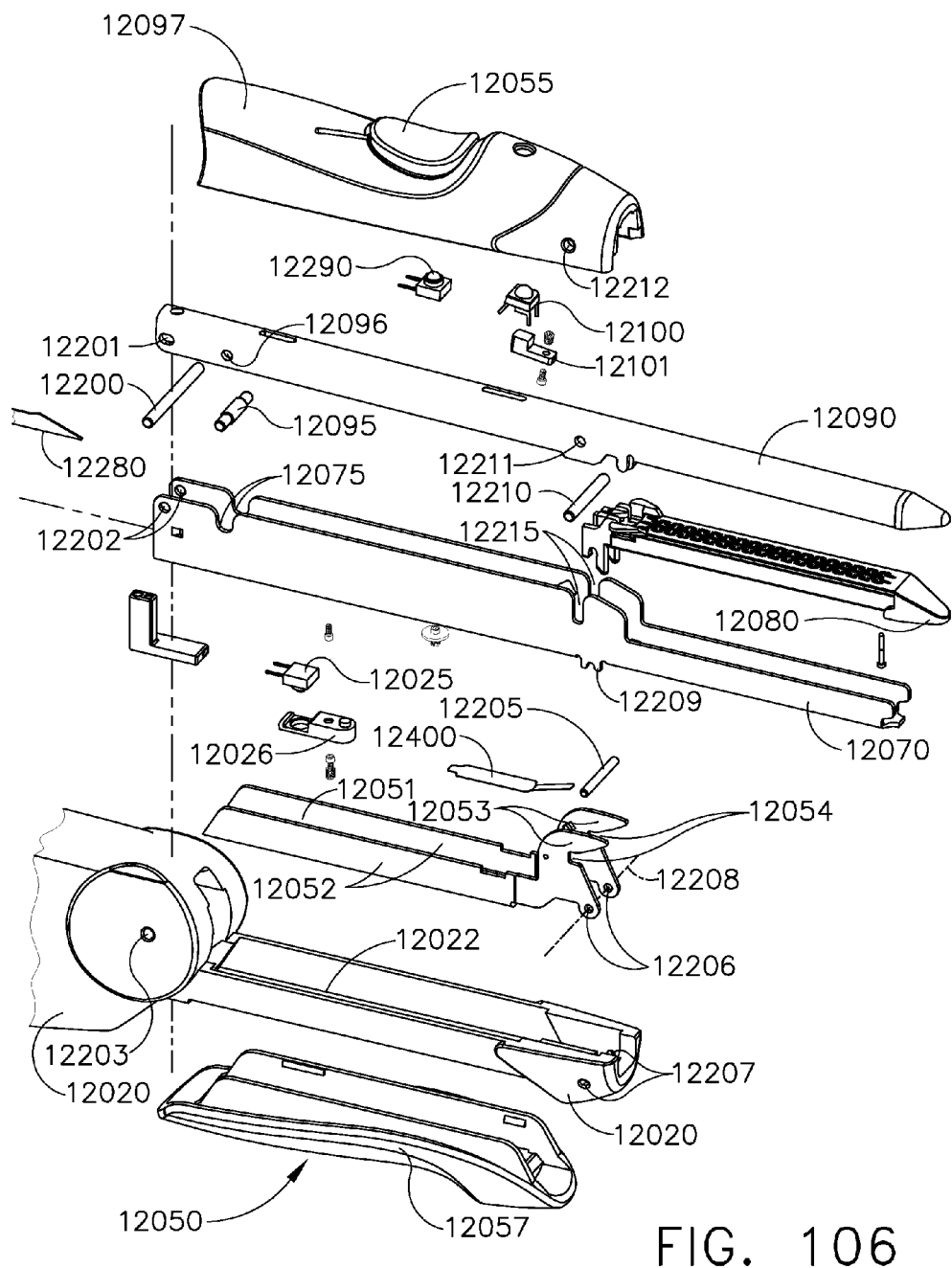
FIG. 106 is an exploded view of a closing drive of the surgical stapling instrument of FIG. 99.

Referring primarily to FIG. 106, the surgical instrument 12010 can include a frame 12020 extending from the handle 12015. The frame 12020 can include a frame channel 12022 defined therein which can be configured to receive and/or support a cartridge channel 12070. The cartridge channel 12070 can include a proximal end and a distal end. The proximal end of the cartridge channel 12070 can be connected to the frame 12020. The distal end of the cartridge channel 12070 can be configured to removably receive a staple cartridge 12080 therein. The frame channel 12022 can include pivot apertures 12207 defined in opposite sides thereof. A pivot pin 12205 can be supported within the pivot apertures 12207 and can extend between the sides of the channel 12022. The closure latch 12050 can include a latch frame 12051 comprising latch bars 12052. The latch bars 12052 can be rotatably mounted to the frame 12020 via the pivot pin 12205 which can extend through pivot apertures 12206 defined in the latch bars 12052. In various instances, the pivot apertures 12206, 12207 and the pivot pin 12205 can define a fixed axis 12208 about which the closure latch 12050 can rotate. The closure latch 12050 can further include a latch housing 12057 mounted to the latch bars 12052. When the latch housing 12057 is moved by the user of the surgical instrument 12010, the latch housing 12057 can move the latch bars 12052. The operation of the closure latch 12050 is described in greater detail further below.

Further to the above, the anvil 12090 can include a proximal end and a distal end. The distal end of the anvil 12090 can include a plurality of staple forming pockets which are alignable, or registerable, with staple cavities defined in the staple cartridge 12080 when the anvil 12090 is in its closed position. The proximal end of the anvil 12090 can be pivotably connected to the frame 12020. The anvil 12090 can include a pivot aperture 12201 which can be aligned with pivot apertures 12202 defined in the cartridge channel 12207 and a pivot aperture 12203 defined in the frame 12020. A pivot pin 12200 can extend through the pivot apertures 12201, 12202, and 12203 and can rotatably connect the anvil 12090 to the cartridge channel 12207. In various instances, the pivot apertures 12201, 12202, and 12203 and the pivot pin 12200 can define a fixed axis about the anvil 12090 can rotate. In certain instances, the pivot apertures 12201, 12202 and/or 12203 can be longitudinally elongate, for example, such that the pivot pin 12200 can slide within the pivot apertures 12201, 12202 and/or 12203. In such instances, the anvil 12090 can rotate about an axis relative to the cartridge channel 12070 and, in addition, translate relative to the cartridge channel 12070. The anvil 12090 can further include an anvil housing 12097 mounted thereto. When the anvil housing 12097 is moved by the user of the surgical instrument 12010, the anvil housing 12097 can move the anvil 12090 such that the anvil 12090 can be rotated between an open position (FIG. 99) and a closed position (FIG. 100).

Further to the above, the anvil 12090 can further include a latch pin 12210. The anvil 12090 can include latch pin apertures 12211 and the anvil housing 12097 can include latch pin apertures 12212 which are configured to receive and support the latch pin 12210. When the anvil 12090 has been moved into its closed position, or a position adjacent to its closed position, the latch 12050 can engage the latch pin 12210 and pull the anvil 12090 toward the staple cartridge 12080. In various instances, the latch bars 12052 of the latch 12050 can each include a latch arm 12053 configured to engage the latch pin 12210. The latch 12050 can be rotated between an unlatched position (FIG. 100) in which the latch arms 12053 are not engaged with the latch pin 12210 and a latched position (FIG. 101). When the latch 12050 is moved between its unlatched position and its latched position, the latch arms 12053 can engage the latch pin 12210 and move the anvil 12090 toward the staple cartridge 12080. Each latch arm 12053 can include a camming surface configured to contact the latch pin 12210. The camming surfaces can be configured to push and guide the latch pin 12210 toward the staple cartridge 12080. When the latch 12050 has reached its latched position, the latch pin 12210 can be captured within latch slots 12054 defined in the latch bars 12052. The latch slots 12054 can be at least partially defined by the latch arms 12053. The opposite sides of the latch slots 12054 can include lift surfaces which can be configured to engage the latch pin 12210 and lift the anvil 12090 away from the staple cartridge 12080 when the latch 12050 is rotated between its latched position and its unlatched position to open the instrument 12010, as discussed in greater detail further below.

As discussed above, the anvil 12090 can be moved toward the staple cartridge 12080. In various instances, the movement of the anvil 12090 toward the staple cartridge 12080 can be stopped when a distal end of the anvil 12090 contacts a distal end of the staple cartridge 12080. In certain instances, the movement of the anvil 12090 can be stopped when the latch pin 12210 contacts the cartridge channel 12070. The cartridge channel 12070 can include slots 12215 defined therein which are configured to receive the latch pin 12210. Each slot 12215 can include an upwardly-facing open end through which the latch pin 12210 can enter the slot 12215 and, in addition, a closed end. In various instances, the latch pin 12210 can contact the closed ends of the slots 12215 when the anvil 12090 reaches its closed position. In certain instances, the latch pin 12210 may not contact the closed ends of the slots 12215 if thick tissue is positioned between the anvil 12090 and the staple cartridge 12080. In at least one instance, the anvil 12090 can further include a stop pin 12095. The stop pin 12095 can be mounted to and supported by the anvil 12090 via pin apertures 12096 defined therein. The stop pin 12095 can be configured to contact the cartridge channel 12070 and stop the movement of the anvil 12090 toward the staple cartridge 12080. Similar to the above, the cartridge channel 12070 can further include stop slots 12075 defined therein which can be configured to receive the stop pin 12095. Each stop slot 12075 can include an upwardly-facing open end through which the stop pin 12095 can enter the stop slot 12275 and, in addition, a closed end. In various instances, the stop pin 12095 can contact the closed ends of the stop slots 12075 when the anvil 12090 reaches its closed position. In certain instances, the stop pin 12095 may not contact the closed ends of the stop slots 12075 if thick tissue is positioned between the anvil 12090 and the staple cartridge 12080.

As discussed above, the cartridge channel 12070 can be mounted to the frame 12020. In various instances, the cartridge channel 12070 can be rigidly and fixedly mounted to the frame 12020. In such instances, the cartridge channel 12070 may not be movable relative to the frame 12020 and/or the handle 12015. In certain instances, the cartridge channel 12070 can be pivotably coupled to the frame 12020. In at least one such instance, the cartridge channel 12070 can include pivot apertures 12202 defined therein which can be configured to receive the pivot pin 12200. In such circumstances, both the anvil 12090 and the cartridge channel 12070 may be rotatable relative to the frame 12020 about the pivot pin 12200. The latch 12050 can hold the anvil 12090 and the cartridge channel 12070 in position when the latch 12050 is engaged with the latch pin 12210.

In certain instances, further to the above, the instrument 12010 can include one or more sensors configured to detect whether the anvil 12090 is in its closed position. In at least one instance, the instrument 12010 can include a pressure sensor positioned intermediate the frame 12020 and the cartridge channel 12070. The pressure sensor can be mounted to the frame channel 12022 or the bottom of the cartridge channel 12070, for example. When the pressure sensor is mounted to the bottom of the cartridge channel 12070, the pressure sensor can contact the frame channel 12022 when the cartridge channel 12070 is moved toward the frame channel 12022. The cartridge channel 12070 can be moved toward the frame channel 12022 if the cartridge channel 12070 is rotatable relative to the frame channel 12022, as discussed above. In addition to or in lieu of the above, the cartridge channel 12070 can be moved toward the frame channel 12022 if the cartridge channel 12070 flexes toward the frame channel 12022. The cartridge channel 12070 can flex toward the frame channel 12022 when a compressive load is generated between the anvil 12090 and the cartridge channel 12070. A compressive load between the anvil 12090 and the cartridge channel 12070 can be generated when the anvil 12090 is moved into its closed position and/or when the anvil 12090 is moved toward the cartridge channel 12070 by the latch 12050. When the anvil 12090 is pushed toward the cartridge channel 12070 and/or when the latch 12050 is used to pull the anvil 12090 toward the cartridge channel 12070, the cartridge channel 12070 can bear against the pivot pin 12205. In various instances, the cartridge channel 12070 can include a slot or groove 12209 defined therein which can be configured to receive the pivot pin 12205. In any event, the pressure sensor can be configured to detect the pressure or force being applied to the cartridge channel 12070. The pressure sensor can be in signal communication with a microprocessor of the surgical instrument 12010. When the pressure or force detected by the pressure sensor exceeds a threshold value, the microprocessor can permit the firing system of the instrument 12010 to be operated. Prior to the pressure or force exceeding the threshold value, the microprocessor can warn the user of the surgical instrument 12010 that the anvil 12090 may not be closed, or sufficiently closed, when the user attempts to operate the firing system. In addition to or in lieu of such a warning, the microprocessor can prevent the firing system of the instrument 12010 from being operated if the pressure or force detected by the pressure sensor has not exceeded the threshold value.

In certain instances, further to the above, the instrument 12010 can include one or more sensors configured to detect whether the latch 12050 is in its latched position. In at least one instance, the instrument 12010 can include a sensor 12025 positioned intermediate the frame 12020 and the cartridge channel 12070. The sensor 12025 can be mounted to the frame channel 12022 or the bottom of the cartridge channel 12070, for example. When the sensor 12025 is mounted to the bottom of the cartridge channel 12070, the latch 12050 can contact the sensor 12025 when the latch 12050 is moved from its unlatched position to its latched position. The sensor 12025 can be in signal communication with the microprocessor of the surgical instrument 12010. When the sensor 12025 detects that the latch 12050 is in its latched position, the microprocessor can permit the firing system of the instrument 12010 to be operated. Prior to the sensor 12025 sensing that the latch 12050 is in its latched position, the microprocessor can warn the user of the surgical instrument 12010 that the anvil 12090 may not be closed, or sufficiently closed, when the user attempts to operate the firing system. In addition to or in lieu of such a warning, the microprocessor can prevent the firing system of the instrument 12010 from being operated if the latch 12050 is not detected in its latched position. In various instances, the sensor 12025 can comprise a proximity sensor, for example. In certain instances, the sensor 12025 can comprise a Hall Effect sensor, for example. In at least one such instance, the latch 12050 can include at least one magnetic element, such as a permanent magnet, for example, which can be detected by the Hall Effect sensor. In various instances, the sensor 12025 can be held in position by a bracket 12026, for example.

Figure 104:
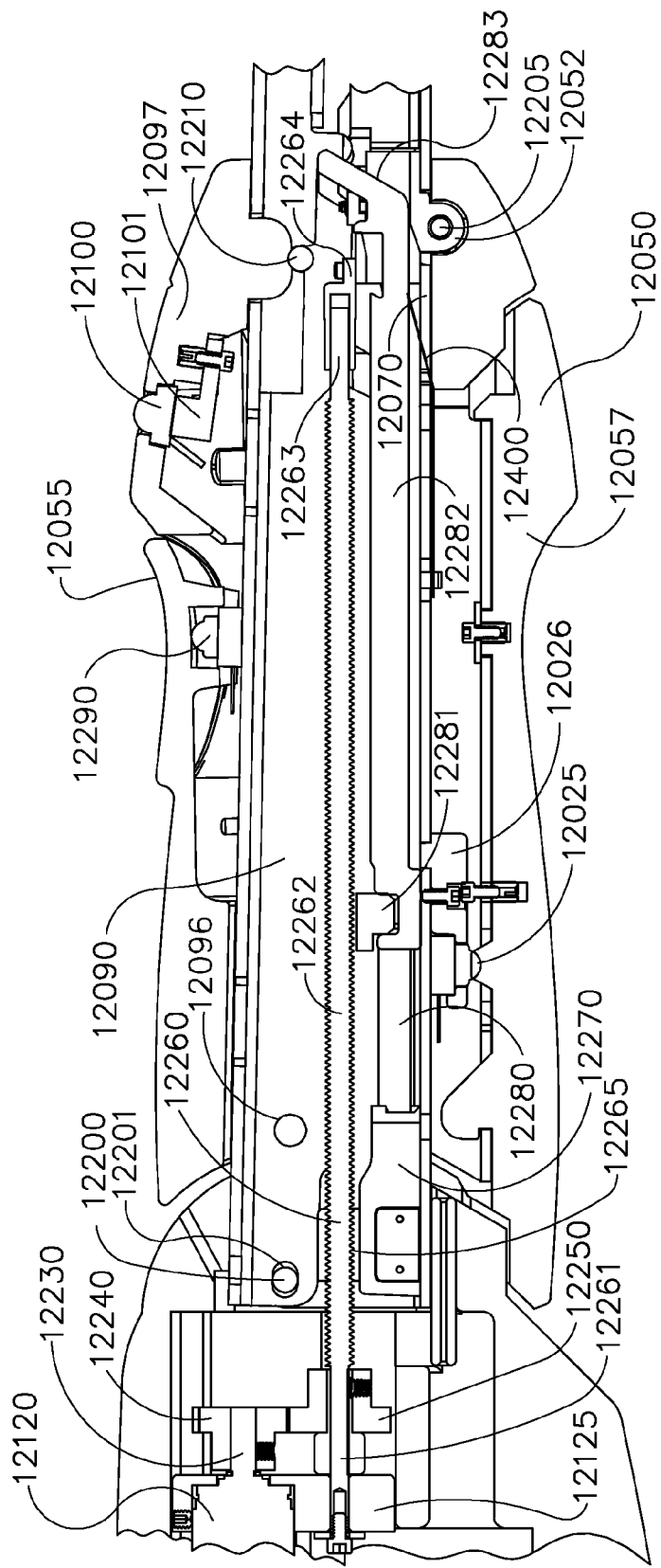
FIG. 104 is a detail cross-sectional view of the surgical stapling instrument of FIG. 99.
Figure 105:
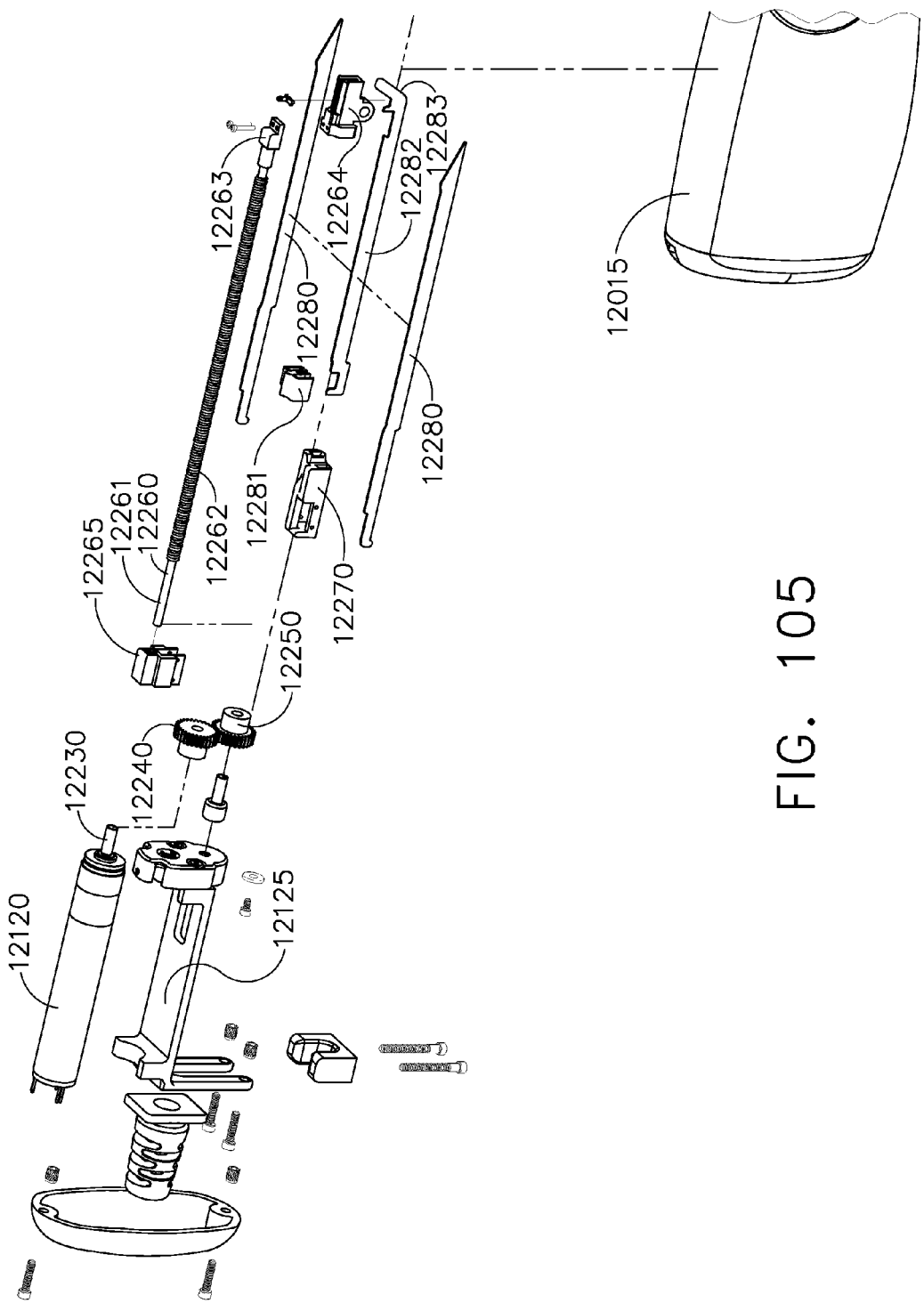
FIG. 105 is an exploded view of a firing drive of the surgical stapling instrument of FIG. 99.

Referring primarily to FIG. 105, the firing system of the surgical instrument 12010 can include a firing motor 12120 configured to rotate a firing shaft 12230. The firing motor 12120 can be mounted to a motor frame 12125 within the handle 12015 of the surgical instrument 12010 such that the firing shaft 12230 extends distally. The firing system can further comprise a gear train including, one, a first firing gear 12240 mounted to the closure shaft 12230 and, two, a lead screw gear 12250 mounted to a lead screw 12260. The first firing gear 12240 can be meshingly engaged with the lead screw gear 12250 such that, when the first firing fear 12240 is rotated by the firing shaft 12230, the first firing gear 12240 can rotate the lead screw gear 12250 and the lead screw gear 12250 can rotate the lead screw 12260. Referring primarily to FIG. 104, the lead screw 12260 can comprise a first end 12261 rotatably 12250 mounted within an aperture defined in the motor block 12125 and a second end 12263 rotatably supported within a bearing mounted to a bearing portion 12264 of the handle 12015. The lead screw 12260 can further include a threaded portion 12262 extending between the first end 12261 and the second end 12263. The firing system can further comprise a firing nut 12265 threadably engaged with the threaded portion 12262 of the lead screw 12260. The firing nut 12265 can be constrained from rotating with the lead screw 12260 such that, when the lead screw 12260 is rotated in a first direction by the firing motor 12120, the lead screw 12260 can advance the firing nut 12265 distally and, correspondingly, when the lead screw 12260 is rotated in a second, or opposite, direction by the firing motor 12120, the lead screw 12260 can retract the firing nut 12265 proximally.

Further to the above, the firing nut 12265 can be mounted to a firing block 12270 which can translate with the firing nut 12265. In various instances, the firing nut 12265 and the firing block 12270 can be integrally formed. Similar to the above, the firing system can further include firing bars 12280 extending therefrom which translate with the firing nut 12265 and the firing block 12270. In various instances, the firing nut 12265, the firing block 12270, and the firing bars 12280 can comprise a firing assembly that is translated proximally and/or distally by the lead screw 12160. When the firing assembly is advanced distally by the lead screw 12260, the firing bars 12280 can enter into the staple cartridge 12080 and eject the staples therefrom. The firing system can further comprise a knife block 12281 and a knife bar 12282 mounted to and extending from the knife block 12281. As the firing block 12270 is advanced distally, the firing bars 12280 can engage the knife block 12281 and advance the knife block 12281 and the knife bar 12282 distally. In various instances, the firing block 12270 can move relative to the knife block 12281 during the initial portion of the firing stroke and then move together during the final portion of the firing stroke. In at least one such instance, the firing bars 12280 can slide through slots defined in the knife block 12281 until one or more raised surfaces extending from the firing bars 12280 contact the knife block 12281 and push the knife block 12281 distally with the firing bars 12280. In various instances, the firing assembly can further include the knife block 12281 and the knife bar 12282 which can move concurrently with the firing block 12270 and the firing bars 12280. In either event, as the knife bar 12282 is advanced distally, a cutting edge 12283 of the knife bar 12282 can incise tissue captured between the anvil 12090 and the staple cartridge 12080. The disclosure of U.S. Pat. No. 4,633,874, entitled SURGICAL STAPLING INSTRUMENT WITH JAW LATCHING MECHANISM AND DISPOSABLE LOADING CARTRIDGE, which issued on Jan. 6, 1987, is incorporated by reference herein in its entirety.

Referring primarily to FIG. 106, the firing system of the surgical instrument 12010 can include a firing button 12055 and a firing switch 12290. When the user of the surgical instrument 12010 depresses the firing button 12055, the firing button 12055 can contact the firing switch 12290 and close a firing circuit which can operate the firing motor 12120. When the user of the surgical instrument 12010 releases the firing button 12055, the firing circuit can be opened and the power supplied to the firing motor 12120 can be interrupted. The firing button 12055 can be pushed once again to operate the firing motor 12120 once again. In certain instances, the firing button 12055 can comprise a bi-directional switch which, when pushed in a first direction, can operate the firing motor 12120 in a first direction and, when pushed in a second direction, can operate the firing motor 12120 in a second, or opposite, direction. The firing switch 12090 and/or any suitable arrangement of firing switches can be in signal communication with the microprocessor of the surgical instrument 12010 which can be configured to control the power supplied to the firing motor 12120. In certain instances, further to the above, the microprocessor may ignore signals from the firing button 12055 until the sensor 12025 has detected that the latch 12050 has been closed. In any event, the firing button 12055 can be pushed in its first direction to advance the firing bars 12280 and the knife 12282 distally and its second direction to retract the firing bars 12280 and the knife 12282 proximally. In certain instances, the surgical instrument 12010 can include a firing button and switch configured to operate the firing motor 12120 in its first direction and a retraction button and switch configured to operate the firing motor 12120 in its second direction. After the firing bars 12280 and the knife 12282 have been retracted, the latch 12050 can be moved from its latched position to its unlatched position to disengage the latch arms 12053 from the latch pin 12210. Thereafter, the anvil 12090 can be pivoted away from the staple cartridge 12080 to return the surgical instrument 12010 to an open, unlatched condition. Similar to the above, the surgical instrument 12010 can include one or more indicators, such as LED 12100, for example, configured to indicate the status of the surgical instrument 12010. The LED 12100 can be in signal communication with the microprocessor of the surgical instrument 12010 and can operate in a similar manner to that described in connection with the LED 11100, for example. The LED 12100 can be held in position by a bracket 12101, for example.

In various instances, the instrument 12010 can include a firing lockout system which can block the advancement of the knife 12282 and/or the firing bars 12280 if the anvil 12090 is not in a closed, or a sufficiently closed, position. Referring to FIGS. 104 and 106, the instrument 12010 can comprise a biasing member 12400 mounted to the cartridge channel 12070, for example, which can bias the knife 12282 into engagement with a lock portion of the handle 12015. When the anvil 12090 is rotated into its closed position, the anvil 12090 can push the knife 12282 downwardly away from the lock portion against the biasing force of the biasing member 12400. At such point, the knife 12282 can be advanced distally. Similarly, the instrument 12010 can include a biasing member which can bias the firing bars 12280 into engagement with a lock portion of the handle 12015 wherein the anvil 12090 can disengage the firing bars 12280 from the lock portion when the anvil 12090 is moved into its closed position.

The surgical instrument 12010 can comprise a manually driven closure system and a motor driven staple firing system. A portion 12040 of the handle 12015 can be gripped by one hand of the user of the surgical instrument 12010 and the anvil 12090 and the latch 12050 can be manipulated by their other hand. As part of closing the latch 12050, in at least one embodiment, the user can move one of their hands in the general direction of their other hand which can reduce the incidental and accidental movement of the surgical instrument 12010. The surgical instrument 12010 can be powered by any suitable power source. For instance, an electrical cable can extend from an external power source and into the handle 12015. In certain instances, a battery can be stored in the handle 12015, for example.

Figure 107:
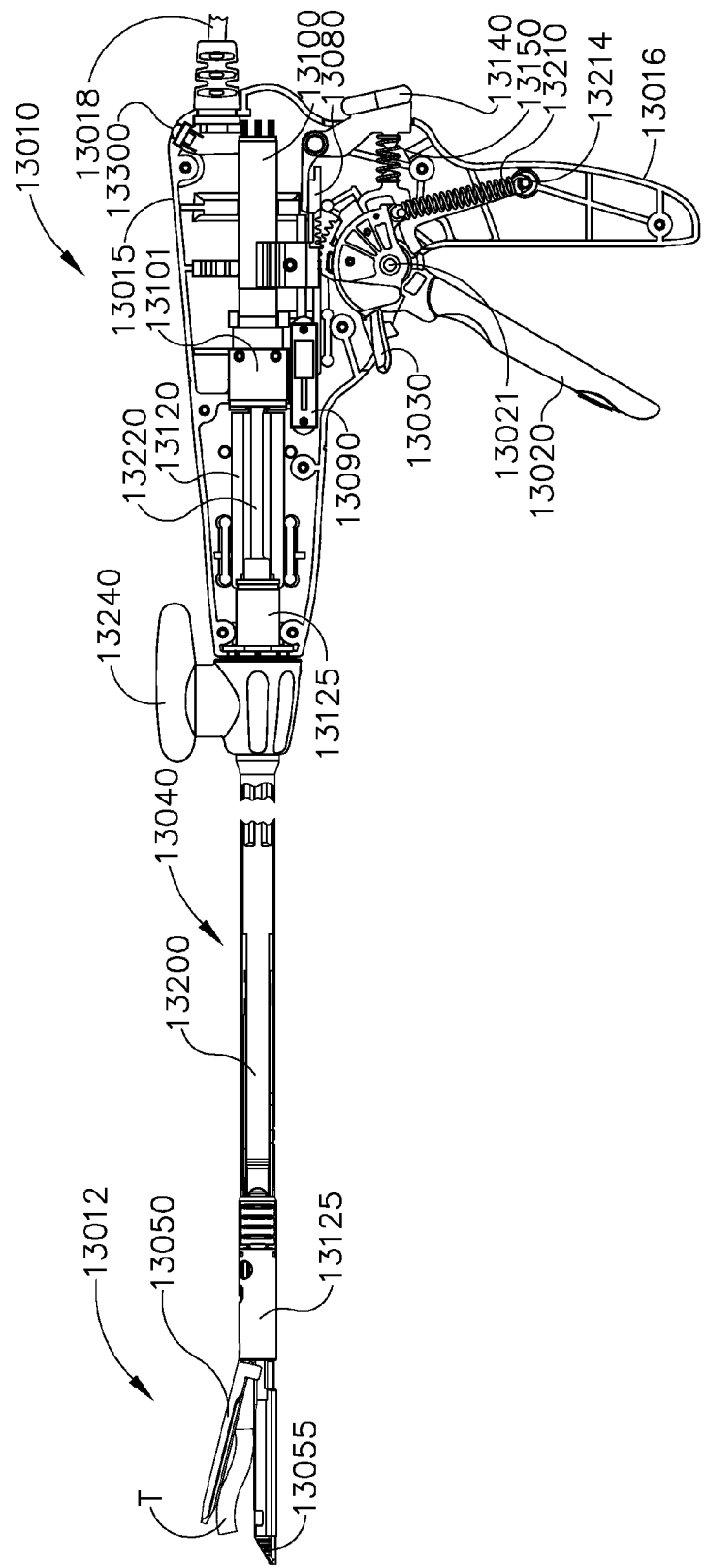
FIG. 107 is a cross-sectional view of a surgical stapling instrument in accordance with at least one embodiment comprising a handle, a shaft, and an end effector.

A surgical stapling instrument 13010 is illustrated in FIGS. 107-110. FIG. 107 is a side view of the surgical instrument 13010 illustrated with some components removed and others shown in cross-section. The instrument 13010 can comprise a handle 13015, a first actuator 13020, a second actuator 13030, a shaft assembly 13040, and an end effector 13012 including an anvil 13050 and a staple cartridge 13055. The shaft portion 13040 and the anvil 13050 can operate as shown and discussed in U.S. Pat. No. 5,704,534, entitled ARTICULATION ASSEMBLY FOR SURGICAL INSTRUMENTS, which issued on Jan. 6, 1998. The disclosure of U.S. Pat. No. 5,704,534, entitled ARTICULATION ASSEMBLY FOR SURGICAL INSTRUMENTS, which issued on Jan. 6, 1998, is incorporated herein by reference by its entirety. An electrical input cable 13018 can connect the instrument 13010 to an external power source. In at least one instance, the external power source can comprise a generator, such as the GEN11 generator manufactured by Ethicon Energy, Cincinnati, Ohio, for example. In various instances, the external power source can comprise an AC to DC adaptor. In certain instances, the instrument 13010 can be powered by an internal battery, such as the batteries shown and discussed in U.S. Pat. No. 8,210,411, entitled MOTOR-DRIVEN SURGICAL CUTTING INSTRUMENT, which issued on Jul. 3, 2012, for example. The disclosure of U.S. Pat. No. 8,210,411, entitled MOTOR-DRIVEN SURGICAL CUTTING INSTRUMENT, which issued on Jul. 3, 2012, is incorporated herein by reference in its entirety.

In various instances, referring primarily to FIG. 107, the anvil 13050 of the end effector 13012 can be movable between an open position, as illustrated in FIG. 107, and a closed position in which the anvil 13050 is positioned adjacent to, or in contact with, the staple cartridge 13055, as described in greater detail further below. In at least one such instance, the staple cartridge 13055 may not be pivotable relative to the anvil 13050. In certain instances, although not illustrated, the staple cartridge 13055 can be pivotable relative to the anvil 13050. In at least one such instance, the anvil 13050 may not be pivotable relative to the staple cartridge 13055. In any event, the user of the instrument 13010 can manipulate the end effector 13012 in order to position tissue T between the anvil 13050 and the cartridge 13055. Once the tissue T has been suitably positioned between the anvil 13050 and the staple cartridge 13055, the user can then pull the first actuator 13020 to actuate the closure system of the instrument 13010. The closure system can move the anvil 13050 relative to the staple cartridge 13055. For example, the first actuator 13020 can be pulled toward a pistol grip portion 13016 of the handle 13015 to close the anvil 13050, as described in greater detail further below.

The closure drive can include a closure motor 13105 (FIG. 110) configured to move the anvil 13050. The closure motor 13105 can be mounted to the handle 13015 via a motor bracket 13101, for example. Squeezing the first actuator 13020 from its open position (FIG. 108) to its closed position (FIG. 109) can energize the closure motor 13105. Referring primarily to FIG. 110, the closure motor 13105 can include a rotatable output shaft which is operably engaged with a closure lead screw 13110. When the closure motor 13105 rotates the output shaft in a first direction, the output shaft can rotate the closure lead screw 13110 in the first direction. The closure lead screw 13110 can be rotatably supported within the handle 13015 and can include a threaded portion. The closure drive can further comprise a closure nut threadably engaged with the threaded portion of the closure lead screw 13110. The closure nut can be constrained from rotating with the closure lead screw 13110 such that the rotational motion of the closure lead screw 13110 can translate the closure nut. The closure nut can be engaged with or integrally formed with a closure yoke 13120. When the closure motor 13015 is rotated in its first direction, the closure lead screw 13110 can advance the closure yoke 13120 distally. In various instances, the closure yoke 13120 can be slidably supported within the handle 13015 by rails 13122 extending from the handle 13015 which can constrain the movement of the closure yoke 13120 to a path defined along a longitudinal axis. Such an axis can be parallel to, substantially parallel to, collinear with, or substantially collinear with a longitudinal axis defined by the shaft assembly 13040. The closure drive can further comprise a closure tube 13125 extending distally from the closure yoke 13120. The closure tube 13125 can also be part of the shaft assembly 13040 and can translate relative to a frame of the shaft assembly 13040. When the closure yoke 13120 is advanced distally by the closure lead screw 13110, the closure yoke 13120 can advance the closure tube 13125 distally. A distal end of the closure tube 13125 can be operably engaged with the anvil 13050 such that, when the closure tube 13125 is advanced distally, the closure tube 13125 can push the anvil 13050 from its open position toward its closed position. U.S. Pat. No. 5,704,534, entitled ARTICULATION ASSEMBLY FOR SURGICAL INSTRUMENTS, which issued on Jan. 6, 1998, discloses a manually-driven closure system.

Figure 108:
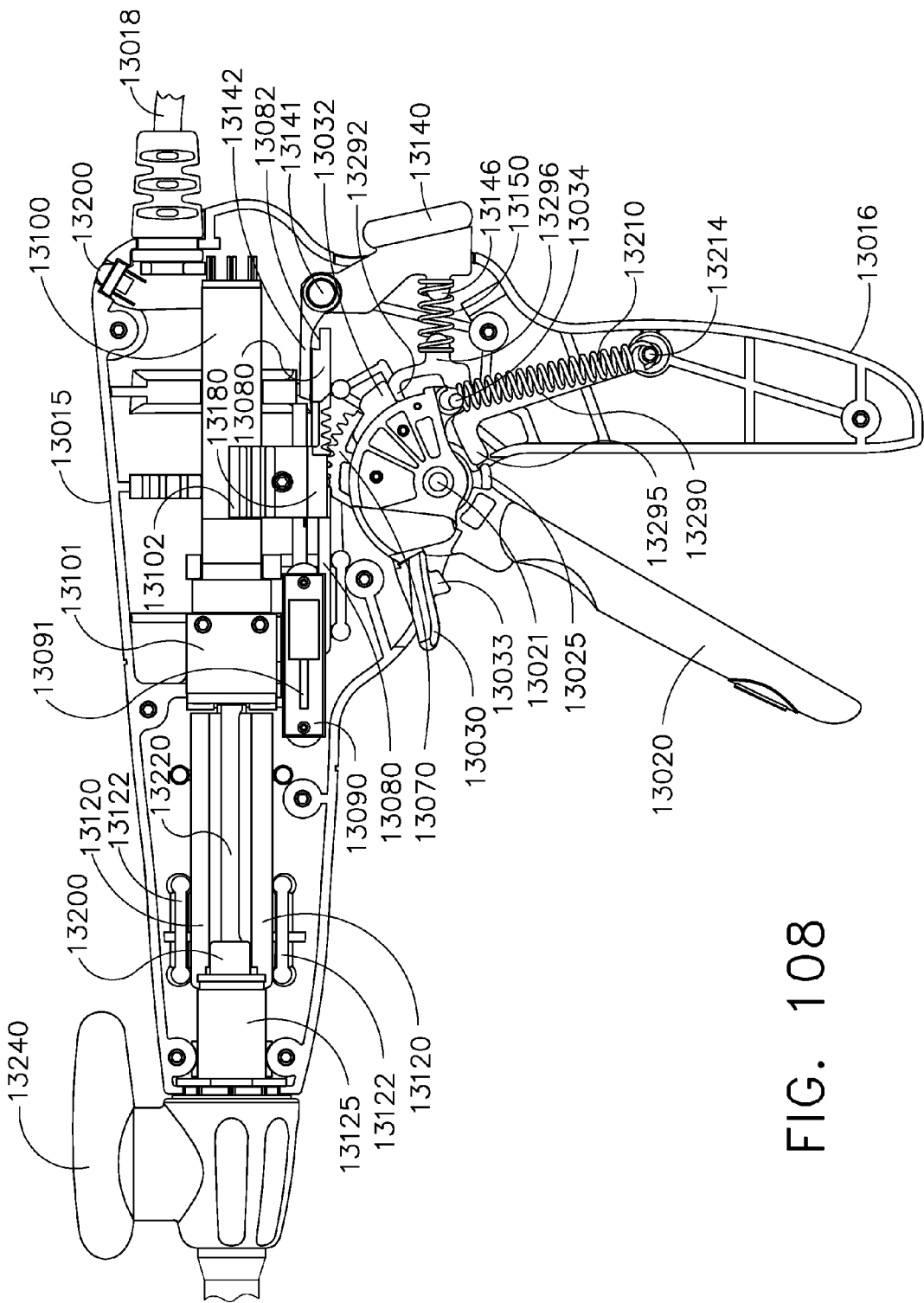
FIG. 108 is a cross-sectional view of the handle of the surgical stapling instrument of FIG. 107 illustrated in an open configuration.
Figure 109:
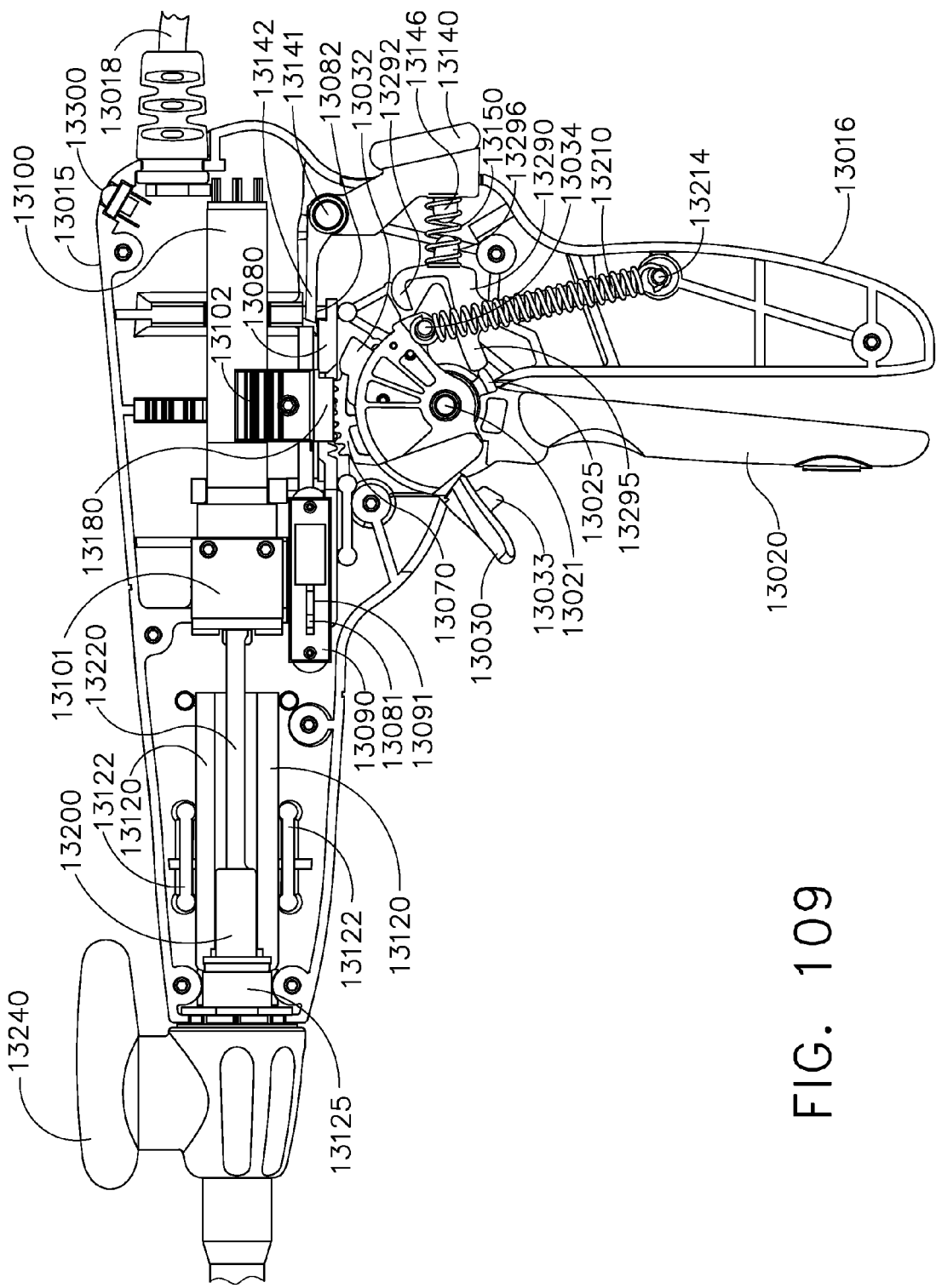
FIG. 109 is a cross-sectional view of the handle of the surgical stapling instrument of FIG. 107 illustrated in a closed configuration.
Figure 110:
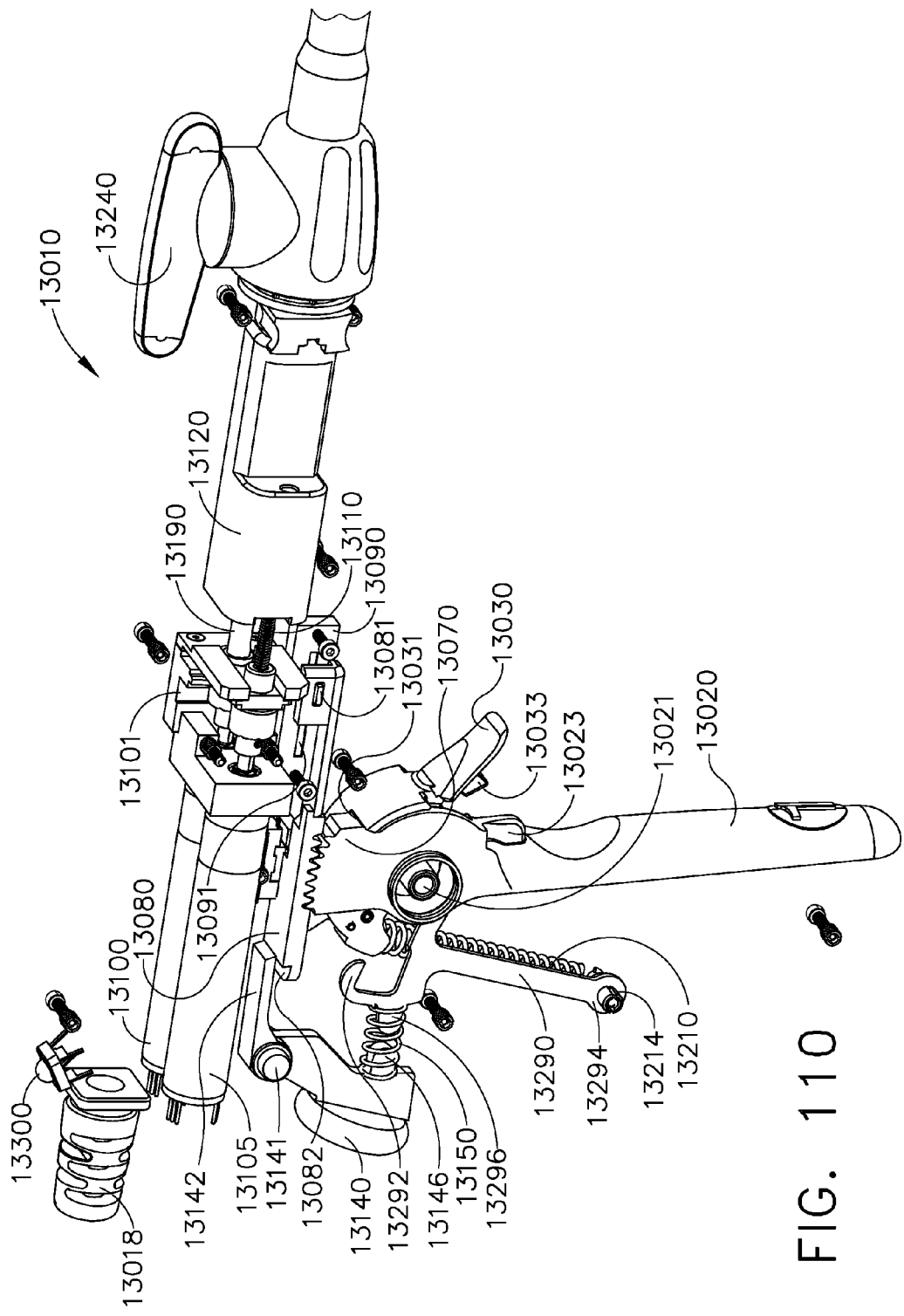
FIG. 110 is a perspective view of the handle of the surgical stapling instrument of FIG. 107 illustrated with some components removed.

In at least one form, the instrument 13010 can include a closure system switch positioned in the handle 13015 which can be closed when the first actuator 13020 is moved from its open position (FIG. 108) toward its closed position (FIG. 109). In certain instances, the closure system switch can be closed when the first actuator 13020 is in its closed position (FIG. 109). In either event, when the closure system switch is closed, a closure system power circuit can be closed to supply electrical power to the closure motor 13105 in order to rotate the closure motor 13105 in its first direction, as discussed above. In certain instances, the surgical instrument 13010 can include a microprocessor and, similar to the above, the closure system switch can be in signal communication with the microprocessor. When the closure system switch sends a signal to the microprocessor indicating that the first actuator 13020 has been closed, the microprocessor can permit power to be supplied the closure motor 13105 to operate the closure motor 13105 in its first direction and move the anvil 13050 toward its closed position. In various instances, the closure motor 13105 can move the anvil 13050 toward its closed position so long as the first actuator 13020 is at least partially actuated and the closure system switch is in a closed state. In the event that the user releases the first actuator 13020 and the first actuator 13020 is returned to its unactuated position, the closure system switch can be opened and the power supplied to the closure motor 13105 can be interrupted. Such instances may leave the anvil 13050 in a partially closed position. When the first actuator 13020 is actuated once again and the closure system switch has been closed, power can be supplied to the closure motor 13105 once again to move the anvil 13050 toward its closed position. In view of the above, the user of the surgical instrument 13010 can actuate the first actuator 13020 and wait for the closure motor 13105 to position the anvil 13050 in its fully closed position.

In at least one form, the movement of the first actuator 13020 can be proportional to the movement of the anvil 13050. The first actuator 13020 can move through a first, or actuator, range of motion when it is moved between its open position (FIG. 108) and its closed position (FIG. 109). Similarly, the anvil 13050 can move through a second, or anvil, range of motion when it is moved between its open position (FIG. 107) and its closed position. The actuator range of motion can correspond to the anvil range of motion. By way of example, the actuator range of motion can be equal to the anvil range of motion. For instance, the actuator range of motion can comprise about 30 degrees and the anvil range of motion can comprise about 30 degrees. In such instances, the anvil 13050 can be in its fully open position when the first actuator 13020 is in its fully open position, the anvil 13050 can be rotated 10 degrees toward its closed position when the first actuator 13020 is rotated 10 degrees toward its closed position, the anvil 13050 can be rotated 20 degrees toward its closed position when the first actuator 13020 is rotated 20 degrees toward its closed position, and so forth. This directly proportional movement between the first actuator 13020 and the anvil 13050 can give the user of the instrument 13010 a sense of the anvil position 13050 relative to the staple cartridge 13055 in the event that the anvil 13050 is obstructed from view in the surgical site.

Further to the above, the anvil 13050 can be responsive to both closing and opening motions of the first actuator 13020. For example, when the first actuator 13020 is moved 10 degrees toward the pistol grip 13016, the anvil 13050 can be moved 10 degrees toward the staple cartridge 13055 and, when the first actuator 13020 is moved 10 degrees away from the pistol grip 13016, the anvil 13050 can be moved 10 degrees away from the staple cartridge 13055. While the movement of the first actuator 13020 and the movement of the anvil 13050 can be directly proportional according to a 1:1 ratio, other ratios are possible. For instance, the movement of the first actuator 13020 and the movement of the anvil 13050 can be directly proportional according to a 2:1 ratio, for example. In such instances, the anvil 13050 will move 1 degree relative to the staple cartridge 13055 when the first actuator 13020 is moved 2 degrees relative to the pistol grip 13016. Moreover, in such instances, the range of motion of the first actuator 13020 may be twice the range of motion of the anvil 13050. In another instance, the movement of the first actuator 13020 and the movement of the anvil 13050 can be directly proportional according to a 1:2 ratio, for example. In such instances, the anvil 13050 will move 2 degrees relative to the staple cartridge 13055 when the first actuator 13020 is moved 1 degree relative to the pistol grip 13016. Moreover, in such instances, the range of motion of the first actuator 13020 may be half the range of motion of the anvil 13050. In various instances, the motion of the first actuator 13020 may be linearly proportional to the motion of the anvil 13050. In other instances, the motion of the first actuator 13020 may be non-linearly proportional to the motion of the anvil 13050. Regardless of the ratio that is used, such embodiments can be possible through the use of a potentiometer, for example, which can evaluate the rotation of the first actuator 13020, as will be discussed in greater detail further below.

Further to the above, referring to FIGS. 108-110, the closure system of the instrument 13010 can comprise a slide potentiometer 13090 which can detect the movement of the first actuator 13020. The first actuator 13020 can be pivotably mounted to the handle 13015 via a pivot 13021. The first actuator 13020 can comprise a gear portion 13070 comprising a plurality of gear teeth extending circumferentially about the pivot 13021. When the first actuator 13020 is rotated proximally toward the pistol grip 13016, further to the above, the gear portion 13070 can be rotated distally. Correspondingly, when the first actuator 13020 is rotated distally away from the pistol grip 13016, the gear portion 13070 can be rotated proximally. The closure system can further comprise a closure yoke rack 13080 which is slidably supported within the handle 13015. The closure yoke rack 13080 can comprise a longitudinal array of teeth extending along a bottom surface thereof which faces the gear portion 13070 of the first actuator 13020. The gear portion 13070 of the first actuator 13020 can be meshingly engaged with the array of teeth defined on the closure yoke rack 13080 such that, when the first actuator 13020 is rotated about the pivot 13021, the first actuator 13020 can displace the closure yoke rack 13080 proximally or distally, depending on the direction in which the first actuator 13020 is rotated. For instance, when the first actuator 13020 is rotated toward the pistol grip 13016, the first actuator 13020 can displace the closure yoke rack 13080 distally. Correspondingly, when the first actuator 13020 is rotated away from the pistol grip 13016, the first actuator 13020 can displace the closure yoke rack 13080 proximally. The handle 13015 can include a guide slot defined therein which can be configured to slidably support the closure yoke rack 13080 and constrain the movement of the closure yoke rack 13080 to a path defined along a longitudinal axis. This longitudinal axis can be parallel to, substantially parallel to, collinear with, or substantially collinear with a longitudinal axis of the shaft assembly 13040.

The closure yoke rack 13080 can include a detectable element 13081 mounted thereon. The detectable element 13081 can comprise a magnetic element, such as a permanent magnet, for example. The detectable element 13081 can be configured to translate within a longitudinal slot 13091 defined in the slide potentiometer 13090 when the closure rack 13080 is translated within the handle 13015. The slide potentiometer 13090 can be configured to detect the position of the detectable element 13081 within the longitudinal slot 13091 and convey that position to the microprocessor of the surgical instrument 13010. For example, when the first actuator 13020 is in its open, or unactuated, position (FIG. 108), the detectable element 13081 can be positioned at the proximal end of the longitudinal slot 13091 and the potentiometer 13090 can transmit a signal to the microprocessor that can indicate to the microprocessor that the first actuator 13020 is in its open position. With this information, the microprocessor can maintain the anvil 13050 in its open position. As the first actuator 13020 is rotated toward the pistol grip 13016, the detectable element 13081 can slide distally within the longitudinal slot 13091. The potentiometer 13090 can transmit a signal, or a plurality of signals, to the microprocessor that can indicate the position of the first actuator 13020. In response to such a signal, or a plurality of signals, the microprocessor can operate the closure motor 13105 to move the anvil 13055 to a position which corresponds to the position of the first actuator 13020. When the first actuator 13020 is in its closed, or fully actuated, position (FIG. 109), the detectable element 13081 can be positioned at the distal end of the longitudinal slot 13091 and the potentiometer 13090 can transmit a signal to the microprocessor that can indicate to the microprocessor that the first actuator 13020 is in its closed position. With this information, the microprocessor can move the anvil 13050 into its closed position.

When the first actuator 13020 is pulled such that it is substantially adjacent to the pistol grip 13016 of the handle 13015, as discussed above, the closure yoke rack 13080 is moved to its most distal position. When the closure yoke rack 13080 is in its most distal position, a closure release button 13140 can engage the closure yoke rack 13080 to releasably hold the closure yoke rack 13080 in its distal most position and, as a result, releasably hold the anvil 13050 in its closed position. Referring primarily to FIG. 108, the closure release button 13140 can be pivotably mounted to the handle 13015 about a pivot 13141. The closure release button 13140 can include a lock arm 13142 extending therefrom. When the first actuator 13120 is in its unactuated position and the closure yoke rack 13080 is in its proximal-most position, the lock arm 13142 may be positioned above and/or against a top surface of the closure yoke rack 13080. In such a position, the closure yoke rack 13080 can slide relative to the lock arm 13142. In some circumstances, the lock arm 13142 can be biased against the top surface of the closure yoke rack 13080. As will be described in greater detail further below, the instrument 13010 can further comprise a lock 13290 configured to releasably hold the first actuator 13020 and the second actuator 13030 in the unactuated configuration depicted in FIG. 108. A spring 13150 can be positioned intermediate the lock 13290 and the firing button 13140 which can rotatably bias the closure release button 13140 about the pivot 13141 and position the lock arm 13142 against the top surface of the closure yoke rack 13080. In various instances, the lock 13290 can include a proximal projection 13296 and the closure release button 13140 can include a distal projection 13146 which can be configured to hold and align the spring 13150 in position between the lock 13290 and the closure release button 13140. When the first actuator 13020 is rotated into its actuated position, as illustrated in FIG. 109, the closure yoke rack 13080 can be in its distal-most position and the lock arm 13142 can be biased into, or drop into, a notch 13082 defined in the proximal end of the closure yoke rack 13080. Moreover, when the first actuator 13020 is moved into its closed, or actuated, position illustrated in FIGS. 109 and 110, the first actuator 13020 can push the lock 13290 proximally and rotate the lock 13290 about pivot 13214. In at least one instance, the first actuator 13020 can include an actuator projection 13025 extending therefrom configured to engage a distal projection 13295 extending from the lock 13290. Such movement of the lock 13290 can compress the spring 13150 between the lock 13290 and the closure release button 13140 and increase the biasing force applied to the closure release button 13140. Once the lock arm 13142 is engaged with the notch 13082, the closure yoke rack 13080 may not be movable, or at least substantially movable, in the proximal direction or the distal direction.

As discussed above, the first actuator 13020 and the second actuator 13030 can be releasably held in and/or biased into their unactuated positions illustrated in FIG. 108. The instrument 13010 can include a return spring 13210 including a first end coupled to the pivot 13214 and a second end coupled to a spring mount 13034 extending from the second actuator 13030. The second actuator 13030 can be rotatably mounted to the handle 13015 about the pivot 13021 and the return spring 13210 can apply a biasing force to the second actuator 13030 to rotate the second actuator 13030 about the pivot 13021. The lock 13290 can stop the rotation of the second actuator 13030 about the pivot 13021. More specifically, the spring 13150, which acts to bias the closure return button 13140 into engagement with the closure yoke rack 13080, can also act to push the lock 13290 distally such that a lock arm 13292 of the lock 13290 is positioned behind a shoulder 13032 defined on the second actuator 13030 which can limit the rotation of the second actuator 13030 and hold the second actuator 13030 in its unactuated position as illustrated in FIG. 108. Referring primarily to FIG. 110, the second actuator 13030 can comprise a shoulder 13031 which can be configured to abut the gear portion 13070 of the first actuator 13020 and bias the first actuator 13020 into its unactuated position (FIG. 108).

When the first actuator 13020 is rotated toward its actuated position (FIG. 109), the first actuator 13020 can at least partially rotate the second actuator 13030 toward the pistol grip 13016 against the biasing force supplied by the spring 13210. In fact, the actuation of the first actuator 13020 can make the second actuator 13030 accessible to the user of the surgical instrument 13010. Prior to the actuation of the first actuator 13020, the second actuator 13030 may be inaccessible to the user. In any event, the reader will recall that the actuation of the first actuator 13020 pushes the lock 13295 proximally. Such proximal movement of the lock 13295 can displace the lock 13295 from behind the shoulder 13032 defined on the second actuator 13030.

Once the first actuator 13020 has been moved and locked into its fully actuated position (FIG. 109) and the anvil 13050 has been moved into its closed position, as discussed above, the instrument 13010 can be used to staple the tissue positioned intermediate the anvil 13050 and the staple cartridge 13055. In the event that the user is unsatisfied with the position of the tissue between the anvil 13050 and the staple cartridge 13055, the user can unlock the anvil 13050 by depressing the closure release button 13140. When the closure release button 13140 is depressed, the lock arm 13142 of the closure release button 13140 can be pivoted upwardly out of the notch 13082 which can permit the closure yoke rack 13080 to move proximally. Moreover, the return spring 13210 can return the first actuator 13120 and the second actuator 13130 to their unactuated positions illustrated in FIG. 109 and, owing to the meshed engagement between the gear portion 13070 and the closure yoke rack 13080, the return spring 13210 can return the closure yoke rack 13080 back into its proximal position. Such movement of the closure yoke rack 13080 can be detected by the slide potentiometer 13090 which can transmit a signal to the microprocessor of the instrument 13010 that the first actuator 13020 has been returned to its unactuated position and that the anvil 13050 should be returned to its open position. In response thereto, the microprocessor can instruct the closure motor 13105 to rotate in its second direction to drive the closure nut of the closing system proximally and retract the closure tube 13125 proximally which will return the anvil 13050 back to its open position. The user can then reposition the anvil 13050 and the staple cartridge 13055 and re-close the anvil 13050 by actuating the first actuator 13020 once again. In various instances, the microprocessor of the instrument 13010 can be configured to ignore input signals from the second actuator 13030 until the potentiometer 13090 detects that the anvil 13050 is in a closed, or a sufficiently closed, position.

Once the user is satisfied with the position of the anvil 13050 and the staple cartridge 13055, further to the above, the user can pull the second actuator 13030 to a closed, or actuated, position such that it is in close proximity to the first actuator 13020. The actuation of the second actuator 13030 can depress or close a firing switch 13180 in the handle 13015. In various instances, the firing switch 13180 can be supported by a motor mount 13102 which can also be configured to support the closure motor 13105 and/or a firing motor 13100. The closure of the firing switch 13180 can operate the firing motor 13100. In certain instances, the firing switch 13180 can be in signal communication with the microprocessor of the surgical instrument 13010. When the microprocessor receives a signal from the firing switch 13180 that the second actuator 13030 has been sufficiently actuated, the microprocessor can supply power to the firing motor 13100. In various embodiments, the closure of the firing switch 13180 can connect the firing motor 13100 directly to a DC or AC power source to operate the firing motor 13100. In at least one instance, the firing switch 13180 can be arranged such that the firing switch 13180 is not closed until the second actuator 13030 has reached its fully closed position. Referring primarily to FIG. 110, the rotation of the second actuator 13030 can be stopped in its fully closed position when it comes into contact with the first actuator 13020. In at least one such instance, the first actuator 13020 can comprise a stop depression 13023 configured to receive a stop projection 13033 extending from the second actuator 13030 when the second actuator 13030 reaches its closed position.

The firing motor 13100 can include a rotatable output shaft which is operably engaged with a firing lead screw 13190 of the firing system. When the firing motor 13100 is operated to rotate its output shaft in a first direction, the output shaft can rotate the firing lead screw 13190 in the first direction. When the firing motor 13100 is operated to rotate its output shaft in a second, or opposite, direction, the output shaft can rotate the firing lead screw 13190 in the second direction. The firing system can further comprise a firing nut which is threadably engaged with a threaded portion of the firing lead screw 13190. The firing nut can be constrained from rotating with the firing lead screw 13190 such that the rotation of the firing lead screw 13190 can translate the firing nut proximally or distally depending on the direction in which the firing lead screw 13190 is rotated. The firing system can further comprise a firing shaft 13220 operatively connected to the firing nut which can be displaced with the firing nut. The firing system can also comprise a knife bar 13200 and staple deploying firing bands which extend distally from the firing shaft 13220. When the firing motor 13020 is rotated in its first direction, the firing lead screw 13190 can displace the firing nut, the firing shaft 13220, the knife bar 13200, and the firing bands distally to eject the staples from the staple cartridge 13055 and incise the tissue positioned intermediate the anvil 13050 and the staple cartridge 13055. Once the knife 13200 and the firing bands reach their end of travel, the microprocessor can rotate the firing motor 13100 in its second, or opposite, direction to bring the knife 13200 and the bands back to their original position. In various instances, the instrument 13010 can include an end of travel sensor in signal communication with the microprocessor which can signal to the microprocessor that the firing drive has reached the end of its firing stroke and that the firing stroke should be retracted. Such an end of travel sensor can be positioned in the anvil 13050 and/or the staple cartridge 13055, for example. In certain instances, an encoder operably coupled to the firing motor 13100 can determine that the firing motor 13100 has been rotated a sufficient number of rotations for the knife 13200 and firing bands to reach their end of travel and signal to the microprocessor that the firing system should be retracted.

Once the second actuator 13030 has been actuated, however, the instrument 13010 is in its firing state and the microprocessor can be configured to ignore any inputs from the first actuator 13020 and/or the slide potentiometer 13090 until the firing system has been returned it to its original position. In various instances, the instrument 13010 can include an abort button which, when depressed, can signal to the microprocessor that the firing assembly should be immediately retracted. In at least one such instance, the firing sequence can be halted when the closure release button 13140 is depressed. As discussed above, pressing the closure release button 13140 moves the closure yoke rack 13080 proximally which, in turn, moves the detectable element 13081 proximally. The proximal movement of the detectable element 13081 can be detected by the slide potentiometer 13090 which can signal to the microprocessor to reverse the rotation of the firing motor 13100 to retract the firing assembly and/or operate the closure motor 13105 to open the anvil 13050.

The instrument 13010 can also include one or more indicators, such as LED 13300, for example, which can be configured to indicate the operating state of the instrument 13010. In various instances, the LED 13300 can operate in a manner similar to that of LED 11100, for example. The instrument 13010 also incorporates the ability to articulate the end effector 13012. This is done through the articulation knob 13240 as discussed in U.S. Pat. No. 5,704,534. Manual rotation of the shaft assembly 13040 is also discussed in U.S. Pat. No. 5,704,534.

In a modular concept of the instrument 13010, the shaft assembly 13040 and the end effector 13012 could be disposable, and attached to a reusable handle 13015. In another embodiment, the anvil 13050 and the staple cartridge 13055 are disposable and the shaft assembly 13040 and the handle 13015 are reusable. In various embodiments, the end effector 13012, including the anvil 13015, the shaft assembly 13040, and the handle 13015 may be reusable and the staple cartridge 13055 may be replaceable.

Figure 111:
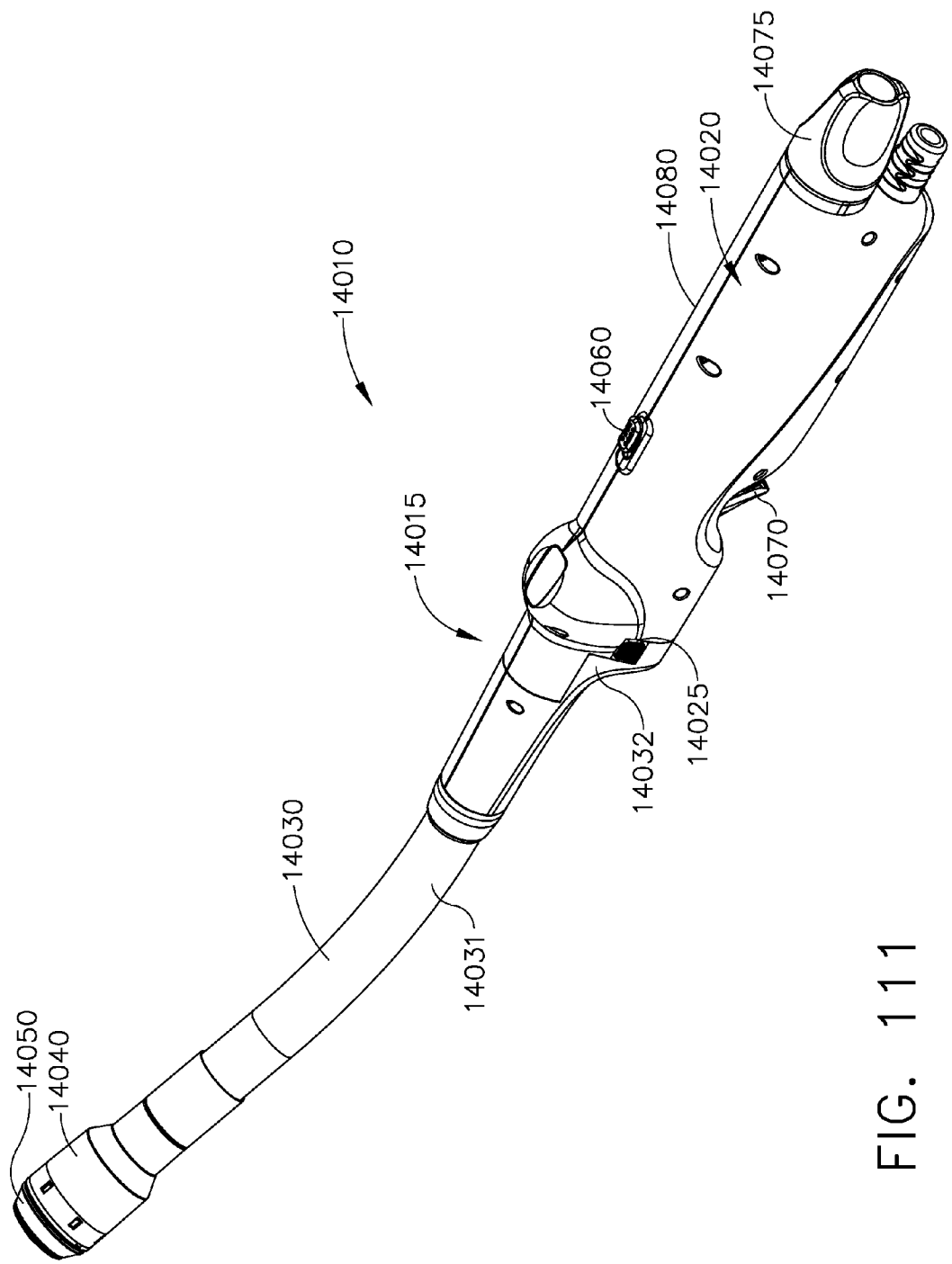
FIG. 111 is a perspective view of a surgical stapling instrument in accordance with at least one embodiment comprising a handle and a shaft.

FIG. 111 is a perspective view of a surgical stapling instrument 14010. The instrument 14010 can comprise an actuator, or handle, 14020, a shaft portion 14030, a tubular cartridge casing 14040, and an anvil 14050. The instrument 14010 can further include a closure system configured to move the anvil 14050 between an open position and a closed position. The actuator 14020 can comprise a rotating closure knob 14075 which can operate the closure system as described in greater detail further below. The instrument 14010 can further include a firing system configured to eject staples which are removably stored in the cartridge casing 14040. The actuator 14020 can further comprise a firing activation trigger 14070 which can operate the firing system as described in greater detail further below. Shaft portion 14030, cartridge casing 14040, and anvil 14050 can operate in a manner similar to that shown and discussed in U.S. Pat. No. 5,292,053, entitled SURGICAL ANASTOMOSIS STAPLING INSTRUMENT, which issued on Mar. 8, 1994. The disclosure of U.S. Pat. No. 5,292,053, entitled SURGICAL ANASTOMOSIS STAPLING INSTRUMENT, which issued on Mar. 8, 1994, is incorporated herein by reference in its entirety.

Further to the above, the actuator 14020 can include a transmission 14000 and a slider button 14060 configured to operate the transmission 14000. The slider button 14060 is movable between a distal position (FIG. 115), which is closer to the cartridge casing 14040, and a proximal position (FIG. 114), which is further away from the cartridge casing 14040. When the slider button 14060 is in its proximal position, the actuator 14020 is in a first operating mode, or closure mode, and can move the anvil 14050 toward and away from the cartridge casing 14040. When the slider button 14060 is in its distal position, the actuator 14020 is in a second operating mode, or firing mode, and can eject staples from the cartridge casing 14040 toward the anvil 14050. When the actuator 14020 is in its closure mode, the rotating closure knob 14075 can be rotated about a longitudinal axis extending through the actuator 14020 in order to move the anvil 14050 proximally or distally depending on the direction in which the closure knob 14075 is rotated. When the actuator 14020 is in its firing mode, the firing activation trigger 14070 can be rotated proximally to eject the staples from the cartridge casing 14040. The closure system and the firing system are discussed in greater detail further below.

Figure 113:
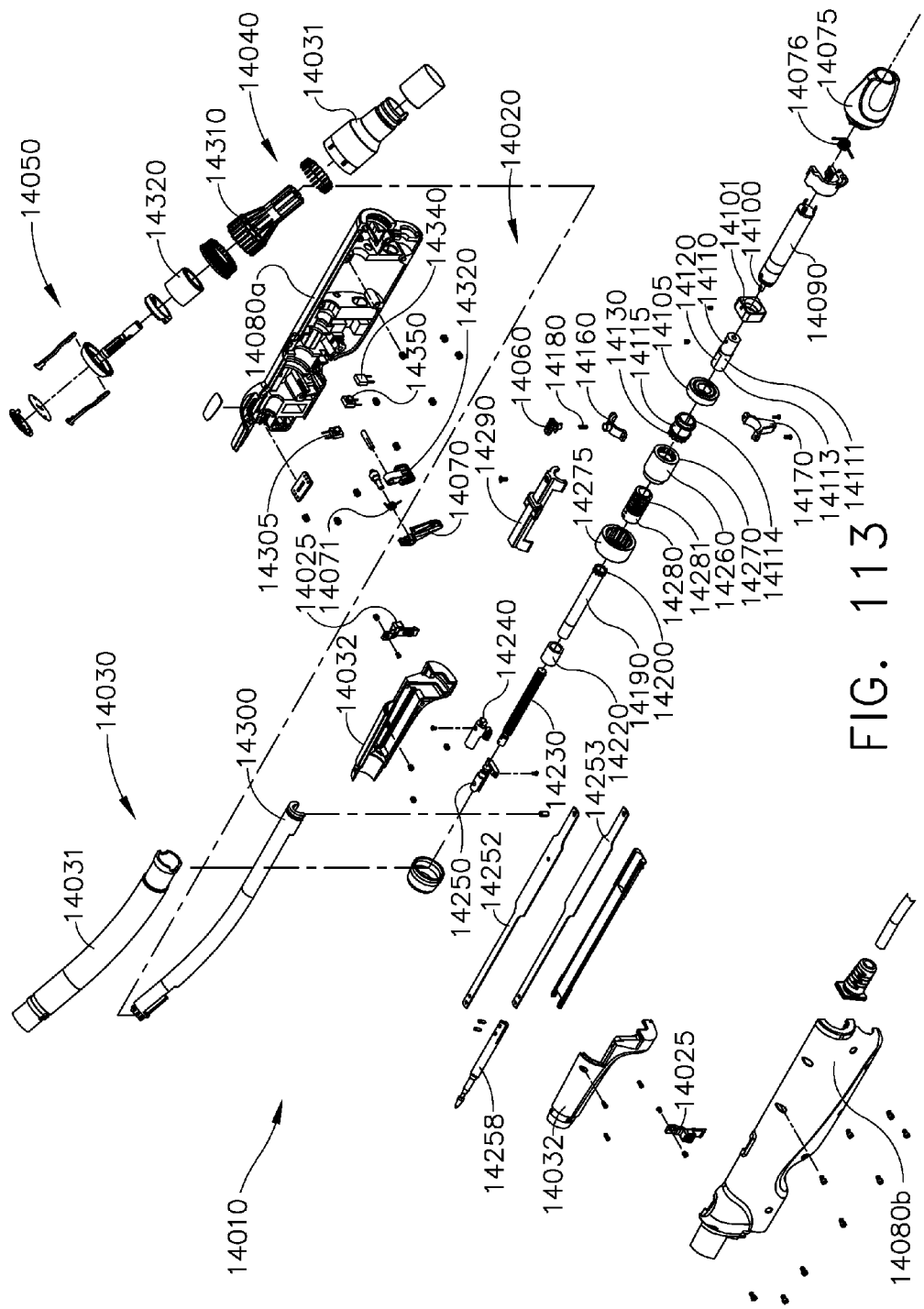
FIG. 113 is an exploded view of the surgical stapling instrument of FIG. 111.

The actuator 14020 can comprise an electric motor, such as motor 14090 (FIGS. 113-115), for example, which can operate the closure drive and the firing drive via the transmission 14000. The motor 14090 can be supported within an actuator housing 14080 of the actuator 14020. Referring primarily to FIG. 113, the actuator housing 14080 can comprise two halves, an actuator housing right half 14080a and an actuator housing left half 14080b. Actuator housing halves 14080a and 14080b can be held together by screws, although any suitable fastening and/or adhesive methods could be used to assemble actuator housing 14080. The motor 14090 can be supported between the actuator housing halves 14080a and 14080b and can include a rotatable shaft 14100 extending distally therefrom. In certain instances, the actuator 14020 can comprise a motor support 14101 positioned in the housing 14080 configured to support the housing of the motor 14100 and constrain the motor housing from rotating relative to the actuator housing 14080. In various instances, the rotatable shaft 14100 can comprise an extender portion 14110 affixed thereto. The shaft 14100 and the extender portion 14110 can be rotatably coupled such that they rotate together.

Figure 115:
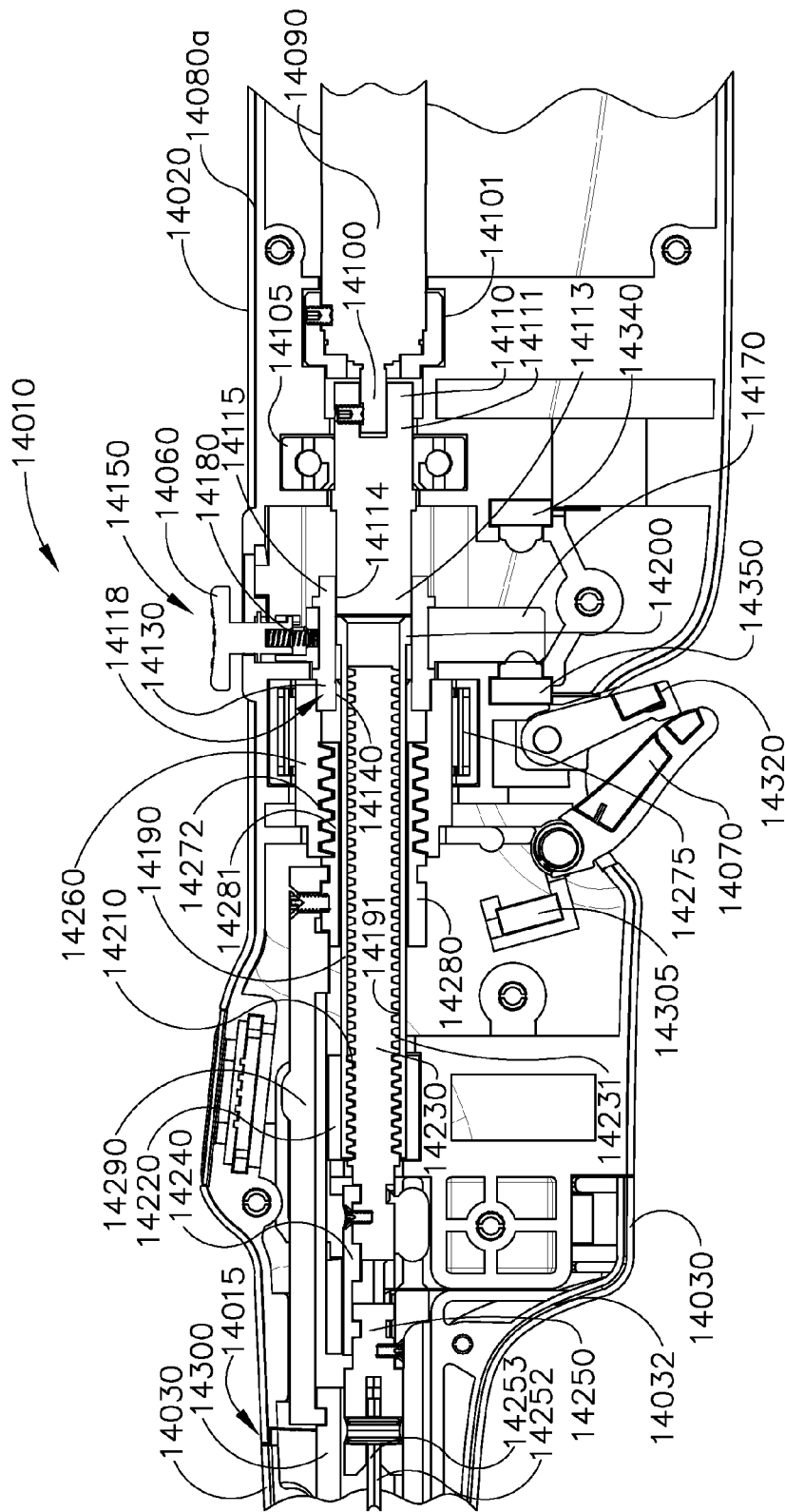
Figure 116:
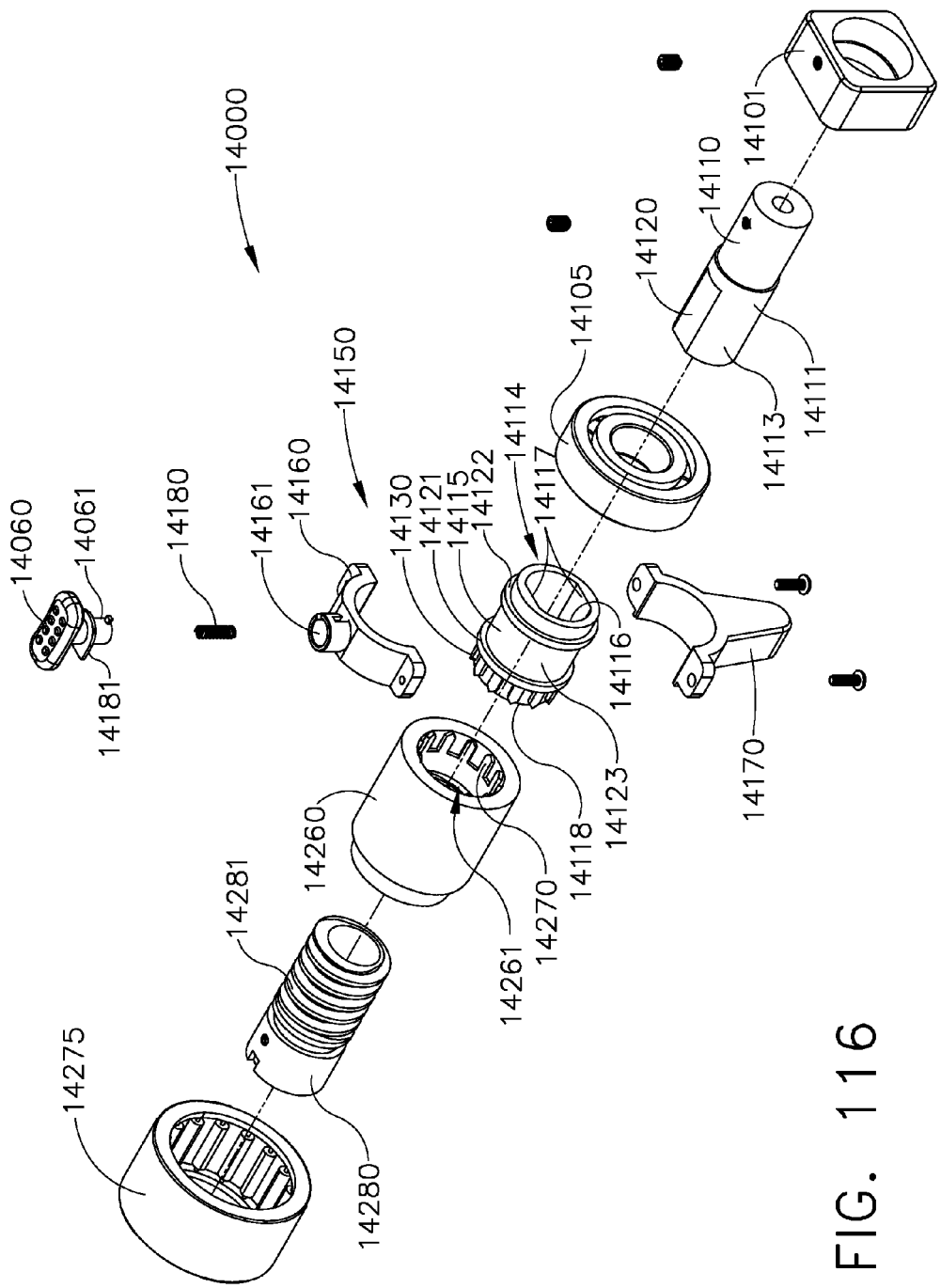

Further to the above, referring primarily to FIG. 116, the extender portion 14110 can comprise a cylindrical, or an at least substantially cylindrical, body 14111 and a flat portion 14120 defined in a distal end 14113 of the extender portion 14110. The cylindrical body 14111 of the extender portion 14110 can be rotatably supported within the actuator housing 14080 by a bearing 14105. The distal end 14113 of the extender portion 14110 can be positioned within a slider aperture 14114 defined in a slider 14115. The slider 14115, as will be discussed in greater detail further below, is part of the transmission 14000 and can be shifted between a proximal position (FIG. 114) in which the slider 14115 transmits the rotary motion of the motor 14090 to the closure system and a distal position (FIG. 115) in which the slider 14115 transmits the rotary motion of the motor 14090 to the firing system. When the slider 14115 is shifted between its proximal position (FIG. 114) and its distal position (FIG. 115), the slider 14115 can slide relative to the extender portion 14110. The slider aperture 14114 defined in the slider 14115 can define a perimeter which matches, or at least substantially matches, the perimeter of the distal end 14113 of the extender portion 14110 such that, one, the extender portion 14110 and the slider 14115 are rotationally coupled together and, two, the slider 14115 can translate relative to the extender portion 14110. In at least one instance, the slider aperture 14114 comprises a cylindrical portion 14116 which matches the cylindrical body 14111 of the extender portion 14110 and a flat portion 14117 which matches the flat portion 14120 defined in the distal end 14113 of the slider 14115.

Figure 114:
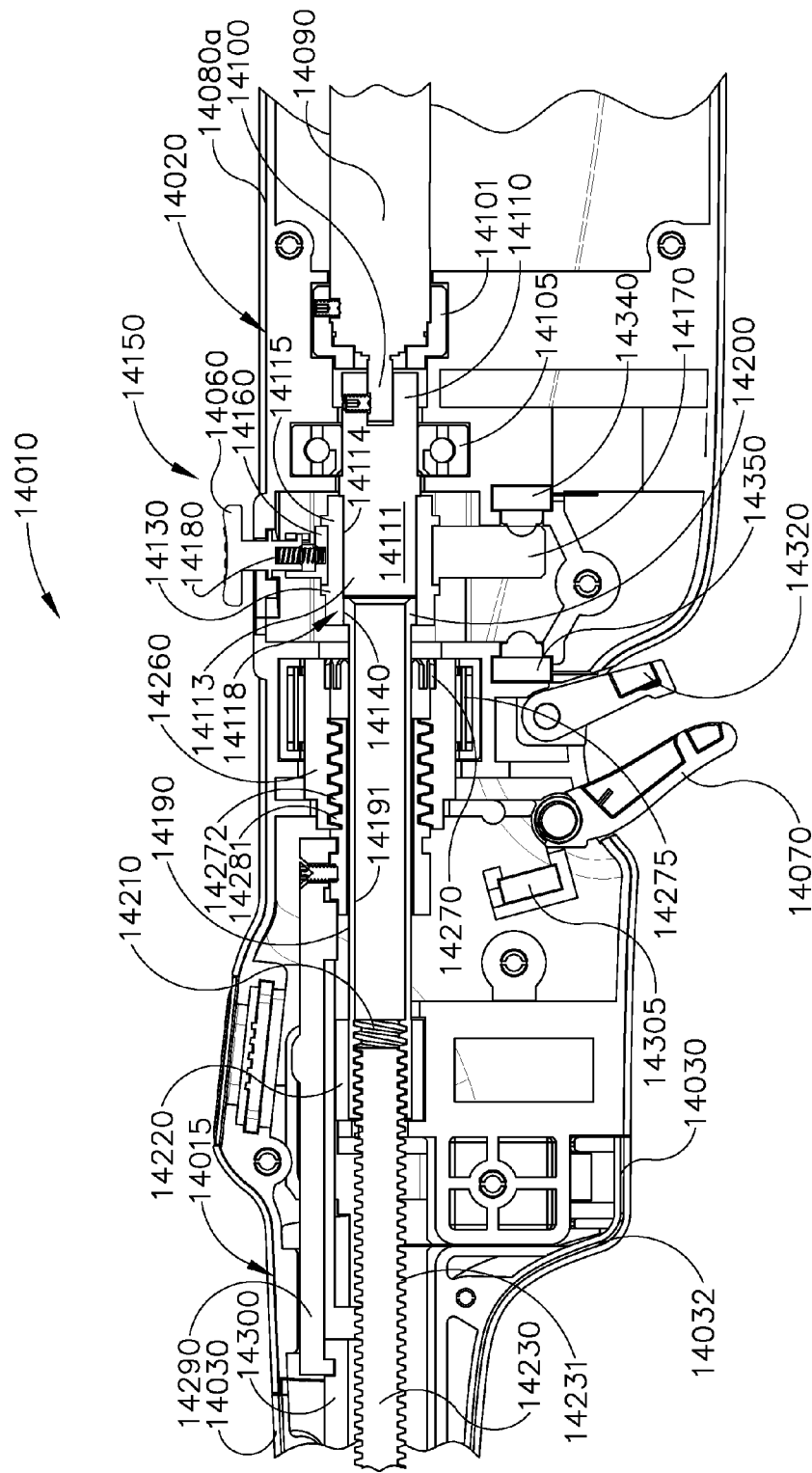
FIG. 114 is a partial cross-sectional view of the handle of FIG. 111 illustrating a transmission operably engaged with a closure system of the surgical stapling instrument of FIG. 111.

Further to the above, the slider 14115 can comprise a tubular, or a generally tubular, structure. The slider 14115 can comprise a distal end 14118 and a plurality of outer circumferential splines 14130 extending around an outer surface of the distal end 14118 which can be operably engaged with the firing drive, as illustrated in FIG. 115. The slider 14115 can further comprise a plurality of internal circumferential splines 14140 defined in the distal end of the slider aperture 14114 which can be operably engaged with the closure drive, as illustrated in FIG. 114. The slider 14115 can be part of a slider assembly 14150. Referring primarily to FIG. 116, the slider assembly 14150 can further comprise an upper journal bearing 14160, a lower journal bearing 14170, the slider button 14060, and a slider spring 14180. The upper journal bearing 14160 and the lower journal bearing 14170 combine to form a journal bearing which can, one, support the slider 14115 loosely enough so that the slider 14115 may rotate within the journal bearing and, two, displace the slider 14115 proximally and distally. Referring primarily to FIG. 116, the slider 14115 can comprise a distal flange 14121 and a proximal flange 14122 extending therefrom which can define a recess 14123 therebetween which is configured to closely receive the journal bearing. When the slider button 14060 is pushed distally, the journal bearing can bear against the distal flange 14121 to push the slider 14115 distally. Correspondingly, when the slider button 14060 is pushed proximally, the journal bearing can bear against the proximal flange 14122 to push the slider 14115 proximally.

The slider assembly 14150 can comprise a lock configured to releasably hold the slider 14115 in position. Referring primarily to FIG. 116, the slider button 14060 can comprise a flange 14181 that can selectively fit into a first depression defined at a first, or proximal, end of a longitudinal slot defined in the actuator housing 14080 and a second depression defined at a second, or distal, end of the longitudinal slot. When the flange 14181 is engaged with the proximal depression, the flange 14181 can hold the slider assembly 14150 in its proximal position which operably engages the slider 14115 and the closure drive with the motor 14090. When the flange 14181 is engaged with the distal depression, the flange 14181 can hold the slider assembly 14150 in its distal position which operably engages the slider 14115 and the firing drive with the motor 14090. The upper journal bearing 14160 can include a journal aperture 14161 configured to slidably receive a shaft 14061 of the button 14060. The button 14060 can be pushed downwardly within the journal aperture 14161 to disengage the flange 14181 from the actuator housing 14080. Once the flange 14181 has been disengaged from the actuator housing 14080, the button 14060 can be slid within the longitudinal slot defined in the actuator housing 14080 to move the slider 14115 between its proximal and distal positions. The spring 14180 can be configured to bias the flange 14181 toward the actuator housing 14080 and, when the user of the surgical instrument 14010 releases the button 14060, the spring 14180 can bias the button 14060 upwardly into engagement with the actuator housing 14080 once again.

When the slider assembly 14150 is in its proximal position, further to the above, the slider 14115 is engaged with a closing nut 14190 of the closure drive. The closing nut 14190 comprises an elongate tubular structure including closing nut external splines 14200 defined at the proximal end thereof. When the slider 14115 is in its proximal position, the internal splines 14140 of the slider 14115 are meshingly engaged with the external splines 14200 of the closing nut 14190 such that, when the slider 14115 is rotated by the motor 14090, the closing nut 14190 is rotated by the slider 14115. The closing nut 14190 can be rotatably supported within the actuator housing 14080 by one or more bearings, such as bushing 14220, for example, which rotatably supports the distal end of the closing nut 14190. The closing nut bushing 14220 may be comprised of Delrin, Nylon, copper, brass, bronze, and/or carbon, for example. In certain instances, the closing nut bushing 14220 can comprise a ball bearing or roller bearing, for example. In various instances, the closing nut bushing 14220 may be an integral portion of the actuator housing 14080.

The closing nut 14190 can comprise a longitudinal aperture 14191 defined therein. The closure system can further comprise a closing rod 14230 which can be at least partially positioned within the longitudinal aperture 14191. The closing rod 14230 can comprise a thread 14231 defined thereon which is threadably engaged with a closing nut thread 14210 defined in the longitudinal aperture 14191. The closing rod 14230 can be constrained from rotating with the closing nut 14190 such that, when the closing nut 14190 is rotated in a first direction by the motor 14090, the closing rod 14230 can be translated proximally by the closing nut 14190. As illustrated in FIG. 115, the closing rod 14230 can move proximally within the longitudinal aperture 14191 of the closing nut 14190. Similarly, when the closing nut 14190 is rotated in an opposite, or second, direction by the motor 14090, the closing rod 14230 can be translated distally by the closing nut 14190. As will be described in greater detail further below, the closing rod 14230 can be operably engaged with the anvil 14050 such that, when the closing rod 14230 is pulled proximally, the anvil 14050 can be moved toward the cartridge casing 14040. Correspondingly, when the closing rod 14230 is pushed distally, the anvil 14050 can be moved away from the cartridge casing 14040. In various instances, a closure stroke length of the closure system can be measured between the open position and the closed position of the anvil 14050. The closing rod 14230 can be at least as long as the closure stroke length to accommodate the same.

As discussed above, the button 14060 of the actuator 14020 is movable between a proximal position (FIG. 114) in which the transmission 14000 is engaged with the closure drive and a distal position (FIG. 115) in which the transmission 14000 is engaged with the firing drive. In this way, the transmission 14000 can be used to selectively couple the closure drive and the firing drive with the motor 14090. When the user of the surgical instrument 14010 is satisfied with the position of the anvil 14050 relative to the cartridge casing 14040, the user can displace the button 14060 distally, as illustrated in FIG. 115, to disengage the slider 14115 from the closing drive and engage the slider 14115 with the firing drive. When the slider 14115 is slid distally, the internal splines 14140 of the slider 14115 are disengaged from the external splines 14200 of the closing nut 14190 such that the subsequent rotation of the slider 14115 is no longer transmitted to the closing nut 14190 and the closure system. Concurrent with the disengagement of the slider from the closure system, the slider 14115 can become engaged with the firing system. Alternatively, the slider 14115 can become disengaged from the closure system as the slider 14115 is displaced distally and, owing to additional distal displacement of the slider 14115, the slider 14115 can become engaged with the firing system. In such circumstances, the transmission 14000 may not operably engage the closure drive and the firing drive with the motor 14090 at the same time. In any event, the firing system can include a firing nut 14260 which can be engaged by the slider 14115 when the slider 14115 is moved distally.

Further to the above, referring primarily to FIG. 116, the firing nut 14260 can include an aperture 14261 defined therein which can be configured to receive the distal end 14118 of the slider 14115 therein when the slider 14115 is advanced into its distal position (FIG. 115). The firing nut aperture 14261 can include firing nut splines 14270 defined around an inner circumference thereof which can intermesh with the outer circumferential splines 14130 of the slider 14115. When the outer circumferential splines 14130 of the slider 14115 are engaged with the firing nut splines 14270 of the firing nut 14260, the slider 14115 can be rotatably coupled with the firing nut 14260 such that the rotation of the slider 14115 is transmitted to the firing nut 14260. The actuator 14020 can further comprise a firing nut bushing 14275 that rotatably supports the firing nut 14260. The firing nut bushing 14275 may comprise a needle bearing, a Delrin, Nylon, and/or other plastic bushing, a metal bushing, or an integral part of the actuator housing 14080, for example. The firing nut 14260 can further comprise internal threads 14272 defined in a distal interior surface of the firing nut aperture 14261. The firing system can further comprise a firing tube 14280 threadably engaged with the internal threads 14272 of the firing nut 14260.

In various instances, further to the above, the firing tube 14280 can include a thread 14281 defined on an outer surface thereof which is threadably engaged with the internal threads 14272. The firing tube 14280 can be constrained from rotating with the firing nut 14260 such that, when the firing nut 14260 is rotated by the motor 14090 and the slider 14115, the firing nut 14260 can translate the firing tube 14280. For instance, when the firing nut 14260 is rotated in a first direction, the firing tube 14280 can be displaced distally by the firing nut 14260 and, when the firing nut 14260 is rotated in a second, or opposite, direction, the firing tube 14280 can be displaced proximally by the firing nut 14260. At least a portion of the firing tube 14280 can be positioned within the aperture 14261 defined in the firing nut 14260. When the firing tube 14280 is displaced proximally, the firing tube 14280 can move proximally within the aperture 14261. When the firing tube 14280 is displaced distally, the firing tube 14280 can move distally within the aperture 14261. As will be described in greater detail below, the firing tube 14280 can be operably connected with a firing member which can eject the staples from the cartridge housing 14040 when the firing tube 14280 is advanced distally. The firing tube 14280 can retract the firing member when the firing tube 14280 is moved proximally. The firing tube 14280 can be long enough to accommodate the firing stroke of the firing member when the firing member is moved between an unfired position and a fired position. In various instances, the threaded portion of the firing tube 14280 is shorter than the threaded portion of the closure rod 14230. In such circumstances, the firing stroke can be shorter than the closure stroke. In other instances, the threaded portion of the firing tube 14280 can be the same length as the threaded portion of the closure rod 14230. In such instances, the firing stroke can be the same length as the closure stroke. In certain instances, the threaded portion of the firing tube 14280 is longer than the threaded portion of the closure rod 14230. In such circumstances, the firing stroke can be longer than the closure stroke.

Figure 34:
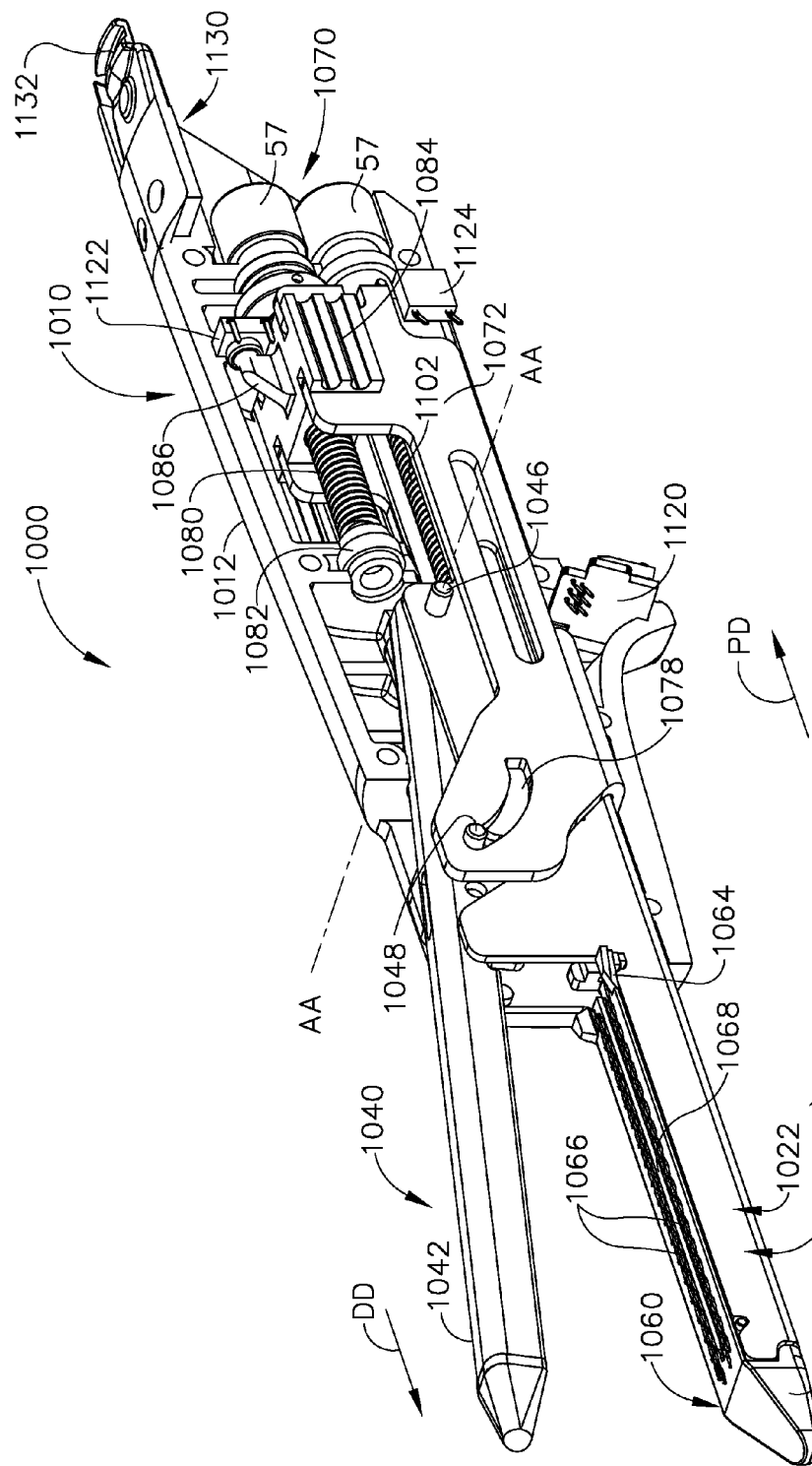
FIG. 34 is a front perspective view of a surgical end effector with a portion of the end effector housing removed for clarity.
Figure 35:
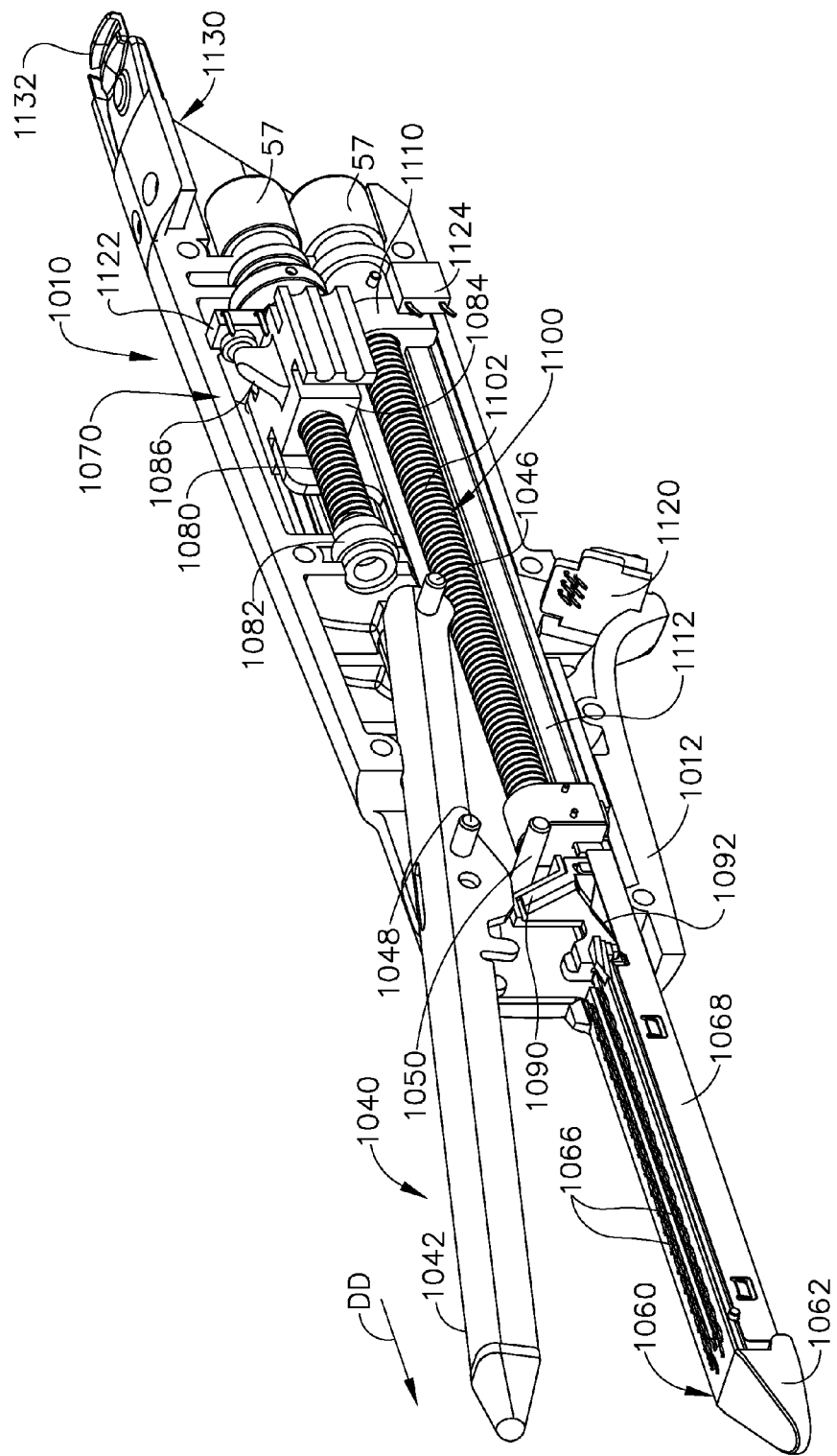
FIG. 35 is another front perspective view of the surgical end effector of FIG. 34 with portions of the closure system and lower jaw omitted for clarity.

Further to the above, the actuator 14020 and the shaft portion 14030 can comprise an integral system. In various instances, the actuator 14020 and the shaft portion 14030 can comprise a unitary assembly. In certain instances, the actuator 14020 can be disassembled from the shaft portion 14030. FIG. 34 is a perspective view of the surgical stapling instrument 14010 depicting the actuator 14020 disassembled from the shaft portion 14030. The instrument 14010 can comprise one or more locks or latches configured to releasably hold the shaft portion 14030 to the actuator 14020. For instance, the actuator 14020 can include latches 14025 on opposite sides thereof which are configured to releasably hold the shaft portion 14030 to the actuator 14020. The latches 14025 can be slid between a first position in which they are engaged with the shaft portion 14030 and a second position in which they have been disengaged from the shaft portion 14030. As described in greater detail below, the actuator 14020 and the shaft portion 14030 can comprise portions of the closure system which are operably assembled together when the shaft portion 14030 is assembled to the actuator 14020. Similarly, the actuator 14020 and the shaft portion 14030 can comprise portions of the firing system which are operably assembled together when the shaft portion 14030 is assembled to the actuator 14020.

Further to the above, referring primarily to FIG. 113, the closure system can further comprise a closing fixture piece 14240 affixed to the distal end of the closing rod 14230. In various instances, a screw can lock the closing fixture piece 14240 to the closing rod 14230 such that the closing fixture piece 14240 is translated distally when the closing rod 14230 is translated distally and, correspondingly, translated proximally when the closing rod 14230 is translated proximally. The closing fixture piece 14240 can comprise one or more lateral extensions that can fit into grooves in the actuator housing 14080 to align the closing fixture piece 14240 and the closing rod 14230. The lateral extensions can also prevent the closing rod 14230 and the closing fixture piece 14240 from rotating when the closing rod 14230 is driven by the closing nut 14190, as discussed above. The closing fixture piece 14240 may comprise a closing drive output of the actuator 14020 and can be attached to a closure drive input of the shaft portion 14030. The closure drive input of the shaft portion 14030 can comprise a second fixture piece 14250 which can be attached to the closing fixture piece 14240 when the shaft portion 14030 is assembled to the actuator 14020. The closing fixture piece 14240 can push the second fixture piece 14250 distally when the closing fixture piece 14240 is advanced distally by the closing rod 14230; correspondingly, the closing fixture piece 14240 can pull the second fixture piece 14250 proximally when the closing fixture piece 14240 is retracted proximally by the closing rod 14230.

The closing drive portion of the shaft portion 14030 can further comprise one or more tension bands 14252 and 14253 mounted to and extending from the second fixture piece 14250. The tension bands 14252 and 14253 can be fastened to the second fixture piece 14250 such that the second fixture piece 14250 can push the tension bands 14252, 14253 distally when the second fixture piece 14250 is advanced distally by the closing fixture piece 14240 and, correspondingly, such that the second fixture piece 14250 can pull the tension bands 14252, 14253 proximally when the second fixture piece 14250 is retracted proximally by the closing fixture piece 14240. In various instances, the shaft portion 14030 can be curved and, in at least one instance, can include a curved shaft housing 14031 extending from a proximal housing mount 14032. In certain instances, the tension bands 14252 and 14253 can be flexible to accommodate a curved path of the closing drive portion of the shaft portion 14030. The closing drive portion of the shaft portion 14030 can further comprise an attachment portion, or trocar, 14258 attached to the tension bands 14253 and 14253. The trocar 14258 can be fastened to the tension bands 14252, 14253 such that the trocar 14258 is advanced and retracted with the tension bands 14252, 14253. The trocar 14258 can comprise a distal end which can be releasably engaged with the anvil 14050 such that the anvil 14050 is advanced and retracted with the trocar 14258 when the anvil 14050 is assembled to the trocar 14258. U.S. Pat. No. 5,292,503, referenced above, discusses this in greater detail.

Further to the above, referring primarily to FIG. 113, the firing system can further comprise a firing fixture piece 14290 affixed to a distal end of the firing tube 14280. In various instances, a screw can lock the firing fixture piece 14290 to the firing tube 14280 such that the firing fixture piece 14290 is translated distally when the firing tube 14280 is translated distally and, correspondingly, translated proximally when the firing tube 14280 is translated proximally. The firing fixture piece 14290 can comprise one or more lateral extensions that can fit into grooves in the actuator housing 14080 to align the firing fixture piece 14290 and the firing tube 14280. The lateral extensions can also prevent the firing tube 14280 and the firing fixture piece 14290 from rotating when the firing tube 14280 is driven by the firing nut 14260, as discussed above. The firing fixture piece 14290 may comprise a firing drive output of the actuator 14020 and can be attached to a firing drive input of the shaft portion 14030. The firing drive input of the shaft portion 14030 can comprise a second fixture piece 14300 which can be attached to the firing fixture piece 14290 when the shaft portion 14030 is assembled to the actuator 14020. The firing fixture piece 14290 can mate in a tongue-in-groove manner with the secondary firing fixture piece 14300. When assembled, the firing fixture piece 14290 can push the second fixture piece 14300 distally when the firing fixture piece 14290 is advanced distally by the firing tube 14280; correspondingly, the firing fixture piece 14290 can pull the second fixture piece 14300 proximally when the firing fixture piece 14290 is retracted proximally by the firing tube 14280.

The firing drive can further comprise a staple driver 14310 coupled to the second fixture piece 14300 such that the staple driver 14310 moves proximally and distally with the second fixture piece 14300. When the staple driver 14310 is moved distally by the second fixture piece 14300, the staple driver 14310 can eject the staples from the cartridge housing 14040. In various instances, the second fixture piece 14300 can advance a knife 14320 distally with the staple driver 14310 to incise tissue captured between the anvil 14050 and the cartridge housing 14040. The second fixture piece 14300 can retract the staple driver 14310 and the knife 14320 proximally when the second fixture piece 14300 is retracted proximally by the firing fixture piece 14290.

Further to the above, it can be noted that portions of the closing system comprising the closing nut 14190 and the closing rod 14230 and portions of the firing system comprising the firing nut 14260 and the firing tube 14280 can be concentric and nested. The firing nut 14260 and the firing tube 14280 may be considered an outer mechanism while the closing nut 14190 and the closing rod 14 230 may be considered an inner mechanism. Together with the slider 14115, the closing nut 14190, the closing rod 14230, the firing nut 14260, and the firing tube 14280 can comprise the transmission 14000. The concentric and nested arrangement of the transmission 14000 can reduce the space required by the closing and firing systems in order to create a smaller and more easily held actuator 14020. This arrangement also allows the outer mechanism to serve as support and provide bearing surfaces for moving parts of the inner mechanism. In the embodiment shown, the translation members of the inner mechanism are shown longer than the translation members of the outer mechanism. The closing rod 14230 may be, for example, of the order of two inches while the firing tube 14280 is of the order of one inch, for example; however, any suitable lengths can be used. Longer translation members are useful when longer translation distances are needed. In the embodiment shown, the inner mechanism, or closure drive, can drive a load a longer distance than the outer mechanism, or firing drive. That said, the firing drive could drive a load a longer distance than the firing drive.

As discussed above, the actuator 14020 and the shaft portion 14030 are designed for easy assembly. The firing fixture piece 14290 comprises a semi-circular lip at the end of a distally extending flange. This semi-circular lip fits into a semi-circular groove at a proximal end of the second firing fixture piece 14300. Because the fit is about a semicircular surface, it is possible to connect firing fixture piece 14290 with the second firing fixture piece 14300 by translating the firing fixture piece 14290 toward the second firing fixture piece 14300 in a direction transverse or orthogonal to a general longitudinal axis of the pieces. Connection of the closure assembly pieces is also facilitated generally in the same manner. For instance, the closing fixture piece 14240 can comprise a distally extending flange. At a distal end of this flange is a semi-circular lip extending from a substantially semi-cylindrical portion of the closing fixture piece 14240. A circumferential groove on a proximal portion of the second fixture piece 14250 receives this semi-circular lip to attach the closing fixture piece 14240 to the second fixture piece 14250. Because of the semi-circular nature of closing fixture piece 14240, the closing fixture piece 14240 and the second fixture piece 14250 may be assembled and disassembled by translation transverse or orthogonal to the general longitudinal axis of the pieces, thus facilitating quick connection and disconnection of the shaft portion 14030 and the actuator 14020.

Referring generally to FIG. 113, the firing trigger 14070 and the closing knob 14075 are further displayed in exploded view to better see their interaction with adjacent parts. The closing knob 14075 is rotatable in a first, or clockwise, direction and a second, or counterclockwise, direction. When the closing knob 14075 is rotated in the first direction, the closing knob 14075 can contact and close a first switch and, when the closing knob 14075 is rotated in the second direction, the closing knob 14075 can contact and close a second switch. When the first switch is closed by the closing knob 14075, the motor 14090 can be energized and operated in a first direction and, when the second switch is closed by the closing knob, the motor 14090 can be energized and operated in a second direction. When the motor 14090 is operated in its first direction, the motor 14090 can drive the closing rod 14230 distally to move the anvil 14050 away from the cartridge casing 14040 and, when the motor 14090 is operated in its second direction, the motor 14090 can drive the closing rod 14230 proximally to move the anvil 14050 toward the cartridge casing 14040. The closing knob 14075 can be positionable in a center, or neutral, position in which neither the first switch nor the second switch are closed and the motor 14090 is not responsive to the closing knob 14075. In various instances, the instrument 14010 can comprise at least one spring, such as spring 14076, for example, configured to bias the closing knob 14075 into its neutral position, for example.

Turning now to the firing trigger 14070, the firing trigger 14070 is rotatably pinned to the actuator housing 14080 and is spring-loaded by a torsion spring 14071 that forces the firing trigger 14070 to a position which is rotated away from the actuator housing 14080. A firing switch 14305 located near the firing trigger 14070 is in a position to be contacted by the firing trigger 14070 when the firing trigger 14070 is rotated toward the actuator housing 14080 against the biasing force of the torsion spring 14071. The firing trigger 14070 can close the firing switch 14305 when the firing trigger 14070 is actuated. When the firing switch 14305 is closed, the motor 14090 can be operated in a first direction to advance the firing tube 14280 and the staple driver 14310 distally. When the firing trigger 14070 is released, the torsion spring 14071 can move the firing trigger 14070 back to its unactuated position and out of contact with the firing switch 14305. At such point, the firing switch 14305 may be in an open condition and the motor 14090 may not be responsive to the firing trigger 14070. In various instances, the instrument 14010 can further comprise a safety latch 14320 rotatably pinned to the actuator housing 14080 which is rotatable between a locked position which blocks the firing trigger 14070 from being actuated and a second position in which the firing trigger 14070 can be actuated to close the firing switch 14035. In any event, the motor 14090 can be operated in a second direction to retract the firing tube 14280 and the staple driver 14310. In certain instances, the motor 14090 can be switched between the first direction and the second direction when the firing system has reached the end of its firing stroke. In some instances, the actuator 14020 can further comprise a reversing button and switch which can be operated to operate the motor 14090 in its second direction.

Figure 112:
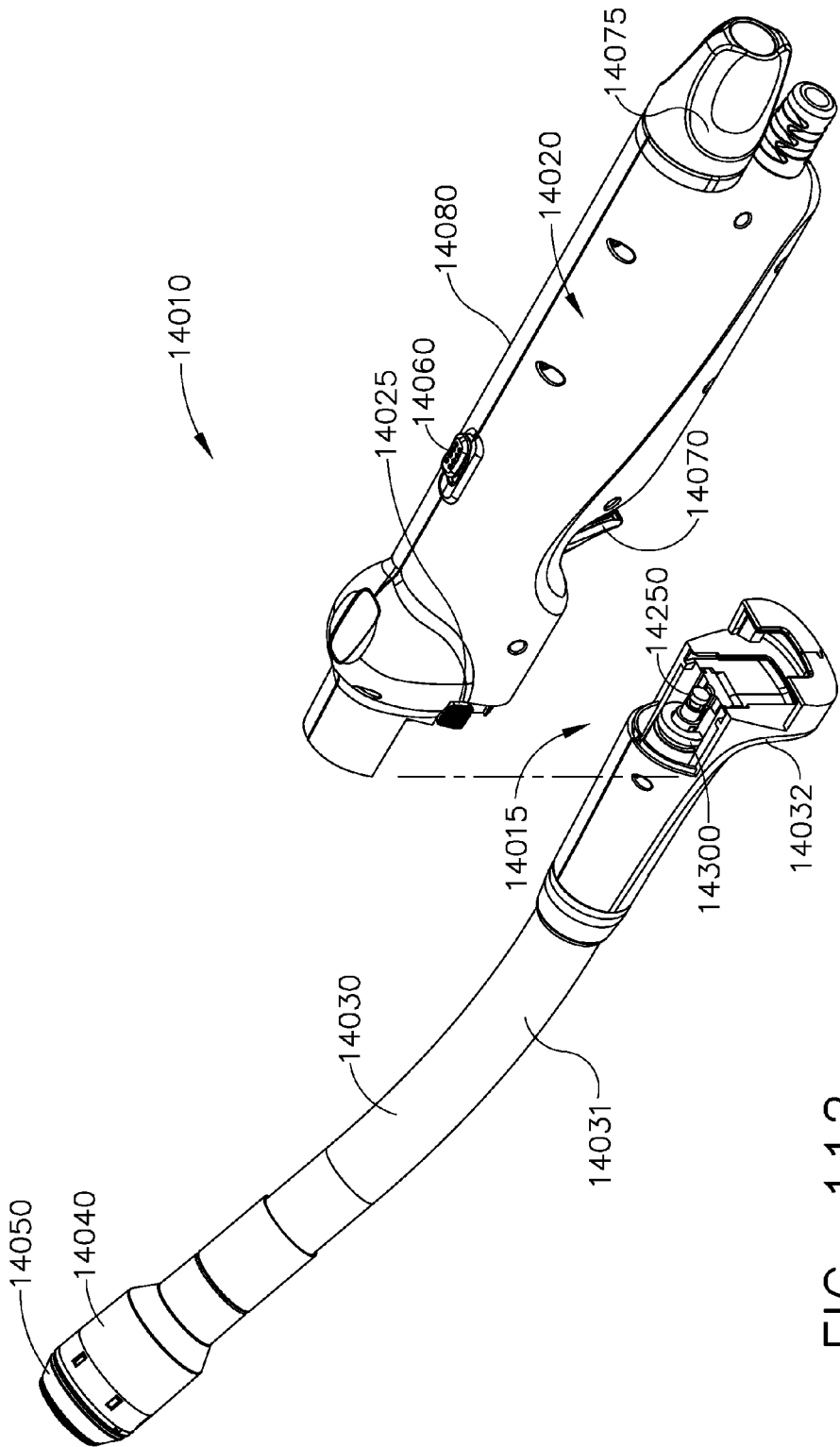
FIG. 112 is a perspective view of the surgical stapling instrument of FIG. 111 illustrating the handle detached from the shaft.

In view of the above, a method of using the instrument 14010 is provided below, although any suitable method could be used. Moreover, it has been described above that the actuator 14020 is capable of providing two outputs and the shaft portion 14030 is capable of receiving two inputs to perform two functions. Such functions have been described as closing functions and firing functions, but the invention is not so limited. The functions could include any suitable functions, such as an articulation function, for example. To use the actuator 14020, in various instances, a user can first assemble the actuator 14020 to the shaft portion 14030 by moving the actuator 14020 toward the shaft portion 14030 perpendicular to the longitudinal axis of the actuator 14020, as seen in FIG. 112. The user can align the open side of the proximal end of the shaft portion 14030 toward the open side of the distal portion of the actuator 14020 and assemble the pieces together. Such assembly can connect the closing and firing fixture pieces as discussed above. As also discussed above, the latches 14025 on the actuator 14020 can grip ledges on the shaft portion housing 14032 to releasably hold the actuator 14020 and the shaft portion 14030 together. After assembling the actuator 14020 and the shaft portion 14030, a user can place the slider assembly 14150 in its first position to use the first desired function of the surgical tool of the attached portion. As discussed above, the button 14060 can be utilized to position the slider assembly 14150 in its first portion.

Referring generally to FIG. 114, the inner splines 14140 on the slider 14115 can engage the external splines 14200 on the closing nut 14190 when the slider assembly 14150 is in its first position. The user would then rotate closing knob 14075 to position the anvil 14050 relative to the cartridge housing 14040. As discussed above, the closing knob 14075 can be rotated in its first direction to close the first closure switch and move the anvil 14050 away from the cartridge housing 14040 and its second direction to close the second closure switch and move the anvil 14050 toward the cartridge housing 14040. In certain instances, the closure of the first closure switch can close a circuit which operates the motor 14090 in its first direction and, correspondingly, the closure of the second closure switch can close a circuit which operates the motor 14090 in its second direction. In certain instances, the first closure switch and the second closure switch can be in communication with a microprocessor of the surgical instrument 14010 which can control the electrical power supplied, including the polarity of the electrical power supplied, to the motor 14090 based on the input from the first closure switch and the second closure switch. As discussed above, the motor 14090 can rotate the rotatable shaft 14100, the extender portion 14110, the slider 14115, and owing to the configuration of the transmission 14000, the closing nut 14190. As discussed above, the closing nut 14190 is threadably engaged with the closing rod 14230 which displaces the anvil 14050 proximally and distally. Alternatively, the closing rod 14230 could perform some other function.

When the slider assembly 14150 is in its first, or proximal, position, as illustrated in FIG. 114, the motor 14090 may be responsive to the closing knob 14075 and not the firing trigger 14070. In at least one instance, the lower journal bearing 14170 of the slider assembly 14150 can contact and close a first transmission switch 14340 when the slider assembly 14150 is in its first position. In various instances, the first transmission switch 14340 can be in communication with the microprocessor of the surgical instrument 14010 which can be configured to ignore input from the firing switch 14305 when the first transmission switch 14340 has been closed. In such circumstances, the user of the surgical instrument 14010 may depress the firing trigger 14070 and the motor 14090 will not be responsive thereto. Rather, in such circumstances, the motor 14090 is responsive to the first and second closure switches which are actuated by the closing knob 14075 to move the anvil 14050. When the slider assembly 14150 is moved toward its second, or distal, position, as illustrated in FIG. 115, the lower journal bearing 14170 is disengaged from the first transmission switch 14340 and the first transmission switch 14340 will return to an open condition. When the slider assembly 14150 is moved into its second, or distal, position, the lower journal bearing 14170 can contact and close a second transmission switch 14350. In various instances, the second transmission switch 14350 can be in communication with the microprocessor of the surgical instrument 14010 which can be configured to ignore input from the closure knob 14075 when the second transmission switch 14350 has been closed. In such circumstances, the user of the surgical instrument 14010 may rotate the closing knob 14075 and the motor 14090 will not be responsive thereto. Rather, in such circumstances, the motor 14090 is responsive to the firing switch 14305 which is actuated by the firing trigger 14070.

In order to move the slider assembly 14150 from its first position to its second position, as discussed above, the user can depress the slider button 14060 to release the slider button 14060 from its detent and move the slider assembly 14150 distally to its second position. In such circumstances, the slider 14115 can be disengaged from the closing nut 14160 and engaged with the firing nut 14260. More particularly, the inner splines 14140 on the slider 14115 can become disengaged from the external splines 14200 on the closing nut 14190 and, furthermore, the outer splines 14130 of the slider 14150 can become engaged with the inner splines 14270 of the firing nut 14260. At such point, the user can rotate the safety latch 14320 to its unlocked position to ready the firing trigger 14070 for firing. The user can fire the firing system by rotating the firing trigger 14070 counterclockwise as depicted in FIG. 115 toward actuator housing 14080. As discussed above, the firing trigger 14070 can contact a firing switch 14305 which can electrically energize the motor 14090. Similar to the first configuration of the transmission 14000, the motor 14090 can rotate the rotatable shaft 14100, the extender portion 14110, and the slider 14115; however, in the second configuration of the transmission 14000, the slider 14115 rotates the firing nut 14260 to translate the firing tube 14280.

In various instances, power can be supplied to the instrument 14010 by an external power source. In certain instances, one or more batteries positioned within the actuator 14020 could be utilized. The batteries could be, for example, lithium rechargeable batteries. In some instances, the batteries and the motor 14090 could be positioned in a sealed, removable housing that is cleanable, sterilizable, and reusable.

After the actuator 14020 has been used during a surgical procedure, the user may disassemble the actuator 14020 from the shaft portion 14030. The user may depress the latches 14025 to disassemble the actuator 14020 from the shaft portion 14030. Thereafter, the actuator 14020 can be cleaned, sterilized, and reused or disposed of. Similarly, the shaft portion 14030 can be cleaned, sterilized, and reused or disposed of. When the shaft portion 14030 is reused, staples can be reloaded into the cartridge housing 14040. In certain instances, the cartridge housing 14040 can include a replaceable cartridge which can be used to reload the staples. In various instances, various portions of the actuator 14020 may also be combined in a sealed, compartmentalized module which can be easily inserted into and removed from the actuator housing 14080. For example, the motor 14090, the rotatable shaft 14100, the extender portion 14110, the slider assembly 14150, the closing nut 14190, the closing rod 14230, the firing nut 14260, and the firing tube 14280 may be combined into a modular assembly removable from the actuator housing 14080. Furthermore, portions of the actuator 14020 may be part of separate assembleable modules. For example, electronic portions of the actuator 14020, such as the motor 14090 and a battery, may comprise one module, while mechanical assemblies containing rotating and/or translating parts may comprise a second module. In such circumstances, the first module may be sterilized by different methods than the second module. Such circumstances can facilitate the use of, for example, gamma radiation for the second module which may be inappropriate for sterilizing the first module.

Various additions to the actuator 14020 are envisioned. For example, microprocessing may be utilized to detect the end-of-stroke positions of the closing system and/or the firing system and to signal the motor 14090 when to stop the closing stroke and/or the firing stroke. Microprocessing could also be utilized to determine the type of shaft assembly that is attached to the actuator 14020. For instance, the actuator 14020 can include a sensor in signal communication with the microprocessor in the actuator 14020 that a circular stapler shaft assembly is attached the actuator 14020 or that a linear cutter shaft assembly is attached to the actuator 14020. It is envisioned that the actuator 14020 can power many types of surgical tools requiring at least one and perhaps two or more longitudinal motion inputs, for example. In various instances, the actuator 14020 can power a circular stapler, a liner stapler, a right-angle stapler, scissors, graspers, and/or other types of surgical instruments, for example.

Further modifications of the actuator 14020 include utilizing multiple motors so that the number of functions employable by the actuator 14020 can be increased. Certain modifications of the actuator 14020 include performing more than two functions with the same motor. For example, a third position of the slider assembly 14150 is envisioned wherein a third function is driven by a third nested mechanism. In some instances, further to the above, the slider assembly 14150 may have a third position which is an idler or neutral position wherein no function is driven by the motor 14090.

Further modifications may include the use of electrical and/or magnetic means to translate the slider 14115 from one position to another. For example, a solenoid may be used to move the slider 14115 from one position to another. A spring may preload the slider 14115 into a default position, and energizing the solenoid may move the slider 14115 from the default position to a second position.

Figure 117:
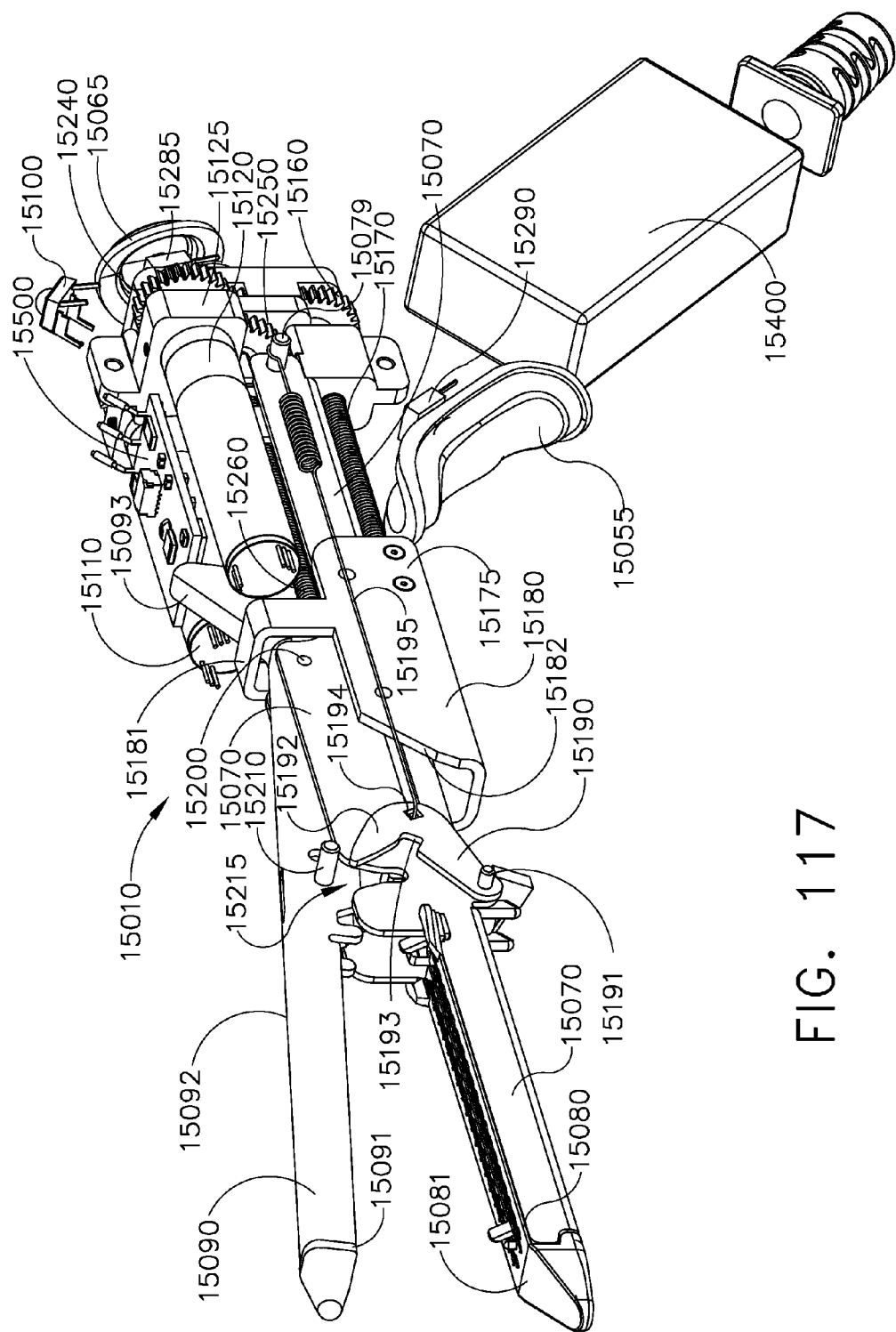
Figure 118:
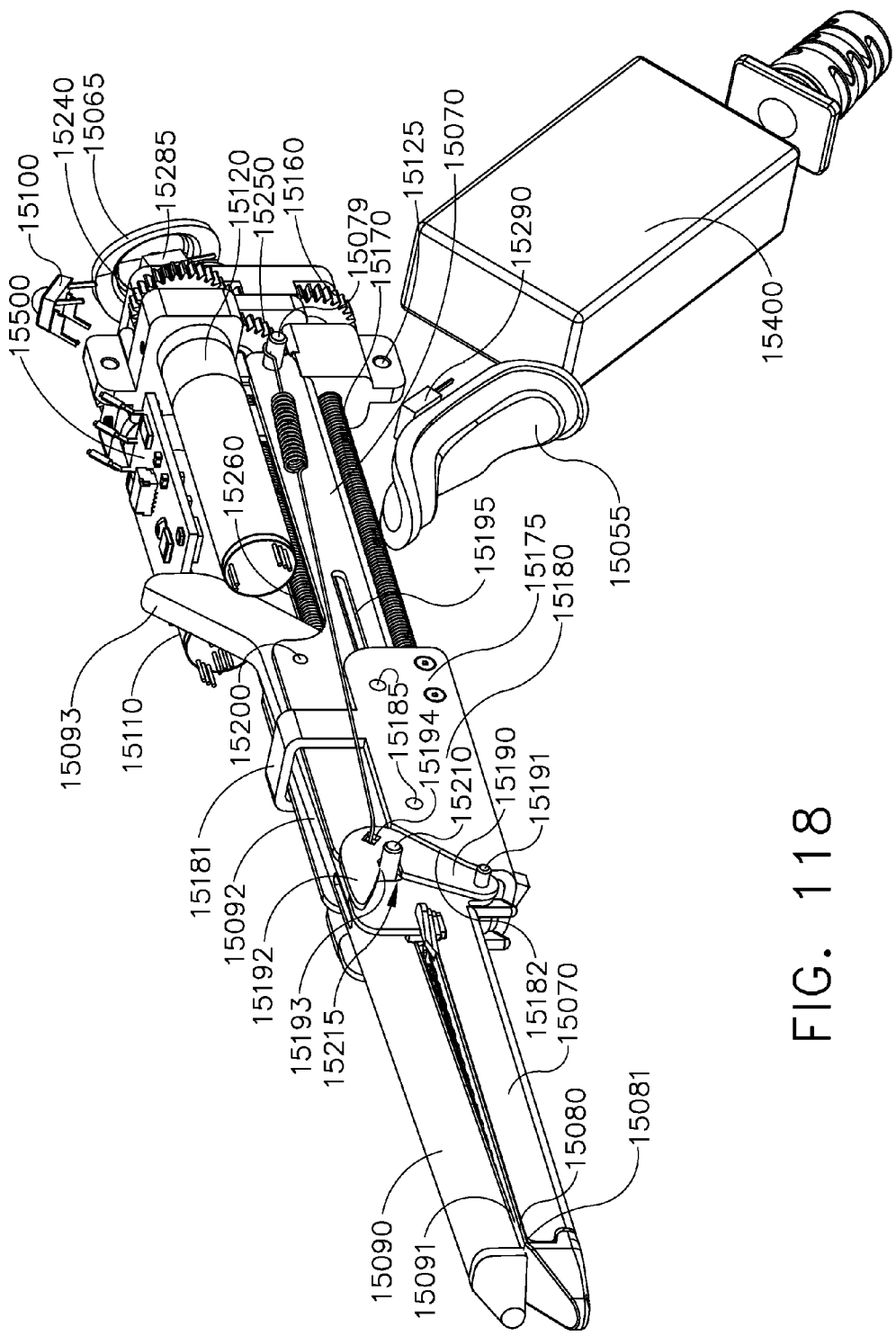

A surgical stapling instrument 15010 is illustrated in FIGS. 117 and 118. Similar to the above, the instrument 15010 can comprise a handle, a closure system configured to move an anvil 15090 between an open position (FIG. 117) and a closed position (FIG. 118) relative to a staple cartridge 15080 and, in addition, a firing system configured to deploy staples from the staple cartridge 15080 and incise tissue captured between the anvil 15090 and the staple cartridge 15080. The housing of the surgical instrument handle has been removed from FIGS. 117 and 118 for the purposes of illustrating various components contained therein. Also similar to the above, the closure system of the instrument 15010 can comprise a closing motor 15110, a closing gear train including closure drive screw gear 15160 operably coupled to the closing motor 15110, and a closure drive screw 15170 operably coupled to the closure drive screw gear 15160. In various instances, the closing motor 15110 can be supported by a motor frame 15125 which can, in addition, rotatably support the closure drive screw gear 15160 and the closure drive lead screw 15170. The closure system can further include a closure button 15065 configured to contact and close a closure switch 15285 which, when closed, can operate the closing motor 15110. In some instances, further to the above, the closure button 15065 can be configured to contact a closure switch configured to operate the closure motor 15110 in a first direction and close the anvil 15090 and an opening switch configured to operate the closure motor 15110 in a second direction and open the anvil 15090.

Further to the above, the closure system can further comprise a carriage 15180 configured to engage the anvil 15090 and move the anvil 15090 between its open position (FIG. 117) and its closed position (FIG. 118). The carriage 15180 can include a threaded nut portion 15175 which is threadably engaged with a threaded portion of the closure drive lead screw 15170. The carriage 15180 can be constrained from rotating with the closure drive lead screw 15170 such that the rotation of the closure drive lead screw 15170 can translate the carriage 15180 proximally and distally, depending on the direction in which the closure drive lead screw 15170 is rotated. When the closure drive lead screw 15170 is rotated in a first direction by the closing motor 15110, the closure drive lead screw 15170 can displace the carriage 15180 distally to close the anvil 15090. Correspondingly, when the closure drive lead screw 15170 is rotated in a second, or opposite, direction, by the closing motor 15110, the closure drive lead screw 15170 can displace the carriage 15180 proximally to open the anvil 15090. The carriage 15180 can be at least partially disposed around a cartridge channel 15070 and, in various instances, can be slidably retained to the cartridge channel 15070. Referring primarily to FIG. 118, the cartridge channel 15070 can include one or more slots 15195 defined in opposite sides thereof which are configured to slidably receive one or more projections 15185 extending inwardly from the carriage 15080. In other circumstances, the channel 15070 can comprise the projections 15185 and the carriage 15080 can comprise the slots 15195. In either event, the slots 15195 and the projections 15185 can be configured to constrain the movement of the carriage 15180 to a longitudinal, or substantially longitudinal, path, for example.

The carriage 15080 is movable from a first, or proximal, position (FIG. 117) to a second, or distal, position (FIG. 118) to close the anvil 15090. The carriage 15080 can include a crossbar 15081 which is configured to contact and move the anvil 15090 when the carriage 15080 is moved relative to the anvil 15090. In various instances, the anvil 15090 can be pivotably coupled to the cartridge channel 15070 about a pivot 15200 and the anvil 15090 can be rotated about the pivot 15200 by the carriage crossbar 15081. More specifically, the carriage crossbar 15181 can be configured to contact a top, or cam, surface 15092 of the anvil 15090 and slide across the top surface 15092 as the carriage 15080 is moved distally to rotate the anvil 15090 toward the cartridge 15080 positioned in the cartridge channel 15070. In some instances, the distal end 15091 of the anvil 15090 can contact the distal end 15081 of the cartridge 15080 when the anvil 15090 reaches its fully closed position. The carriage 15180 can be advanced distally until it reaches its distal-most position and/or the anvil 15090 is in its fully closed position, which is illustrated in FIG. 118. In various circumstances, the carriage 15180 can contact and close an end-of-stroke sensor when the carriage 15180 reaches its distal-most position. In certain instances, the end-of-stroke sensor can be in signal communication with a microprocessor of the surgical instrument 15010. When the end-of-stroke sensor is closed by the carriage 15180, the microprocessor can interrupt the power supplied to the closing motor 15110 and stop the advancement of the carriage 15180.

As discussed above, the crossbar 15181 of the carriage 15180 can cam the anvil 15090 toward the staple cartridge 15080 by pushing the cam surface 15092 downwardly. The anvil 15090 can further comprise a latch pin 15210 extending from the sides thereof which can be received in slots 15215 defined in the sides of the cartridge channel 15070 when the anvil 15090 is rotated toward the staple cartridge 15080. In various instances, the latch pin 15210 can contact the closed ends of the slots 15215 when the anvil 15090 reaches its closed position, for example. In some instances, the anvil 15090 may be in a closed position and the latch pin 15210 may not be in contact with the closed ends of the slots 15215. In certain instances, the closure system can comprise one or more latches 15190 configured to engage the latch pin 15210 and/or move the anvil 15090 closer to the staple cartridge 15080. The latches 15190 can be rotatably coupled to the cartridge channel 15070 by a pivot pin 15191 and can be rotated about a pivot axis to engage the latch pin 15210. In some instances, the latches 15190 can engage the latch pin 15210 and position the latch pin 15210 against the closed ends of the slots 15215. Each latch 15190 can comprise a latch arm 15192 which can slide over the latch pin 15210 and push the latch pin 15210 downwardly as the latch 15190 is rotated distally into its closed position. Each latch arm 15192 can at least partially define a latch slot 15193 which can be configured to receive the latch pin 15210 as the latches 15190 are moved into their actuated positions. The latch arms 15192 and the closed ends of the slots 15215 can co-operate to trap and/or hold the latch pin 15210 in position.

Further to the above, the latches 15190 can be moved between an unlatched position (FIG. 117) and a latched position (FIG. 118) by the carriage 15180 when the carriage 15180 is advanced distally. To the extent that the anvil 15090 is not moved into its fully closed position by the crossbar

15181, the latches 15190 can move the anvil 15090 into its fully closed position. In various instances, the carriage 15180 can include distal cam surfaces 15182 defined thereon which can engage the latches 15190 when the carriage 15180 is advanced distally. In at least one such instance, each cam surface 15182 can comprise a sloped or angled surface, for example. When the closure drive lead screw 15170 is rotated in its second direction and the carriage 15180 is retracted proximally by the closure drive lead screw 15170, the latches 15190 can be returned to their unactuated positions. In various instances, the instrument 15010 can further comprise one or more biasing springs 15195, for example, which can be configured to rotate the latches 15190 proximally when the distal cam surfaces 15182 are retracted away from the latches 15190. Each latch 15190 can include an aperture 15194 defined therein configured to receive a first end of a spring 15195. A second end of each spring 15195 can be engaged with a spring post 15079 extending from the cartridge channel 15070. When the latches 15190 are rotated distally from their unlatched positions to the their latched positions by the carriage 15180, as discussed above, the springs 15195 can be resiliently stretched such that, when the carriage 15180 is retracted, the springs 15195 can elastically return to their original condition thereby applying a force to the latches 15090 via the apertures 15194, for example. In any event, when the latches 15190 have been returned to their unlatched positions, the anvil 15090 can be moved relative to the staple cartridge 15080 once again.

As discussed above, the crossbar 15181 of the carriage 15180 can contact the cam surface 15092 of the anvil 15090 to rotate the anvil 15090 toward the staple cartridge 15080. The carriage 15180 can also be configured to rotate the anvil 15090 away from the staple cartridge 15080. In at least one such instance, the anvil 15090 can comprise a second cam surface 15093 defined thereon which can be contacted by the crossbar 15181 of the carriage 15080 as the carriage 15080 is moved proximally by the closure drive lead screw 15170. As the reader will appreciate, the closing cam surface 15092 can be defined on a first side of the pivot pin 15200 and the opening cam surface 15093 can be defined on a second, or opposite, side of the pivot pin 15200. The opening cam surface 15093 can extend at an angle with respect to the closing cam surface 15092. In various instances, the crossbar 15181 can contact and slide relative to the opening cam surface 15093 as the carriage 15180 is retracted. The opening cam surface 15093 can be configured such that the degree, or amount, in which the anvil 15090 is opened relative to the staple cartridge 15080 is dependent upon the distance in which the crossbar 15181 is retracted proximally. For instance, if the crossbar 15181 is retracted a first distance proximal to the pivot 15200, the crossbar 15181 can pivot the anvil 15090 upwardly away from the staple cartridge 15080 a first degree and, if the crossbar 15181 is retracted a second distance proximal to the pivot 14200 which is larger than the first distance, the crossbar 15181 can pivot the anvil 15090 upwardly away from the staple cartridge 15080 a second degree which is larger than the first degree.

The closing system discussed above can permit the user of the surgical instrument to pivot the anvil 15090 between an open and a closed position without having to manipulate the anvil 15090 by hand. The closing system discussed above can also latch or lock the anvil 15090 in its closed position automatically without requiring the use of a separate actuator. To the extent that the user is unsatisfied with the positioning of the tissue between the anvil 15090 and the staple cartridge 15080 when the anvil 15090 is in its closed position, the user can reopen the anvil 15090, reposition the anvil 15090 and the staple cartridge 15080 relative to the tissue, and then close the anvil 15090 once again. The user can open and close the anvil 15090 as many times as needed prior to actuating the firing system of the instrument 15010. The firing system can comprise a firing motor 15120 mounted to the motor frame 15125, a firing drive gear train operably coupled to the firing motor 15120 including a firing gear 15240, a firing lead screw gear 15250, and a firing drive lead screw 15260. Similar to the above, the firing drive gear train and/or the firing drive lead screw 15260 can be rotatably supported by the motor frame 15125. The firing drive can further comprise a firing trigger 15055 configured to close a firing switch 15290 when the firing trigger 15055 is depressed to operate the firing motor 15120. When the firing motor 15120 is operated in a first direction to rotate the firing drive lead screw 15260 in a first direction, the firing drive can deploy the staples removably stored in the staple cartridge 15080 and incise the tissue captured between the anvil 15090 and the staple cartridge 15080. When the firing motor 15120 is operated in a second direction to rotate the firing drive lead screw 15260 in a second, or opposite, direction, the firing drive can be retracted. Thereafter, the anvil 15090 can be reopened to remove the tissue from between the anvil 15090 and the staple cartridge 15080. In some instances, the firing drive may not need to be retracted to open the anvil 15090. In such instances, the firing drive may not engage the anvil 15090 as it is advanced distally. In at least one such instance, the firing drive can enter into the staple cartridge 15080 to eject the staples therefrom and a knife edge may travel between the staple cartridge 15080 and the anvil 15090 to incise the tissue. The firing drive may not lock the anvil 15090 in its closed position, although embodiments are envisioned in which the firing drive could lock the anvil 15090 in its closed position. Such embodiments could utilize an I-beam, for example, which can engage the anvil 15090 and the staple cartridge 15080 and hold them in position relative to each other as the I-beam is advanced distally.

The instrument 15010 can be powered by an external power source and/or an internal power source. A cable can enter into the actuator housing 15080 to supply power from an external power source, for example. One or more batteries, such as battery 15400, for example, can be positioned within the handle of the instrument 15010 to supply power from an internal power source, for example. The instrument 15010 can further comprise one or more indicators, such as LED indicator 15100, for example, which can indicate the operating state of the instrument 15010, for example. The LED indicator 15100 can operate the same manner as or a similar manner to the LED indicator 11100 described above, for example. The LED indicator 15100 can be in signal communication with the microcontroller of the instrument 15010 which can be positioned on a printed circuit board 15500, for example.

Previous surgical instruments have utilized a manually-driven closure system configured to move an anvil between an open position and a closed position. Various embodiments disclosed herein utilize a motor-driven closure system configured to move an anvil between an open position and a closed position relative to a fixed staple cartridge. Other embodiments are envisioned in which an anvil can be fixed and a motor-driven closure system could move a staple cartridge between an open position and a closed position. In either event, the motor of the closure system can set the tissue gap between the anvil and the staple cartridge. In various instances, the closure system of the surgical instrument is separate and distinct from the firing system. In other instances, the closure system and the firing system can be integral. When the closure system and the firing system are separate and distinct, the user of the surgical instrument can evaluate the position of the anvil and the staple cartridge relative to the tissue that is to be stapled and incised before operating the firing system.

As discussed above, an end effector of a surgical instrument, such as end effector 1000, for example, can be configured to clamp tissue between an anvil jaw 1040 and a staple cartridge 1060 thereof. When the anvil jaw 1040 is in its closed position, a tissue gap can be defined between the anvil jaw 1040 and the staple cartridge 1060. In certain instances, the end effector 1000 may be suitable for use with thin tissue, thick tissue, and tissue having a thickness intermediate the thin tissue and the thick tissue. The thinnest tissue and the thickest tissue in which the end effector 1000 can be suitably used to staple can define a tissue thickness range for the end effector 1000. In various instances, a surgical instrument system can include a handle and a plurality of end effectors which can be assembled to the handle, wherein one or more of the end effectors can have different tissue thickness ranges. For instance, a first end effector can have a first tissue thickness range and a second end effector can have a second tissue thickness range which is different than the first tissue thickness range. In some instances, the first tissue thickness range and the second tissue thickness range can be discrete while, in other instances, the first tissue thickness range and the second tissue thickness range can partially overlap. Surgical instrument systems can utilize any suitable number of end effectors having different tissue thickness ranges where some of the tissue thickness ranges may at least partially overlap and other tissue thickness ranges may not overlap at all.

In various instances, further to the above, a staple cartridge of an end effector, such as staple cartridge 1060 of end effector 1000, for example, can be replaceable. In various instances, the staple cartridge 1060 can be removably locked into position within the lower jaw 1020 of the end effector 1000. Once locked into position, the deck, or tissue contacting, surface of the staple cartridge 1060 may not move, or at least substantially move, relative to the lower jaw 1020. Thus, when the anvil jaw 1040 is moved into its closed position, a fixed distance, or tissue gap, can be defined between the anvil jaw 1040 and the deck surface of the staple cartridge 1060. To change this fixed distance, the staple cartridge 1060 can be removed from the lower jaw 1020 and a different staple cartridge can be removably locked within the lower jaw 1020. The deck surface of the different staple cartridge can be configured to provide a different tissue gap than the tissue gap provided by the staple cartridge 1060. Embodiments are envisioned in which a surgical instrument system includes a handle, a plurality of end effectors which can be assembled to the handle, and a plurality of staple cartridges which can be replaceably inserted into the end effectors. Such an embodiment can allow a user to select an end effector capable of being used with a range of tissue thicknesses and the staple cartridge selected for use with the end effector can adjust or fine tune the range of tissue thicknesses that can be stapled by the end effector. In certain instances, a first staple cartridge of the surgical instrument system can include a first type of staple and a second staple cartridge can include a second type of staple. For example, the first staple cartridge can include staples having a first unformed, or unfired, height, and the second staple cartridge can include staples having a second unformed, or unfired, height which is different that the first height.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, filed Jan. 31, 2006, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, filed Sep. 23, 2008, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, filed Oct. 10, 2008, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Patent Application Publication No. 2012/0074198;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012, now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

As described earlier, sensors may be configured to detect and collect data associated with the surgical device. The processor processes the sensor data received from the sensor(s).

The processor may be configured to execute operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the data associated with motion, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the controller 2016 and/or the controller 2022 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:
1. A surgical instrument, comprising:
a motor including a motor output shaft;
a first rotary drive system;
a second rotary drive system;
a transmission assembly in operable engagement with the motor output shaft and being selectively shiftable between a first drive position wherein rotation of the motor output shaft is imparted to the first rotary drive system and a second drive position wherein rotation of the motor output shaft is imparted to the second rotary drive system; and
a locking assembly supported by the transmission assembly and configured to mechanically prevent actuation of the second rotary drive system when the transmission assembly is in the first drive position, said locking assembly further configured to prevent actuation of the first rotary drive system when the transmission assembly is in the second drive position.
2. The surgical instrument of claim 1 wherein the transmission assembly is axially shiftable between the first and second drive positions by a solenoid operably coupled thereto.

3. The surgical instrument of claim 1 wherein the transmission assembly comprises:
a transmission carriage in operable engagement with the motor output shaft, the transmission carriage being supported for selective axial travel between the first and second drive positions;
a transmission link operably coupled to the transmission carriage; and
a firing trigger coupled to the transmission link such that when the firing trigger is depressed, the transmission link moves the transmission carriage from the first drive position to the second drive position.
4. The surgical instrument of claim 1 wherein the first rotary drive system comprises a first rotary drive shaft including a first drive gear non-rotatably supported thereon and wherein the second rotary drive system comprises a second rotary drive shaft including a second drive gear non-rotatably supported thereon and an intermediate drive gear rotatably supported thereon in meshing engagement with the first drive gear and wherein the transmission assembly comprises a transmission carriage rotatably supporting a carriage gear thereon, the transmission carriage supported for axial travel between the first drive position wherein the carriage gear is in meshing engagement with a motor gear on the motor output shaft and the intermediate gear and the second drive position wherein the carriage gear is in meshing engagement with the motor gear and the second drive gear.
5. The surgical instrument of claim 4 wherein the locking assembly comprises:
a first drive lock on the transmission carriage, the first drive lock positioned to lockingly engage the second drive gear when the transmission carriage is in the first drive position to prevent rotation of the second drive gear; and
a second drive lock on the transmission carriage, the second drive lock positioned to lockingly engage the intermediate drive gear when the transmission carriage is in the second drive position to prevent rotation of the intermediate drive gear.
6. The surgical instrument of claim 4 wherein the first rotary drive shaft defines a first shaft axis and wherein the second rotary drive shaft defines a second shaft axis that is parallel to the first shaft axis.
7. The surgical instrument of claim 1 wherein the first rotary drive system comprises a rotary drive shaft having a first drive gear non-rotatably attached thereto and wherein the second rotary drive system comprises:
a second rotary drive shaft;
a planetary gear assembly comprising:
a planetary gear carrier non-rotatably attached to the second rotary drive shaft;
a plurality of planetary gears rotatably supported on the planetary gear carrier, each said planetary gear in meshing engagement with a sun gear non-rotatably attached to the motor output shaft and wherein the second rotary drive system further comprises:
a ring gear assembly rotatably supported on the second rotary drive shaft, the ring gear assembly including an internal ring gear in meshing engagement with the planetary gears and an external ring gear in meshing engagement with the first drive gear and wherein the locking assembly comprises:
a first lock lug portion on the transmission assembly configured to lockingly engage the planetary gear carrier when the transmission assembly is in said first drive position to prevent rotation of the planetary gear carrier and the second rotary drive shaft such that rotation of the motor output shaft causes the planetary gears to rotate relative to the planetary gear carrier and impart rotary motion to the ring gear assembly and the first drive gear; and a second lock lug portion on the transmission assembly configured to lockingly engage the ring gear assembly when the transmission assembly is in the second drive position to prevent rotation of the ring gear assembly such that rotation of the motor output shaft causes the planetary gears to rotate the planetary gear carrier and impart rotary motion to the second rotary drive shaft.

8. The surgical instrument of claim 7 wherein the transmission assembly is axially shiftable between the first and second drive positions by a solenoid operably coupled thereto.

9. The surgical instrument of claim 1 wherein the first rotary drive system is configured to be operably coupled to a first rotary driven system operably supported in a surgical end effector that is attached to the surgical instrument and wherein the second rotary drive system is configured to be operably coupled to a second rotary driven system in the surgical end effector.

10. A surgical instrument, comprising:
a motor including a motor output shaft;
a first rotary drive system;
a second rotary drive system;
a transmission assembly in operable engagement with the motor output shaft and being selectively shiftable between a first rotary drive position wherein rotation of the motor output shaft is imparted to the first rotary drive system and a second rotary drive position wherein rotation of the motor output shaft is imparted to the second rotary drive system; and
means for mechanically preventing rotation of the second rotary drive system when the transmission assembly is in the first rotary drive position, said means for mechanically preventing further configured to prevent rotation of the first rotary drive system when the transmission assembly is in the second rotary drive position.

11. A surgical instrument, comprising:
a housing;
a motor supported by the housing and including a motor output shaft;
a first rotary drive system operably supported by the housing;
a second rotary drive system operably supported by the housing;
a transmission assembly movably supported in the housing in operable engagement with the motor output shaft and being selectively shiftable between a first rotary drive position wherein rotation of the motor output shaft is imparted to the first rotary drive system and a second rotary drive position wherein rotation of the motor output shaft is imparted to the second rotary drive system wherein the first rotary drive system comprises:
a first rotary drive shaft supported by the housing and including a first drive pulley non-rotatably coupled thereto and wherein the second rotary drive system comprises:
a second rotary drive shaft supported by the housing and including a second drive pulley non-rotatably attached thereto and wherein the motor output shaft includes a first motor pulley non-rotatably attached thereto and a second motor pulley non-rotatably attached thereto and wherein the surgical instrument further comprises:
a first drive belt in slack engagement with the first motor pulley and the first drive pulley; and
a second drive belt in slack engagement with the second motor pulley and the second drive pulley and wherein the transmission assembly comprises:
an idler carriage supporting a first idler pulley and a second idler pulley, the idler carriage being selectively laterally movable between the first rotary drive position wherein the first drive pulley engages the first drive belt to remove slack therefrom such that rotation of the first motor pulley results in the rotation of the first drive pulley and the first rotary drive shaft, and the second rotary drive position wherein the second drive pulley engages the second drive belt to remove slack therefrom such that rotation of the second motor pulley results in rotation of the second drive pulley and the second rotary drive shaft.

12. The surgical instrument of claim 11 wherein the first rotary drive shaft defines a first shaft axis and wherein the second rotary drive shaft defines a second shaft axis that is parallel to the first shaft axis.

13. A surgical instrument, comprising:
a housing;
a motor supported by the housing and including a motor output shaft;
a first rotary drive system operably supported by the housing;
a second rotary drive system operably supported by the housing;
a transmission assembly movably supported in the housing in operable engagement with the motor output shaft and being selectively shiftable between a first rotary drive position wherein rotation of the motor output shaft is imparted to the first rotary drive system and a second rotary drive position wherein rotation of the motor output shaft is imparted to the second rotary drive system wherein the first rotary drive system comprises a first rotary drive shaft supported by the housing and includes a first drive pulley non-rotatably coupled thereto and wherein the second rotary drive system comprises a second rotary drive shaft supported by the housing and includes a second drive pulley non-rotatably attached thereto and wherein the transmission assembly further comprises a transmission shaft assembly movably supported on the motor output shaft for axial travel thereon and rotation therewith, the transmission shaft assembly configured for selective meshing engagement with first and second motor pulleys rotatably supported thereon such that when the transmission shaft assembly is in the first rotary drive position, the first motor pulley rotates with the transmission shaft assembly and the second motor pulley is freewheeling thereon and when the transmission shaft assembly is in the second rotary drive position, the second motor pulley rotates with the transmission shaft assembly and the first motor pulley is freewheeling thereon and wherein the transmission assembly further comprises:
a first drive belt in driving engagement with the first drive pulley and the first motor pulley; and
a second drive belt in driving engagement with the second drive pulley and the second motor pulley.

14. The surgical instrument of claim 13 wherein the transmission assembly further comprises a transmission carriage axially movable within the housing and operably coupled to the transmission shaft assembly to axially move the transmission shaft assembly between the first and second rotary drive positions while enabling the transmission shaft assembly to rotate relative to the transmission carriage.

15. The surgical instrument of claim 14 wherein the transmission carriage is axially shiftable by a solenoid operably coupled thereto.

16. A surgical instrument, comprising:
   a motor including a motor output;
   a first drive system;
   a second drive system;
   a transmission assembly in operable engagement with the motor output and being selectively shiftable between a first drive position wherein the motor output is imparted to the first drive system and a second drive position wherein the motor output is imparted to the second drive system; and
   a locking assembly configured to prevent actuation of the second drive system when the transmission assembly is in the first drive position, said locking assembly further configured to prevent actuation of the first drive system when the transmission assembly is in the second drive position.

17. A surgical instrument, comprising:
   a motor including a motor output;
   a first drive system comprising a first drive gear;
   a second drive system comprising a second drive gear and an intermediate drive gear wherein the intermediate drive gear is in meshing engagement with the first drive gear;
   a transmission assembly in operable engagement with the motor output and being selectively shiftable between a first drive position wherein the motor output is imparted to the first drive system and a second drive position wherein the motor output is imparted to the second drive system; and
   a locking assembly, comprising:
      a first drive lock positioned to engage the second drive gear when the transmission assembly is in the first drive position to resist rotation of the second drive gear; and
      a second drive lock positioned to engage the intermediate drive gear when the transmission assembly is in the second drive position to resist rotation of the intermediate drive gear.

18. A surgical instrument, comprising:
   a motor including a motor output;
   a first drive system;
   a second drive system;
   a transmission assembly in operable engagement with the motor output and being selectively shiftable between a first drive position wherein the motor output is imparted to the first drive system and a second drive position wherein the motor output is imparted to the second drive system; and
   a locking assembly configured to stop the second drive system when the transmission assembly is in the first drive position, said locking assembly further configured to stop the first drive system when the transmission assembly is in the second drive position.

* * * * *